US011046938B2

(12) United States Patent
Karhumaa et al.

(10) Patent No.: US 11,046,938 B2
(45) Date of Patent: Jun. 29, 2021

(54) RECOMBINANT YEAST STRAINS FOR PENTOSE FERMENTATION

(71) Applicant: Novozymes A/S, Bagsvaerd (DK)

(72) Inventors: Kaisa Karhumaa, Södra Sandby (SE); Malin Sendelius, Staffanstorp (SE); Violeta Sánchez I Nógue, Lund (SE)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 16/471,490

(22) PCT Filed: Dec. 19, 2017

(86) PCT No.: PCT/EP2017/083586

§ 371 (c)(1),
(2) Date: Jun. 19, 2019

(87) PCT Pub. No.: WO2018/114973

PCT Pub. Date: Jun. 28, 2018

(65) Prior Publication Data

US 2019/0352620 A1 Nov. 21, 2019

Related U.S. Application Data

(60) Provisional application No. 62/436,648, filed on Dec. 20, 2016, provisional application No. 62/436,687, filed on Dec. 20, 2016, provisional application No. 62/436,706, filed on Dec. 20, 2016, provisional application No. 62/436,723, filed on Dec. 20, 2016.

(51) Int. Cl.
*C12N 9/12* (2006.01)
*C12P 7/10* (2006.01)
*C12P 19/02* (2006.01)

(52) U.S. Cl.
CPC .............. *C12N 9/1205* (2013.01); *C12P 7/10* (2013.01); *C12P 19/02* (2013.01); *C12Y 207/01017* (2013.01)

(58) Field of Classification Search
CPC .......... C12N 9/1205; C12N 1/18; C12N 1/22; C12N 9/0006; C12N 9/12; C12N 9/88; C12N 9/90; C12N 9/92; C12N 15/52; C12P 7/10; C12P 19/02; C12P 2203/00; C12Y 207/01017; Y02E 50/10; C07K 14/395
See application file for complete search history.

(56) References Cited

U.S. PATENT DOCUMENTS

| | | | | |
|---|---|---|---|---|
| 2009/0246857 | A1 | 10/2009 | Ho et al. | |
| 2012/0270289 | A1 | 10/2012 | Jeffries et al. | |
| 2012/0309093 | A1 | 12/2012 | Ma et al. | |
| 2014/0038253 | A1 * | 2/2014 | Jessen ...................... | C12P 7/10 435/161 |

FOREIGN PATENT DOCUMENTS

| | | | |
|---|---|---|---|
| JP | 2015177760 | A | 10/2015 |
| WO | 1995013362 | A1 | 5/1995 |
| WO | 2009017441 | A1 | 2/2009 |
| WO | 2010039692 | A1 | 4/2010 |
| WO | 2010059095 | A1 | 5/2010 |
| WO | 2012045088 | A2 | 4/2012 |
| WO | 2012135110 | A1 | 10/2012 |

OTHER PUBLICATIONS

Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Branden et al., Introduction to Protein Structure, Garland Publishing Inc., New York, p. 247, 1991.*
Sadowski et al., Current Opinion in Structural Biology 19:357-362, 2009.*
Guo et al., Gen Bank accession No. AAY87404, Jun. 21, 2016, 2006.*
Hector et al., Biotechnology for Biofuels 6:84, pp. 1-12, 2013.*
Varghese et al., Gen Bank accession No. SEV86969, Oct. 29, 2016.*
Chang et al, 1988, Appl Biochem Biotechnol 17, 313-318.
Eliasson et al, 2001, Enzyme Microb Technol 29, 288-297.
Gietz et al, 2007, Nature protocols 2, 31-34.
Guo et al, 2006, J Appl Microbiol 101(1), 139-150.
Hou, 2012, Appl Microbiol Biotechnol 94, 205-214.
Inoue et al, 1990, Gene 96, 23-28.
Jin et al, 2003, Appl Environ Microbiol 69(1), 495-503.
Johansson et al, 2001, Appl Environ Microbiol 67(9), 4249-4255.
Johansson et al, 2002, Yeast 19(3), 225-231.
Karhumaa et al, 2005, Yeast 22(5), 359-368.
Karhumaa et al, 2007, Micro Cell Fac 6(5), 1-10.
Karhumaa et al, 2009, Yeast 26, 371-382.
Kim et al, 2013, Biotechnol Adv 31, 851-861.
Kuyper et al, 2005, FEMS Yeast Research 5(4-5), 399-409.
Linden et al, 1992, Appl Environ Microbiol 58(5), 1661-1669.
Lonn et al, 2003, Enzyme Microb Technol 32, 567-573.
Madhavan et al, 2009, Appl Microbiol Biotechnol 82, 1067-1078.
Matsushika et al, 2011, Enzyme Microb Technol 48, 466-471.
Mollapour et al, 2001, Mol Microbiol 42(4), 919-930.
Mumberg et al, 1995, Gene 156, 119-122.
Needleman et al, 1970, J Mol Biol 48, 443-453.
Nguyen et al, 2006, Mycological research 110, 1232-1241.
Parachin et al, 2011, Metabolic Engineering 13, 508-517.
Rice et al, 2000, Trends Genet 16, 276-277.
Runquist et al, 2010, Appl Environ Microbiol 76(23), 7796-7802.
Shamanna et al, 1979, J Bacteriol 139, 64-70.
Tiwari et al, 2008, Biochem Biophys Res Com 366, 340-345.
Walther et al, 2012, FEBS Letters 586(23), 4114-4118.
Wohlbach et al, 2011, PNAS 108(32), 1-29.
Wohlbach et al, 2011, PNAS 108(32), 13212-13217.
Xu et al, 2013, Molecular Systems Biology 9(665), 1-12.

* cited by examiner

*Primary Examiner* — Delia M Ramirez
(74) *Attorney, Agent, or Firm* — Eric Fechter

(57) ABSTRACT

Described herein are recombinant yeast cells expressing a xylulose kinase (XK) which are suitable for fermentation of pentoses. Also described are recombinant yeast cells with higher tolerance to formic and/or acetic acid and suitable for fermentation of pentoses. Also described are recombinant yeast cells expressing an enolase, a phosphofructokinase beta subunit, a 6-phosphofructo-2-kinase, a glucose-6-phosphate isomerase, a phosphoglycerate mutase and/or a triose-phosphate isomerase, and suitable for fermentation of pentoses. Also described are recombinant yeast cells expressing a phosphoglucomutase and/or phosphoribomutase which are suitable for fermentation of pentoses. Further described are methods of using or producing such recombinant yeast cells and related materials.

20 Claims, 37 Drawing Sheets

Specification includes a Sequence Listing.

RECOMBINANT YEAST STRAINS FOR PENTOSE FERMENTATION

CROSS-REFERENCE TO RELATED APPLICATIONS

This application is a 35 U.S.C. 371 national application of PCT/EP2017/083586, filed Dec. 19, 2017, which claims priority or the benefit from U.S. Provisional Application Ser. No. 62/436,648, filed Dec. 20, 2016, U.S. Provisional Application Ser. No. 62/436,687, filed Dec. 20, 2016, U.S. Provisional Application Ser. No. 62/436,706, filed Dec. 20, 2016, and U.S. Provisional Application Ser. No. 62/436,723, filed Dec. 20, 2016. The contents of these applications are fully incorporated herein by reference.

FIELD OF THE INVENTION

Described herein are genetically modified recombinant yeast cells and strains capable of fermenting pentoses, as well as to the preparation and use of such cells and strains.

REFERENCE TO A SEQUENCE LISTING

This application contains a Sequence Listing in computer readable form, which is incorporated herein by reference.

BACKGROUND

Bioethanol production from renewable feedstock by baker's yeast *Saccharomyces cerevisiae* has become an attractive alternative to fossil fuels, but the use of lignocellulosic feedstocks for such purposes poses challenges. For example, a substantial fraction of lignocellulosic material consists of pentoses such as xylose and arabinose. Native *Saccharomyces* species cannot ferment these pentoses, but genetic engineering techniques to provide *Saccharomyces* with this ability are now well-established (Kim et al., 2013). These include heterologous expression of xylose reductase (XR) and xylitol dehydrogenase (XDH) from naturally xylose fermenting yeasts such as *Scheffersomyces* (*Pichia*) *stipitis* and various *Candida* species, as well as the overexpression of xylulokinase (XK) and the four enzymes in the non-oxidative pentose phosphate pathway (PPP), namely transketolase (TKL), transaldolase (TAL), ribose-5-phosphate ketol-isomerase (RKI) and D-ribulose-5-phosphate 3-epimerase (RPE). Modifying the co-factor preference of *S. stipitis* XR towards NADH in such systems has been found to provide metabolic advantages as well as improving anaerobic growth, and replacing the XR/XDH with heterologous XI has been reported to reduce unwanted xylitol by-product. These and other modifications have been described in, e.g., WO2009/017441, WO2010/059095, WO2012/135110, Karhumaa et al., 2005; Karhumaa et al., 2007; Kuyper et al., 2005).

Some degree of overexpression of XK is generally considered necessary for ethanol formation, directing the xylose metabolism towards central metabolism (Chang and Ho, 1988; Eliasson et al., 2001), and XK from various species, e.g., *S. cerevisiae, E. coli, Pichia stipitis* and *P. tannophilus*, have been used or proposed (WO 95/13362; US 2009/0246857). It has also been reported that XK reduces the production of unwanted xylitol and acetate byproducts (Johansson et al., 2001; Parachin et al., 2011; Matsushika et al., 2011). Several investigators have concluded, however, that it is necessary to limit the levels of XK since XK overexpression inhibited growth of *S. cerevisiae* on xylose (Jin et al., 2003; Matsushika et al., 2011), reduced xylose consumption (Johansson et al., 2001), or drained ATP (Eliasson et al., 2001), suggesting that moderate or low XK levels are needed for optimal xylose fermentation. A lower XK activity could, however, limit the metabolic flux.

Some yeast species are naturally capable of fermenting xylose, e.g., *Pichia stipites, Spathaspora passalidarum, Candida jeffriesii* and *Candida tenuis* (Nguyen et al., 2006; US 2012/270289 A1; Wohlbach et al., 2011). Wohlbach and co-workers applied a comparative genomic approach to identify genes involved in xylose metabolism in *Spathaspora passalidarum* and *Candida tenuis*, and found that a Cten aldo/keto reductase, CtAKR, significantly improved xylose consumption in engineered *S. cerevisiae* strains during both aerobic and anaerobic growth, although this did not result in improved ethanol production. Hou (2012) then found that the ability of *Spathaspora passalidarum* to utilize xylose under anaerobic conditions was possibly due to the balance of cofactors in the XR-XDH pathway.

Lignocellulosic hydrolysates contain complex mixtures of other compounds, many of which are inhibitory to microbial fermentation, growth or viability. When the lignocellulosic material is heated during pretreatment, some of the sugars are dehydrated to furans such as furfural (from pentoses) and HMF (from hexoses), which are toxic to most microorganisms. Further, when the hemicellulose is hydrolysed to release the monomeric sugars, acetic acid is formed by the deacetylation of this fraction. More acids are formed if the lignocellulosic hydrolysate containing furfural and HMF is further heated, since these compounds can degrade into formic and levulinic acids, which are even more potent inhibitors of microorganisms than acetic acid. The toxicity and acidity of the pretreated and hydrolysed lignocellulosic material presents a strong limitation on the fermenting micro-organism.

WO 2009/017441 describes a mutant of alcohol dehydrogenase (ADH1) from *S. cerevisiae*, which was capable of reducing HMF.

Mollapour and Piper (Molecular Microbiology (2001) 42(4):919-930) describes that the YME2p gene from the food spoilage yeast *Zygosaccharomyces bailii*, heterologously expressed in *S. cerevisiae* cells, could enable growth of the latter on benzoate, sorbate and phenylalanine.

For the purpose of further examining the factors improving xylose utilization, Karhumaa et al. (2009) compared the proteome of mutant *S. cerevisiae* strain TMB 3400, which has good xylose fermentation properties, with that of its parental strain. Although the level of acetaldehyde dehydrogenase (Ald6) and some other proteins were found to be increased, the most significant changes detected by proteome analysis were 6-10-fold increased levels of XR, XDH and TKL1 in the mutant, which was in accordance with previous knowledge from rational engineering of xylose metabolism in yeast.

WO 2010/059095 describes that increased levels of phosphoglucomutase obtained by constitutive overexpression of the PGM2 gene with a constitutive promoter improved ethanol production from xylose.

Tiwari et al. (2008) describes that PGM1, PGM2 encode minor and major isozymes of phosphoglucomutase, and further notes that the protein product of YMR278w exhibits phosphoglucomutase activity, designating YMR278w as PGM3. PGM3 has now, however, also been named PRM15 (Xu et al., 2013, Walther et al., 2012), since the enzyme, apart from phosphoglucomutase activity, also has a significant phosphoribomutase activity (Xu et al., 2013).

Despite these and other advances in the art, there is still a need for improved yeast strains providing for cost-effective production of ethanol and other fermentation products from pentoses such as xylose.

SUMMARY

Described herein are improved recombinant yeast cells for production of ethanol and other fermentation products. This is based, at least in part, on the discovery of xylulokinases (XKs) which, even if present or expressed at high XK activities, have one or more improved properties such as high aerobic or anaerobic growth rates, increased xylose consumption and/or improved ethanol production.

Accordingly, in one aspect is a recombinant yeast cell, such as a recombinant *Saccharomyces* cell, which is capable of fermenting xylose and which comprises a heterologous gene encoding a xylulokinase (XK), wherein the XK can have an enzymatic activity for converting D-xylulose to xylulose 5-phosphate at least twice that of *S. cerevisiae* XK (SEQ ID NO: 32), and can provide for an anaerobic growth rate of the recombinant cell on xylose which is higher than that provided by a *S. cerevisiae* XK, or both. In one embodiment, the XK can further provide for an aerobic growth rate of the cell on xylose which is higher than that provided by *S. cerevisiae* XK. Representative assays for measuring these activities are provided by the Examples. For example, the enzymatic activity for converting D-xylulose to xylulose 5-phosphate can be measured according to Example 7, and the anaerobic growth rate can be measured according to Example 9.

In one aspect is a recombinant yeast cell capable of fermenting xylose and which comprises an heterologous gene encoding a xylulokinase (XK) comprising the amino acid sequence of SEQ ID NO: 6, SEQ ID NO: 22, or a catalytically active variant or fragment of any thereof.

In one embodiment of any preceding aspect or embodiment, the recombinant cell is derived from a *Saccharomyces, Rhodotorula, Schizosaccharomyces, Kluyveromyces, Pichia, Hansenula, Rhodosporidium, Candida, Yarrowia, Lipomyces, Cryptococcus*, or *Dekkera* sp. cell. In one embodiment, the recombinant cell is derived from a *Saccharymyces* cell, such as a *Saccharomyces cerevisiae, bayanus* or *carlsbergensis* cell. In a particular embodiment, the recombinant cell is derived from a *Saccharomyces cerevisiae* cell.

In one embodiment, the recombinant yeast cell comprises a heterologous gene encoding a xylose reductase (XR), a heterologous gene encoding a xylitol dehydrogenase (XDH), and/or a heterologous gene encoding a xylose isomerase (XI). In one embodiment, the XR is *Pichia stipitis* XR or an NADH-preferring variant thereof. In one embodiment, the XDH is *Pichia stipitis* XDH or a catalytically active variant thereof. In a particular embodiment, the XR is *Pichia stipitis* XR comprising one or more amino acid substitutions selected from N272D, K270R and P275Q. The cell may also comprise a heterologous gene encoding a transaldolase (TAL), a heterologous gene encoding a transketolase (TKL), and/or a heterologous gene encoding a ribose 5-phosphate ketol-isomerase (RKI). In some embodiments, the recombinant yeast cell is isolated.

In one aspect is a vector comprising a gene encoding a xylulokinase (XK) comprising the amino acid sequence of SEQ ID NO: 6, SEQ ID NO: 22 or a catalytically active variant or fragment of any thereof. In some embodiments, the vector further comprises a gene encoding a xylose reductase (XR), a gene encoding a xylitol dehydrogenase (XDH), and/or a gene encoding a xylose isomerase (XI). The vector may further comprise regulatory sequences for expressing the genes in a yeast host cell such as a *Saccharomyces* or *Saccaromyces cerevisiae* host cell.

In one aspect, is a process for producing a recombinant cell described herein (e.g., a *Saccharomyces* cell), comprising transforming the cell with a heterologous gene (e.g., a vector) that encodes a xylulokinase (XK) comprising the amino acid sequence of SEQ ID NO: 6, the amino acid sequence of SEQ ID NO: 22 or a catalytically active variant or fragment of any thereof.

In one embodiment of any preceding aspect or embodiment, the XK comprises the amino acid sequence of SEQ ID NO: 6, or a catalytically active variant or fragment thereof. For example, the XK may have a sequence identity of at least 80% with the amino acid sequence of SEQ ID NO: 6, such as at least 90%, 95%, 97%, 98%, or 99% with the amino acid sequence of SEQ ID NO: 6. In a particular embodiment, the XK comprises the amino acid sequence of SEQ ID NO: 6.

In an alternative embodiment of any preceding aspect or embodiment, the XK the amino acid sequence comprises SEQ ID NO: 22, or a catalytically active variant or fragment thereof. For example, the XK may have a sequence identity of at least 80% with SEQ ID NO: 22, such as at least 90%, 95%, 97%, 98%, or 99% with the amino acid sequence of SEQ ID NO: 22. In a particular embodiment, the XK comprises the amino acid sequence of SEQ ID NO: 22.

Also described herein are improved recombinant yeast cells more tolerant to e.g. formic acid and acetic acid, useful for production of ethanol and other fermentation products from fermentation media derived from lignocellulosic hydrolysates. The invention is based, at least in part, on the discovery that expression of the YME2p gene product in a recombinant yeast cell increases the tolerance of the cell to inhibitors such as formic acid, providing for improved anaerobic growth rates and more cost-efficient production of fermentation products such as ethanol.

Accordingly, in one aspect is a recombinant yeast cell which is capable of fermenting xylose and which comprises a heterologous gene encoding an Yme2p polypeptide comprising the amino acid sequence of SEQ ID NO: 50 or a catalytically active variant, fragment or yeast ortholog thereof, wherein the Yme2p polypeptide can provide for an increased tolerance of the recombinant cell to formic acid, acetic acid, or both. In separate and specific embodiments, the Yme2p polypeptide can provide for an increased anaerobic growth rate on xylose, an increased xylose consumption rate, an increased ethanol production rate, or a combination of two or more of any thereof, of the recombinant cell in the presence of formic acid. In other separate and specific embodiments, the Yme2p polypeptide can provide for an increased xylose consumption rate, an increased ethanol production rate, or a combination thereof, of the recombinant cell in the presence of acetic acid. Representative assays for measuring these activities are provided by the Examples. For example, the anaerobic growth, xylose consumption, ethanol production rate, or combination in the presence of formic acid can measured according to Example 14, and the xylose consumption rate, ethanol production rate or combination in the presence of acetic acid can be measured according to Example 13.

In one embodiment, the recombinant cell is derived from a *Saccharomyces, Rhodotorula, Schizosaccharomyces, Kluyveromyces, Pichia, Hansenula, Rhodosporidium, Candida, Yarrowia, Lipomyces, Cryptococcus*, or *Dekkera* sp. cell. In one embodiment, the recombinant cell is derived from a *Saccharymyces* cell, such as a *Saccharomyces cerevisiae, bayanus* or *carlsbergensis* cell. In a particular embodiment, the recombinant cell is derived from a *Saccharomyces cerevisiae* cell.

In one embodiment, the recombinant yeast cell comprises a heterologous gene encoding a xylose reductase (XR), a heterologous gene encoding a xylitol dehydrogenase (XDH), and/or a heterologous gene encoding a xylose isomerase (XI). In one embodiment, the XR is *Pichia stipitis* XR or an NADH-preferring variant thereof. In one embodiment, the XDH is *Pichia stipitis* XDH or a catalytically active variant thereof. In a particular embodiment, the XR is *Pichia stipitis* XR comprising one or more amino acid substitutions selected from N272D, K270R and P275Q. The cell may also comprise a heterologous gene encoding a transaldolase (TAL), a heterologous gene encoding a transketolase (TKL), and/or a heterologous gene encoding a ribose 5-phosphate ketol-isomerase (RKI). In some embodiments, the recombinant yeast cell is isolated.

In one aspect is a vector comprising a gene encoding an Yme2p polypeptide comprising the amino acid sequence of SEQ ID NO: 50 or a catalytically active variant or fragment thereof. In some embodiments, the vector further comprises a gene encoding a xylose reductase (XR), a gene encoding a xylitol dehydrogenase (XDH), a gene encoding a xylulose kinase (XK), and/or a gene encoding a xylose isomerase (XI). The vector may also comprise regulatory sequences for expressing the genes in a *Saccharomyces* host cell.

In one aspect is a process for producing a recombinant cell described herein (e.g., a *Saccharomyces* cell), comprising transforming the cell with a heterologous gene (e.g., a vector) that encodes an Yme2p polypeptide comprising the amino acid sequence of SEQ ID NO: 50 or a catalytically active variant or fragment thereof.

In one aspect is a method for increasing the tolerance of a cell described herein (e.g., a yeast cell such as a *Saccharomyces* cell) to formic acid, comprising transforming the cell with a gene (e.g., a vector) encoding a Yme2p polypeptide comprising the amino acid sequence of SEQ ID NO: 50 or a catalytically active variant, fragment or yeast ortholog thereof, and expressing the gene. The gene can, for example, be operably linked to an inducible, a regulated or a constitutive promoter.

In one embodiment of any preceding aspect or embodiment, the Yme2p polypeptide has a sequence identity of at least 70% with the amino acid sequence of SEQ ID NO: 50, such as at least 80%, at least 90%, at least 95%, or at least 97%, or at least 98%, or at least 99% identity. In one embodiment, the Yme2p polypeptide comprises the amino acid sequence of SEQ ID NO: 50.

Also described herein are improved recombinant yeast cells for production of ethanol and other fermentation products. This is based, at least in part, on the discovery of genes providing one or more improved properties such as a higher aerobic or anaerobic growth rates, increased xylose consumption and/or improved ethanol production.

Accordingly, in one aspect is a recombinant yeast cell, such as a recombinant *Saccharomyces* cell, which is capable of fermenting xylose and which comprises a heterologous gene encoding an enolase comprising the amino acid sequence of SEQ ID NO: 132, a phosphofructokinase beta subunit polypeptide comprising the amino acid sequence of SEQ ID NO: 134, a 6-phosphofructo-2-kinase comprising the amino acid sequence of SEQ ID NO: 136, a glucose-6-phosphate isomerase comprising the amino acid sequence of SEQ ID NO: 138, a phosphoglycerate mutase comprising the amino acid sequence of SEQ ID NO: 140, a triose-phosphate isomerase comprising the amino acid sequence of SEQ ID NO: 142, a catalytically active variant, fragment or yeast ortholog of any one of the aforementioned enzymes, or a combination of any two or more of the aforementioned enzymes and catalytically active variants, fragments or yeast orthologs thereof. In one embodiment, the heterologous gene or combination can provide for an increased anaerobic growth rate on xylose, an increased aerobic growth rate on xylose, an increased ethanol production from xylose, or a combination of any two or all thereof. Representative assays for measuring these activities are provided by the Examples. The anaerobic growth rate can, for example, be measured according to Example 23, the aerobic growth according to Example 17, and/or the ethanol production according to Example 24.

In one embodiment, the recombinant yeast cell is derived from a *Saccharomyces, Rhodotorula, Schizosaccharomyces, Kluyveromyces, Pichia, Hansenula, Rhodosporidium, Candida, Yarrowia, Lipomyces, Cryptococcus*, or *Dekkera* sp. cell. In one embodiment, the recombinant cell is derived from a *Saccharymyces* cell, such as a *Saccharomyces cerevisiae, bayanus* or *carlsbergensis* cell. In a particular embodiment, the recombinant cell is derived from a *Saccharomyces cerevisiae* cell.

In one embodiment, the recombinant yeast cell comprises a heterologous gene encoding a xylose reductase (XR), a heterologous gene encoding a xylitol dehydrogenase (XDH), a heterologous gene encoding a xylulose kinase (XK) and/or a heterologous gene encoding a xylose isomerase (XI). In one embodiment, the XR is *Pichia stipitis* XR or an NADH-preferring variant thereof. In one embodiment, the XDH is *Pichia stipitis* XDH or a catalytically active variant thereof. In a particular embodiment, the XR is *Pichia stipitis* XR comprising one or more amino acid substitutions selected from N272D, K270R and P275Q. The cell may also comprise a heterologous gene encoding a transaldolase (TAL), a heterologous gene encoding a transketolase (TKL), and/or a heterologous gene encoding a ribose 5-phosphate ketol-isomerase (RKI). In some embodiments, the recombinant yeast cell is isolated.

In one aspect is a vector comprising a gene encoding a polypeptide comprising the amino acid sequence of SEQ ID NO: 132, 84, 86, 88, 90 or 92 or a catalytically active variant, fragment or yeast ortholog of any thereof. In some embodiments, the vector further comprises a gene encoding a xylose reductase (XR), a gene encoding a xylitol dehydrogenase (XDH), a gene encoding a xylulose kinase (XK), and/or a gene encoding a xylose isomerase (XI). The vector may further comprise regulatory sequences for expressing the genes in a *Saccharomyces* host cell.

In one aspect is a process for producing a recombinant cell described herein (e.g., a yeast cell such as a *Saccharomyces* cell), comprising transforming the cell with a heterologous gene (e.g., a vector) that encodes an polypeptide comprising the amino acid sequence of SEQ ID NO: 132, 134, 136, 138, 140 or 142 or a catalytically active variant or fragment of any thereof.

In one embodiment of any preceding aspect or embodiment, the gene encodes an enolase comprising the amino acid sequence of SEQ ID NO: 132 or a catalytically active variant, fragment or yeast ortholog thereof. In one embodiment, the gene encodes a phosphofructokinase beta subunit polypeptide comprising the amino acid sequence of SEQ ID NO: 134 or a catalytically active variant, fragment or yeast ortholog thereof. In one embodiment, the gene encodes a 6-phosphofructo-2-kinase comprising the amino acid sequence of SEQ ID NO: 136 or a catalytically active variant, fragment or yeast ortholog thereof. In one embodiment, the gene encoding a glucose-6-phosphate isomerase comprising the amino acid sequence of SEQ ID NO: 138 or a catalytically active variant, fragment or yeast ortholog thereof. In one embodiment, the gene encodes a phosphoglycerate mutase comprising the amino acid sequence of SEQ ID NO: 140 or a catalytically active variant, fragment or yeast ortholog thereof. In one embodiment, the gene encodes a triose-phosphate isomerase comprising the amino acid sequence of SEQ ID NO: 142 or a catalytically active variant, fragment or yeast ortholog thereof. In one embodiment, the catalytically active variant or yeast ortholog of has a least 50% sequence identity to the amino acid sequence of SEQ ID NO: 132, 134, 136, 138, 140 or 142, such as at least 70%, at least 80%, at least 90%, at least 95%, at least 97%, at least 98%, or at least 99% sequence identity to SEQ ID NO: 132, 84, 86, 88, 90 or 92.

Also described herein are improved recombinant yeast cells for production of ethanol and other fermentation products. This is based, at least in part, on the discovery that overexpression of PGM3 (SEQ ID NO: 150) provides one or more improved properties such as a higher aerobic or anaerobic growth rates, increased xylose consumption and/or improved ethanol production.

Accordingly, in one aspect, is a recombinant yeast cell which is capable of fermenting xylose and which comprises a heterologous gene encoding a phosphoglucomutase and/or phosphoribomutase comprising the amino acid sequence of SEQ ID NO: 150 or a catalytically active variant or fragment thereof. In separate and specific embodiments, the heterologous gene can provide for an increased anaerobic growth rate on xylose, an increased xylose consumption, an increased ethanol production from xylose, or a combination of any two or all thereof. Representative assays for measuring these activities are provided by the Examples.

For example, the anaerobic growth rate can be measured according to Example 26, the anaerobic growth can be measured according to Example 27, and/or the ethanol production can be measured according to Example 27.

In one embodiment, the recombinant cell is derived from a *Saccharomyces, Rhodotorula, Schizosaccharomyces, Kluyveromyces, Pichia, Hansenula, Rhodosporidium, Candida, Yarrowia, Lipomyces, Cryptococcus*, or *Dekkera* sp. cell. In one embodiment, the recombinant cell is derived from a *Saccharymyces* cell, such as a *Saccharomyces cerevisiae, bayanus* or *carlsbergensis* cell. In a particular embodiment, the recombinant cell is derived from a *Saccharomyces cerevisiae* cell.

In one embodiment, the recombinant yeast cell comprises a heterologous gene encoding a xylose reductase (XR), a heterologous gene encoding a xylitol dehydrogenase (XDH), a heterologous gene encoding a xylulose kinase (XK) and/or a heterologous gene encoding a xylose isomerase (XI). In one embodiment, the XR is *Pichia stipitis* XR or an NADH-preferring variant thereof. In one embodiment, the XDH is *Pichia stipitis* XDH or a catalytically active variant thereof. In a particular embodiment, the XR is *Pichia stipitis* XR comprising one or more amino acid substitutions selected from N272D, K270R and P275Q. The cell may also comprise a heterologous gene encoding a transaldolase (TAL), a heterologous gene encoding a transketolase (TKL), and/or a heterologous gene encoding a ribose 5-phosphate ketol-isomerase (RKI). In some embodiments, the recombinant yeast cell is isolated.

In one aspect is a vector comprising a gene encoding a polypeptide comprising a phosphoglucomutase and/or phosphoribomutase comprising the amino acid sequence of SEQ ID NO: 150 or a catalytically active variant, fragment or yeast ortholog thereof. In some embodiments, the vector further comprises a gene encoding a xylose reductase (XR), a gene encoding a xylitol dehydrogenase (XDH), a gene encoding a xylulose kinase (XK), and/or a gene encoding a xylose isomerase (XI). The vector can also comprise regulatory sequences for expressing the genes in a *Saccharomyces* host cell.

In one aspect is a process for producing a recombinant cell described herein (e.g., a yeast cell such as a *Saccharomyces* cell), comprising transforming the cell with a heterologous gene (e.g., a vector) that encodes a phosphoglucomutase and/or phosphoribomutase comprising the amino acid sequence of SEQ ID NO: 150 or a catalytically active variant or fragment thereof.

In one embodiment of any preceding aspect or embodiment, the phosphoglucomutase and/or phosphoribomutase has a sequence identity of at least 30%, at least 50%, at least 70%, at least 80%, at least 90%, at least 95%, or at least 97%, or at least 98%, or at least 99% with the amino acid sequence of SEQ ID NO: 150. In one embodiment, the phosphoglucomutase and/or phosphoribomutase comprises the amino acid sequence of SEQ ID NO: 150.

In any preceding aspect or embodiment, each gene can be operably linked to an inducible, a regulated or a constitutive promoter, and/or can optionally be integrated into the genome of the cell.

In one aspect is a strain or clone comprising the recombinant cell or vector(s) of any of the aspects or embodiments.

In one aspect is a method for producing a fermentation product, comprising contacting any recombinant yeast cell, strain or clone described herein with a medium comprising a carbon source comprising a pentose such as xylose or arabinose under anaerobic conditions, and isolating the fermentation product from the medium. This method is suitable for producing, for example, a fermentation product comprising at least one of ethanol, butanol, isobutanol, isopentanol, lactate, isoamylacetate, glycerol, sorbitol, mannitol, xylitol, arabinitol; 3-hydroxybutyrolactone; hydrogen gas; L-ascorbic acid, 2,5-furan dicarboxylic acid, 3-hydroxy propionic acid, aspartic acid, glutaric acid, glutamic acid, itaconic acid, levulinic acid; succinic acid, fumaric acid, malic acid or other 1,4-diacid; a fatty acid, a fatty acid derived molecule; an isoprenoid, an isoprenoid-derived molecule; and an alkane. In particular, the method is suitable for producing a fermentation product comprising ethanol from a carbon source comprising xylose.

These and other aspects and embodiments are described in more detail below.

DEFINITIONS

Figure 1:
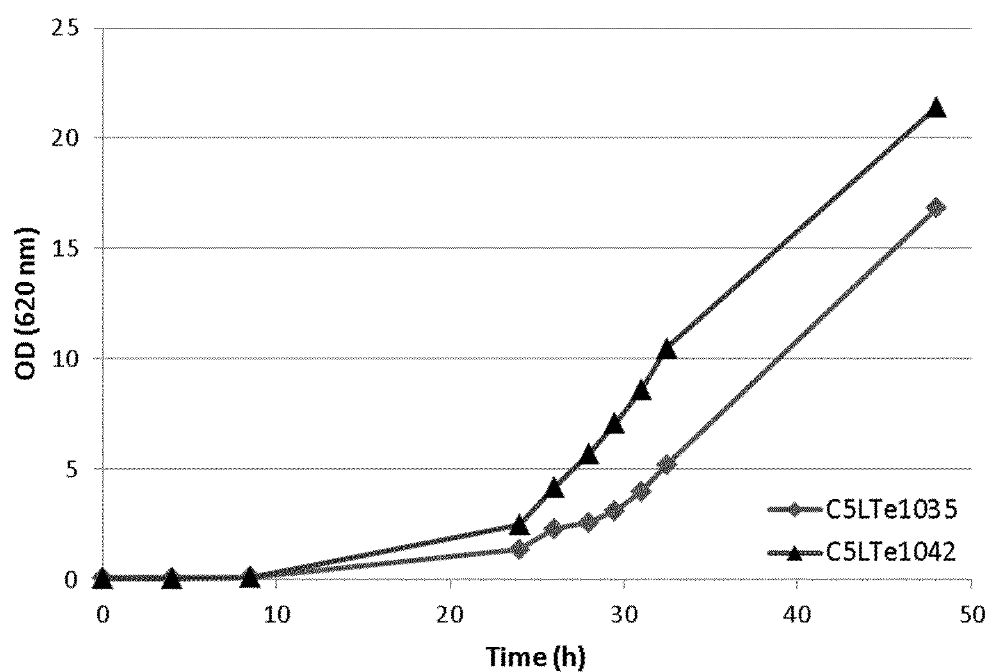
FIG. 1: Curves for the aerobic growth on xylose for C5LTe1035 (diamonds) and C5LTe1042 (triangles).

The term "pathway", "biometabolic pathway" and the like herein refers to an enzymatic pathway present in a cell, typically a yeast cell, which converts or processes an initial substrate to an intermediate or a final product in a series of enzyme-catalyzed reactions.

The term "gene" refers to a nucleic acid sequence that is capable of being expressed as a specific protein, such as an enzyme, optionally including regulatory sequences preceding (5' non-coding sequences) and following (3' non-coding sequences) the coding sequence.

The term "transformation" refers to the transfer of a nucleic acid sequence such as, e.g., a gene, into a host cell, typically a yeast host cell, resulting in genetically stable inheritance.

As used herein, "recombinant" refers to a host cell into which a nucleic acid sequence, such as a gene, has been transferred, typically by transformation.

A "yeast" is any of various small, single-celled eukaryotic fungi of the phylum Ascomycota that reproduce by fission or budding, and that are capable of fermenting carbohydrates into alcohol and carbon dioxide. Preferably, a yeast cell as used herein refers to a cell of a genus selected form the group consisting of *Saccharomyces, Rhodotorula, Schizosaccharomyces, Kluyveromyces, Pichia, Hansenula, Rhodosporidium, Candida, Yarrowia, Lipomyces, Cryptococcus*, and *Dekkera* sp.

A metabolic pathway, protein, polypeptide, enzyme, nucleic acid sequence or gene may be "heterologous" or "foreign" to a host cell, meaning that the pathway, enzyme, nucleic acid sequence or gene is not normally found in the host cell, typically a yeast host cell of a specific taxonomic classification. "Endogenous" refers to a pathway, protein, polypeptide, enzyme, nucleic acid or gene normally present in the host cell, typically a yeast host cell of a specific taxonomic classification.

The term "heterologous gene" is defined herein as a gene that is not native to the host cell; a native gene in which structural modifications have been made to the coding region; a native gene whose expression is quantitatively altered (e.g., "overexpressed") as a result of a manipulation of the DNA by recombinant DNA techniques, e.g., a different (foreign) promoter; or a gene in a host cell having one or more extra copies of the coding sequence to quantitatively alter expression. For avoidance of doubt, as used herein, a described *Saccharomyces* gene shall be considered a "heterologous gene" when expressed in a *Saccharomyces* host so long as the gene is not in its native form and is altered by any means as described above (e.g., transformed into the host).

As used herein, an "overexpressed" gene encoding an enzyme means that the enzyme is produced at a higher level of specific enzymatic activity as compared to the unmodified host cell under identical conditions. Usually this means that the enzymatically active protein (or proteins in case of multi-subunit enzymes) is produced in greater amounts, or rather at a higher steady state level as compared to the unmodified host cell under identical conditions. Typically, this is the result of the mRNA coding for the enzymatically active protein being produced in greater amounts, or again rather at a higher steady state level as compared to the unmodified host cell under identical conditions. Overexpression of an enzyme is thus preferably determined by measuring the level of the enzyme specific activity in the host cell using appropriate enzyme assays as described herein. Alternatively, overexpression of the enzyme may be determined indirectly by quantifying the specific steady state level of enzyme protein, e.g. using antibodies specific for the enzyme, or by quantifying the specific steady level of the mRNA coding for the enzyme. The latter may particularly be suitable for enzymes of the pentose phosphate pathway for which enzymatic assays are not easily feasible as substrates for the enzymes are not commercially available. Preferably, in the host cells described herein, a heterologous gene is overexpressed by at least a factor 1.1, 1.2, 1.5, 2, 5, 10 or 20 as compared to a host cell which is genetically identical except for the genetic modification causing the overexpression. It is to be understood that these levels of overexpression may apply to the steady state level of the enzyme's activity, the steady state level of the enzyme's protein as well as to the steady state level of the transcript coding for the enzyme.

The term "isolated" means a substance in a form or environment that does not occur in nature. Non-limiting examples of isolated substances include (1) any non-naturally occurring substance, (2) any substance including, but not limited to, any host cell, enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated.

The term "operably linked" means a configuration in which a control sequence is placed at an appropriate position relative to the coding sequence of a polynucleotide such that the control sequence directs expression of the coding sequence.

A "variant" of a reference enzyme as used herein is similar in its amino acid sequence to the reference enzyme, such as a "parent" or wild-type enzyme, having an amino acid sequence identity of at least 30%, such as at least 40%, such as at least 50%, such as at least 60%, such as at least 70%, such as at least 80%, such as at least 90%, such as at least 95%, such as at least 98%, such as at least 99% to the amino acid sequence of the reference. Enzyme variants can be made by a wide variety of different mutagenesis techniques well known to those skilled in the art. In addition, mutagenesis kits are also available from many commercial molecular biology suppliers. Methods are available to make specific substitutions at defined amino acids (site-directed), specific or random mutations in a localized region of the gene (regio-specific) or random mutagenesis over the entire gene (e.g., saturation mutagenesis). Numerous suitable methods are known to those in the art to generate enzyme variants, including but not limited to site-directed mutagenesis of single-stranded DNA or double-stranded DNA using PCR, cassette mutagenesis, gene synthesis, error-prone PCR, shuffling, and chemical saturation.

As used herein, a "fragment" of a reference enzyme such as a parent or wild-type enzyme comprises a segment of the reference enzyme amino acid sequence. The amino acid sequence of the fragment typically comprises at least 50%, such as at least 60%, such as at least 70%, such as at least 80%, such as at least 90%, such as at least 95% of the amino acid sequence of the reference enzyme, lacking either an N-terminal portion, a C-terminal portion, or both N-terminal and C-terminal portions of the reference. Typically, a fragment is a catalytically active, at least retaining the enzyme activity of the reference enzyme, though fragments having improved enzyme activity, improved thermostability, altered co-factor dependency, or the like, are also encompassed. The fragment can be designed and expressed using recombinant methods, simply omitting the coding sequences for the relevant N-terminal and/or C-terminal portions.

An "ortholog" of a wild-type reference enzyme from a particular organism can readily be identified as being similar in its amino acid sequence to the reference enzyme though being encoded by a gene from another organism. Preferred orthologs are yeast orthologs, which can be readily identified by, e.g., searching public genomic sequence databases or screening EST libraries for nucleic acid sequences which hybridize to the wild-type nucleic acid sequence encoding the reference enzyme under moderate or stringent hybridization conditions. Typically, the ortholog has an amino acid sequence identity of at least 30%, such as at least 40%, such as at least 50%, such as at least 60%, such as at least 70%, such as at least 80%, such as at least 90%, such as at least 95%, such as at least 98%, such as at least 99% to the amino acid sequence of the reference enzyme, and is catalytically active such that it at least retains the enzyme activity of the reference enzyme, though orthologs having improved enzyme activity, improved thermostability, altered co-factor dependency, or the like, are also encompassed.

The relatedness between two amino acid sequences or between two nucleotide sequences is described by the parameter "sequence identity".

For purposes described herein, the degree of sequence identity between two amino acid sequences is determined using the Needleman-Wunsch algorithm (Needleman and Wunsch, 1970) as implemented in the Needle program of the EMBOSS package (Rice et al., 2000), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

(Identical Residues×100)/(Length of the Referenced Sequence−Total Number of Gaps in Alignment)

For purposes described herein, the degree of sequence identity between two deoxyribonucleotide sequences is determined using the Needleman-Wunsch algorithm (Needleman and Wunsch, 1970) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the—nobrief option) is used as the percent identity and is calculated as follows:

(Identical Deoxyribonucleotides×100)/(Length of Referenced Sequence−Total Number of Gaps in Alignment)

The variants, fragments, and orthologs of reference enzymes as described herein are typically "catalytically active", meaning that at least retain the enzyme activity of the reference enzyme, though variants, fragments and orthologs having improved enzyme activity, improved thermostability, altered co-factor dependency, improved affinity, improved catalytic rate, or the like, are also encompassed. For example, a catalytically active variant, fragment or ortholog of Sp. *passalidarum* XK (SEQ ID NO: 6) or *K. marxianus* XK (SEQ ID NO: 22) thus has, e.g., at least twice the enzymatic activity of *S. cerevisiae* XK (SEQ ID NO: 32) for converting D-xylulose to xylulose 5-phosphate, preferably when measured according to Example 7, and provides for an anaerobic growth rate of a recombinant *S. cerevisiae* or other yeast cell on xylose which is higher than that provided by a *S. cerevisiae* XK, preferably when measured according to Example 8. In another example, a functional variant, fragment or ortholog of YME2p from *Zygosaccharomyces bailii* (SEQ ID NO: 50) thus provides for one or more, preferably all, of an increased anaerobic growth, an increased xylose consumption rate, and an increased ethanol production rate of a recombinant yeast cell in the presence of formic acid and/or acetic acid, preferably when measured according to Example 14 or 13, respectively. In another example, a catalytically active variant, fragment or yeast ortholog of *S. cerevisiae* ENO1, PFK2, PFK26, PGI1, GPM1 or TPI1 thus provides for one or more, preferably all, of an increased aerobic growth on xylose, an increased anaerobic growth rate on xylose, an increased xylose consumption rate, and an increased ethanol production rate from xylose, preferably when measured according to Example 17, 18, 23 and/or 24. In another example, a catalytically active variant, fragment or ortholog of *S. cerevisiae* PGM3/PRM15 thus provides for one or more, preferably all, of an increased anaerobic growth on xylose, an increased xylose consumption rate, and an increased ethanol production rate from xylose, preferably when measured according to Example 26 and/or 27 and, typically, substantially retained or improved phosphoglucomutase activity, phosphoribomutase activity, or both. Phosphoglucomutase activity and phosphoribomutase activity can be determined as known in the art (e.g., See Xu et al., 2013).

Reference to "about" a value or parameter herein includes aspects that are directed to that value or parameter per se. For example, description referring to "about X" includes the aspect "X". When used in combination with measured values, "about" includes a range that encompasses at least the uncertainty associated with the method of measuring the particular value, and can include a range of plus or minus two standard deviations around the stated value.

As used herein and in the appended claims, the singular forms "a," "or," and "the" include plural referents unless the context clearly dictates otherwise. It is understood that the aspects described herein include "consisting" and/or "consisting essentially of" aspects.

Unless defined otherwise or clearly indicated by context, all technical and scientific terms used herein have the same meaning as commonly understood by one of ordinary skill in the art.

DETAILED DESCRIPTION

Recombinant Cells

Table 1 below summarizes some key results from the Examples. When tested in cell extracts of recombinant *S. cerevisiae* cells capable of fermenting xylose, the extracts from those cells overexpressing *Sp. passalidarium* XK (SEQ ID NO: 6) had a consistently higher XK activity than the control strains overexpressing *S. cerevisiae* XK (SEQ ID NO: 32). Surprisingly, the anaerobic growth rate on xylose of the cells overexpressing XK from either Sp. *passalidarium* or *K. marxianus* (SEQ ID NO: 22) was nonetheless higher than those of the control strains overexpressing *S. cerevisiae* XK or *E. coli* XK (SEQ ID NO: 18). In addition, the cell overexpressing *Sp. passalidarium* XK also provided for higher xylose consumption and ethanol production in fermentation on xylose than the corresponding *S. cerevisiae* XK control strains.

TABLE 1

Overview of strains constructed and tested as described in the Examples.

| | | | | | Anaerobic fermentation on xylose 72 h | |
|---|---|---|---|---|---|---|
| Strain | Heterologous genes | XK activity (U/mg) | Aerobic growth on xylose ($h^{-1}$) | Anaerobic growth on xylose ($h^{-1}$) | Consumed xylose (g/L) | Produced ethanol (g/L) |
| C5LTe1000 | None | 0.11 ± 0.00 | | | | |
| C5LTe1001 | *S. cerevisiae* TAL1<br>*S. cerevisiae* TKL1<br>*S. cerevisiae* RKI1 | | | | | |
| C5LTe1035 | *P. stipitis* mXR(N272D)<br>*P. stipitis* XDH<br>*S. cerevisiae* XK<br>*S. cerevisiae* TAL1<br>*S. cerevisiae* TKL1<br>*S. cerevisiae* RKI1 | 1.65 ± 0.27 | 0.16 | | 42 | 21 |
| C5LTe1036 | *P. stipitis* mXR(N272D)<br>*P. stipitis* XDH<br>*S. cerevisiae* XK<br>*S. cerevisiae* TAL1<br>*S. cerevisiae* TKL1<br>*S. cerevisiae* RKI1 | 0.84 ± 0.20 | | | 21 | 15 |
| C5LTe1040 | *P. stipitis* mXR(N272D)<br>*P. stipitis* XDH<br>*E. coli* XK<br>*S. cerevisiae* TAL1<br>*S. cerevisiae* TKL1<br>*S. cerevisiae* RKI1 | | | Slower than e1035 | | |
| C5LTe1042 | *P. stipitis* mXR(N272D)<br>*P. stipitis* XDH<br>*S. passalidarum* XK<br>*S. cerevisiae* TAL1<br>*S. cerevisiae* TKL1<br>*S. cerevisiae* RKI1 | 5.21 ± 0.37 | 0.19 | Faster than e1035 | 46 | 23 |

TABLE 1-continued

Overview of strains constructed and tested as described in the Examples.

| Strain | Heterologous genes | XK activity (U/mg) | Aerobic growth on xylose ($h^{-1}$) | Anaerobic growth on xylose ($h^{-1}$) | Anaerobic fermentation on xylose 72 h | |
|---|---|---|---|---|---|---|
| | | | | | Consumed xylose (g/L) | Produced ethanol (g/L) |
| C5LTe1043 | *P. stipitis* mXR(N272D) *P. stipitis* XDH *K. marxianus* XK *S. cerevisiae* TAL1 *S. cerevisiae* TKL1 *S. cerevisiae* RKI1 | | | Faster than e1035 | | |
| C5LTe1048 | *P. stipitis* mXR(N272D) *P. stipitis* XDH *S. passalidarum* XK *S. cerevisiae* TAL1 *S. cerevisiae* TKL1 *S. cerevisiae* RKI1 | 4.31 ± 0.06 | | | 35 | 19 |
| C5LTe1204 | *P. stipitis* mXR(N272D) *P. stipitis* XDH *S. cerevisiae* XK *S. cerevisiae* TAL1 *S. cerevisiae* TKL1 *S. cerevisiae* RKI1 | 0.92 ± 0.27 | | | 25 | 15 |
| C5LTe1208 | *P. stipitis* mXR(N272D) *P. stipitis* XDH *S. passalidarum* XK *S. cerevisiae* TAL1 *S. cerevisiae* TKL1 *S. cerevisiae* RKI1 | 3.67 ± 0.19 | | | 37 | 19 |

Accordingly, in one aspect, is a recombinant yeast cell such as a *Saccharomyces* cell, optionally a *S. cerevisiae* cell, which is capable of fermenting xylose and which comprises a heterologous gene encoding a polypeptide having enzymatic xylulokinase (XK) activity.

In one aspect, is a recombinant yeast cell such as a *Saccharomyces* cell, optionally a *S. cerevisiae* cell, which is capable of fermenting xylose and which comprises a heterologous gene encoding a xylulokinase (XK) providing an enzymatic activity for converting D-xylulose to xylulose 5-phosphate which is higher than that provided by *S. cerevisiae* XK (SEQ ID NO: 32) and yet provides for an anaerobic growth rate which is higher than that provided by *S. cerevisiae* XK, *E. coli* XK, or both.

In one aspect, is a recombinant *Saccharomyces* cell which is capable of fermenting xylose and which comprises a heterologous gene encoding a xylulokinase (XK), wherein the XK has an enzymatic XK activity, which is higher than that of *S. cerevisiae* XK, and provides for an anaerobic growth rate of the recombinant cell on xylose which is higher than that provided by a *S. cerevisiae* XK.

In one aspect, is a recombinant yeast cell such as a *Saccharomyces* cell, optionally a *S. cerevisiae* cell, capable of fermenting xylose and which comprises a heterologous gene encoding a xylulokinase (XK) comprising SEQ ID NO: 6 or a catalytically active variant thereof.

In separate and specific embodiments of any aforementioned aspect, the XK provides for an enzymatic XK activity which is at least 1.1, e.g., at least 1.2, at least 1.5, at least 1.7, at least twice (2), at least 2.5 or at least 3 times that provided by *S. cerevisiae* XK. In one embodiment, the XK has an enzymatic activity for converting D-xylulose to xylulose 5-phosphate at least twice that of *S. cerevisiae* XK. In one embodiment, the XK further provides for an aerobic growth rate of the cell on xylose which is higher than that provided by *S. cerevisiae* XK, *E. coli* XK, or both. For example, the XK may provide for an aerobic growth rate which is 1.1, 1.2, 1.3, 1.4 or 1.5 times that provided by *S. cerevisiae* XK. Additionally, the XK may provide for a higher xylose consumption, a higher ethanol production, or both, of the recombinant cell than that provided by *S. cerevisiae* XK, *E. coli* XK or both.

Advantageously, the XK activity, anaerobic and aerobic growth rates, and xylose consumption and ethanol production, can be tested in the assays and strain constructs according to the Examples. For example, in one embodiment, the enzymatic activity for converting D-xylulose to xylulose 5-phosphate is measured according to Example 7. In an additional or alternative embodiment, the anaerobic growth rate can be measured according to Example 9. Likewise, the aerobic growth rate can be measured according to Example 8, and/or the xylose consumption and ethanol production can be measured according to Example 10. In these tests, the recombinant strains can, for example, be prepared from C5LTe1000 or an equivalent or similar laboratory or commercially available *S. cerevisiae* strain, for example CEN.PK or s288c, and then tested in the form of live cells or cell extracts as described. Typically, for conducting such test assays, *S. cerevisiae* cells are transformed with genes encoding *P. stipitis* mXR with an N272D mutation, *P. stipitis* XDH, the XK to be examined or control *S. cerevisiae* or *E. coli* XK, and *S. cerevisiae* TAL1, TKL1, and RKI1, so that each gene is chromosomally integrated and operably linked to a constitutive promoter.

In one embodiment of any preceding aspect or embodiment, the XK comprises the amino acid sequence of SEQ ID NO: 6, the amino acid sequence of SEQ ID NO: 22 or a catalytically active variant or fragment of any thereof. In one embodiment, the XK is a catalytically active variant of SEQ ID NO: 6, comprising an amino acid sequence which is at least 50%, such as at least 60%, such as at least 70%, such as at least 80%, such as at least 90%, such as at least 95%, such as at least 98%, such as at least 99% identical to SEQ ID NO: 6. In one embodiment, the XK is a variant of SEQ ID NO: 22, comprising an amino acid sequence which is at least 50%, such as at least 60%, such as at least 70%, such as at least 80%, such as at least 90%, such as at least 95%, such as at least 98%, such as at least 99% identical to SEQ ID NO: 6. In one embodiment, the XK is a fragment (e.g., a catalytically active fragment) of SEQ ID NO: 6 corresponding to at least 50%, at least 80%, at least 90%, at least 95%, at least 96%, at least 97%, at least 98% or at least 99% of the full-length enzyme amino acid sequence. In one embodiment, the XK is a fragment (e.g., a catalytically active fragment) of SEQ ID NO: 22 corresponding to at least 50%, at least 80%, at least 90%, at least 95%, at least 96%, at least 97%, at least 98% or at least 99% of the full-length enzyme amino acid sequence.

Table 2 below additionally summarizes additional key results from the Examples. Surprisingly, expressing the heterologous YME2 gene (i.e., overexpressing the YME2 gene) in recombinant *S. cerevisiae* cells capable of fermenting xylose resulted in a higher anaerobic growth rate, more efficient xylose consumption and increased ethanol production in fermentation on xylose.

increased ethanol production rate, or (d) a combination of two or all of (a) to (c), of the recombinant cell in the presence of formic acid. In one embodiment, the Yme2p polypeptide further provides for (a) an increased xylose consumption rate, (b) an increased ethanol production rate, or (c) a combination of (a) and (b), of the recombinant cell in the presence of acetic acid.

Advantageously, the anaerobic growth, xylose consumption, ethanol production rate, or combination can be measured according to Examples 13 or 14. Notably, these Example show that xylose fermentation in presence of formic or acetic acid was improved in yeast overexpressing YME2. Specifically, xylose consumption and ethanol production increased by 13% and 12%, respectively, in the presence of acetic acid, and by 7% and 12%, respectively, in the presence of formic acid. Formic acid is common in lignocellulosic hydrolysates, and strongly contributes to the toxicity of such hydrolysates.

In separate and specific embodiments of any aforementioned aspect or embodiment, the Yme2p polypeptide comprising the amino acid sequence of SEQ ID NO: 50 or a functional variant, fragment or yeast ortholog thereof, provides for a xylose consumption which is at least 5%, e.g., at least 10% higher, an ethanol production which is at least 5%, e.g., at least 10% higher, or both, of the recombinant cell when tested according to Example 14. In these tests, the recombinant strains can, for example, be prepared from TMB 3000 or an equivalent or similar laboratory or commercially available *S. cerevisiae* strain, and then tested in as

TABLE 2

Overview of strains constructed and tested in the presence of formic acid as described in the Examples. The growth and fermentation experiments reported here were conducted on xylose and under anaerobic conditions.

| | | | Fermentation in the presence of acetic acid, 144 h | | Fermentation in the presence of formic acid, 144 h | |
|---|---|---|---|---|---|---|
| Strain | Heterologous genes | Growth in the prescence of formic acid ($h^{-1}$) | Consumed xylose (g/L) | Consumed ethanol (g/L) | Consumed xylose (g/L) | Consumed ethanol (g/L) |
| C5LTe 1202 | *P. stipitis* mXR(N272D)<br>*P. stipitis*[a] XDH<br>*S. cerevisiae* XK<br>*S. cerevisiae* TAL1<br>*S. cerevisiae* TKL1<br>*S. cerevisiae* RKI1 | 0.03 | 37.6 | 25.4 | 42.7 | 27.1 |
| C5LTe 1212 | *P. stipitis* mXR(N272D)<br>*P. stipitis*[a] XDH<br>*S. cerevisiae* XK<br>*S. cerevisiae* TAL1<br>*S. cerevisiae* TKL1<br>*S. cerevisiae* RKI1<br>*Z. bailii* YME2 | 0.05 | 42.4 | 28.3 | 45.8 | 30.3 |

Accordingly, in one aspect is a recombinant yeast cell such as a *Saccharomyces* cell, optionally a *S. cerevisiae* cell, which is capable of fermenting xylose and which comprises a heterologous gene encoding an Yme2p polypeptide comprising the amino acid sequence of SEQ ID NO: 50 or a catalytically active variant, fragment or yeast ortholog thereof, wherein the Yme2p polypeptide provides for an increased tolerance of the recombinant cell to formic acid, acetic acid, or both. In one embodiment, the Yme2p polypeptide further provides for (a) an increased anaerobic growth, (b) an increased xylose consumption rate, (c) an described. Typically, for conducting such test assays, *S. cerevisiae* cells are transformed with genes encoding *P. stipitis* mXR with an N272D mutation, *P. stipitis* XDH, the Yme2p polypeptide to be examined, and *S. cerevisiae* XK, TAL1, TKL1, and RKI1, so that each gene is chromosomally integrated and operably linked to a constitutive promoter.

In one embodiment of any preceding aspect or embodiment, the Yme2p polypeptide comprises the amino acid sequence of SEQ ID NO: 50 or a functional variant, fragment or yeast ortholog thereof. In one embodiment, the Yme2p polypeptide is a functional variant or yeast ortholog of the amino acid sequence of SEQ ID NO: 50, comprising an amino acid sequence which is at least 50%, such as at least 60%, such as at least 70%, such as at least 80%, such as at least 90%, such as at least 95%, such as at least 97%, such as at least 98%, such as at least 99% identical to the amino acid sequence of SEQ ID NO: 50. In one embodiment, the Yme2p polypeptide is a functional fragment of the amino acid sequence of SEQ ID NO: 50 corresponding to at least 50%, at least 80%, at least 90%, at least 95%, at least 96%, at least 97%, at least 98% or at least 99% of the full-length enzyme amino acid sequence.

Tables 3 and 8 below additionally summarize some key results from the Examples, showing that overexpression of genes encoding ENO1, PFK2, PFK26, PGI1, GPM1 or TPI1 in recombinant *S. cerevisiae* cells capable of fermenting xylose resulted in a higher anaerobic growth rate, more efficient xylose consumption and/or increased ethanol production in fermentation on xylose.

TABLE 3

Overview of strains constructed and tested as described in the Examples. See also Table 8, for results on xylose consumption and ethanol production.

| Strain | Heterologous genes | Aerobic growth on xylose | Anaerobic growth on xylose ($h^{-1}$) | Xylose consumed in 140 h, (g/L) | Ethanol produced in 140 h (g/L) |
|---|---|---|---|---|---|
| C5LTe1035 | *P. stipitis* mXR(N272D)<br>*P. stipitis*[a] XDH<br>*S. cerevisiae* XK<br>*S. cerevisiae* TAL1<br>*S. cerevisiae* TKL1<br>*S. cerevisiae* RKI1 | | 0.058 | | |
| C5LTe1051 | *P. stipitis* mXR(N272D)<br>*P. stipitis*[a] XDH<br>*S. cerevisiae* XK<br>*S. cerevisiae* TAL1<br>*S. cerevisiae* TKL1<br>*S. cerevisiae* RKI1<br>*S. cerevisiae* ENO1 | | 0.066 | | |
| C5LTe1052 | *P. stipitis* mXR(N272D)<br>*P. stipitis*[a] XDH<br>*S. cerevisiae* XK<br>*S. cerevisiae* TAL1<br>*S. cerevisiae* TKL1<br>*S. cerevisiae* RKI1<br>*S. cerevisiae* PFK2 | | 0.063 | | |
| C5LTe1054 | *P. stipitis* mXR(N272D)<br>*P. stipitis*[a] XDH<br>*S. cerevisiae* XK<br>*S. cerevisiae* TAL1<br>*S. cerevisiae* TKL1<br>*S. cerevisiae* RKI1<br>*S. cerevisiae* PGI1 | | 0.071 | | |
| C5LTe1055 | *P. stipitis* mXR(N272D)<br>*P. stipitis*[a] XDH<br>*S. cerevisiae* XK<br>*S. cerevisiae* TAL1<br>*S. cerevisiae* TKL1<br>*S. cerevisiae* RKI1<br>*S. cerevisiae* PFK26 | | 0.075 | | |
| MC2 | *P. stipitis* mXR(N272D)<br>*P. stipitis*[a] XDH<br>*S. cerevisiae* XK<br>*S. cerevisiae* TAL1<br>*S. cerevisiae* TKL1<br>*S. cerevisiae* RKI1<br>*S. cerevisiae* RPE1<br>*S. cerevisiae* PGI1 | Faster than average | Faster than average | 51 | 18 |
| MC3 | *P. stipitis* mXR(N272D)<br>*P. stipitis*[a] XDH<br>*S. cerevisiae* XK<br>*S. cerevisiae* TAL1<br>*S. cerevisiae* TKL1<br>*S. cerevisiae* RKI1<br>*S. cerevisiae* RPE1<br>*S. cerevisiae* PFK26 | Slower than average | Faster than average | 53 | 21 |
| MC4 | *P. stipitis* mXR(N272D)<br>*P. stipitis*[a] XDH<br>*S. cerevisiae* XK<br>*S. cerevisiae* TAL1<br>*S. cerevisiae* TKL1<br>*S. cerevisiae* RKI1<br>*S. cerevisiae* RPE1<br>*S. cerevisiae* PFK2 | Faster than average | Faster than average | 50 | 22 |

TABLE 3-continued

Overview of strains constructed and tested as described in the Examples. See also Table 8, for results on xylose consumption and ethanol production.

| Strain | Heterologous genes | Aerobic growth on xylose | Anaerobic growth on xylose ($h^{-1}$) | Xylose consumed in 140 h, (g/L) | Ethanol produced in 140 h (g/L) |
|---|---|---|---|---|---|
| MC11 | *P. stipitis* mXR(N272D)<br>*P. stipitis*[a] XDH<br>*S. cerevisiae* XK<br>*S. cerevisiae* TAL1<br>*S. cerevisiae* TKL1<br>*S. cerevisiae* RKI1<br>*S. cerevisiae* RPE1<br>*S. cerevisiae* PFK2 | Slower than average | Faster than average | 50 | 18 |
| MC14 | *P. stipitis* mXR(N272D)<br>*P. stipitis*[a] XDH<br>*S. cerevisiae* XK<br>*S. cerevisiae* TAL1<br>*S. cerevisiae* TKL1<br>*S. cerevisiae* RKI1<br>*S. cerevisiae* RPE1<br>*S. cerevisiae* ENO1 | Faster than average | Faster than average | 54 | 20 |
| MC22 | *P. stipitis* mXR(N272D)<br>*P. stipitis*[a] XDH<br>*S. cerevisiae* XK<br>*S. cerevisiae* TAL1<br>*S. cerevisiae* TKL1<br>*S. cerevisiae* RKI1<br>*S. cerevisiae* RPE1<br>*S. cerevisiae* ENO1 | Slower than average | Faster than average | 51 | 18 |
| Control | *P. stipitis* mXR(N272D)<br>*P. stipitis*[a] XDH<br>*S. cerevisiae* XK<br>*S. cerevisiae* TAL1<br>*S. cerevisiae* TKL1<br>*S. cerevisiae* RKI1<br>*S. cerevisiae* RPE1<br>URA3+ | — | — | 36 | 13 |

Accordingly, in one aspect is a recombinant yeast cell such as a *Saccharomyces* cell, optionally a *S. cerevisiae* cell, which is capable of fermenting xylose and which comprises a heterologous gene encoding an enolase comprising the amino acid sequence of SEQ ID NO: 132 (ENO1), a phosphofructokinase beta subunit polypeptide comprising the amino acid sequence of SEQ ID NO: 134 (PFK2), a 6-phosphofructo-2-kinase comprising the amino acid sequence of SEQ ID NO: 136 (PFK26), a glucose-6-phosphate isomerase comprising the amino acid sequence of SEQ ID NO: 138 (PGI1), a phosphoglycerate mutase comprising the amino acid sequence of SEQ ID NO: 140 (GPM1), a triose-phosphate isomerase comprising the amino acid sequence of SEQ ID NO: 142 (TPI1), or a catalytically active variant, fragment or yeast ortholog of any one of ENO1, PFK2, PFK26, PGI1, GPM1 and TPI1, or a combination of any two or more of ENO1, PFK2, PFK26, PGI1, GPM1 and TPI1 thereof, such as three, four, five or all of ENO1, PFK2, PFK26, PGI1, GPM1 and TPI1. In one embodiment, the heterologous gene or combination provides for an increased anaerobic growth rate on xylose, an increased aerobic growth rate on xylose, an increased ethanol production from xylose, or a combination of any two or all thereof. Advantageously, the anaerobic growth rate can be measured according to Example 23, the aerobic growth can be measured according to Example 5, and/or the ethanol production can be measured according to Example 24.

In separate and specific embodiments of any aforementioned aspect or embodiment, the ENO1, PFK2, PFK26, PGI1, GPM1, TPI1 or catalytically active variant, fragment or yeast ortholog of any thereof, provides for an ethanol yield from xylose which is at least 5%, e.g., at least 10% higher, at least 15% higher, or at least 20% higher, of the recombinant cell when tested according to Example 12. In these tests, the recombinant strains can, for example, be prepared from CEN.PK or an equivalent or similar laboratory or commercially available *S. cerevisiae* strain, and then tested in as described. Typically, for conducting such test assays, *S. cerevisiae* cells are transformed with genes encoding *P. stipitis* mXR with an N272D mutation, *P. stipitis* XDH, the ENO1, PFK2, PFK26, PGI1, GPM1, or TPI1 to be examined, and *S. cerevisiae* XK, TAL1, TKL1, and RKI1, so that each gene is chromosomally integrated and operably linked to a constitutive promoter.

In one embodiment or any preceding aspect or embodiment, the cell comprises a heterologous gene encoding an enolase comprising the amino acid sequence of SEQ ID NO: 132 or a catalytically active variant, fragment or yeast ortholog thereof. In one embodiment, the catalytically active variant or yeast ortholog has a sequence identity of at least 80%, e.g., at least 90%, at least 95%, at least 97%, at least 98%, or at least 99% to the amino acid sequence of SEQ ID NO: 132. In one embodiment, the heterologous gene encodes the amino acid sequence of SEQ ID NO: 132.

In one embodiment or any preceding aspect or embodiment, the cell comprises a heterologous gene encoding a phosphofructokinase beta subunit polypeptide comprising the amino acid sequence of SEQ ID NO: 134 or a catalytically active variant, fragment or yeast ortholog thereof. In one embodiment, the catalytically active variant or yeast ortholog has a sequence identity of at least 80%, e.g., at least 90%, at least 95%, at least 97%, at least 98%, or at least 99% to the amino acid sequence of SEQ ID NO: 134. In one embodiment, the heterologous gene encodes the amino acid sequence of SEQ ID NO: 134.

In one embodiment or any preceding aspect or embodiment, the cell comprises a heterologous gene encoding a 6-phosphofructo-2-kinase comprising the amino acid sequence of SEQ ID NO: 136 or a catalytically active variant, fragment or yeast ortholog thereof. In one embodiment, the catalytically active variant or yeast ortholog has a sequence identity of at least 80%, e.g., at least 90%, at least 95%, at least 97%, at least 98%, or at least 99% to the amino acid sequence of SEQ ID NO: 136. In one embodiment, the heterologous gene encodes the amino acid sequence of SEQ ID NO: 136.

In one embodiment or any preceding aspect or embodiment, the cell comprises a heterologous gene encoding a glucose-6-phosphate isomerase comprising the amino acid sequence of SEQ ID NO: 138 or a catalytically active variant, fragment or yeast ortholog thereof. In one embodiment, the catalytically active variant or yeast ortholog has a sequence identity of at least 80%, e.g., at least 90%, at least 95%, at least 97%, at least 98%, or at least 99% to the amino acid sequence of SEQ ID NO: 138. In one embodiment, the heterologous gene encodes the amino acid sequence of SEQ ID NO: 138.

In one embodiment or any preceding aspect or embodiment, the cell comprises a heterologous gene encoding a phosphoglycerate mutase comprising the amino acid sequence of SEQ ID NO: 140 or a catalytically active variant, fragment or yeast ortholog thereof. In one embodiment, the catalytically active variant or yeast ortholog has a sequence identity of at least 80%, e.g., at least 90%, at least 95%, at least 97%, at least 98%, or at least 99% to the amino acid sequence of SEQ ID NO: 140. In one embodiment, the heterologous gene encodes the amino acid sequence of SEQ ID NO: 140.

In one embodiment or any preceding aspect or embodiment, the cell comprises a heterologous gene encoding a triose-phosphate isomerase comprising the amino acid sequence of SEQ ID NO: 142 or a catalytically active variant, fragment or yeast ortholog thereof. In one embodiment, the catalytically active variant or yeast ortholog has a sequence identity of at least 80%, e.g., at least 90%, at least 95%, at least 97%, at least 98%, or at least 99% to the amino acid sequence of SEQ ID NO: 142. In one embodiment, the heterologous gene encodes the amino acid sequence of SEQ ID NO: 142.

In one embodiment, the heterologous gene encodes a fragment of the amino acid sequence of SEQ ID NO: 132, 134, 136, 138, 140 or 142 corresponding to at least 50%, at least 80%, at least 90%, at least 95%, at least 96%, at least 97%, at least 98% or at least 99% of the full-length amino acid sequence.

Table 4 below additionally summarizes some key results from the Examples, showing that overexpression of PGM3 in recombinant *S. cerevisiae* cells capable of fermenting xylose resulted in a higher anaerobic growth rate, and more efficient xylose consumption and increased ethanol production in anaerobic fermentation of xylose.

TABLE 4

Overview of strains constructed and tested as described in the Examples.

| Strain | Heterologous genes | Anaerobic growth on xylose ($h^{-1}$) | Anaerobic growth on xylose 120 h, consumed xylose (g/L) | Anaerobic growth on xylose 120 h, produced ethanol (g/L) |
|---|---|---|---|---|
| Parent strain | *P. stipitis* mXR(N272D)<br>*P. stipitis* XDH<br>*S. cerevisiae* XK<br>*S. cerevisiae* TAL1<br>*S. cerevisiae* TKL1<br>*S. cerevisiae* RKI1<br>*S. cerevisiae* RPE1 | 0.010 | 20 | 6.6 |
| PGM1 | *P. stipitis* mXR(N272D)<br>*P. stipitis* XDH<br>*S. cerevisiae* XK<br>*S. cerevisiae* TAL1<br>*S. cerevisiae* TKL1<br>*S. cerevisiae* RKI1<br>*S. cerevisiae* RPE1<br>*S. cerevisiae* PGM1 | 0.009 | 24 | 7.3 |
| PGM3 | *P. stipitis* mXR(N272D)<br>*P. stipitis* XDH<br>*S. cerevisiae* XK<br>*S. cerevisiae* TAL1<br>*S. cerevisiae* TKL1<br>*S. cerevisiae* RKI1<br>*S. cerevisiae* RPE1<br>*S. cerevisiae* PGM3 | 0.019 | 40 | 14.3 |

Accordingly, in one aspect is a recombinant yeast cell such as a *Saccharomyces* cell, optionally a *S. cerevisiae* cell, which is capable of fermenting xylose and which comprises an heterologous gene encoding a phosphoglucomutase and/or phosphoribomutase comprising the amino acid sequence of SEQ ID NO: 150 (PGM3) or a catalytically active variant or fragment thereof. In one embodiment, the heterologous gene or combination provides for an increased anaerobic growth rate on xylose, an increased xylose consumption, an increased ethanol production from xylose, or a combination of any two or all thereof.

In separate and specific embodiments of any aforementioned aspect or embodiment, the PGM3 or catalytically active fragment or variant provides for an anaerobic growth rate of the recombinant cell which is at least 10%, e.g., at least 20%, at least 50%, at least 80%, or at least 100% higher than a relevant control not comprising the heterologous PGM3 gene (in which the PGM3 is not overexpressed), (e.g., when tested according to Example 26). In separate and specific embodiments of any aforementioned aspect or embodiment, the PGM3 or catalytically active fragment or variant also or alternatively provides for a xylose consumption rate in anaerobic fermentation which is at least 10%, e.g., at least 20%, at least 50%, at least 80%, or at least 100% higher than a relevant control not comprising the heterologous PGM3 gene (in which the PGM3 is not overexpressed), (e.g., when tested according to Example 27). In separate and specific embodiments of any aforementioned aspect or embodiment, the PGM3 or catalytically active fragment or variant also or alternatively provides for an ethanol yield in anaerobic fermentation which is at least 10%, e.g., at least 20%, at least 50%, at least 80%, or at least 100% higher than a relevant control not comprising the heterologous PGM3 gene (in which the PGM3 is not overexpressed), (e.g., when tested according to Example 27). In these tests, the recombinant strains can, for example, be prepared from CEN.PK or an equivalent or similar laboratory or commercially available *S. cerevisiae* strain, and then tested in as described. Typically, for conducting such test assays, *S. cerevisiae* cells are transformed with genes encoding *P. stipitis* mXR with an N272D mutation, *P. stipitis* XDH, the PGM3 or catalytically active fragment or variant to be examined, and *S. cerevisiae* XK, TAL1, TKL1, and RKI1, so that each gene is chromosomally integrated and operably linked to a constitutive promoter.

In one embodiment or any preceding aspect or embodiment, the cell comprises a heterologous gene encoding a PGM3 comprising the amino acid sequence of SEQ ID NO: 150 or a catalytically active variant or fragment thereof. In one embodiment, the catalytically active variant has a sequence identity of at least 30%, such as at least 50%, such as at least 80%, such as at least 90%, such as least 95%, such as at least 97%, such as at least 98%, such as at least 99% to the amino acid sequence of SEQ ID NO: 150. In one embodiment, the heterologous gene encodes a PGM3 comprising the amino acid sequence of SEQ ID NO: 150.

In one embodiment, the heterologous gene encoding PGM3 or catalytically active fragment or variant encodes a fragment of SEQ ID NO: 150 corresponding to at least 50%, at least 80%, at least 90%, at least 95%, at least 96%, at least 97%, at least 98% or at least 99% of the full-length amino acid sequence.

The skilled artisan is well aware that variants and fragments of an enzyme sequence can be modified by replacing, inserting, or deleting amino acids using standard recombinant techniques while still retaining, or even improving, the enzyme activity of interest. Although such variants include those having amino acid sequences with one or more conservative or non-conservative substitutions relative to the amino acid sequence of SEQ ID NO: 6, 22, 50, 132, 134, 136, 138, 140, 142 and/or 150, conservative substitutions are typically of most interest. As used herein, the term "conservative substitution" refers to the substitution of a residue for another residue that does not generally alter the specific activity of the encoded polypeptide. An exemplary conservative substitution is a substitution that is within the same group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine, proline, cysteine and methionine). Amino acid substitutions that do not generally alter the specific activity are well-known in the art. The most commonly occurring exchanges are Ala/Ser, Val/Ile, Asp/Glu, Thr/Ser, Ala/Gly, Ala/Thr. Ser/Asn, Ala/Val, Ser/Gly, Tyr/Phe, Ala/Pro, Lys/Arg, Asp/Asn, Leu Ile, Leu/Val, Ala/Glu, and Asp/Gly, as well as these in reverse. In some embodiments, the substitutions are of a low percentage, typically less than about 10%, more typically less than 5%, and often less than about 2% of the amino acids of the polypeptide sequence, with a conservatively selected amino acid of the same conservative substitution group. In one preferred embodiment of any preceding aspect or embodiment, the XK comprises SEQ ID NO: 6. In another preferred embodiment of any preceding aspect or embodiment, the XK comprises SEQ ID NO: 22. In another preferred embodiment of any preceding aspect or embodiment, the Yme2p comprises the amino acid sequence of SEQ ID NO: 50. In another preferred embodiment of any preceding aspect, the enzyme comprises the amino acid sequence of SEQ ID NO: 134, 136, 138, 140, 142 or 150.

Essential amino acids of enzymes can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for enzymatic activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identities of essential amino acids can also be inferred from analysis of identities with other enzymes that are related to the referenced enzymes.

Additional guidance on the structure-activity relationship of the enzymes herein can be determined using multiple sequence alignment (MSA) techniques well-known in the art. Based on the teachings herein, the skilled artisan could make similar alignments with any number of enzymes described herein or known in the art. Such alignments aid the skilled artisan to determine potentially relevant domains (e.g., binding domains or catalytic domains), as well as which amino acid residues are conserved and not conserved among the different enzyme sequences. It is appreciated in the art that changing an amino acid that is conserved at a particular position between the disclosed enzyme will more likely result in a change in biological activity (Bowie et al., 1990, *Science* 247: 1306-1310: "Residues that are directly involved in protein functions such as binding or catalysis will certainly be among the most conserved"). In contrast, substituting an amino acid that is not highly conserved among the enzymes will not likely or significantly alter the biological activity.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active enzymes (e.g., xylulokinases) can be recovered from the host cells and rapidly sequenced using standard methods in the art. These methods allow the rapid determination of the importance of individual amino acid residues in a polypeptide.

The host cells for preparing the recombinant cells of the invention can be from any suitable yeast strain, including, but not limited to, a *Saccharomyces, Rhodotorula, Schizosaccharomyces, Kluyveromyces, Pichia, Hansenula, Rhodosporidium, Candida, Yarrowia, Lipomyces, Cryptococcus*, or *Dekkera* sp. cell. In particular, *Saccharomyces* host cells are contemplated, such as *Saccharomyces cerevisiae, bayanus* or *carlsbergensis* cells. Preferably, the yeast cell is a *Saccharomyces cerevisiae* cell. Suitable cells can, for example, be derived from commercially available strains and polyploid or aneuploid industrial strains, including but not limited to those from Superstart™, THERMOSACC®, etc. (Lallemand); RED STAR and ETHANOL RED® (Fermentis/Lesaffre); FALI (AB Mauri); Baker's Best Yeast, Baker's Compressed Yeast, etc. (Fleishmann's Yeast); BIOFERM AFT, XP, CF, and XR (North American Bioproducts Corp.); Turbo Yeast (Gert Strand AB); and FERMIOL® (DSM Specialties). Other useful yeast strains are available from biological depositories such as the American Type Culture Collection (ATCC) or the Deutsche Sammlung von Mikroorganismen and Zellkulturen GmbH (DSMZ), such as, e.g., BY4741 (e.g., ATCC 201388); Y108-1 (ATCC PTA.10567) and NRRL YB-1952 (ARS Culture Collection). Still other *S. cerevisiae* strains suitable as host cells DBY746, [Alpha][Eta]22, S150-2B, GPY55-15Ba, CEN.PK, USM21, TMB3500, TMB3400, VTT-A-63015, VTT-A-85068, VTT-c-79093 and their derivatives as well as *Saccharomyces* sp. 1400, 424A (LNH-ST), 259A (LNH-ST) and derivatives thereof.

As previously mentioned, some wild-type yeast cells, e.g., *Saccharomyces* cells, cannot naturally ferment xylose. However, it is now well within the level of skill in the art to apply genetic engineering technology to prepare recombinant *Saccharomyces* cells which are capable of fermenting xylose. For example, XR and XDH enzymes from naturally xylose fermenting yeasts such as *Scheffersomyces* (*Pichia*) *stipitis* and various *Candida* species can be expressed in *Saccharomyces* cells to provide this ability and/or an XI enzyme suitable for expression in a yeast host cell. Additionally, it is contemplated to use catalytically active variants of XR and/or XDH. For example, variants of *P. stipitis* XR exist which change the cofactor preference of the XR from NADPH to NADH. These variants are referred to herein as "NADH-preferring" XR variants, and include, but are not limited to, N272D, K270R and P275Q. Still other variants of XR and XK are described in WO 2012/135110. As for XI, XI from the fungus *Piromyces* sp. (Kuyper et al., 2005) or other sources (Madhavan et al., 2009) have been expressed in *S. cerevisiae* host cells. Still other XIs suitable for expression in yeast have been described in US 2012/0184020 (an XI from *Ruminococcus flavefaciens*), WO 2011/078262 (several XIs from *Reticulitermes speratus* and *Mastotermes darwiniensis*) and WO 2012/009272 (constructs and fungal cells containing an XI from *Abiotrophia defectiva*). Optionally, additional improvements in xylose fermentation can also be achieved by strain adaptation to selective conditions, according to techniques known in the art. Additionally, the xylose fermentative capability of a yeast cell can also be increased by increasing the flux of the pentose-phosphate pathway (PPP) by overexpressing one or more genes encoding enzymes of the non-oxidative pathway, which includes TAL (EC 2.2.1.2), TKL (EC 2.2.1.1), RKI (EC 5.3.1.6) and RPE (EC 5.1.3.4) (Karhumaa et al., 2005). Preferably, in the yeast cells of the invention, the genes encoding TAL, TKL and RKI are overexpressed. Typically, although not necessarily, the endogenous genes of the PPP are overexpressed. An increased flux in the PPP can be measured by metabolic flux analysis with 13C-labeled glucose as described in, e.g., van Winden et al. (2005, FEMS Yeast Research 5:559-568).

Accordingly, in one embodiment of any preceding aspect or embodiment, the recombinant cell comprises a heterologous gene encoding a transaldolase (TAL), a heterologous gene encoding a transketolase (TKL), and/or a heterologous gene encoding a ribose 5-phosphate ketol-isomerase (RKI). In some embodiments, the recombinant cell comprises a heterologous gene encoding a transaldolase (TAL), a heterologous gene encoding a transketolase (TKL), and a heterologous gene encoding a ribose 5-phosphate ketol-isomerase (RKI).

In one embodiment of any preceding aspect or embodiment, the recombinant cell comprises a heterologous gene encoding a xylose reductase (XR), a heterologous gene encoding a xylitol dehydrogenase (XDH), and/or a heterologous gene encoding a xylose isomerase (XI). Preferred XRs are *Pichia stipitis* XR and NADH-preferring variants thereof, such as *Pichia stipites* XR comprising one or more amino acid substitutions selected from N272D, K270R and P275Q. Most preferred is *Pichia stipitis* XR(N272D). Preferred XDHs are *Pichia stipitis* XDH and catalytically active variants thereof. Preferred TALs, TKLs and RKIs are those that are endogenous to the cell.

The specific coding or amino acid sequences for the various *S. cerevisiae* or other yeast or fungal enzymes referred to above can be identified in the literature and in bioinformatics databases well known to the skilled person, such as the BRENDA comprehensive enzyme information system and the *Saccharomyces* genome database Particular XR, XDH, XK, TAL, TKL and RKI nucleic acid and amino acid sequences can also be prepared as described in the Examples, or are provided in the accompanying sequence listing.

In another aspect is a method for increasing the tolerance of a yeast cell such as a *Saccharomyces* cell to formic acid, comprising transforming the cell with a gene encoding a Yme2p polypeptide comprising the amino acid sequence of SEQ ID NO: 50 or a catalytically active variant, fragment or yeast ortholog thereof, and expressing the gene.

In one embodiment, each of the heterologous gene or genes in the recombinant cell according to the invention is operably linked to an inducible, a regulated or a constitutive promoter. Optionally, one or more, optionally all, of the genes are integrated into the genome of the cell. In a specific embodiment, the gene encoding an XK is operably linked to a constitutive promoter endogenous to the cell. Related recombinant techniques are described in more detail below.

Strains or clones of the recombinant cells of any of the preceding aspects or embodiments are also provided by the invention. A "clone" in this context refers to a number of cells which all are derived from the same parent cell by cell division.

Recombinant Methods

The invention also relates to vectors comprising genes encoding an XK as described in the preceding aspects and embodiments which can be used for transforming a yeast host cell, optionally a *Saccharomyces* cell, such as an *S. cerevisiae* cell. The yeast host cell can either be naturally capable of fermenting xylose, or may be transformed with genes providing this capability, as described above.

Accordingly, in one aspect is a process for producing a recombinant cell described herein (e.g., a *Saccharomyces* cell), comprising transforming the cell with a heterologous gene (e.g., a vector) that encodes a XK comprising the amino acid sequence of SEQ ID NO: 6, the amino acid sequence of SEQ ID NO: 22 or a catalytically variant or fragment of any thereof.

In one embodiment, the process comprises transforming the cell with a heterologous gene (e.g., a vector) that encodes a XK comprising the amino acid sequence of SEQ ID NO: 6, the amino acid sequence of SEQ ID NO: 22 or a catalytically variant or fragment of any thereof; a heterologous gene (e.g., a vector) that encodes a XR, and a heterologous gene (e.g., a vector) that encodes a XDH. The heterologous genes may be in the form of one or more vectors.

In one embodiment, the process comprises transforming the cell with a heterologous gene (e.g., a vector) that encodes a XK comprising the amino acid sequence of SEQ ID NO: 6, the amino acid sequence of SEQ ID NO: 22 or a catalytically variant or fragment of any thereof; and a heterologous gene (e.g., a vector) that encodes an XI. The heterologous genes may be in the form of one or more vectors.

In one aspect is a vector comprising a gene encoding a xylulokinase (XK) comprising the amino acid sequence of SEQ ID NO: 6, SEQ ID NO: 22 or a catalytically active variant or fragment of any thereof. In some embodiments, the vector further comprises a gene encoding a xylose reductase (XR), a gene encoding a xylitol dehydrogenase (XDH), and/or a gene encoding a xylose isomerase (XI). The vector may further comprise regulatory sequences for expressing the genes in a yeast host cell such as a *Saccharomyces* or *Saccaromyces cerevisiae* host cell.

The invention also relates to vectors comprising genes encoding an Yme2p as described in the preceding aspects and embodiments which can be used for transforming a yeast host cell, optionally a *Saccharomyces* cell, such as an *S. cerevisiae* cell. The yeast host cell can either be naturally capable of fermenting xylose, or may be transformed with genes providing this capability, as described above.

Accordingly, in one aspect is a process for producing a recombinant cell described herein (e.g., a *Saccharomyces* cell), comprising transforming the cell with a heterologous gene (e.g., a vector) that encodes a Yme2p comprising the amino acid sequence of SEQ ID NO: 50, or a catalytically variant or fragment of any thereof.

In one embodiment, the process comprises transforming the cell with a heterologous gene (e.g., a vector) that encodes a Yme2p comprising the amino acid sequence of SEQ ID NO: 50 or a catalytically variant or fragment of any thereof; a heterologous gene (e.g., a vector) that encodes a XR, and a heterologous gene (e.g., a vector) that encodes a XDH. The heterologous genes may be in the form of one or more vectors.

In one embodiment, the process comprises transforming the cell with a heterologous gene (e.g., a vector) that encodes a Yme2p comprising the amino acid sequence of SEQ ID NO: 50 or a catalytically variant or fragment of any thereof; and a heterologous gene (e.g., a vector) that encodes an XI. The heterologous genes may be in the form of one or more vectors.

In one aspect is a vector comprising a gene encoding a Yme2p comprising the amino acid sequence of SEQ ID NO: 50 or a catalytically active variant or fragment of any thereof. In some embodiments, the vector further comprises a gene encoding a xylose reductase (XR), a gene encoding a xylitol dehydrogenase (XDH), and/or a gene encoding a xylose isomerase (XI). The vector may further comprise regulatory sequences for expressing the genes in a yeast host cell such as a *Saccharomyces* or *Saccaromyces cerevisiae* host cell.

The invention also relates to vectors comprising genes encoding an ENO1, PFK2, PFK26, PGI1, GPM1, TPI1 polypeptide or catalytically active variant, fragment or yeast ortholog thereof as described in the preceding aspects and embodiments which can be used for transforming a yeast host cell, optionally a *Saccharomyces* cell, such as an *S. cerevisiae* cell. The yeast host cell can either be naturally capable of fermenting xylose, or may be transformed with genes providing this capability, as described above.

Accordingly, in one aspect is a process for producing a recombinant cell described herein (e.g., a *Saccharomyces* cell), comprising transforming the cell with one or more heterologous genes (e.g., vectors) that encode ENO1, PFK2, PFK26, PGI1, GPM1, TPI1 or a catalytically active variant, fragment or yeast ortholog of any thereof.

In one embodiment, the process comprises transforming the cell with one or more heterologous genes (e.g., vectors) that encodes ENO1, PFK2, PFK26, PGI1, GPM1, TPI1 or a catalytically active variant, fragment or yeast ortholog of any thereof; a heterologous gene (e.g., a vector) that encodes a XR, and a heterologous gene (e.g., a vector) that encodes a XDH. In some embodiments, the process further comprises transforming the cell with a heterologous gene encoding a xylulose kinase (XK). The heterologous genes may be in the form of one or more vectors.

In one embodiment, the process comprises transforming the cell with one or more heterologous genes (e.g., vectors) that encodes ENO1, PFK2, PFK26, PGI1, GPM1, TPI1 or a catalytically active variant, fragment or yeast ortholog of any thereof; and a heterologous gene (e.g., a vector) that encodes an XI. In some embodiments, the process further comprises transforming the cell with a heterologous gene encoding a xylulose kinase (XK). The heterologous genes may be in the form of one or more vectors.

In another aspect is a vector comprising one or more heterologous genes encoding ENO1, PFK2, PFK26, PGI1, GPM1, TPI1 or a functional variant, fragment or yeast ortholog of any thereof. In some embodiments, the vector further comprises a gene encoding a xylose reductase (XR), a gene encoding a xylitol dehydrogenase (XDH), In some embodiments, the process further comprises transforming the cell with a heterologous gene encoding a xylulose kinase (XK), and/or a gene encoding a xylose isomerase (XI). The vector may further comprise regulatory sequences for expressing the genes in a yeast host cell such as a *Saccharomyces* or *Saccaromyces cerevisiae* host cell.

The invention also relates to vectors comprising genes encoding an PGM3 polypeptide or a catalytically active variant or fragment thereof as described in the preceding aspects and embodiments which can be used for transforming a yeast host cell, optionally a *Saccharomyces* cell, such as an *S. cerevisiae* cell. The yeast host cell can either be naturally capable of fermenting xylose, or may be transformed with genes providing this capability, as described above.

Accordingly, in one aspect is a process for producing a recombinant cell described herein (e.g., a *Saccharomyces* cell), comprising transforming the cell with a heterologous gene (e.g., a vector) that encodes the PGM3 comprising the amino acid sequence of SEQ ID NO: 150 or a catalytically active variant or fragment thereof.

In one embodiment, the process comprises transforming the cell with a heterologous gene (e.g., a vector) that encodes a PGM3 comprising the amino acid sequence of SEQ ID NO: 150 or a catalytically variant or fragment of any thereof; a heterologous gene (e.g., a vector) that encodes a XR, and a heterologous gene (e.g., a vector) that encodes a XDH. The heterologous genes may be in the form of one or more vectors.

In one embodiment, the process comprises transforming the cell with a heterologous gene (e.g., a vector) that encodes a PGM3 comprising the amino acid sequence of SEQ ID NO: 150 or a catalytically variant or fragment of any thereof; and a heterologous gene (e.g., a vector) that encodes an XI. The heterologous genes may be in the form of one or more vectors.

In another aspect is a vector comprising a gene encoding the PGM3 comprising the amino acid sequence of SEQ ID NO: 150 or a functional variant or fragment thereof. In some embodiments, the vector further comprises a gene encoding a xylose reductase (XR), a gene encoding a xylitol dehydrogenase (XDH), and/or a gene encoding a xylose isomerase (XI). The vector may further comprise regulatory sequences for expressing the genes in a yeast host cell such as a *Saccharomyces* or *Saccaromyces cerevisiae* host cell.

Many methods for genetic modification, including transformation of yeast host cells are known to one skilled in the art and may be used to create the present recombinant cells, some of which are exemplified below. Standard recombinant DNA and molecular cloning techniques useful for transforming microbial cells with a desired nucleic acid sequence or gene, or otherwise manipulate the microbial cell, are described, e.g., in Sambrook, J., Fritsch, E. F. and Maniatis, T., Molecular Cloning: A Laboratory Manual, Second Edition, Cold Spring Harbor Laboratory Press, Cold Spring Harbor, N.Y. (1989); and by Silhavy, T. J., Bennan, M. L. and Enquist, L. W., Experiments with Gene Fusions, Cold Spring Harbor Laboratory Press, Cold Spring Harbor, N.Y. (1984); Ausubel et al., Short Protocols in Molecular Biology, 3rd ed., Wiley & Sons, 1995; and by Ausubel, F. M. et al., Current Protocols in Molecular Biology, published by Greene Publishing Assoc. and Wiley-Interscience (1987). Additional methods used here are in Methods in Enzymology, Volume 194, Guide to Yeast Genetics and Molecular and Cell Biology (Part A, 2004, Christine Guthrie and Gerald R. Fink (Eds.), Elsevier Academic Press, San Diego, Calif.).

Overexpressing a gene can be achieved by increasing the copy number of the gene coding for the enzyme in the cell, e.g. by integrating additional copies of the gene in the cell genome, expressing the gene from an episomal multicopy expression vector or introducing an episomal expression vector that comprises multiple copies of the gene; upregulating the endogenous gene, and the like. In a preferred embodiment, the gene is introduced into the microbial cell via, e.g., transformation with one or more expression vectors. For example, for a yeast host cell, the level of a recombinantly expressed enzyme in the cell can be increased by clone one or more recombinant genes in a multicopy plasmid in the manner described by Mumberg et al. (1995).

The gene can either be synthesized or cloned from a host organism in which the corresponding DNA sequence is endogenous (see, e.g., Examples 1-5). Standard cloning procedures used in genetic engineering can be used to relocate a nucleic acid sequence from its natural location to a different site where it will be reproduced. The cloning procedures may involve excision and isolation of a desired DNA fragment comprising the DNA sequence encoding the polypeptide of interest, insertion of the fragment into a vector molecule, and incorporation of the recombinant vector into a host cell where multiple copies or clones of the DNA sequence will be replicated. An isolated DNA sequence may be manipulated in a variety of ways to provide for expression of the polypeptide of interest. Manipulation of the DNA sequence prior to its insertion into a vector may be desirable or necessary depending on the expression vector and the host cell.

For example, to increase the likelihood that a, e.g., a bacterial enzyme gene is expressed in a yeast cell, the nucleotide sequence encoding the heterologous sequence may be adapted to optimize its codon usage to that of the yeast cell. The adaptiveness of a nucleotide sequence encoding enzyme to the codon usage of the host cell may be expressed as codon adaptation index (CAI). The CAI is herein defined as a measurement of the relative adaptiveness of the codon usage of a gene towards the codon usage of highly expressed genes. The relative adaptiveness (w) of each codon is the ratio of the usage of each codon, to that of the most abundant codon for the same amino acid. The CAI is defined as the geometric mean of these relative adaptiveness values. Non-synonymous codons and termination codons (dependent on genetic code) are excluded. CAI values range from 0 to 1, with higher values indicating a higher proportion of the most abundant codons (see Sharp and Li, 1987, Nucleic Acids Research 15: 1281-1295; also see: Jansen et al., 2003, Nucleic Acids Res. 31(8):2242-51). An adapted or "optimized" nucleotide sequence preferably has a CAI of at least 0.2, 0.3, 0.4, 0.5, 0.6 or 0.7.

The nucleotide sequence to be introduced into the DNA of the host cell may be integrated in vectors comprising the nucleotide sequence operably linked to one or more control sequences that direct the expression of the coding sequence in a suitable host cell under conditions compatible with the control sequences. The control sequence may be an appropriate promoter sequence, a nucleotide sequence which is recognized by a host cell for expression of the nucleotide sequence. The promoter sequence contains transcriptional control sequences, which mediate the expression of the coding sequence. The promoter may be any nucleotide sequence which shows transcriptional activity in the host cell of choice including native, mutant, truncated, and hybrid promoters, and may be obtained from genes encoding extracellular or intracellular polypeptides either homologous or heterologous to the host cell. The promoter may be a weak or a strong promoter that is constitutive or regulated in the host to be used. Strong, constitutive promoters are generally preferred for overexpression of the genes. Examples of suitable promoters for directing the transcription of the genes and vector constructs of the present invention in a yeast host cell are promoters obtained for example from the genes for *Saccharomyces cerevisiae* enolase (ENO1), *S. cerevisiae* galactokinase (GAL1), *S. cerevisiae* alcohol dehydrogenase 2 (ADH2), *S. cerevisiae* glyceraldehyde-3-phosphate dehydrogenase (TDH1), *S. cerevisiae* glyceraldehyde-3—phosphate dehydrogenase (TDH3), *S. cerevisiae* alcohol dehydrogenase 1 (ADH1), *S. cerevisiae* 3-phosphoglycerate kinase (PGK1) or *S. cerevisiae* cytochrome C (CYC1) (Karhumaa et al, 2005), translation elongation factor 1alpha (TEF1/TEF2) (Mumberg et al., 1995), PDC1 pyruvate decarboxylase (PDC1), pyruvate kinase (PYK1), and the constitutive truncated HXT7 promoter (Hauf et al. Enzym Microb Technol (2000) 26:688-698.) Other suitable vectors and promoters for use in yeast expression are further described in EP A-73,657 to Hitzeman, which is hereby incorporated by reference. Preferred promoters for overexpressing a gene encoding an XK in a recombinant yeast cell according to the invention include, but are not limited to, PGK1, TPI1, HXT7, TDH3, ADH2 and TEF2 promoters. Preferably, the promoter for overexpressing a gene encoding an XK according to the invention is TPI1. Promoters for overexpressing the genes encoding an XR, an XDH, an XI, a TAL, a TKL and an RPI in a recombinant yeast cell according to the invention are preferably separately selected from the following: PGK1, TDH3, TEF2, PDC1, HXT truncated, TPI1 and PYK1.

The above disclosed vectors may comprise a gene encoding the enzyme polypeptide, a promoter, and transcriptional and translational stop signals as well as other regulatory or structural DNA sequences known to a person of skill in the art. The vector may be any vector or nucleic acid (e.g., a plasmid, virus, integration vector or integration fragment), which can be conveniently subjected to recombinant procedures and can bring about the expression of the gene in the yeast host cell. The choice of the vector will typically depend on the compatibility of the vector with the host cell into which the vector is to be introduced. The vectors may be linear or closed circular plasmids, and may contain any means for assuring self-replication.

Alternatively, the vector may be one which, when introduced into the host cell, is integrated into the genome and replicated together with the chromosome(s) into which it has been integrated. The vector system may be a single vector or plasmid or two or more vectors or plasmids, which together contain the total DNA to be introduced into the genome of the host cell, or a transposon. The vector may also be an integration vector comprising solely the gene or part of the gene to be integrated. For integration, the vector may rely on the DNA sequence encoding the polypeptide of interest or any other element of the vector for stable integration of the vector into the genome by homologous or non homologous recombination. More than one copy of a DNA sequence encoding a polypeptide of interest may be inserted into the host cell to amplify expression of the DNA sequence.

Optionally, the vectors of the present invention may contain one or more selectable markers, which permit easy selection of transformed cells. A selectable marker is a gene the product of which provides for biocide or viral resistance, resistance to heavy metals, prototrophy to auxotrophs and the like. Useful expression vectors for yeast cells include, for example, the 2 [mu] (micron) plasmid and derivatives thereof, the Yip, YEp and YCp vectors described by Gietz and Sugino (1988. "New yeast vectors constructed with in vitro mutagenized yeast genes lacking six-base pair restriction sites", Gene 74:527-534), the vectors described in Mumberg et al. (1995, supra), YEplac-HXT vector (Karhumaa et al., 2005), the POT1 vector (U.S. Pat. No. 4,931,373), the pJS037 vector described in Okkels, Ann. New York Acad. Sci. 782, 202-207, 1996, the pPICZ A, B or C vectors (Invitrogen).

To achieve overexpression of an endogenous gene, promoter replacement methods may also be used to exchange the endogenous transcriptional control elements of the gene for another promoter (see, e.g., Mnaimneh et al. (2004) Cell 118(1):31-44). Deletions of DNA control elements preventing a high expression of an endogenous target gene may be made using mitotic recombination as described in Wach et al. ((1994) Yeast 10:1793-1808). This method involves preparing a DNA fragment that contains a selectable marker between genomic regions that may be as short as 20 bp, and which bound a target DNA sequence. This DNA fragment can be prepared by PCR amplification of the selectable marker gene using as primers oligonucleotides that hybridize to the ends of the marker gene and that include the genomic regions that can recombine with the yeast genome. The linear DNA fragment can be efficiently transformed into a cell and recombined into the genome resulting in gene replacement including with deletion of the target DNA sequence (as described in Methods in Enzymology, v 194, pp 281-301 (1991)).

For yeasts such as for *Saccharomyces cerevisiae*, DNA sequences surrounding a target gene coding sequence can be identified, e.g., in the complete genome sequence coordinated by Genome Project ID9518 of Genome Projects coordinated by NCBI (National Center for Biotechnology Information) with identifying GOPID #13838. Additional examples of yeast genomic sequences include that of *Yarrowia lipolytica*, GOPIC #13837, and of *Candida albicans*, which is included in GPID #10771, #10701 and #16373. Additional genomes have been completely sequenced and annotated and are publicly available for the following yeast strains Candida glabrata CBS 138, *Kluyveromyces lactis* NRRL Y-1140, Pichia stipitis CBS 6054, and *Schizosaccharomyces pombe* 972 h-.

Fermentation Methods

In one aspect is a method for producing a fermentation product, comprising contacting the recombinant cell of any one of the preceding aspects and embodiments with a medium comprising a carbon source comprising xylose and/or arabinose under anaerobic conditions, and recovering or isolating the fermentation product from the medium.

The fermentation product may be or comprise, for example, at least one of ethanol, butanol, isobutanol, isopentanol, lactate, isoamylacetate, glycerol, sorbitol, mannitol, xylitol, arabinitol; 3-hydroxybutyrolactone; hydrogen gas; L-ascorbic acid, 2,5-furan dicarboxylic acid, 3-hydroxy propionic acid, aspartic acid, glutaric acid, glutamic acid, itaconic acid, levulinic acid; succinic acid, fumaric acid, malic acid or other 1,4-diacid; a fatty acid, a fatty acid derived molecule; an isoprenoid, an isoprenoid-derived molecule; and an alkane.

However, it is contemplated that other fermentation products can also be produced using the methods of the present invention. Preferably, the carbon source comprises xylose and the fermentation product comprises ethanol.

In some embodiments, the medium, i.e., the fermentation medium, is feedstock from a cellulosic saccharification process and/or feedstock from a hemicellulose pre-treatment process. Such feedstocks include, but are not limited to carbohydrates (e.g., lignocellulose, xylans, cellulose, starch, etc.), other sugars (e.g., glucose, xylose, arabinose, etc.), and other compositions. Compositions of fermentation media suitable for the growth of yeast are well known in the art and there are various reference texts that provide recipes for these media.

Typically, the fermentation takes place under conditions known to be suitable for generating the fermentation product. Fermentation conditions suitable for generating desired fermentation products are well known in the art and any suitable method finds use in the present invention. In some embodiments, the fermentation process is carried out under aerobic or microaerophilic (i.e., where the concentration of oxygen is less than that in air), or anaerobic conditions. In some embodiments, fermentation is conducted under anaerobic conditions (i.e., no detectable oxygen), or less than about 5, about 2.5, or about 1 mmol/L/h oxygen. In the absence of oxygen, the NADH produced in glycolysis cannot be oxidized by oxidative phosphorylation. Under anaerobic conditions, pyruvate or a derivative thereof may be utilized by the host cell as an electron and hydrogen acceptor in order to generate NAD+.

The fermentation process is typically run at a temperature that is optimal for the recombinant fungal cell. For example, in some embodiments, the fermentation process is performed at a temperature in the range of from about 25° C. to about 42° C. Typically the process is carried out a temperature that is less than about 38° C., less than about 35° C., less than about 33° C., or less than about 38° C., but at least about 20° C., 22° C., or 25° C. Example 10 describes an exemplary assay for evaluating xylose consumption and/or ethanol production during fermentation of a xylose-containing fermentation medium.

In some embodiments, the recombinant cells of the present invention are grown under batch or continuous fermentation conditions. Classical batch fermentation is a closed system, wherein the composition of the medium is set at the beginning of the fermentation and is not subject to artificial alterations during the fermentation. A variation of the batch system is a fed-batch fermentation, which also finds use in the present invention. In this variation, the substrate is added in increments as the fermentation progresses. Fed-batch systems are useful when catabolite repression is likely to inhibit the metabolism of the cells and/or where it is desirable to have limited amounts of substrate in the medium. Batch and fed-batch fermentations are common and well known in the art. Continuous fermentation is an open system where a defined fermentation generally maintains the culture at a constant high density where cells are primarily in log phase growth. Continuous fermentation systems strive to maintain steady state growth conditions. Methods for modulating nutrients and growth factors for continuous fermentation processes, as well as techniques for modulating nutrients and growth factors for continuous fermentation processes as well as techniques for maximizing the rate of product formation are well known in the art of industrial microbiology.

The invention may further be described in the following numbered paragraphs:

Paragraph [1]. A recombinant *Saccharomyces* cell which is capable of fermenting xylose and which comprises a heterologous gene encoding a xylulokinase (XK), wherein the XK:

provides an enzymatic activity for converting D-xylulose to xylulose 5-phosphate at least twice that provided by *S. cerevisiae* XK (SEQ ID NO: 32), and provides for an anaerobic growth rate of the recombinant cell on xylose which is higher than that provided by a *S. cerevisiae* XK.

Paragraph [2]. The recombinant cell of paragraph [1], wherein the XK further provides for an aerobic growth rate of the cell on xylose which is higher than that provided by *S. cerevisiae* XK.

Paragraph [3]. The recombinant cell of paragraph [1] or [2], wherein (a) the enzymatic activity for converting D-xylulose to xylulose 5-phosphate is measured according to Example 7, (b) the anaerobic growth rate is measured according to Example 9, or (c) both (a) and (b).

Paragraph [4]. The recombinant cell any one of the preceding paragraphs, wherein the XK comprises the amino acid sequence of SEQ ID NO: 6, the amino acid sequence of SEQ ID NO: 22 or a catalytically active variant or fragment of any thereof.

Paragraph [5]. A recombinant yeast cell capable of fermenting xylose and which comprises a heterologous gene encoding a xylulokinase (XK) comprising the amino acid sequence of SEQ ID NO: 6 or a catalytically active variant or fragment thereof.

Paragraph [6]. The recombinant yeast cell of paragraph [5], which is derived from a *Saccharomyces, Rhodotorula Schizosaccharomyces, Kluyveromyces, Pichia, Hansenula, Rhodosporidium, Candida, Yarrowia, Lipomyces, Cryptococcus*, or *Dekkera* sp. cell.

Paragraph [7]. The recombinant cell of any one of the preceding paragraphs, wherein the XK has a sequence identity of at least 80% with the amino acid sequence of SEQ ID NO: 6.

Paragraph [8]. The recombinant cell of any one of the preceding paragraphs, wherein the XK has a sequence identity of at least 90% with the amino acid sequence of SEQ ID NO: 6.

Paragraph [9]. The recombinant cell of any one of the preceding paragraphs, which comprises a heterologous gene encoding a transaldolase (TAL), a heterologous gene encoding a transketolase (TKL), and a heterologous gene encoding a ribose 5-phosphate ketol-isomerase (RKI), and (a) a heterologous gene encoding a xylose reductase (XR) and a heterologous gene encoding a xylitol dehydrogenase (XDH), and/or (b) a heterologous gene encoding a xylose isomerase (XI).

Paragraph [10]. The recombinant cell of paragraph [9], wherein the XR is *Pichia stipitis* XR or an NADH-preferring variant thereof, and the XDH is *Pichia stipitis* XDH or a catalytically active variant thereof.

Paragraph [11]. The recombinant cell of any one of paragraphs [9] and [10], wherein the XR is *Pichia stipitis* XR comprising one or more amino acid substitutions selected from N272D, K270R and P275Q.

Paragraph [12]. The recombinant cell of any one of paragraphs [9] to [11], wherein the TAL, TKL and RKI coding sequences are endogenous to the cell.

Paragraph [13]. The recombinant cell of any one of the preceding paragraphs, which is derived from a *Saccharomyces cerevisiae, bayanus* or *carlsbergensis* cell.

Paragraph [14]. The recombinant cell of any one of the preceding paragraphs, which is derived from a *Saccharomyces cerevisiae* cell.

Paragraph [15]. The recombinant cell of any one of the preceding paragraphs, wherein each of said gene or genes is operably linked to an inducible, a regulated or a constitutive promoter, and is optionally integrated into the genome of the cell.

Paragraph [16]. The recombinant cell of any one of the preceding paragraphs, wherein the gene encoding an XK is operably linked to a strong constitutive promoter endogenous to the cell.

Paragraph [17]. A strain or clone comprising the recombinant cell of any one of the preceding paragraphs.

Paragraph [18]. A method for producing a fermentation product, comprising (a) contacting the recombinant cell of any one of paragraphs [1] to [16] or the strain or clone of paragraph [17] with a medium comprising a carbon source comprising xylose or arabinose under anaerobic conditions, and (b) isolating the fermentation product from the medium.

Paragraph [19]. The method of paragraph [18], wherein the fermentation product comprises at least one of ethanol, butanol, isobutanol, isopentanol, lactate, isoamylacetate, glycerol, sorbitol, mannitol, xylitol, arabinitol; 3-hydroxybutyrolactone; hydrogen gas; L-ascorbic acid, 2,5-furan dicarboxylic acid, 3-hydroxy propionic acid, aspartic acid, glutaric acid, glutamic acid, itaconic acid, levulinic acid; succinic acid, fumaric acid, malic acid or other 1,4-diacid; a fatty acid, a fatty-acid derived molecule; an isoprenoid, an isoprenoid-derived molecule; and an alkane.

Paragraph [20]. The method of any one paragraph [18] or [19], wherein the carbon source comprises xylose and the fermentation product comprises ethanol.

Paragraph [21]. A vector comprising genes encoding an XK comprising the amino acid sequence of SEQ ID NO: 6, the amino acid sequence of SEQ ID NO: 22 or a catalytically active variant or fragment of any thereof, an XR, and an XDH; and optionally, regulatory sequences for expressing the genes in a *Saccharomyces* host cell.

Paragraph [22]. A process for producing a recombinant *Saccharomyces* cell, comprising transforming a *Saccharomyces* cell with one or more vectors comprising genes encoding an XK comprising the amino acid sequence of SEQ ID NO: 6, the amino acid sequence of SEQ ID NO: 22 or a catalytically active variant or fragment of any thereof, an XR, and an XDH, and optionally, regulatory sequences for expressing the genes in the host cell.

Paragraph [23]. A recombinant yeast cell which is capable of fermenting xylose and which comprises a heterologous gene encoding an Yme2p polypeptide comprising the amino acid sequence of SEQ ID NO: 50 or a catalytically active variant, fragment or yeast ortholog thereof, wherein the Yme2p polypeptide provides for an increased tolerance of the recombinant cell to formic acid, acetic acid, or both.

Paragraph [24]. The recombinant yeast cell of paragraph [23], wherein the Yme2p polypeptide provides for (a) an increased anaerobic growth on xylose, (b) an increased xylose consumption rate, (c) an increased ethanol production rate, or (d) a combination of two or all of (a) to (c), of the recombinant cell in the presence of formic acid.

Paragraph [25]. The recombinant yeast cell of paragraph [24], wherein the anaerobic growth, xylose consumption, ethanol production rate, or combination is measured according to Example 14.

Paragraph [26]. The recombinant yeast cell of any one of paragraphs [23] to [25], wherein the Yme2p polypeptide provides for (a) an increased xylose consumption rate, (b) an increased ethanol production rate, or (c) a combination of (a) and (b), of the recombinant cell in the presence of acetic acid.

Paragraph [27]. The recombinant yeast cell of paragraph [26], wherein the xylose consumption rate, ethanol production rate or combination is measured according to Example 13.

Paragraph [28]. The recombinant yeast cell of any one of paragraphs [23] to [27], wherein the Yme2p polypeptide has a sequence identity of at least 70% with the amino acid sequence of SEQ ID NO: 50.

Paragraph [29]. The recombinant yeast cell of any one of paragraphs [23] to [28], wherein the Yme2p polypeptide comprises the amino acid sequence of SEQ ID NO: 50.

Paragraph [30]. The recombinant yeast cell of any one of paragraphs [23] to [29], which comprises a heterologous gene encoding a transaldolase (TAL), a heterologous gene encoding a transketolase (TKL), and a heterologous gene encoding a ribose 5-phosphate ketol-isomerase (RKI), a heterologous gene encoding a xylulokinase (XK), and (a) a heterologous gene encoding a xylose reductase (XR) and a heterologous gene encoding a xylitol dehydrogenase (XDH), and/or (b) a heterologous gene encoding a xylose isomerase (XI).

Paragraph [31]. The recombinant yeast cell of paragraph [30], wherein the XR is *Pichia stipitis* XR or an NADH-preferring variant thereof, and the XDH is *Pichia stipitis* XDH or a catalytically active variant thereof.

Paragraph [32]. The recombinant yeast cell of paragraph [30] or [31], wherein the XR is *Pichia stipitis* XR comprising one or more amino acid substitutions selected from N272D, K270R and P275Q.

Paragraph [33]. The recombinant yeast cell of any one of paragraphs [30] to [32], wherein the TAL, TKL, RKI and XK coding sequences are endogenous to the cell.

Paragraph [34]. The recombinant yeast cell of any one of paragraphs [23] to [33], wherein the yeast cell is derived from a *Saccharomyces, Rhodotorula Schizosaccharomyces, Kluyveromyces, Pichia, Hansenula, Rhodosporidium, Candida, Yarrowia, Lipomyces, Cryptococcus*, or *Dekkera* sp. cell.

Paragraph [35]. The recombinant yeast cell of any one of paragraphs [23] to [34], which is derived from a *Saccharomyces cerevisiae, bayanus* or *carlsbergensis* cell.

Paragraph [36]. The recombinant yeast cell of any one of paragraphs [23] to [35], which is derived from a *Saccharomyces cerevisiae* cell.

Paragraph [37]. The recombinant yeast cell of any one of paragraphs [23] to [36], wherein each of said gene or genes is operably linked to an inducible, a regulated or a constitutive promoter, and is optionally integrated into the genome of the cell.

Paragraph [38]. The recombinant yeast cell of any one of paragraphs [23] to [38], wherein the gene encoding an Yme2p polypeptide is operably linked to a strong constitutive promoter endogenous to the cell.

Paragraph [39]. A strain or clone comprising the recombinant yeast cell of any one of paragraphs [23] to [38].

Paragraph [40]. A method for producing a fermentation product, comprising (a) contacting the recombinant yeast cell of any one of paragraphs [23] to [38] or the strain or clone of paragraph [39] with a medium comprising a carbon source comprising xylose or arabinose under anaerobic conditions, and (b) isolating the fermentation product from the medium.

Paragraph [41]. The method of paragraph [40], wherein the fermentation product comprises at least one of ethanol, butanol, isobutanol, isopentanol, lactate, isoamylacetate, glycerol, sorbitol, mannitol, xylitol, arabinitol; 3-hydroxybutyrolactone; hydrogen gas; L-ascorbic acid, 2,5-furan dicarboxylic acid, 3-hydroxy propionic acid, aspartic acid, glutaric acid, glutamic acid, itaconic acid, levulinic acid; succinic acid, fumaric acid, malic acid or other 1,4-diacid; a fatty acid, a fatty-acid derived molecule; an isoprenoid, an isoprenoid-derived molecule; and an alkane.

Paragraph [42]. The method of paragraph [40] or [41], wherein the carbon source comprises xylose and the fermentation product comprises ethanol.

Paragraph [43]. A vector comprising genes encoding an Yme2p polypeptide comprising the amino acid sequence of SEQ ID NO: 50 or a catalytically active variant or fragment thereof, an XR, an XDH, and an XK; and optionally, regulatory sequences for expressing the genes in a *Saccharomyces* host cell.

Paragraph [44]. A process for producing a recombinant *Saccharomyces* cell, comprising transforming a *Saccharomyces* cell with one or more vectors comprising genes encoding an Yme2p polypeptide comprising the amino acid sequence of SEQ ID NO: 50 or a catalytically active variant or fragment thereof, an XR, an XDH, an XK, and optionally, regulatory sequences for expressing the genes in the host cell.

Paragraph [45]. A method for increasing the tolerance of a *Saccharomyces* cell to formic acid, comprising transforming the cell with a gene encoding a Yme2p polypeptide comprising the amino acid sequence of SEQ ID NO: 50 or a catalytically active variant, fragment or yeast ortholog thereof, and expressing the gene.

Paragraph [46]. The method of paragraph 23, wherein the gene is operably linked to an inducible, a regulated or a constitutive promoter.

Paragraph [47]. A recombinant yeast cell which is capable of fermenting xylose and which comprises a heterologous gene encoding (a) an enolase comprising the amino acid sequence of SEQ ID NO: 132, (b) a phosphofructokinase beta subunit polypeptide comprising the amino acid sequence of SEQ ID NO: 134, (c) a 6-phosphofructo-2-kinase comprising the amino acid sequence of SEQ ID NO: 136, (d) a glucose-6-phosphate isomerase comprising the amino acid sequence of SEQ ID NO: 138, (e) a phosphoglycerate mutase comprising the amino acid sequence of SEQ ID NO: 140, (f) a triose-phosphate isomerase comprising the amino acid sequence of SEQ ID NO: 142, (g) a catalytically active variant, fragment or yeast ortholog of any one of (a) to (f), or (h) a combination of any two or more of (a) to (g).

Paragraph [48]. The recombinant yeast cell of paragraph [47], wherein the heterologous gene or combination provides for an increased anaerobic growth rate on xylose, an increased aerobic growth rate on xylose, an increased ethanol production from xylose, or a combination of any two or all thereof.

Paragraph [49]. The recombinant yeast cell of paragraph [48], wherein the anaerobic growth rate is measured according to Example 23, the aerobic growth is measured according to Example 17, and/or the ethanol production is measured according to Example 24.

Paragraph [50]. The recombinant yeast cell of any one of paragraphs [47] to [49], comprising a heterologous gene encoding an enolase comprising the amino acid sequence of SEQ ID NO: 132 or a catalytically active variant, fragment or yeast ortholog thereof.

Paragraph [51]. The recombinant yeast cell of any one of paragraphs [47] to [49], comprising a heterologous gene encoding an a phosphofructokinase beta subunit polypeptide comprising the amino acid sequence of SEQ ID NO: 134 or a catalytically active variant, fragment or yeast ortholog thereof.

Paragraph [52]. The recombinant yeast cell of any one of paragraphs [47] to [49], comprising a heterologous gene encoding a 6-phosphofructo-2-kinase comprising the amino acid sequence of SEQ ID NO: 136 or a catalytically active variant, fragment or yeast ortholog thereof.

Paragraph [53]. The recombinant yeast cell of any one of paragraphs [47] to [49], comprising a heterologous gene encoding a glucose-6-phosphate isomerase comprising the amino acid sequence of SEQ ID NO: 138 or a catalytically active variant, fragment or yeast ortholog thereof.

Paragraph [54]. The recombinant yeast cell of any one of paragraphs [47] to [49], comprising a heterologous gene encoding a phosphoglycerate mutase comprising the amino acid sequence of SEQ ID NO: 140 or a catalytically active variant, fragment or yeast ortholog thereof.

Paragraph [55]. The recombinant yeast cell of any one of paragraphs [47] to [49], comprising a heterologous gene encoding a triosephosphate isomerase comprising the amino acid sequence of SEQ ID NO: 142 or a catalytically active variant, fragment or yeast ortholog thereof.

Paragraph [56]. The recombinant yeast cell of any one of paragraphs [47] to [55], wherein the catalytically active variant or yeast ortholog of has a least 90% sequence identity to the amino acid sequence of SEQ ID NO: 132, 134, 136, 138 140 or 142.

Paragraph [57]. The recombinant yeast cell of any one of paragraphs [47] to [56], wherein the catalytically active variant or yeast ortholog of has a least 95% sequence identity to the amino acid sequence of SEQ ID NO: 132, 134, 136, 138 140 or 142.

Paragraph [58]. The recombinant yeast cell of any one of paragraphs [47] to [57], which comprises a heterologous gene encoding a transaldolase (TAL), a heterologous gene encoding a transketolase (TKL), and a heterologous gene encoding a ribose 5-phosphate ketol-isomerase (RKI), a heterologous gene encoding an XK, and at least one of (a) a heterologous gene encoding a xylose reductase (XR) and an overexpressed gene encoding a xylitol dehydrogenase (XDH), and/or (b) a heterologous gene encoding a xylose isomerase (XI).

Paragraph [59]. The recombinant yeast cell of paragraph [58], wherein the XR is *Pichia stipitis* XR or an NADH-preferring variant thereof, and the XDH is *Pichia stipitis* XDH or a catalytically active variant thereof.

Paragraph [60]. The recombinant yeast cell of paragraph [58] or [59], wherein the XR is *Pichia stipitis* XR comprising one or more amino acid substitutions selected from N272D, K270R and P275Q.

Paragraph [61]. The recombinant yeast cell of any one of paragraphs [58] to [60], wherein the TAL, TKL, RKI and XK are endogenous to the cell.

Paragraph [62]. The recombinant yeast cell of any one of paragraphs [47] to [61], wherein the yeast cell is derived from a *Saccharomyces, Rhodotorula, Schizosaccharomyces, Kluyveromyces, Pichia, Hansenula, Rhodosporidium, Candida, Yarrowia, Lipomyces, Cryptococcus*, or *Dekkera* sp. cell.

Paragraph [63]. The recombinant yeast cell of any one of paragraphs [47] to [62], which is derived from a *Saccharomyces cerevisiae, bayanus* or *carlsbergensis* cell.

Paragraph [64]. The recombinant yeast cell of any one of paragraphs [47] to [63]— which is derived from a *Saccharomyces cerevisiae* cell.

Paragraph [65]. The recombinant yeast cell of any one of paragraphs [47] to [64], wherein each of said gene or genes is operably linked to an inducible, a regulated or a constitutive promoter, and is optionally integrated into the genome of the cell.

Paragraph [66]. The recombinant yeast cell of any one of paragraphs [47] to [65], wherein the gene encoding an enolase, phosphofructokinase beta subunit polypeptide, 6-phosphofructo-2-kinase, glucose-6-phosphate isomerase, phosphoglycerate mutase or triose-phosphate isomerase is operably linked to a strong constitutive promoter endogenous to the cell.

Paragraph [67]. A strain or clone comprising the recombinant yeast cell of any one of paragraphs [47] to [66], Paragraph [68]. A method for producing a fermentation product, comprising (a) contacting the recombinant cell of any one of paragraphs [47] to [66], 0 or the strain or clone of paragraph [67] with a medium comprising a carbon source comprising xylose or arabinose under anaerobic conditions, and (b) isolating the fermentation product from the medium.

Paragraph [69]. The method of paragraph [68], wherein the fermentation product comprises at least one of ethanol, butanol, isobutanol, isopentanol, lactate, isoamylacetate, glycerol, sorbitol, mannitol, xylitol, arabinitol; 3-hydroxybutyrolactone; hydrogen gas; L-ascorbic acid, 2,5-furan dicarboxylic acid, 3-hydroxy propionic acid, aspartic acid, glutaric acid, glutamic acid, itaconic acid, levulinic acid; succinic acid, fumaric acid, malic acid or other 1,4-diacid; a fatty acid, a fatty-acid derived molecule; an isoprenoid, an isoprenoid-derived molecule; and an alkane.

Paragraph [70]. The method of paragraph [68] or [69], wherein the carbon source comprises xylose and the fermentation product comprises ethanol.

Paragraph [71]. A vector comprising genes encoding a polypeptide comprising the amino acid sequence of SEQ ID NO: 132, 134, 136, 138 140 or 142 or a catalytically active variant, fragment or yeast ortholog of any thereof, a XR, a XDH, and a XK; and optionally, regulatory sequences for expressing the genes in a *Saccharomyces* host cell.

Paragraph [72]. A process for producing a recombinant *Saccharomyces* cell, comprising transforming a *Saccharomyces* cell with one or more vectors comprising genes encoding a polypeptide comprising the amino acid sequence of SEQ ID NO: 132, 134, 136, 138 140 or 142 or a catalytically active variant or fragment of any thereof, an XR, an XDH, an XK, and, optionally, regulatory sequences for expressing the genes in a *Saccharomyces* host cell.

Paragraph [73]. A recombinant yeast cell which is capable of fermenting xylose and which comprises a heterologous gene encoding a phosphoglucomutase and/or phosphoribomutase comprising the amino acid sequence of SEQ ID NO: 150 or a catalytically active variant or fragment thereof.

Paragraph [74]. The recombinant yeast cell of paragraph [73], wherein the heterologous gene provides for an increased anaerobic growth rate on xylose, an increased xylose consumption, an increased ethanol production from xylose, or a combination of any two or all thereof.

Paragraph [75]. The recombinant yeast cell of paragraph [74], wherein the anaerobic growth rate is measured according to Example 26, the anaerobic growth is measured according to Example 27, and/or the ethanol production is measured according to Example 27.

Paragraph [76] The recombinant yeast cell of any one of paragraphs [73] to [75], wherein the catalytically active variant has a sequence identity of at least 30%, at least 50%, at least 70%, at least 80%, at least 90% or at least 95% with the amino acid sequence of SEQ ID NO: 150.

Paragraph [77]. The recombinant yeast cell of any one of paragraphs [73] to [76], wherein the phosphoglucomutase and/or phosphoribomutase comprises the amino acid sequence of SEQ ID NO: 150.

Paragraph [78]. The recombinant yeast cell of any one of paragraphs [73] to [77], which comprises heterologous gene encoding a transaldolase (TAL), a heterologous gene encoding a transketolase (TKL), a heterologous gene encoding a ribose 5-phosphate ketol-isomerase (RKI), a heterologous gene encoding a xylulokinase (XK), and at least one of:

(a) a heterologous gene encoding a xylose reductase (XR) and a heterologous gene encoding a xylitol dehydrogenase (XDH), and/or (b) a heterologous gene encoding a xylose isomerase (XI).

Paragraph [79]. The recombinant yeast cell of paragraph [78], wherein the XR is *Pichia stipitis* XR or an NADH-preferring variant thereof, and the XDH is *Pichia stipitis* XDH or a catalytically active variant thereof.

Paragraph [80]. The recombinant yeast cell of paragraph [78] or [79], wherein the XR is *Pichia stipitis* XR comprising one or more amino acid substitutions selected from N272D, K270R and P275Q.

Paragraph [81]. The recombinant yeast cell of any one of paragraphs [78] to [80], wherein the TAL, TKL, RKI and XK coding sequences are endogenous to the cell.

Paragraph [82]. The recombinant yeast cell of any one of paragraphs [73] to [81], wherein the yeast cell is derived from a *Saccharomyces, Rhodotorula, Schizosaccharomyces, Kluyveromyces, Pichia, Hansenula, Rhodosporidium, Candida, Yarrowia, Lipomyces, Cryptococcus*, or *Dekkera* sp. cell.

Paragraph [83]. The recombinant yeast cell of any one of paragraphs [73] to [82], which is derived from a *Saccharomyces cerevisiae, bayanus* or *carlsbergensis* cell.

Paragraph [84]. The recombinant yeast cell of any one of paragraphs [73] to [83], which is derived from a *Saccharomyces cerevisiae* cell.

Paragraph [85]. The recombinant yeast cell of any one of paragraphs [73] to [84], wherein each of said gene or genes is operably linked to an inducible, a regulated or a constitutive promoter, and is optionally integrated into the genome of the cell.

Paragraph [86]. The recombinant yeast cell of any one of paragraphs [73] to [85], wherein the overexpressed gene encoding a phosphoglucomutase and/or phosphoribomutase is operably linked to a strong constitutive promoter endogenous to the cell.

Paragraph [87]. A strain or clone comprising the recombinant yeast cell of any one of paragraphs [73] to [86].

Paragraph [88]. A method for producing a fermentation product, comprising (c) contacting the recombinant cell of any one of paragraphs [73] to [86] or the strain or clone of paragraph [87] with a medium comprising a carbon source comprising xylose or arabinose under anaerobic conditions, and (d) isolating the fermentation product from the medium.

Paragraph [89]. The method of paragraph [88], wherein the fermentation product comprises at least one of ethanol, butanol, isobutanol, isopentanol, lactate, isoamylacetate, glycerol, sorbitol, mannitol, xylitol, arabinitol; 3-hydroxybutyrolactone; hydrogen gas; L-ascorbic acid, 2,5-furan dicarboxylic acid, 3-hydroxy propionic acid, aspartic acid, glutaric acid, glutamic acid, itaconic acid, levulinic acid; succinic acid, fumaric acid, malic acid or other 1,4-diacid; a fatty acid, a fatty-acid derived molecule; an isoprenoid, an isoprenoid-derived molecule; and an alkane.

Paragraph [90]. The method of paragraph [88] or [89], wherein the carbon source comprises xylose and the fermentation product comprises ethanol.

Paragraph [91]. A vector comprising genes encoding a polypeptide comprising the amino acid sequence of SEQ ID NO: 150 or a catalytically active variant, fragment or yeast ortholog thereof, an XR, an XDH, and an XK; and optionally, regulatory sequences for expressing the genes in a *Saccharomyces* host cell.

Paragraph [92]. A process for producing a recombinant *Saccharomyces* cell, comprising transforming a *Saccharomyces* cell with one or more vectors comprising genes encoding a polypeptide comprising the amino acid sequence of SEQ ID NO: 150 or a catalytically active variant or fragment thereof, an XR, an XDH, an XK, and, optionally, regulatory sequences for expressing the genes in a *Saccharomyces* host cell.

The following examples are provided by way of illustration and are not intended to be limiting of the invention.

EXAMPLES

Example 1: Construction of a Genetically Modified *S. cerevisiae* Strain Overexpressing Three of the Genes in the Pentose Phosphate Pathway (TAL1 (Transaldolase), TKL1 (Transketolase) and RKI1 (Ribose 5-Phosphate Ketol Isomerase)

Strains, Media and Genetic Techniques

*Escherichia coli* strain DH5α (Life Technologies, Rockville, Md., USA) was used for subcloning. *E. coli* was grown in LB-medium (Ausubel et al., 1995). Yeast cells from freshly streaked YPD plates (Ausubel et al., 1995) were used for inoculation. Plasmid DNA was prepared with the GeneJET™ Plasmid Miniprep Kit (Fermentas UAB, Vilnius, Lithuania). Agarose gel DNA extraction was made with QIAquick® Gel Extraction Kit (Qiagen GmbH, Hilden, Germany). Primers from MWG-Biotech AG (Ebersberg, Germany) and Pfu DNA Polymerase and dNTP from Fermentas (Vilnius, Lithuania) were used for polymerase chain reactions (PCR). PCR product purification was made with the E.Z.N.A.® Cycle Sequencing Kit (Omega Bio-tek Inc., Doraville, Ga., USA). Sequencing was performed by MWG-Biotech AG (Ebersberg, Germany). Restriction endonucleases, FastAP Thermosensitive Alkaline Phosphatase and T4 DNA Ligase from Fermentas (Vilnius, Lithuania) were used for DNA manipulation. Competent *E. coli* DH5α cells were transformed as described elsewhere (Inoue et al., 1990) and transformed *E. coli* cells were selected on LB plates (Ausubel et al., 1995) containing 100 mg/l ampicillin (IBI Shelton Scientific Inc., Shelton, Conn., USA). *E. coli* strains were grown in LB medium containing 100 mg/l ampicillin for plasmid amplifications. Yeast strains were transformed with the lithium acetate method (Gietz and Schiestl, 2007) and transformed yeast strains were selected on YPD plates with a pH set to 7.5 containing 50 μg/ml zeocin (Invitrogen, Groningen, The Netherlands).

Construction of YlpTAL Containing the *S. cerevisiae* Transaldolase (TAL1) Gene

Plasmid pB3 PGK TAL1 (Johansson and Hahn-Hägerdal, 2002) containing the *S. cerevisiae* transaldolase (TAL1) gene under control of the PGK1 promoter and the GCY1 terminator from *S. cerevisiae* was digested with restriction enzymes XcmI and EheI, and ends of the resulting fragment were made blunt by the use of T4 DNA polymerase (Boehringer Mannheim, Indianapolis, Ind.) and the vector was re-ligated resulting in YlpTAL. Correct orientations and sequences of the inserts were verified by restriction analysis and sequencing.

Construction of YlpTALTKL Containing the *S. cerevisiae* Transaldolase (TAL1) Gene and Transketolase (TKL1) Gene The DNA cassette PGKp-TKL1-GCYt containing the *S. cerevisiae* transketolase (TKL1) gene under control of the PGK1 promoter and the GCY1 terminator from *S. cerevisiae* was PCR amplified having as template plasmid pB3 PGK TKL1 (Johansson and Hahn-Hägerdal, 2002) and using primers FwdTKL and RevTKL identified by

```
                                        (SEQ ID NO: 1)
GGTACCGAGCTCTAACTGATCTATCCAAAACTG
and

                                        (SEQ ID NO: 2)
GGTACCGATCAGCATGCGATCGCTCGACATTTGATATAC,
```

which were including the restriction site KpnI at the ends of the amplified DNA cassette. The PCR product PGKp-TKL1-GCYt was then digested with KpnI restriction enzyme. The resulting purified DNA fragment was inserted into the plasmid YlpTAL, which had also been cleaved with the restriction enzyme KpnI and which had been dephosphorylated. The resulting plasmid was named YlpTALTKL. Correct orientations and sequences of the inserts were verified by restriction analysis and sequencing.

Construction of YlpTTR Containing the *S. cerevisiae* Transaldolase (TAL1) Gene, Transketolase (TKL1) Gene and Ribose 5-Phosphate Ketol Isomerase (RKI1) Gene The DNA cassette PGKp-RKI1-GCYt containing the *S. cerevisiae* ribose 5-phosphate ketol isomerase (RKI1) gene under control of the PGK1 promoter and the GCY1 terminator from *S. cerevisiae* was PCR amplified having as template plasmid pB3 PGK RKI1 (Johansson and Hahn-Hägerdal, 2002) and using primers FwdRKI and RevRKI identified by 5'-CCGCGGGAGCTCTAACTGATCTATCCAAAACTG-3' (SEQ ID NO: 3) and 5'-CCGCGGGATCAGCATGCGATCGCTCGACATTTGATATAC-3' (SEQ ID NO: 4) which were including the restriction site SacII at the ends of the amplified DNA cassette. The PCR product PGKp-RKI1-GCYt was then digested with SacII restriction enzyme. The resulting purified DNA fragment was inserted into the plasmid YlpTALTKL, which also had been cleaved with the restriction enzyme Kpnl and which had been dephosphorylated. The resulting plasmid was named YlpTTR. Correct orientations and sequences of the inserts were verified by restriction analysis and sequencing.

Construction of C5LTe1001 Containing YlpTTR

YlpTTR was cleaved with Spel within the RKI1 gene and transformed into strain C5LTe1000. This resulted in strain C5LTe1001. Strain C5LTe1000 was deposited in accordance with the terms of the Budapest Treaty on 4 Nov. 2014 with DSMZ—Deutsche Sammlung von Mikroorganismen and Zellkulturen GmbH, Inhoffenstr. 7B, 38124 Braunschweig, Germany—under DSMZ accession number DSM 29597.

Example 2: Strains, Media and Genetic Techniques

*Escherichia coli* strain NEB 5-alpha (New England BioLabs, Ipswich, Mass., USA) was used for subcloning. *E. coli* was grown in LB-medium (Ausubel et al., 1995). Yeast cells from freshly streaked YPD plates (Ausubel et al., 1995) were used for inoculation. Plasmid DNA was prepared with the GeneJET™ Plasmid Miniprep Kit (Fermentas UAB, Vilnius, Lithuania). Agarose gel DNA extraction was made with QIAquick® Gel Extraction Kit (Qiagen GmbH, Hilden, Germany). Primers from Eurofins MWG Operon (Ebersberg, Germany) and Phusion Hot Start II High-Fidelity DNA Polymerase and dNTP from Fermentas (Vilnius, Lithuania) were used for polymerase chain reactions (PCR). PCR product purification was made with the E.Z.N.A.® Cycle Sequencing Kit (Omega Bio-tek Inc., Doraville, Ga., USA). Sequencing was performed by Eurofins MWG Operon (Ebersberg, Germany). Restriction endonucleases from Fermentas (Vilnius, Lithuania) were used for DNA manipulation. Competent *E. coli* cells were transformed as described elsewhere (Inoue et al., 1990) and transformed *E. coli* cells were selected on LB plates (Ausubel et al., 1995) containing 100 mg/l ampicillin (IBI Shelton Scientific Inc., Shelton, Conn., USA). *E. coli* strains were grown in LB medium containing 100 mg/l ampicillin for plasmid amplifications. Yeast strains were transformed with the lithium acetate method (Gietz and Schiestl, 2007) and transformed yeast strains were selected on Yeast Nitrogen Base plates (YNB) (6.7 g/l Difco Yeast Nitrogen Base without amino acids; Becton Dickinson and Company, Sparks, Md., USA) supplemented with 40 g/l xylose and buffered at pH 5.5 with 10.21 g/l potassium hydrogen phthalate.

Example 3: Construction of an *S. cerevisiae* Strain Overexpressing Three of the Genes in the Pentose Phosphate Pathway and Expressing a *Spathaspora passalidarum* Xylulose Kinase Gene, a *Scheffersomyces stipitis* Xylitol Dehydrogenase (XDH) Gene and a Mutated *Scheffersomyces stipitis* Xylose Reductase (XR(N272D)) Gene Strains, Media and Genetic Techniques The strains, media and genetic techniques described in Example 2 were used.

Construction of Synthetic Xylulose Kinase Gene Encoding *Spathaspora passalidarum* Xylulose Kinase Based on NCBI Accession Code XP 007373112 Under Control of the TPI1 Promoter and the PGK1 Terminator from *S. cerevisiae*

The entire *Spathaspora passalidarum* xylulose kinase gene (XKsp) was synthesized and assembled by Eurofins MWG Operon (Ebersberg, Germany). Codon usage in the sequence was optimised based on the yeast codon usage table from the Kazusa codon usage database. The TPI1 promoter from *S. cerevisiae* and the PGK1 terminator from *S. cerevisiae* were also included in the synthetic construct; the TPI1 promoter before the ATG-start codon and the PGK1 terminator after the stop-codon. The nucleotide sequence of TPI1 promoter, XKsp and PGK1 terminator is identified as SEQ ID NO: 5, showing the synthesized DNA sequence. The corresponding amino acid sequence of the coding region of XKsp is identified in SEQ ID NO: 6. The harboring plasmid was named pC5e0022.

Construction of pC5e0049 Containing a *Spathaspora passalidarum* Xylulose Kinase Gene, a *Scheffersomyces stipitis* Xylitol Dehydrogenase (XDH) Gene and a Mutated *Scheffersomyces stipitis* Xylose Reductase (XR(N272D)) Gene The DNA cassette TPI1p-XKsp-PGK1t was PCR amplified having as template plasmid pC5e0022 and using the following primers.

```
TPI1p_fwd (SEQ ID NO: 7):
5'-TCTTC CACAC CTGCA GTATA TCTAG GAACC CATCA G-3'

reverse-PGK1t (SEQ ID NO: 8):
5'-ATCAG TTAGA CTGCA GGAAC ATAGA AATAT CGAAT

GGGAA-3'
```

The resulting purified DNA fragment was inserted into plasmid YlpDR7 (Runquist et al. 2010), containing a *Scheffersomyces stipitis* xylitol dehydrogenase (XDH) gene under control of the PGK1 promoter and the PGK1 terminator from *S. cerevisiae* and a mutated *Scheffersomyces stipitis* xylose reductase (XR(N272D)) gene under control of the TDH3 promoter and the ADH1 terminator from *S. cerevisiae*. YlpDR7 which had been cleaved with restriction enzyme Pstl and the DNA fragment was inserted by In-Fusion cloning (Clontech, California, Calif., USA). The resulting plasmid was named pC5e0049. Correct orientations and sequences of the inserts were verified by restriction analysis and sequencing.

Construction of C5LTe1042 Containing YlpTTR and pC5e0049

The Plasmid pC5e0049 was digested with restriction enzyme EcoRV within the URA3 gene and it was thereafter transformed into strain C5LTe1001. This resulted in strain C5LTe1042.

Example 4: Construction of an *S. cerevisiae* Strain Overexpressing Three of the Genes in the Pentose Phosphate Pathway and a Xylulose Kinase (XK) Gene and Expressing a *Scheffersomyces stipitis* Xylitol Dehydrogenase (XDH) Gene and a Mutated *Scheffersomyces stipitis* Xylose Reductase (XR(N272D)) Gene Strains, Media and Genetic Techniques The strains, media and genetic techniques described in Example 2 were used.

Construction of pC5e0024 Containing a *S. cerevisiae* Xylulose Kinase Gene, a *Scheffersomyces Stipitis* Xylitol Dehydrogenase (XDH) Gene and a Mutated *Scheffersomyces stipitis* Xylose Reductase (XR(N272D)) Gene The TPI1 promoter from *S. cerevisiae* (TPI1p) was PCR amplified having as template plasmid pC5e0022 and using the following primers.

```
TPI1p_fwd (SEQ ID NO: 9):
5'-TCTTC CACAC CTGCA GTATA TCTAG GAACC CATCA G-3'

R_TPI1p (SEQ ID NO: 10):
5'-CTGTC TCTGA ATTAC TGAAC ACAAC ATTTT TAGTT TATGT

ATGTG TTT-3'
```

The PGK1 terminator from *S. cerevisiae* (PGK1t) was PCR amplified having as template plasmid pC5e0022 and using the following primers.

```
fwdS_PGK1t (SEQ ID NO: 11):
5'-GCGAACTGGAAAAGACTCTCATCTAAAGATCTCCCATGTCTCTACTG

G-3'

reverse_PGK1t (SEQ ID NO: 12):
5'-ATCAGTTAGACTGCAGGAACATAGAAATATCGAATGGGAA-3'
```

The *S. cerevisiae* xylulose kinase gene (Xkcere; SEQ ID NO: 31), encoding *S. cerevisiae* XK (SEQ ID NO: 32) was PCR amplified having as template plasmid YlpXK (Lönn et al., 2003) and using the following primers

```
XKcere_fwd (SEQ ID NO: 13):
5'-AAACACATACATAAACTAAAAATGTTGTGTTCAGTAATTCAGAGACA

G-3'

XKcere_rev (SEQ ID NO: 14):
5'-CCAGTAGAGACATGGGAGATCTTTAGATGAGAGTCTTTTCCAGTTCG

C-3'
```

The DNA cassette TPI1p-XKcere-PGK1t was PCR amplified by overlap extension PCR having as template the three purified DNA fragments TPI1p, PGK1t and XKcere using the following primers

```
TPI1p_fwd (SEQ ID NO: 15):
5'-TCTTCCACACCTGCAGTATATCTAGGAACCCATCAG-3'

reverse_PGK1t (SEQ ID NO: 16):
5'-ATCAGTTAGACTGCAGGAACATAGAAATATCGAATGGGAA-3'
```

The resulting purified DNA fragment was inserted into the plasmid YlpDR7 (Runquist et al. 2010), which had been cleaved with restriction enzyme Pstl. The DNA fragment was inserted by In-Fusion cloning (Clontech, California, Calif., USA). The resulting plasmid was named pC5e0024. Correct orientations and sequences of the inserts were verified by restriction analysis and sequencing.

Construction of C5LTe1035 Containing YlpTTR and pC5e0024

Plasmid pC5e0024 was cleaved with restriction enzyme EcoRV within the URA3 gene and it was thereafter transformed into strain C5LTe1001. This resulted in strain C5LTe1035.

Example 5: Construction of an *S. cerevisiae* Strain Overexpressing Three of the Genes in the Pentose Phosphate Pathway and Expressing an *Escherichia coli* Xylulose Kinase (XK) Gene, a *Scheffersomyces stipitis* Xylitol Dehydrogenase (XDH) Gene and a Mutated *Scheffersomyces stipitis* Xylose Reductase (XR(N272D)) Gene Strains, Media and Genetic Techniques The strains, media and genetic techniques described in Example 2 were used.

Construction of Synthetic Xylulose Kinase Gene Encoding *Escherichia coli* Xylulose Kinase Based on NCBI Accession Code YP_001460359 Under Control of the TPI1 Promoter and the PGK1 Terminator from *S. cerevisiae*

The entire *E. coli* xylulose kinase gene (XKcoli) was synthesized and assembled by Eurofins MWG Operon (Ebersberg, Germany). Codon usage in the sequence was optimised based on the yeast codon usage table from the Kazusa codon usage database. The TPI1 promoter from *S. cerevisiae* and the PGK1 terminator from *S. cerevisiae* were also included in the synthetic construct; the TPI1 promoter before the ATG-start codon and the PGK1 terminator after the stop-codon. The nucleotide sequence of TPI1 promoter, XKcoli and PGK1 terminator is identified as SEQ ID NO: 17, showing the synthesized DNA sequence. The corresponding amino acid sequence of the coding region of XKcoli is identified in SEQ ID NO: 18. The harboring plasmid was named pC5e0012.

Construction of pC5e0046 Containing a *E. coli* Xylulose Kinase Gene, a *Scheffersomyces stipitis* Xylitol Dehydrogenase (XDH) Gene and a Mutated *Scheffersomyces stipitis* Xylose Reductase (XR(N272D)) Gene The DNA cassette TPI1p-XKcoli-PGK1t was PCR amplified having as template plasmid pC5e0012 and using the following primers.

```
TPI1p_fwd (SEQ ID NO: 19):
5'-TCTTCCACACCTGCAGTATATCTAGGAACCCATCAG-3'

reverse-PGK1t (SEQ ID NO: 20):
5'-ATCAGTTAGACTGCAGGAACATAGAAATATCGAATGGGAA-3'.
```

The resulting purified DNA fragment was inserted into plasmid YlpDR7 (Runquist et al. 2010), containing a *Scheffersomyces stipitis* xylitol dehydrogenase (XDH) gene under control of the PGK1 promoter and the PGK1 terminator from *S. cerevisiae* and a mutated *Scheffersomyces stipitis* xylose reductase (XR(N272D)) gene under control of the TDH3 promoter and the ADH1 terminator from *S. cerevisiae*. YlpDR7 which had been cleaved with restriction enzyme Pstl and the DNA fragment was inserted by In-Fusion cloning (Clontech, California, Calif., USA). The resulting plasmid was named pC5e0046. Correct orientations and sequences of the inserts were verified by restriction analysis and sequencing.

Construction of C5LTe1040 Containing YlpTTR and pC5e0046

Plasmid pC5e0046 was digested with restriction enzyme EcoRV within the URA3 gene and it was thereafter transformed into strain C5LTe1001. This resulted in strain C5LTe1040.

Example 6: Construction of an *S. cerevisiae* Strain Overexpressing Three of the Genes in the Pentose Phosphate Pathway and Expressing a *Kluyveromyces marxianus* Xylulose Kinase (XK) Gene, a *Scheffersomyces stipitis* Xylitol Dehydrogenase (XDH) Gene and a Mutated *Scheffersomyces stipitis* Xylose Reductase (XR(N272D)) Gene Strains, Media and Genetic Techniques The strains, media and genetic techniques described in Example 2 were used.

Construction of Synthetic Xylulose Kinase Gene Encoding *Kluyveromyces marxianus* Xylulose Kinase Based on NCBI Accession Code ADW23548

The entire *Kluyveromyces marxianus* xylulose kinase gene (XKmarx) was synthesized and assembled by Eurofins MWG Operon (Ebersberg, Germany). Codon usage in the sequence was optimised based on the yeast codon usage table from the Kazusa codon usage database. The nucleotide sequence of XKmarx is identified as SEQ ID NO: 21, showing the synthesized DNA sequence. The corresponding amino acid sequence of the coding region of XKmarx is identified in SEQ ID NO: 22. The harboring plasmid was named pC5e0043.

Construction of pC5e0051 Containing a *Kluyveromyces marxianus* Xylulose Kinase Gene, a *Scheffersomyces stipitis* Xylitol Dehydrogenase (XDH) Gene and a Mutated *Scheffersomyces stipitis* Xylose Reductase (XR(N272D)) Gene The TPI1 promoter from *S. cerevisiae* (TPI1p) was PCR amplified having as template plasmid pC5e0022 and using the following primers.

```
TPI1p_fwd (SEQ ID NO: 23):
5'-TCTTCCACACCTGCAGTATATCTAGGAACCCATCAG-3'

Rev_TPI1p (SEQ ID NO: 24):
5'-GCCTAAGTAATATGGAGTCGACATTTTTAGTTTATGTATGTGTTT-

3'.
```

The PGK1 terminator from *S. cerevisiae* (PGK1t) was PCR amplified having as template plasmid pC5e0022 and using the following primers.

```
PGK1t_forS (SEQ ID NO: 25):
5'-CTTTAGCACAATCTCAGGGTCAATAAAGATCTCCCATGTCTCTACTG

G-3'

reverse_PGK1t (SEQ ID NO: 26):
5'-ATCAGTTAGACTGCAGGAACATAGAAATATCGAATGGGAA-3'
```

The *Kluyveromyces marxianus* kinase gene (XKmarx) was PCR amplified having as template plasmid pC5e0043 and using the following primers

```
XKmarx_fwd (SEQ ID NO: 27):
5'-AAACACATACATAAACTAAAAATGTCGACTCCATATTACTTAGGC-

3'

XKmarx_rev (SEQ ID NO: 28):
5'-CCAGTAGAGACATGGGAGATCTTTATTGACCCTGAGATTGTGCTAAA

G-3'
```

The DNA cassette TPI1p-XKmarx-PGK1t was PCR amplified by overlap extension PCR having as template the three purified DNA fragments TPI1p, PGK1t and XKmarx using the following primers:

```
TPI1p_fwd (SEQ ID NO: 29):
5'-TCTTCCACACCTGCAGTATATCTAGGAACCCATCAG-3'

reverse_PGK1t (SEQ ID NO: 30):
5'-ATCAGTTAGACTGCAGGAACATAGAAATATCGAATGGGAA-3'
```

The resulting purified DNA fragment was inserted into the plasmid YlpDR7 (Runquist et al. 2010), which had been cleaved with restriction enzyme PstI. The DNA fragment was inserted by In-Fusion cloning (Clontech, California, Calif., USA). The resulting plasmid was named pC5e0051. Correct orientations and sequences of the inserts were verified by restriction analysis and sequencing.

Construction of C5LTe1043 Containing YlpTTR and pC5e0051

Plasmid pC5e0051 was digested with restriction enzyme EcoRV within the URA3 gene and it was thereafter transformed into strain C5LTe1001. This resulted in strain C5LTe1043.

Example 7: Enzyme Activity Assays

Cell extracts for activity assays were prepared from exponentially growing aerobic batch cultures. Cells were collected by centrifugation, washed with sterile water, resuspended in an appropriate amount of Y-PER reagent (Pierce; Rockford, Ill., USA), and processed according to the instructions. Protein concentrations were determined with the Bradford Protein Assay (Pierce, Rockford, Ill., USA) against a bovine serum albumin standard. Xylulose kinase (XK) and xylitol dehydrogenase (XDH) were measured as described by Shamanna and Sanderson (1979). XK activity was determined in two steps. First, the XDH activity was determined in the absence of ATP, and then the sum of the XK and XDH activities in the presence of ATP was determined, the XK activity being the difference. All enzyme activity measurements were performed at 30° C. Specific activities are expressed as units per milligram of protein. One unit of enzyme activity is defined as 1 μmol of substrate converted per minute.

As shown in Table 5, strains C5LTe1042, C5LTe1048 and C5LT1208 had higher XK activity than their corresponding control strains. All strains with a heterologous XK gene had higher XK activity when compared to the wild-type strain C5LTe1000.

TABLE 5

XK activities in constructed strains.

| Strain | XK activity |
|---|---|
| C5LTe1000 | 0.11 ± 0.00 |
| C5LTe1035 | 1.65 ± 0.28 |
| C5LTe1042 | 5.21 ± 0.37 |
| C5LTe1036 | 0.84 ± 0.20 |
| C5LTe1048 | 4.31 ± 0.06 |
| C5LTe1204 | 0.92 ± 0.27 |
| C5LTe1208 | 3.67 ± 0.19 |

Example 8: Aerobic Growth on Xylose

Cells were grown on YPD medium (Yeast extract, Peptone and 20 g/l glucose) overnight, and inoculated into mineral medium with xylose as the sole carbon source (13.4 g/l Yeast Nitrogen Base and 50 g/l xylose, buffered with 10.2 g/l potassium hydrogen phthalate to pH 5.5). Starting OD at 620 nm was around 0.1. Growth was measured by increase in OD 620 nm. Maximum specific growth rate was calculated from time points 8 to 30 hours, and they were 0.16 h-1 for C5LTe1035 and 0.19 h-1 for C5LTe1042. See FIG. 1, which shows curves for the aerobic growth on xylose for C5LTe1035 and C5LTe1042.

In conclusion, strains C5LTe1042, C5LTe1048 and C5LT1208 grew more than their corresponding control strains.

Example 9: Anaerobic Growth on Xylose

Yeast strains were analysed for anaerobic growth on xylose in 96-well microplate yeast cultures. Prior to experiments, yeast was grown in semi-aerobic precultures in YNB medium with 50 g/l xylose, in microplates, overnight. For measurement of anaerobic growth, cells were inoculated in 200 μl of the same medium where solution of ergosterol and Tween80 had been added at final concentration of 0.03 and 1.2 g/l, respectively. 50 μl mineral oil was added on top of each well to keep culture anaerobic. 20 μl of pre-cultured cells were added. The growth was followed in Multiskan FC (Thermo Scientific) at 30° C. and growth was measured as increase of OD (620 nm).

Figure 2:
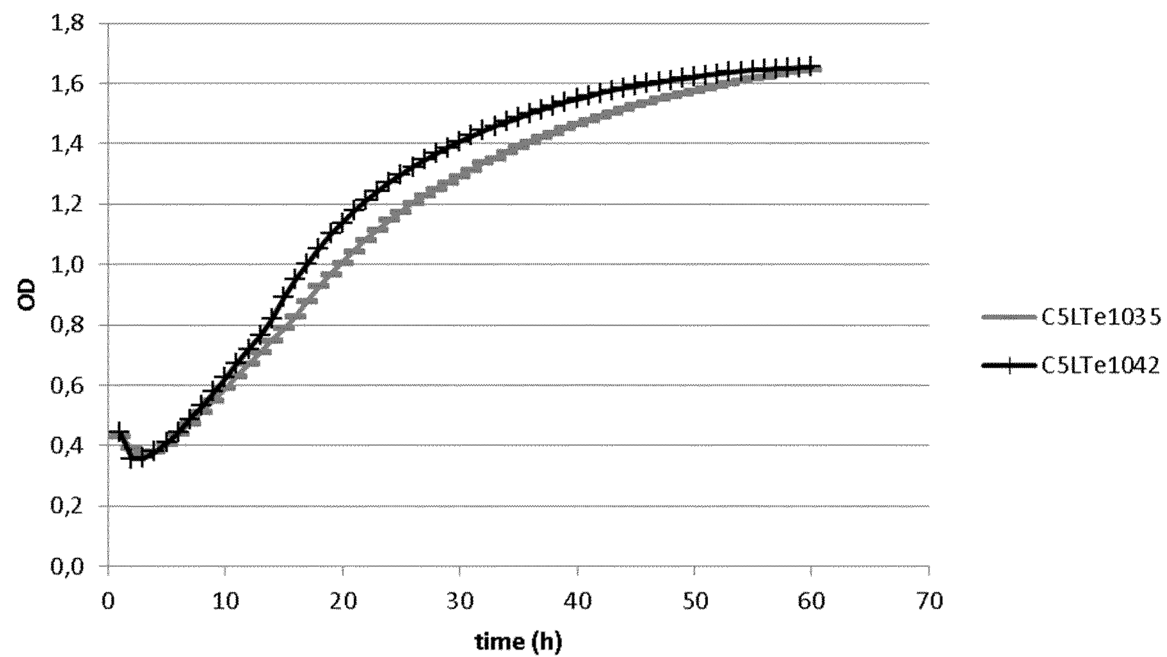
FIG. 2: Curves over anaerobic growth of strain C5LTe1042 ("+") compared with control strain C5LTe1035 ("−").
Figure 3:
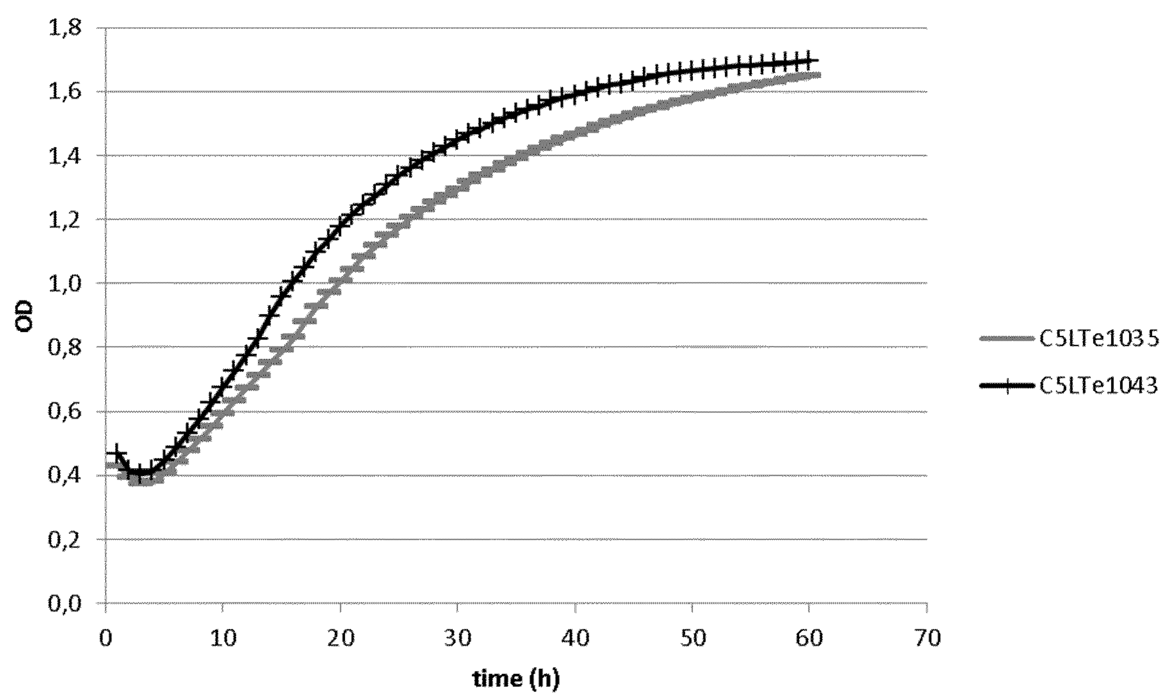
FIG. 3: Curves over anaerobic growth of strain C5LTe1043 ("+") compared with control strain C5LTe1035 ("−").
Figure 4:
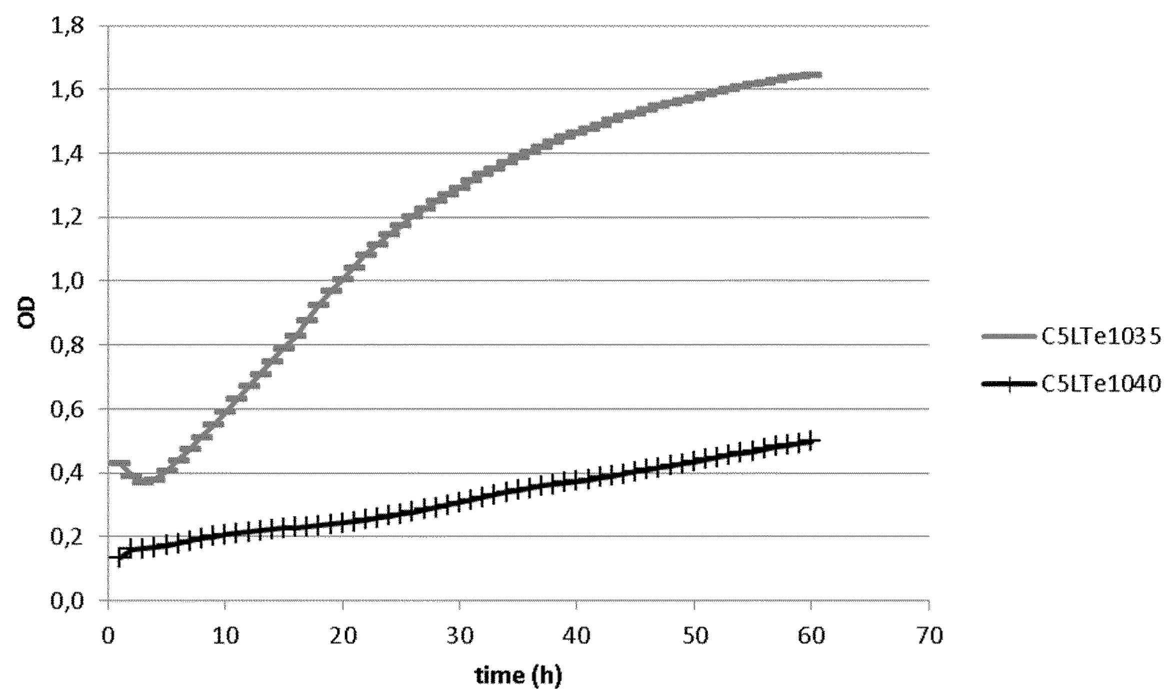
FIG. 4: Curves over anaerobic growth of strain C5LTe1040 ("+") compared with control strain C5LTe1035 ("−").

In conclusion, strains with *K. marxianus* XK or *S. passalidarium* XK grow faster and more under anaerobic conditions than the control strain with *S. cerevisiae* XK. See FIG. 2, which shows curves over anaerobic growth of C5LTe1042 compared with control strain C5LTe1035, FIG. 3, which shows curves over anaerobic growth of C5LTe1043 compared with control strain C5LTe1035, and FIG. 4, which shows curves over anaerobic growth of C5LTe1040 compared with control strain C5LTe1035.

Example 10: Anaerobic Fermentation on Xylose

Cells were pre-grown on mineral medium with glucose as a carbon source (YNB 6.7 g/l and 20 g/l glucose). Cells were then inoculated in fermenters (Applikon) at starting biomass concentration of about 0.15 g/l cell dry weight. Mixing was set at 200 rpm and the gas outlet was closed by a waterlock. Fermentation medium consisted of YNB (6.7 g/l) with 50 g/l xylose and 20 g/l glucose, supplemented with Tween80 (1.2 g/l) and ergosterol (0.03 g/l). The pH was controlled at 5.5 with KOH.

Figure 5:
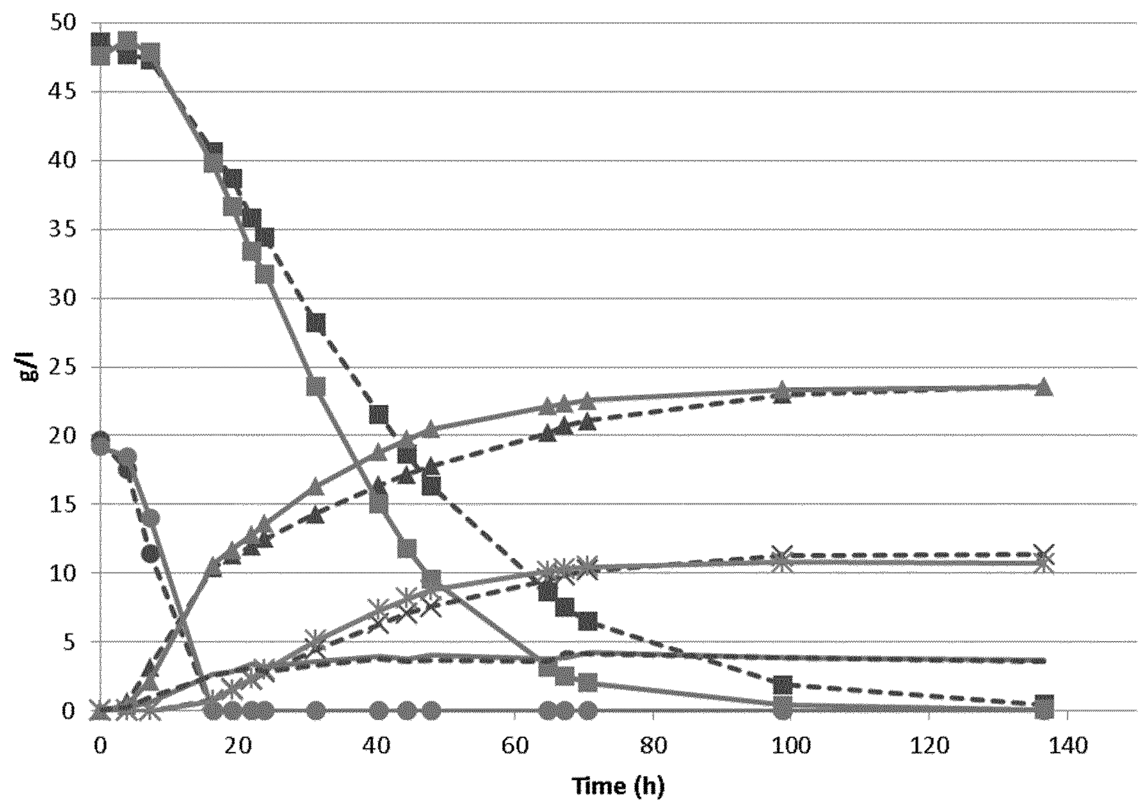
FIG. 5: Graph showing xylose fermentation by strains C5LTe1035 (dashed line) and C5LTe1042 (solid line). Glucose: circles, Xylose: squares, Xylitol: stars, Biomass: line.
Figure 6:
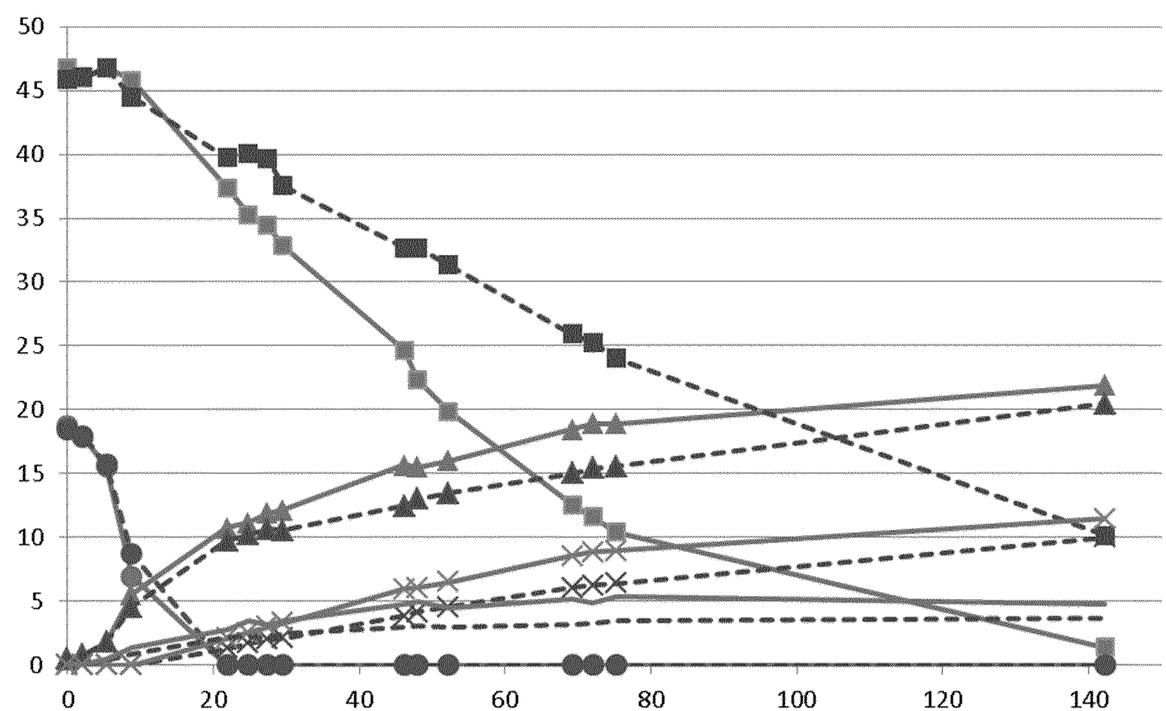
FIG. 6: Graph showing xylose fermentation by strains C5LTe1036 (dashed line) and C5LTe1048 (solid line). Glucose: circles, Xylose: squares, Xylitol: stars, Biomass: line.
Figure 7:
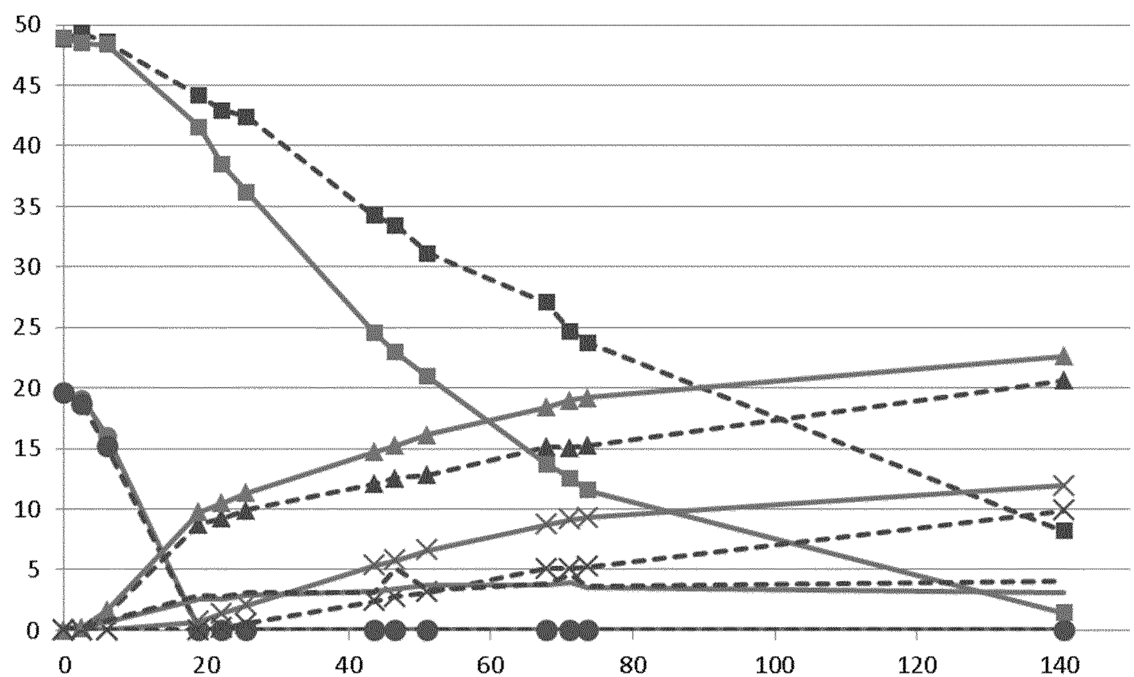
FIG. 7: Graph showing xylose fermentation by 5 strains C5LTe1204 (dashed line) and C5LTe1208 (solid line). Glucose: circles, Xylose: squares, Xylitol: stars, Biomass: line.

Concentrations of glucose, xylose, ethanol, glycerol, and xylitol were determined by high performance liquid chromatography (Waters, Milford, Mass., USA). The compounds were separated with a Shodex SUGAR SP0810 Pb2+ copolymer-based column (Showa Denko America, NY, USA) preceded by a Micro-Guard Carbo-C guard column (Bio-Rad, Hercules, Calif., USA). Separation was performed at 80° C., with H2O at a flow rate of 0.6 ml min-1 as mobile phase. Compounds were quantified by refractive index detection (Waters). A seven-point calibration curve was made for each compound to calculate concentrations. See FIG. 5, which shows xylose fermentation by strains C5LTe1035 (dashed line) and C5LTe1042 (solid line). Glucose: circles, Xylose: squares, Xylitol: stars, Biomass: line. See also FIG. 6, which shows xylose fermentation by strains C5LTe1036 (dashed line) and C5LTe1048 (solid line). Glucose: circles, Xylose: squares, Xylitol: stars, Biomass: line. And, see also FIG. 7, which shows xylose fermentation by strains C5LTe1204 (dashed line) and C5LTe1208 (solid line). Glucose: circles, Xylose: squares, Xylitol: stars, Biomass: line.

TABLE 6

Figure 8:
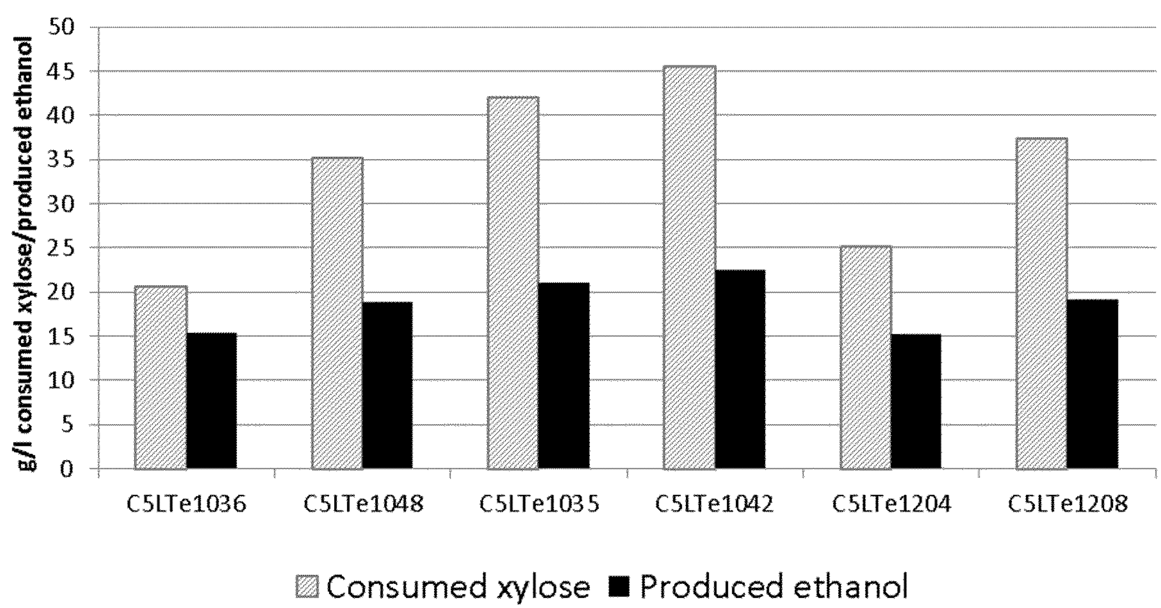
FIG. 8: Graph showing a summary of xylose consumption and ethanol production in anaerobic xylose fermentation of 50 g/l xylose and 20 g/l glucose in mineral medium within 72 hours of fermentation.

Summary of xylose consumption and ethanol production in anaerobic xylose fermentation of 50 g/l xylose and 20 g/l glucose in mineral medium within 72 hours of fermentation. See also a graphic depiction of this data in FIG. 8.

| Strain | Consumed xylose (g/L) | Produced ethanol (g/L) | Xylitol yield (g/g xylose consumed) | Biomass yield (g/g total sugar consumed) |
|---|---|---|---|---|
| C5LTe1036 | 21 | 15 | 0.30 | 0.08 |
| C5LTe1048 | 35 | 19 | 0.25 | 0.09 |
| C5LTe1035 | 42 | 21 | 0.24 | 0.07 |
| C5LTe1042 | 46 | 23 | 0.14 | 0.06 |
| C5LTe1204 | 25 | 15 | 0.21 | 0.10 |
| C5LTe1208 | 37 | 19 | 0.25 | 0.07 |

In conclusion, these data show that strains C5LTe1042, C5LTe1048 and C5LT1208 carrying *S. passalidarium* XK consumed more xylose and produced more ethanol than their corresponding control strains C5LTe1035, C5LTe1036 and C5LT1204, respectively.

Example 11: Construction of an *S. cerevisiae* Strain Overexpressing Three of the Genes in the Pentose Phosphate Pathway and a Xylulose Kinase (XK) Gene and Expressing a *Scheffersomyces stipitis* Xylitol Dehydrogenase (XDH) Gene and a Mutated *Scheffersomyces stipitis* Xylose Reductase (XR(N272D)) Gene Strains, Media and Genetic Techniques Yeast cells from freshly streaked YPD plates (Ausubel et al., 1995) were used for inoculation. Plasmid DNA was prepared with the GeneJET™ Plasmid Miniprep Kit (Fermentas UAB, Vilnius, Lithuania). Agarose gel DNA extraction was made with QIAquick® Gel Extraction Kit (Qiagen GmbH, Hilden, Germany). Primers from Eurofins MWG Operon (Ebersberg, Germany) and Phusion Hot Start II High-Fidelity DNA Polymerase and dNTP from Fermentas (Vilnius, Lithuania) were used for polymerase chain reactions (PCR). PCR product purification was made with the E.Z.N.A.® Cycle Sequencing Kit (Omega Bio-tek Inc., Doraville, Ga., USA). Sequencing was performed by Eurofins MWG Operon (Ebersberg, Germany). Restriction endonucleases from Fermentas (Vilnius, Lithuania) were used for DNA manipulation. Competent *E. coli* cells were transformed as described elsewhere (Inoue et al., 1990) and transformed *E. coli* cells were selected on LB plates (Ausubel et al., 1995) containing 100 mg/l ampicillin (IBI Shelton Scientific Inc., Shelton, Conn., USA). *E. coli* strains were grown in LB medium containing 100 mg/l ampicillin for plasmid amplifications. Yeast strains were transformed with the lithium acetate method (Gietz et al., 2007) and transformed yeast strains were selected on Yeast Nitrogen Base plates (YNB) (6.7 g/l Difco Yeast Nitrogen Base without amino acids; Becton Dickinson and Company, Sparks, Md., USA) supplemented with 40 g/l xylose and buffered at pH 5.5 with 10.21 g/l potassium hydrogen phthalate.

Construction of C5LTe1201 Containing YlpTTR

YlpTTR was cleaved with SpeI within the RKI1 gene and transformed into strain TMB 3000, a robust strain of *Saccharomyces cerevisiae* (Linden et al., 1992). This resulted in strain\C5LTe1201.

Construction of C5LTe1202 Containing YlpTTR and pC5e0024

Plasmid pC5e0024 was cleaved with restriction enzyme EcoRV within the URA3 gene and it was thereafter transformed into strain C5LTe1201. This resulted in strain C5LTe1202.

Example 12: Preparation of Plasmid pC50042 and Transformant C5LTe1212

Generation of Fragments

YME2-PGK1t was synthesized and assembled by Eurofins MWG Operon (Ebersberg, Germany) and that the harboring plasmid was named pEX-A1-YME2. The fragment YME2-PGK1t was generated by PCR using the plasmid pEX-A1-YME2 as template and the following primers (Eurofins MWG Operon):

```
                                   (SEQ ID NO: 45)
5'-GATCCCCGGGCTGCAATGTTGCCCATTTCTGGACCTT-3'

                                   (SEQ ID NO: 46)
5'-CGCTGCAGGTCGACGTGTTACATGCGTACACGCGTCT-3'
```

The vector pUG6-HXT7'p was generated by PCR using the plasmid pUG6-HXT-PGM2 (WO2010/059095 A1) as template and the following primers (Eurofins MWG Operon):

```
                                   (SEQ ID NO: 47)
5'-CGTCGACCTGCAGCGTAC-3'

                                   (SEQ ID NO: 48)
5'-TGCAGCCCGGGGATCCTTTTT-3'
```

The three PCR products were purified using QIAquick Gel Extraction Kit (Qiagen, Venlo, Netherlands) and DNA concentration was determined.

SEQ ID NO: 49 shows the nucleic acid sequence for codon-optimized YME2 tolerance gene, whereas SEQ ID NO: 50 shows the encoded amino acid sequence.

In-Fusion Cloning and *E. coli* Transformation

Fragment YME2-PGK1t and vector pUG6-HXT7'p were introduced into NEB5α *E. coli* competent cells (New England Biolabs, Ipswich Mass., USA) using In-Fusion HD Cloning Kit (Clontech, Mountain View Calif., USA) following the manufacturer instructions procedure. Transformants were selected on LB agar plates containing 100 μg/mL ampicillin and incubated overnight.

Four colonies were randomly selected and growth overnight on LB containing 100 μg/mL ampicillin. Plasmid DNA was prepared using the GeneJET Plasmid MiniPrep Kit (Thermo Scientific, Walthman Mass., USA) by following the manufacturer instructions and concentration was determined.

Plasmid DNA was digested with restriction enzymes XhoI and SmaI (Thermo Scientific) by following the manufacturer instructions. All the evaluated clones containing the YME2-plasmid displayed the expected size fragments (1904 and 3105 bp) and one of them was chosen to be sequenced (Eurofins MWG Operon) using the following primers:

5'-CCTGCGTGTTCTTCTGAGGTTC-3' (SEQ ID NO: 21)

5'-ATATTGTCGTTAGAACGCGG-3' (SEQ ID NO: 22)

The obtained sequence was as predicted when using in silico cloning tools and the plasmid was named pC5e0042.

Genomic Integration of Linearized Plasmid pC50042 into C5LTe1202

5 μg of plasmid was linearized with BmrI (New England Biolabs) following the manufacturer instructions procedure and kept on ice until used in the transformation system.

Strain C5LTe1202 was transformed using a lithium acetate-based method (Gietz and Schiestl, 2007) and 20 μL of linearized pC50042 were used in the transformation system. YPD agar plates supplemented with 20 g/L glucose and 500 mg/L geneticin were incubated aerobically at 30° C. and transformant C5LTe1212 was selected after 2 days.

Example 13: Toxicity of Formic Acid on Yeast Growing on Xylose

The inhibitory effect of acetic and formic acids on cells growing on xylose was initially demonstrated with strain C5LTe1202.

Figure 9A:
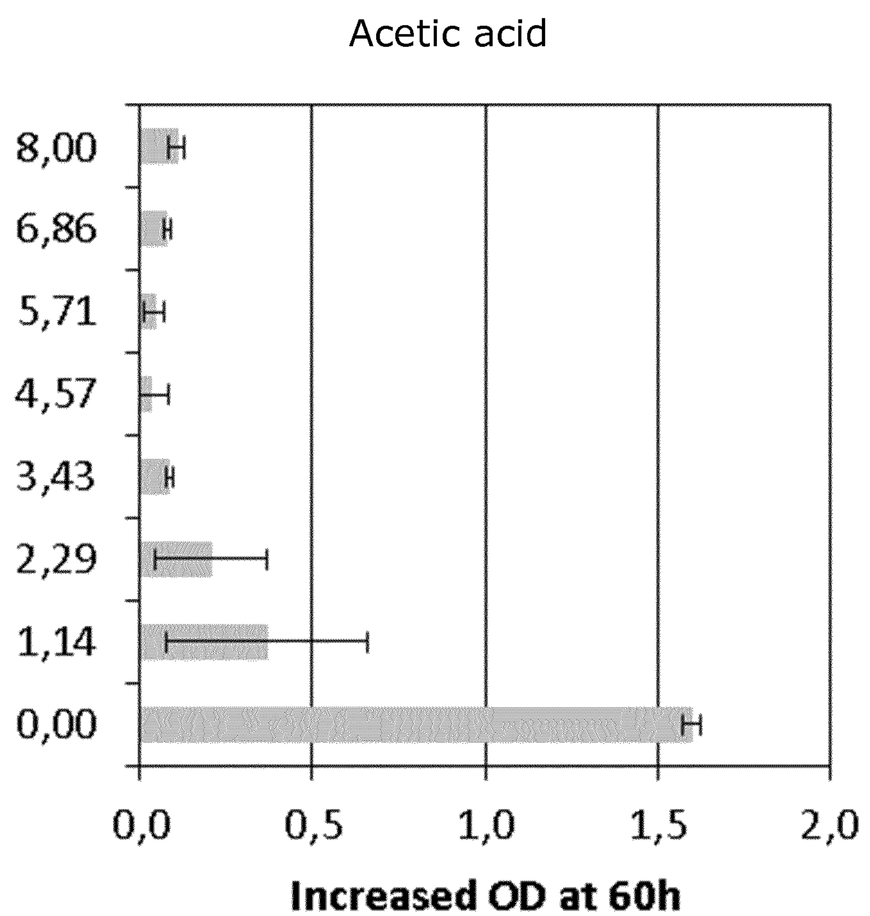
FIG. 9: Graph showing change in OD (620 nm) in microplate experiments of cells growing on xylose in the presence of various concentrations of acetic (A) and formic (B) acids (g/g, vertical axis).
Figure 9B:
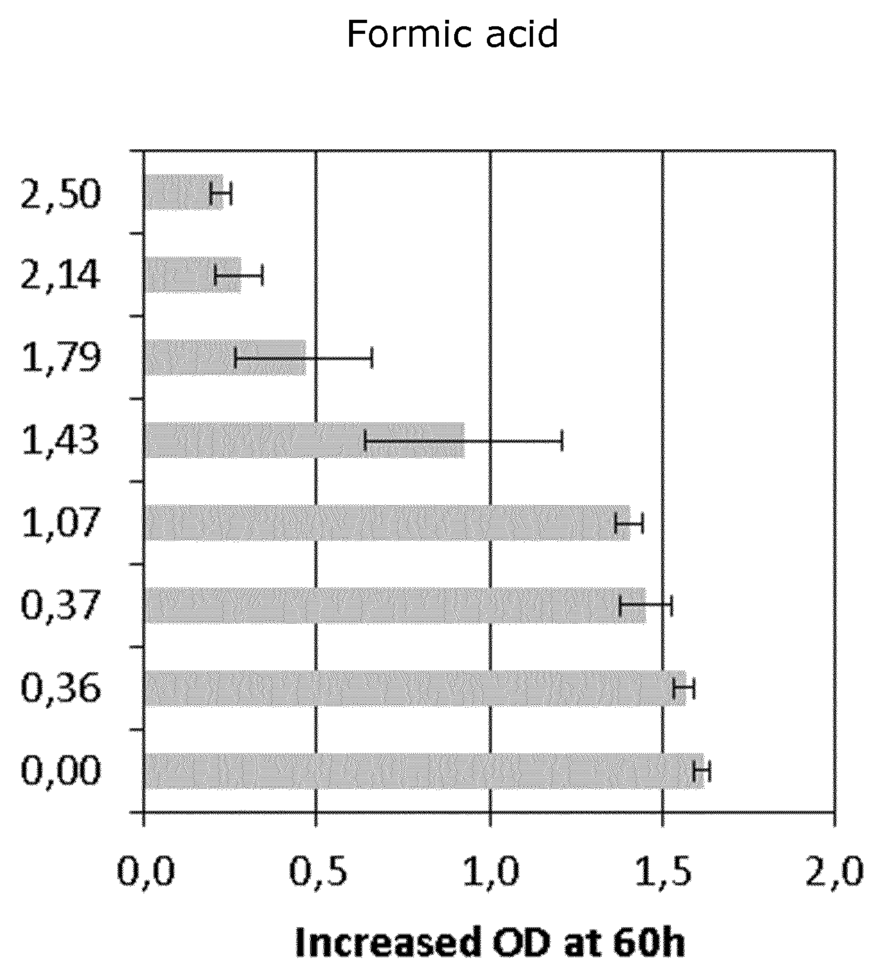

Mineral medium supplemented with 110 g/L of xylose, 50 mM potassium phthalate buffer and containing the concentrations (in g/L) of single inhibitors indicated in FIG. 9. Anaerobic growth was followed in Multiskan FC (Thermo Scientific) at 30° C. and growth was measured as increase of OD (620 nm). The increment of OD after 60 hours of cultivation was chosen to estimate the tolerance to single lignocellulosic inhibitors, since no exponential growth can be observed when using initial high concentration of xylose.

Example 14: Fermentation in the Presence of Acetic Acid

Cells aerobically grown overnight on YNB medium supplemented with 20 g/L glucose were used to inoculate a serum flask containing 30 mL of YNB medium supplemented with glucose (20 g/L) and xylose (50 g/L) as carbon source and acetic acid (8 g/L) at initial concentration of 1 g cell dry weight/L.

Concentrations of glucose, xylose, ethanol, glycerol, xylitol and acetic acid were determined by high performance liquid chromatography (Waters, Milford, Mass., USA). The compounds were separated with a Shodex SUGAR SP0810 Pb2+ copolymer-based column (Showa Denko America, NY, USA), or a Rezex H+ column, preceded by a Micro-Guard Carbo-C guard column (Bio-Rad, Hercules, Calif., USA). Separation was performed at 80° C., with H2O at a flow rate of 0.6 ml min-1 as mobile phase. Compounds were quantified by refractive index detection (Waters). A seven-point calibration curve was made for each compound to calculate concentrations.

Figure 10A:
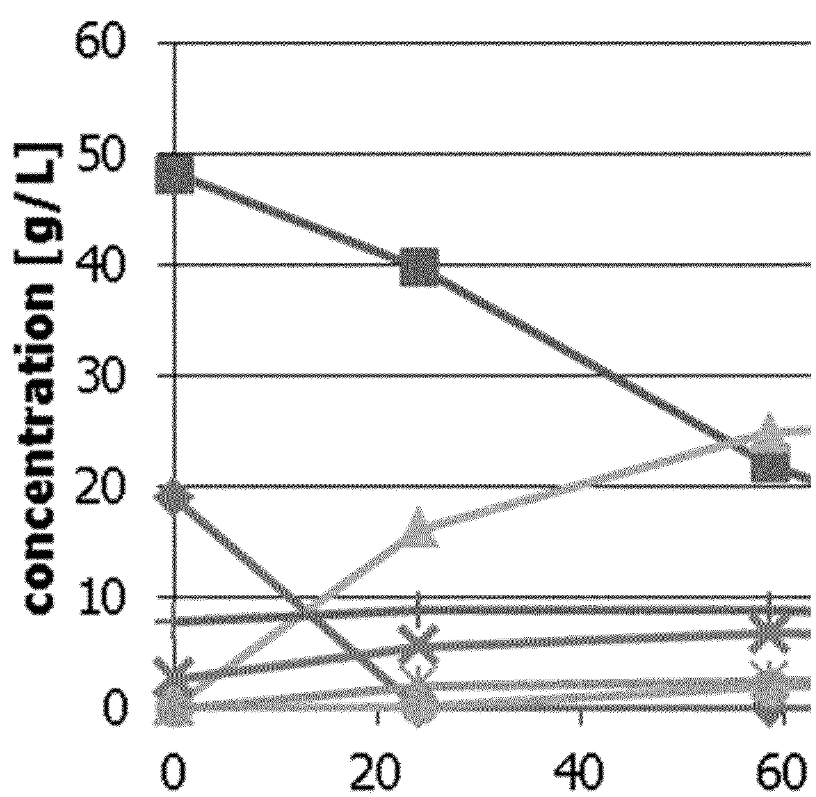
FIG. 10: Graph showing fermentation results of fermentation of xylose in the presence of acetic acid with strains C5LTe1202 (A) and C5LTe1212 (B).
Figure 10B:
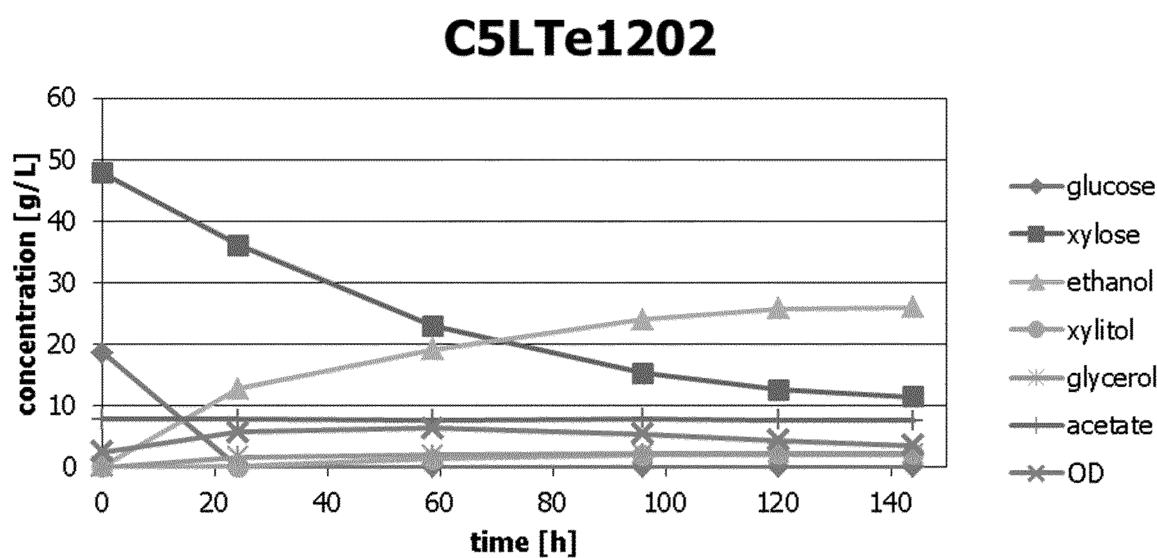
Figure 11:
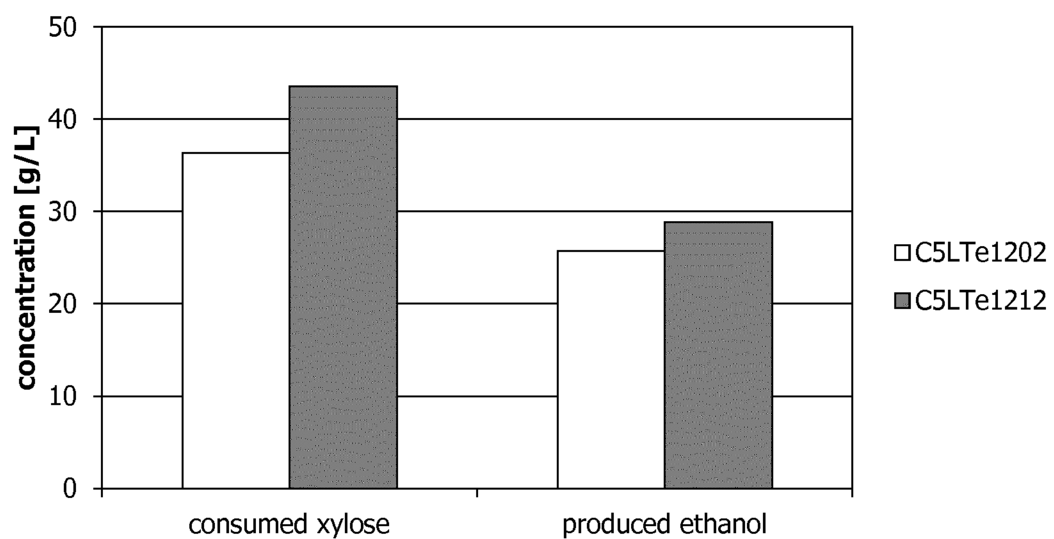
FIG. 11: Graph showing fermentation profiles of strains C5LTe1202 and C5LTe1212 in mineral medium in the presence of acetic acid.
Figure 12A:
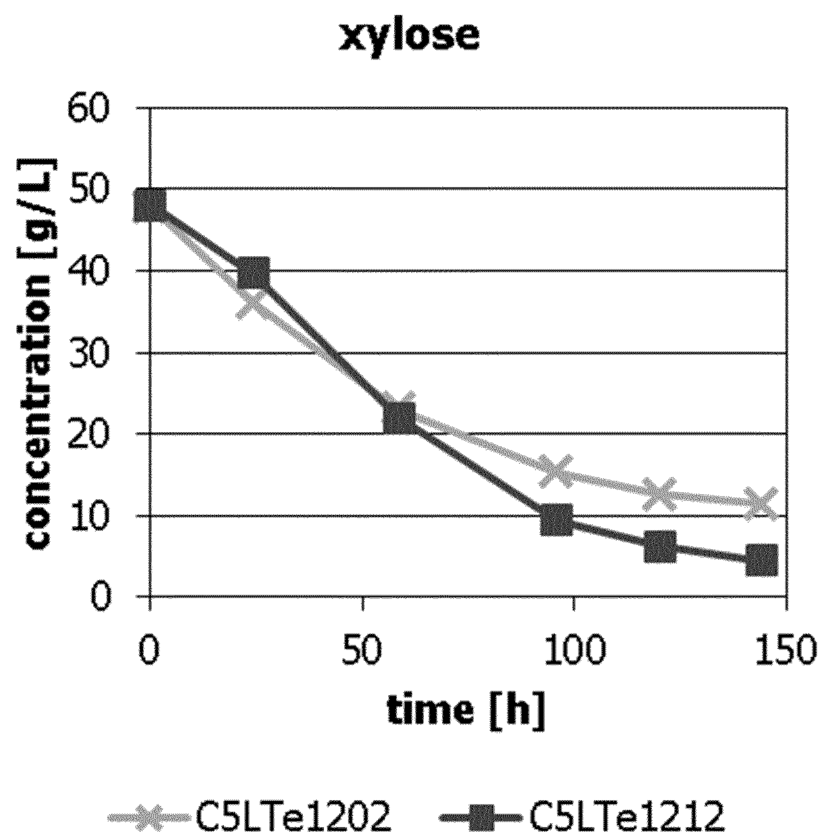
FIG. 12: Graph showing overlay of xylose consumption (A) and ethanol production (B) profiles of strains C5LTe1202 and C5LTe1212.
Figure 12B:
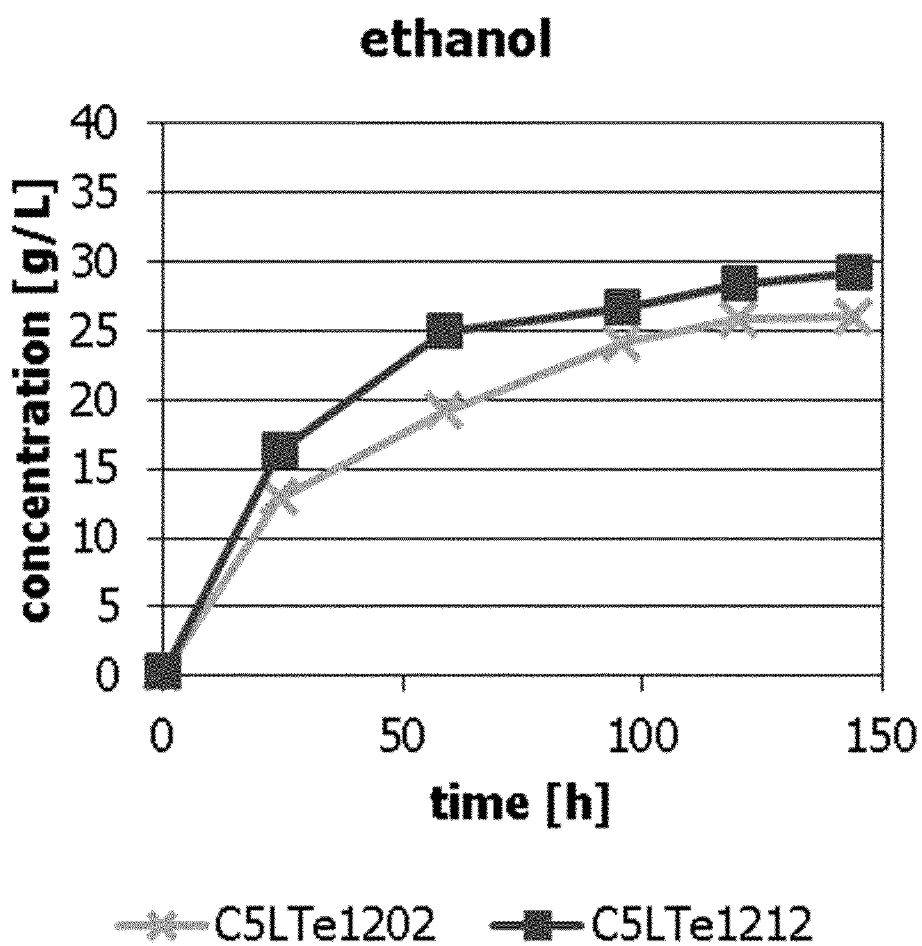

Results are presented graphically in FIG. 10, FIG. 11, and FIG. 12. In conclusion, more xylose was consumed, and more ethanol was produced, in strain C5LTe1212 expressing the YME2 gene.

Example 15: Fermentation and Growth Characteristics in the Presence of Formic Acid Cells aerobically grown overnight on YNB medium supplemented with 20 g/L glucose were used to inoculate a serum flask containing 30 mL of YNB medium supplemented with glucose (20 g/L) and xylose (50 g/L) as carbon source and formic acid (4.5 g/L) at initial concentration of 1 g CDW/L. Glucose, xylose, ethanol, xylitol, glycerol and acetate were analysed using HPLC (Waters) using the same procedure as in Example 7.

Figure 13A:
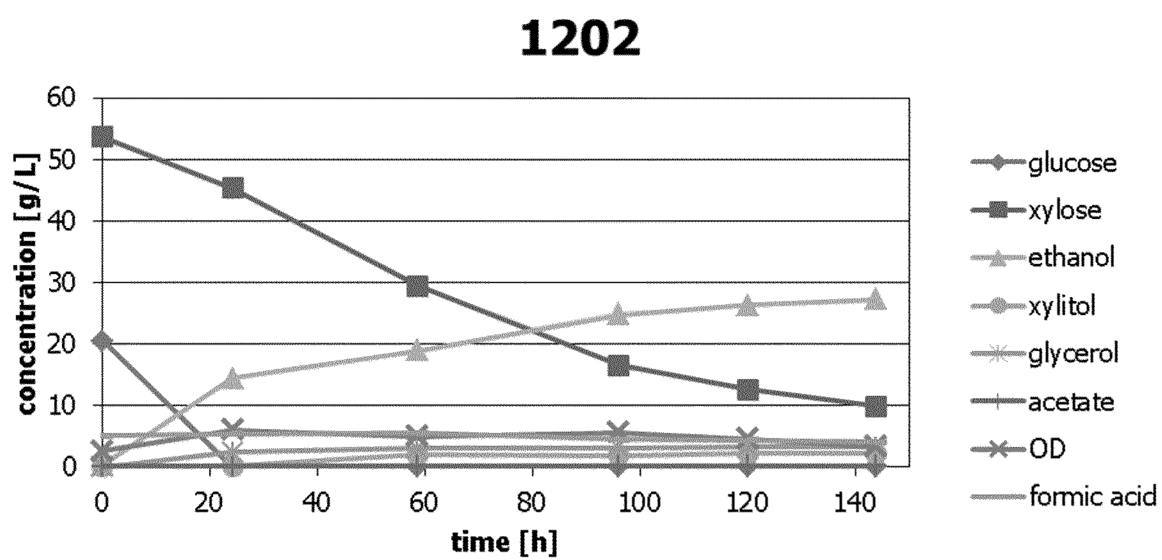
FIG. 13: Graph showing fermentation profiles of strains C5Lte1202 (A) and C5Lte1212 (B) in mineral medium in the presence of formic acid.
Figure 13B:
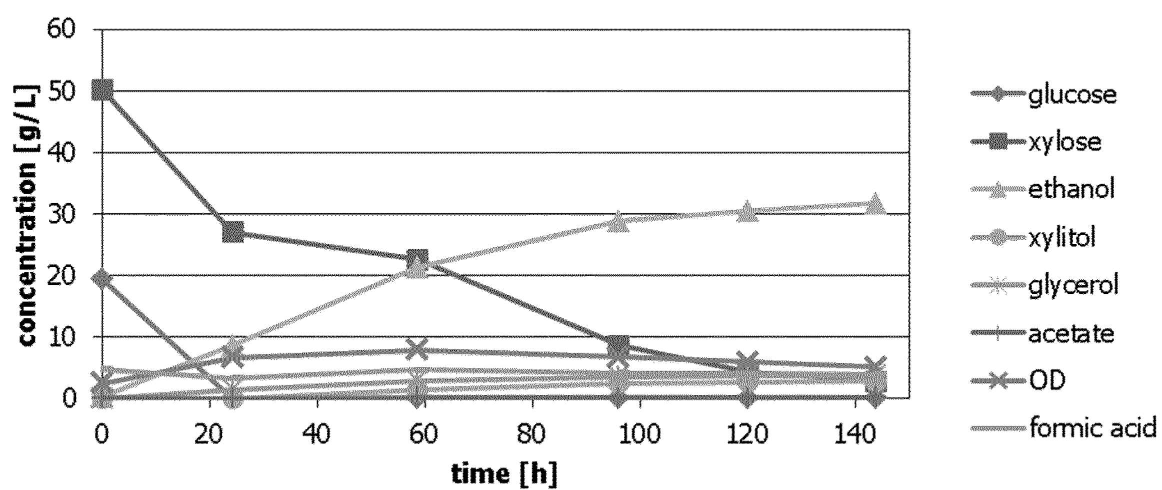
Figure 14:
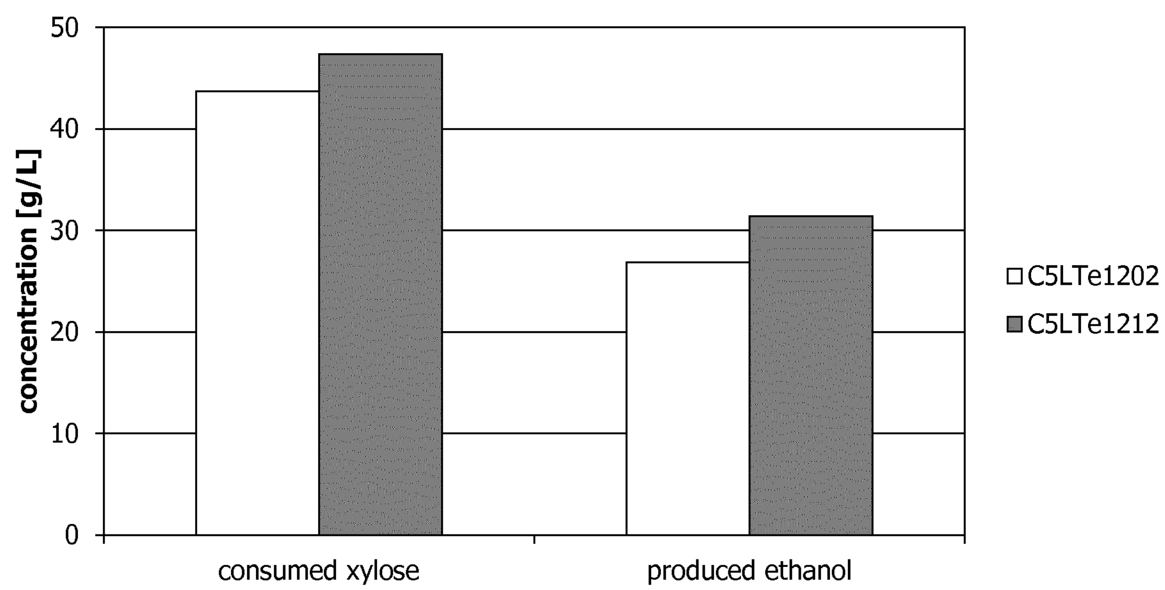
FIG. 14: Graph showing fermentation results of fermentation of xylose in the presence of formics acid with strains C5LTe1202 and C5LTe1212.
Figure 15A:
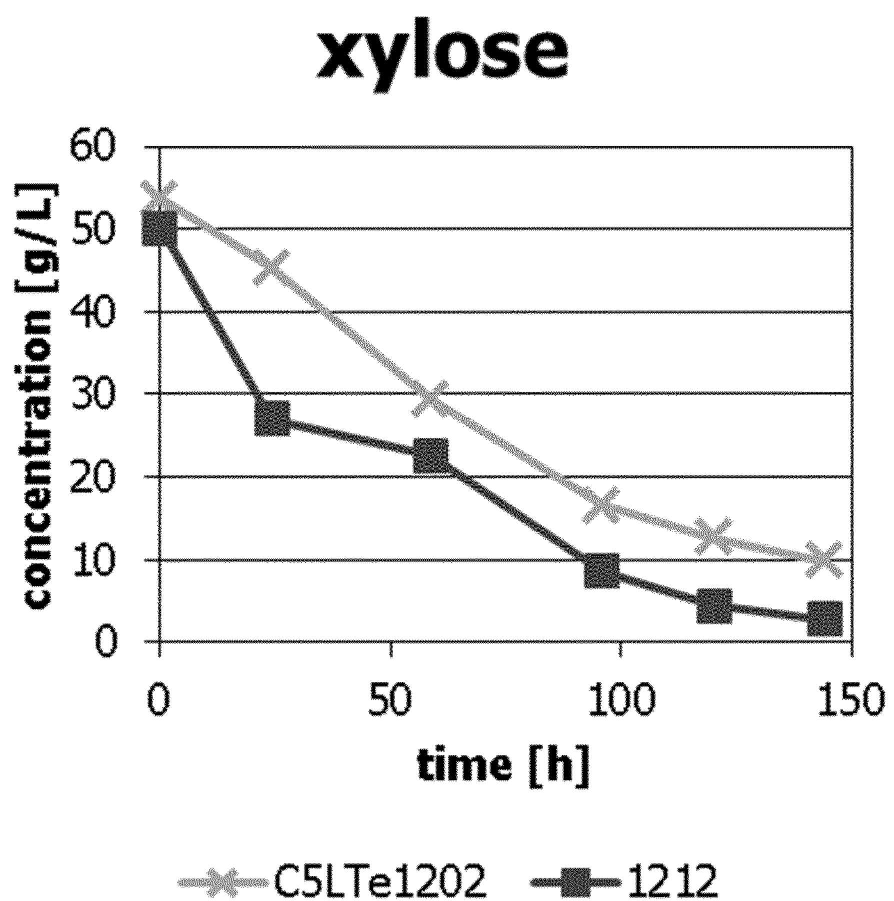
FIG. 15: Graph showing overlay of xylose consumption (A) and ethanol production (B) profiles of strains C5LTe1202 and C5LTe1212.
Figure 15B:
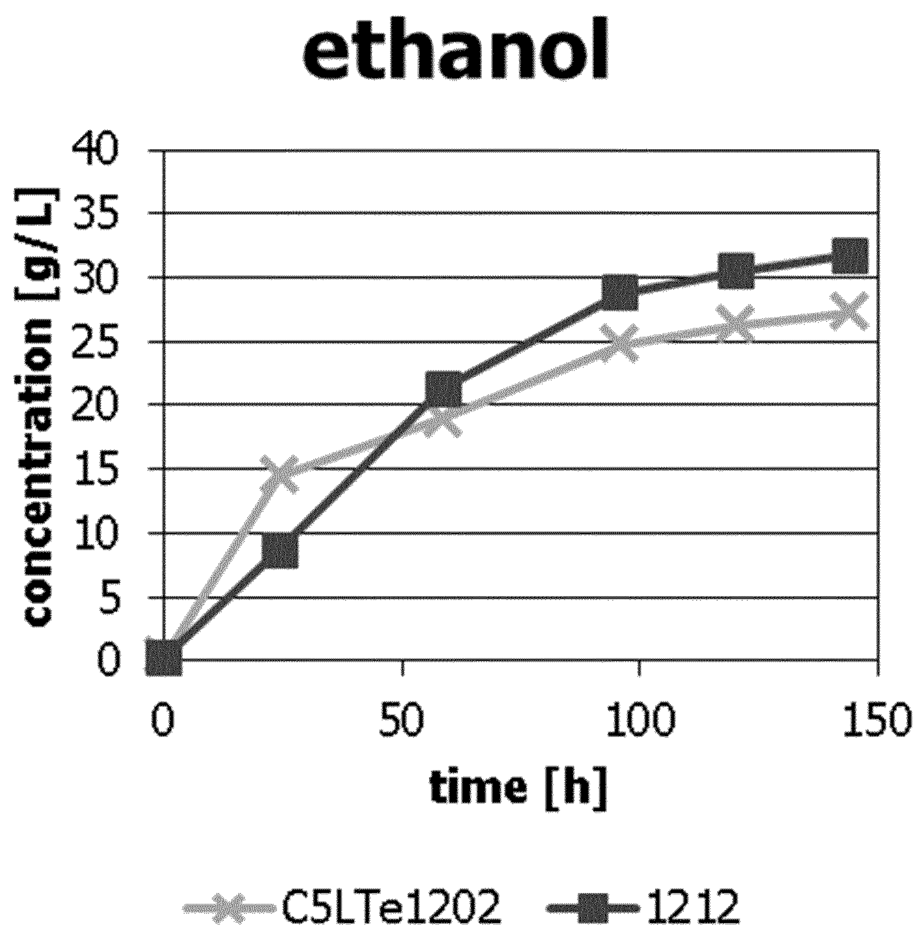

Results are shown graphically in FIG. 13, FIG. 14, and FIG. 15. In conclusion, the more xylose was consumed, and more ethanol was produced, in strain C5LTe1212 expressing the YME2 gene.

Figure 16:
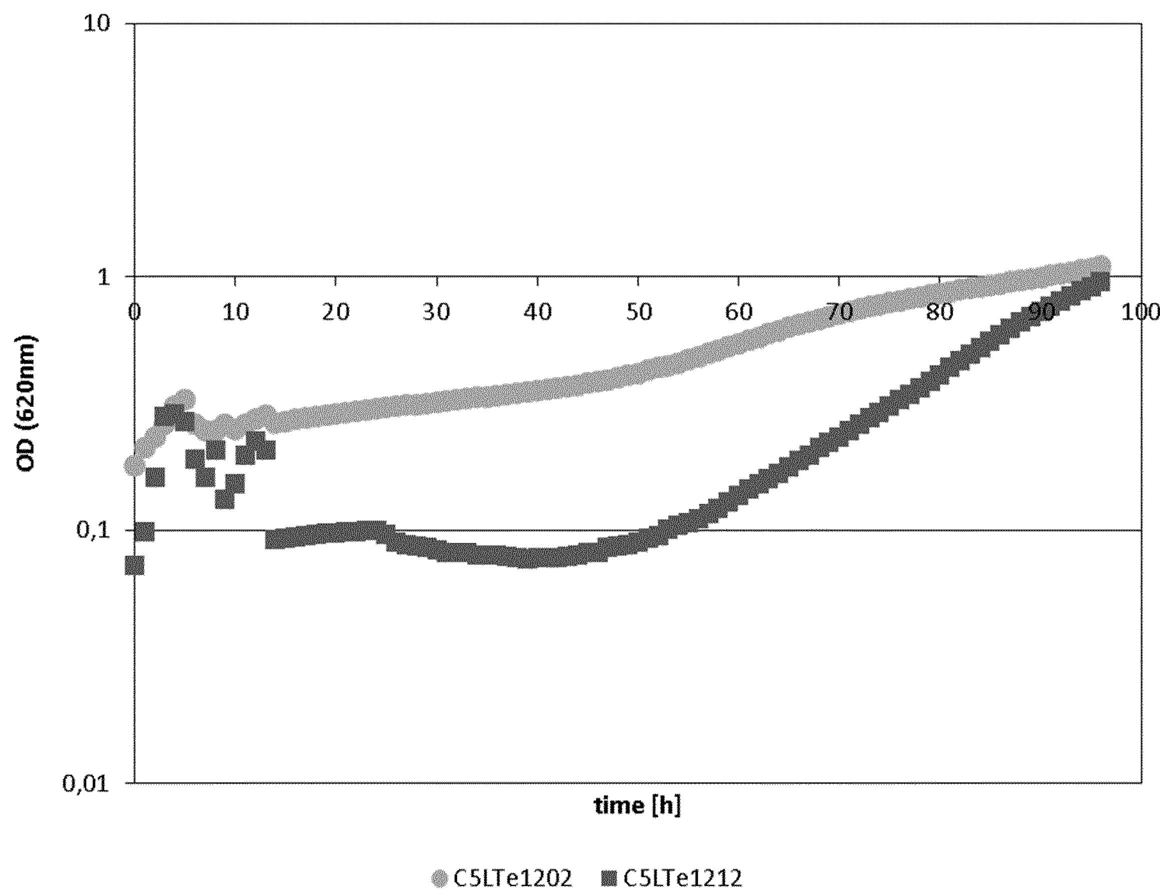
FIG. 16: Graphic representation of the growth characteristics (measured as change in OD at 620 nm) of strains C5LTe1202 (upper curve) and C5LTe1212 (lower curve).

In another tolerance experiment, cells grown overnight on YNB medium supplemented with 50 g/L xylose were used to inoculate a microtiter plate containing YNB medium supplemented with 110 g/L xylose as carbon source and 4.5 g/L formic acid. FIG. 16 shows a graphic representation of the anaerobic growth characteristics (measured as change in OD at 620 nm) of strains C5LTe1202 (upper curve) and C5LTe1212 (lower curve).

To conclude, overexpression of the YME2 gene clearly improves tolerance towards both formic acid and acetic acid. Xylose fermentation in presence of formic or acetic acid was improved in yeast overexpressing YME2. Specifically, xylose consumption and ethanol production increased by 13% and 12%, respectively, in the presence of acetic acid, and by 7% and 12%, respectively, in the presence of formic acid. Formic acid is common in lignocellulosic hydrolysates, and strongly contributes to the toxicity of such hydrolysates.

Example 16: Construction and Selection of MC Strains

For this Example, certain *S. cerevisiae* genes coding for enzymes in the main pathways of the central metabolism were tested.

Yeast strain C5LTe1101 was constructed by transforming yeast strain TMB 3043 (Karhumaa et al. 2005) in its ura3 locus with a DNA fragment containing URA3 gene, TDH3p-XYL1(N272D)-ADH1t, and PGK1p-XYL2-PGK1t. Selection was made on YNB (Yeast nitrogen base 6,7 g/l and 20 g/l glucose, 20 g/l agar) plates supplemented with 200 mg/L leucine. To C5LTe1101 were transformed DNA fragments obtained with PCR with primers shown in Table 7 together with the plasmid p245GPD (Mumberg et al., 1995) linearized with SmaI. A control strain was constructed by transforming with unlinearized plasmid p245GPD. Selection was made on YNB agar plates with 20 g/l glucose as a carbon source. Selected colonies were tested by colony PCR and clones with PCR-products indicating right size of plasmid insert were chosen.

TABLE 7

| Genes Included: | | | |
|---|---|---|---|
| Strain | Gene | Forward primer (5' → 3') (SEQ ID NO:) | Reverse primer (5' → 3') (SEQ ID NO:) |
| MC1 | GLK1 | CTAGAACTAGTGGATCCCCCATGTCA TTCGACGACTTACACAAAG (63) | ATATCGAATTCCTGCAGCCCTCATGCT ACAAGCGCACACAA (64) |
| MC2 | PGI1 | CTAGAACTAGTGGATCCCCCATGTCC AATAACTCATTCACTAACTTCA (65) | ATATCGAATTCCTGCAGCCCTCACATC CATTCCTTGAATTG (66) |
| MC3 | PFK26 | CTAGAACTAGTGGATCCCCCATGTTC AAACCAGTAGACTTCTCTGA (67) | ATATCGAATTCCTGCAGCCCTTAAACG TGACTTTGGCTGC (68) |
| MC4 | PFK2 | CTAGAACTAGTGGATCCCCCATGACT GTTACTACTCCTTTTGTGAATG (69) | ATATCGAATTCCTGCAGCCCTTAATCAA CTCTCTTTCTTCCAACC (70) |
| MCS | PFK27 | CTAGAACTAGTGGATCCCCCATGGG TGGTTCTTCCGATTCA (71) | ATATCGAATTCCTGCAGCCCTCAAGCA AATCCGTTGCTTTC (72) |
| MC6 | FBA1 | CTAGAACTAGTGGATCCCCCATGGG TGTTGAACAAATCTTAAAGAG (73) | ATATCGAATTCCTGCAGCCCTTAATCAA CTCTCTTTCTTCCAACC (74) |
| MC7 | TDH1 | CTAGAACTAGTGGATCCCCCATGATC AGAATTGCTATTAACGGTTTC (75) | ATATCGAATTCCTGCAGCCCTTAAGCC TTGGCAACATATTCG (76) |
| MC8 | TDH2/3 | CTAGAACTAGTGGATCCCCCATGGTT AGAGTTGCTATTAACGGTTTC (77) | ATATCGAATTCCTGCAGCCCTTAAGCC TTGGCAACGTGTT (78) |
| MC11 | GPM1 | CTAGAACTAGTGGATCCCCCATGCCA AAGTTAGTTTTAGTTAGACACG (79) | ATATCGAATTCCTGCAGCCCTTATTTCT TACCTTGGTTGGCAAC (80) |
| MC12 | GPM2 | CTAGAACTAGTGGATCCCCCATGACT GCAAGCACACCATCCAAT (81) | ATATCGAATTCCTGCAGCCCTTAAGGA TTTTTTATGAAACCCTCA (82) |
| MC13 | GPM3 | CTAGAACTAGTGGATCCCCCATGACT GTTACTGACACTTTTAAACTG (83) | ATATCGAATTCCTGCAGCCCTCATGGA TTCTTTTCGAAACCC (84) |
| MC14 | ENO1 | CTAGAACTAGTGGATCCCCCATGGC TGTCTCTAAAGTTTACGC (85) | ATATCGAATTCCTGCAGCCCTTATAATT TGTCACCGTGGTGG (86) |
| MC15 | PYK1 | CTAGAACTAGTGGATCCCCCATGTCT AGATTAGAAAGATTGACCTCA (87) | ATATCGAATTCCTGCAGCCCTTAAACG GTAGAGACTTGCAAAGTG (88) |
| MC16 | PYK2 | CTAGAACTAGTGGATCCCCCATGCCA GAGTCCAGATTGCA (89) | ATATCGAATTCCTGCAGCCCCTAGAAT TCTTGACCAACAGTAGAAATG (90) |
| MC17 | PDC1 | CTAGAACTAGTGGATCCCCCATGTCT GAAATTACTTTGGGTAAA (91) | ATATCGAATTCCTGCAGCCCTTATTGC TTAGCGTTGGTAGCAG (92) |
| MC18 | PDC6 | CTAGAACTAGTGGATCCCCCATGTCT GAAATTACTCTTGGAAAATACT (93) | ATATCGAATTCCTGCAGCCCTTATTGTT TGGCATTTGTAGCGG (94) |

TABLE 7-continued

| Strain | Gene | Forward primer (5' → 3') (SEQ ID NO:) | Reverse primer (5' → 3') (SEQ ID NO:) |
|---|---|---|---|
| | | Genes Included: | |
| MC19 | ALD6 | CTAGAACTAGTGGATCCCCCATGACT AAGCTACACTTTGACACTGC (95) | ATATCGAATTCCTGCAGCCCTTACAAC TTAATTCTGACAGCTTTTAC (96) |
| MC20 | ADH5 | CTAGAACTAGTGGATCCCCCATGCCT TCGCAAGTCATTCCT (97) | ATATCGAATTCCTGCAGCCCTCATTTA GAAGTCTCAACAACATATC (98) |
| MC21 | ADH6 | CTAGAACTAGTGGATCCCCCATGTCT TATCCTGAGAAATTTGAAGGT (99) | ATATCGAATTCCTGCAGCCCCTAGTCT GAAAATTCTTTGTCGTAGCC (100) |
| MC22 | TPI1 | CTAGAACTAGTGGATCCCCCATGGC TAGAACTTTCTTTGTCGG (101) | ATATCGAATTCCTGCAGCCCTTAGTTT CTAGAGTTGATGATATCAACA (102) |
| MC23 | GPD1 | CTAGAACTAGTGGATCCCCCATGTCT GCTGCTGCTGATAGATT (103) | ATATCGAATTCCTGCAGCCCCTAATCTT CATGTAGATCTAATTCTTCA (104) |
| MC24 | GPD2 | CTAGAACTAGTGGATCCCCCATGCTT GCTGTCAGAAGATTAACA (105) | ATATCGAATTCCTGCAGCCCCTATTCG TCATCGATGTCTAGCTCT (106) |
| MC25 | HOR2 | CTAGAACTAGTGGATCCCCCATGGG ATTGACTACTAAACCTCTATCT (107) | ATATCGAATTCCTGCAGCCCTTACCATT TCAACAGATCGTCC (108) |
| MC26 | SNF3 | CTAGAACTAGTGGATCCCCCATGGAT CCTAATAGTAACAGTTCTAGCG (109) | ATATCGAATTCCTGCAGCCCTTATTTCA AATCATTATTTTCATTTACAGGTTG (110) |
| MC27 | RGT2 | CTAGAACTAGTGGATCCCCCATGAAC GATAGCCAAAACTGC (111) | ATATCGAATTCCTGCAGCCCTTATTGG GGGGAAGTGTATTG (112) |
| MC28 | MIG1 | CTAGAACTAGTGGATCCCCCATGCAA AGCCCATATCCAATG (113) | ATATCGAATTCCTGCAGCCCTCAGTCC ATGTGTGGGAAGG (114) |
| MC29 | STD1 | CTAGAACTAGTGGATCCCCCATGTTT GTTTCACCACCTCCA (115) | ATATCGAATTCCTGCAGCCCCTAGGAC ATTCCATCAGGCTT (116) |
| MC30 | ADH1 | CTAGAACTAGTGGATCCCCCATGTCT ATCCCAGAAACTCAAAAAGG (117) | ATATCGAATTCCTGCAGCCCTTATTTAG AAGTGTCACAACGTATCTACC (118) |
| MC31 | PGM1 | CTAGAACTAGTGGATCCCCCATGAAC GATAGCCAAAACTGC (119) | ATATCGAATTCCTGCAGCCCTTATTGG GGGGAAGTGTATTG (120) |
| MC32 | PGM3 | CTAGAACTAGTGGATCCCCCATGTTG CAAGGAATTTTAGAAACCG (121) | ATATCGAATTCCTGCAGCCCTCAAAATT TTGTAACTATATTCATTTCATCTG (122) |
| MC33 | GAL3 | CTAGAACTAGTGGATCCCCCATGAAT ACAAACGTTCCAATATTCAG (123) | ATATCGAATTCCTGCAGCCCTTATTGTT CGTACAAACAAGTACCC (124) |
| MC34 | GAL1 | CTAGAACTAGTGGATCCCCCATGACT AAATCTCATTCAGAAGAAGTGA (125) | ATATCGAATTCCTGCAGCCCTTATAATT CATATAGACAGCTGCCCA (126) |
| MC35 | GAL4 | CTAGAACTAGTGGATCCCCCATGAA GCTACTGTCTTCTATCGAACAAG (127) | ATATCGAATTCCTGCAGCCCTTACTCTT TTTTTGGGTTTGGTGG (128) |
| MC36 | GAL1 | CTAGAACTAGTGGATCCCCCATGACT GCTGAAGAATTTGATTTTTC (129) | ATATCGAATTCCTGCAGCCCTTACAGT CTTTGTAGATAATGAATCTGACC (130) |

The nucleic acid and amino acid sequences of ENO1 are shown in SEQ ID NOs: 131 and 132, respectively. The nucleic acid and amino acid sequences of PFK2 are shown in SEQ ID NOs: 133 and 134, respectively. The nucleic acid and amino acid sequences of PFK26 are shown in SEQ ID NOs: 135 and 136, respectively. The nucleic acid and amino acid sequences of PGI1 are shown in SEQ ID NOs: 137 and 138, respectively. The nucleic acid and amino acid sequences of GMP1 are shown in SEQ ID NOS: 139 and 140, respectively. The nucleic acid and amino acid sequences of TPI1 are shown in SEQ ID NOs: 141 and 142, respectively.

Example 17: Aerobic Growth on Xylose

Figure 17:
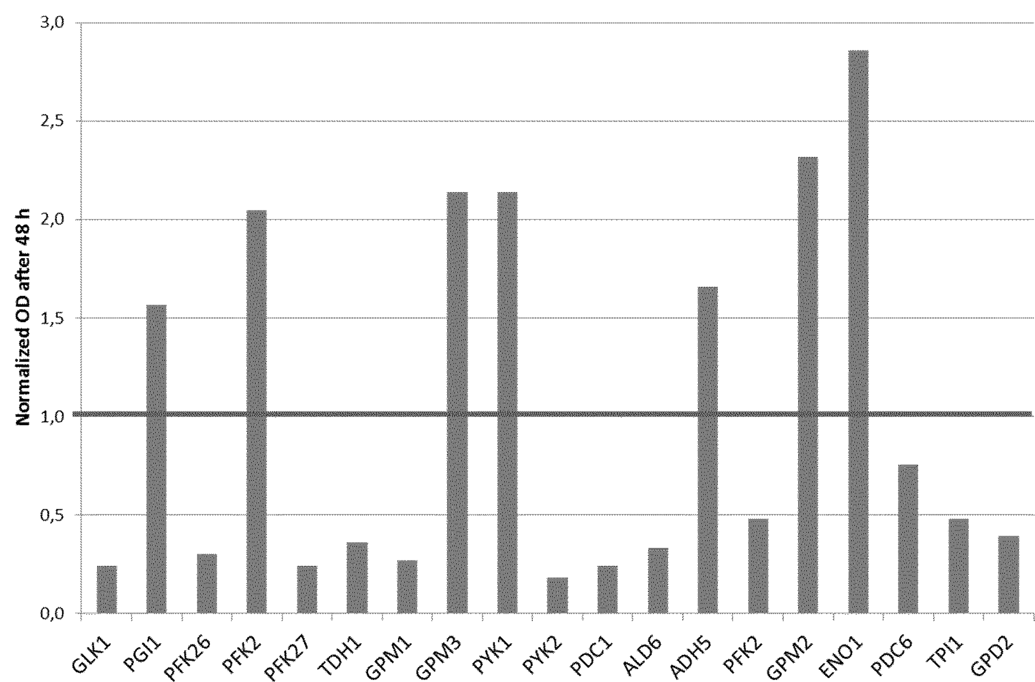
FIG. 17: Graph showing aerobic growth on xylose of clones expressing various glycolytic genes. Normalized OD (620 nm) for clones with the expressed genes is shown.

Aerobic growth on xylose was measured in mineral medium (Yeast nitrogen base, 13.4 g/l, xylose 50 g/l) in 5 ml cultures in 50 ml falcon tubes. Samples were taken and OD at 620 nm was measured. See FIG. 17: For clarity result is presented as normalized OD, against average of all results, for OD at time point of 48 h. Values exceeding 1 indicate that the strain is better than the average of the strains in the experiment.

Example 18: Anaerobic Growth on Xylose

Figure 18:
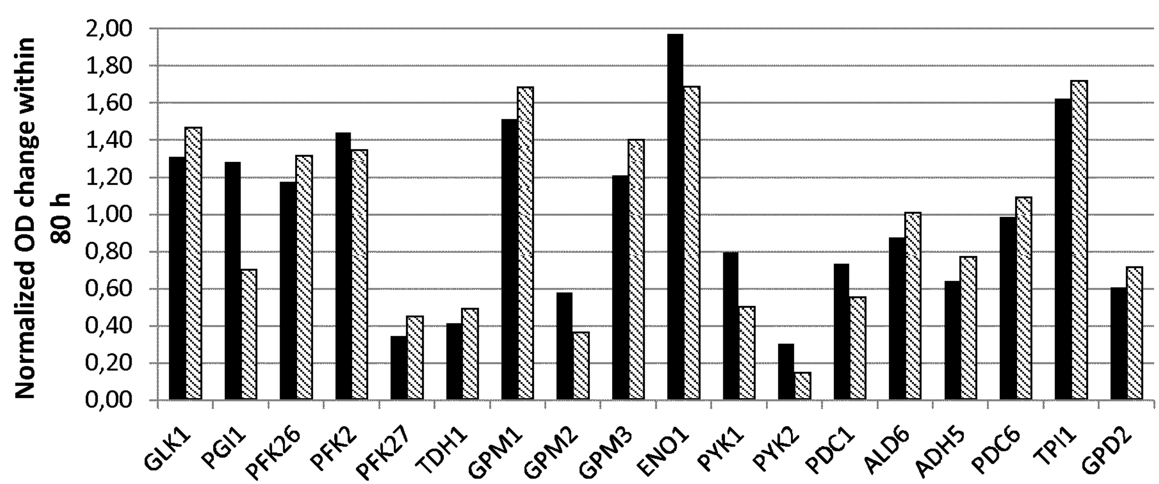
FIG. 18: Graph showing anaerobic growth on xylose of clones expressing various glycolytic genes. Normalized OD (620 nm) for clones with the expressed genes is shown, the black bars and the striped bars representing results from two independent experiments.
Figure 19:
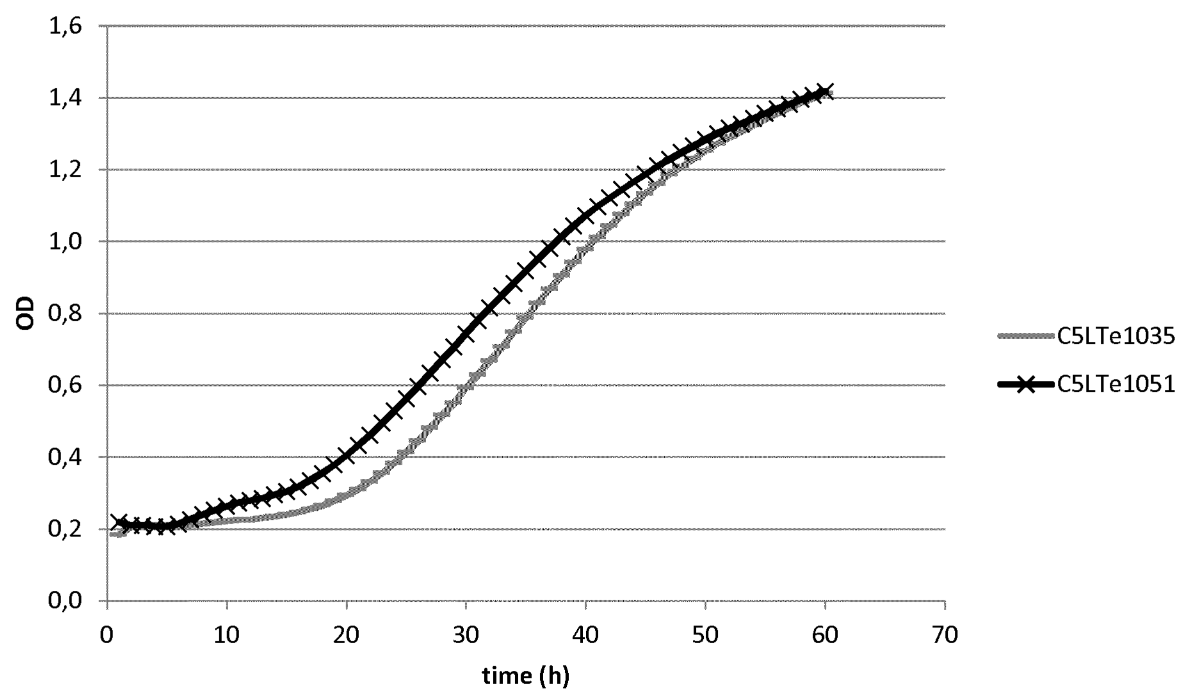
FIG. 19: Graph showing anaerobic growth of C5LTe1051 ("x") compared with control strain C5LTe1035 ("–").
Figure 20:
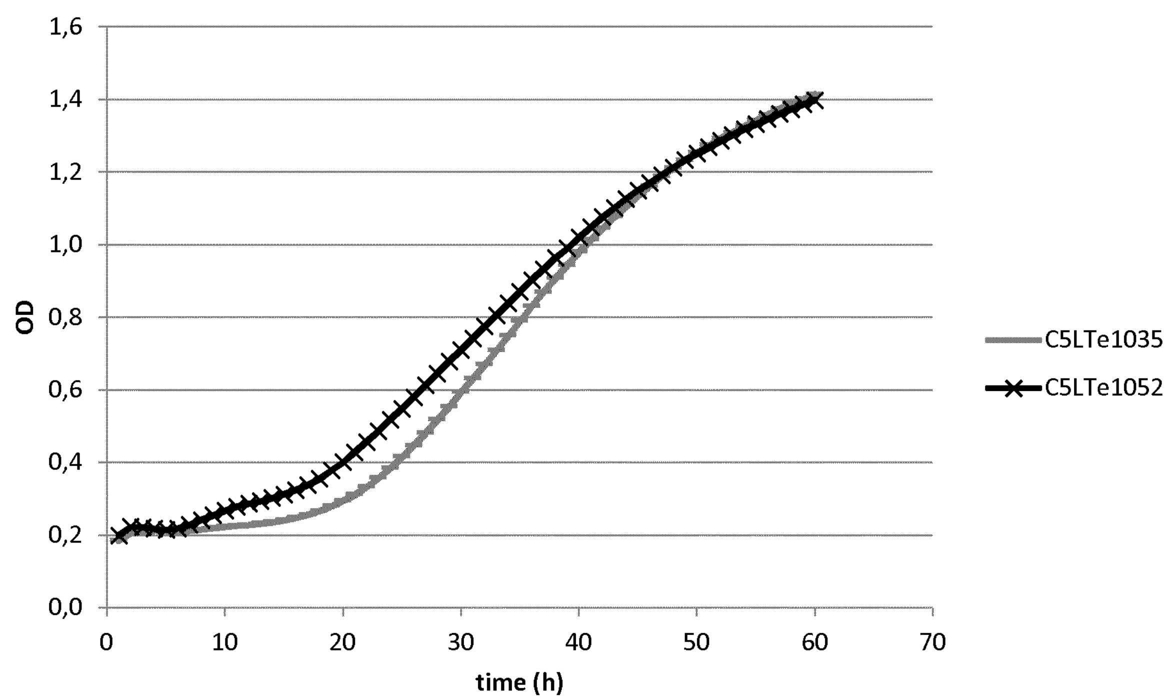
FIG. 20: Graph showing anaerobic growth of C5LTe1052 compared with control strain C5LTe1035.
Figure 21:
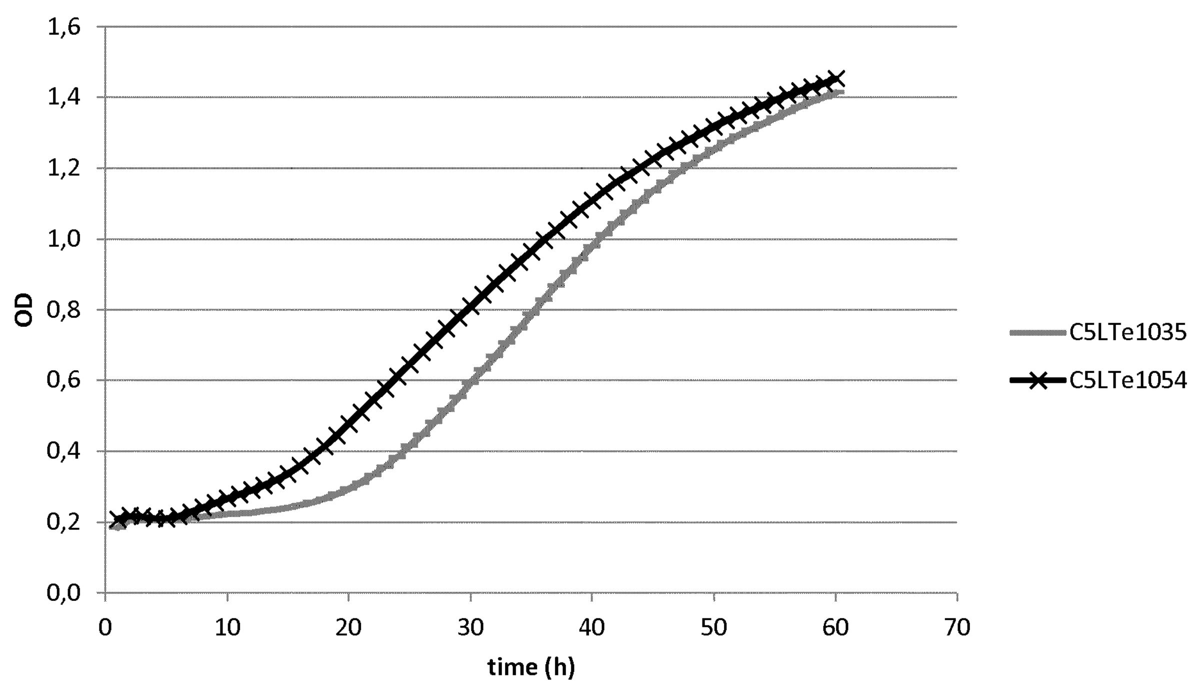
FIG. 21: Graph showing anaerobic growth of C5LTe1054 compared with control strain C5LTe1035.
Figure 22:
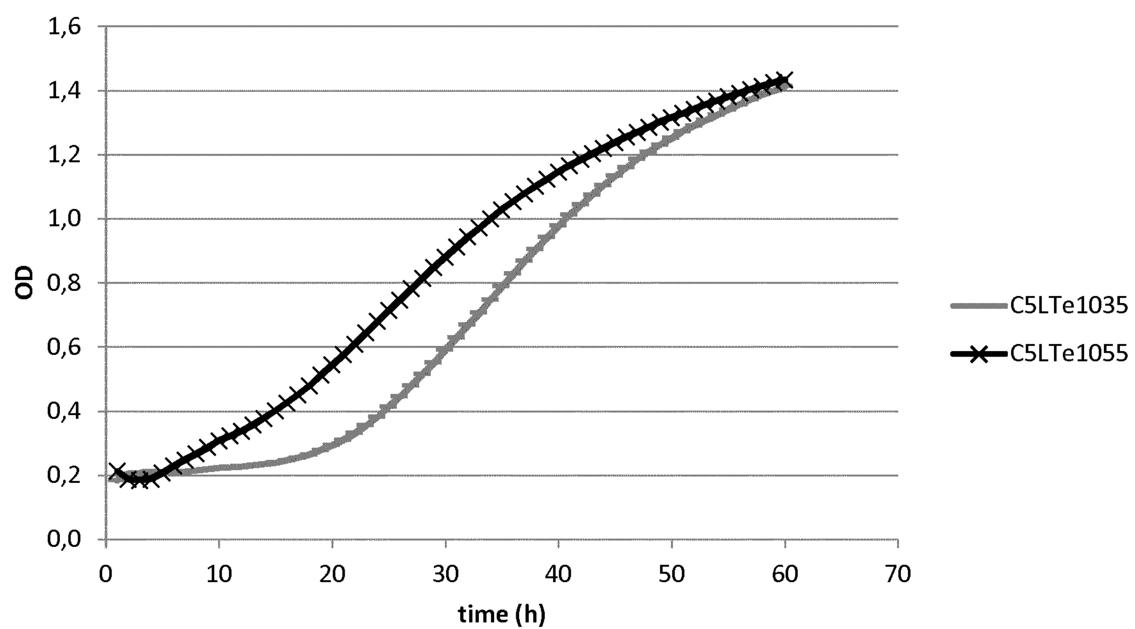
FIG. 22: Graph showing anaerobic growth of C5LTe1055 compared with control strain C5LTe1035.
Figure 23A:
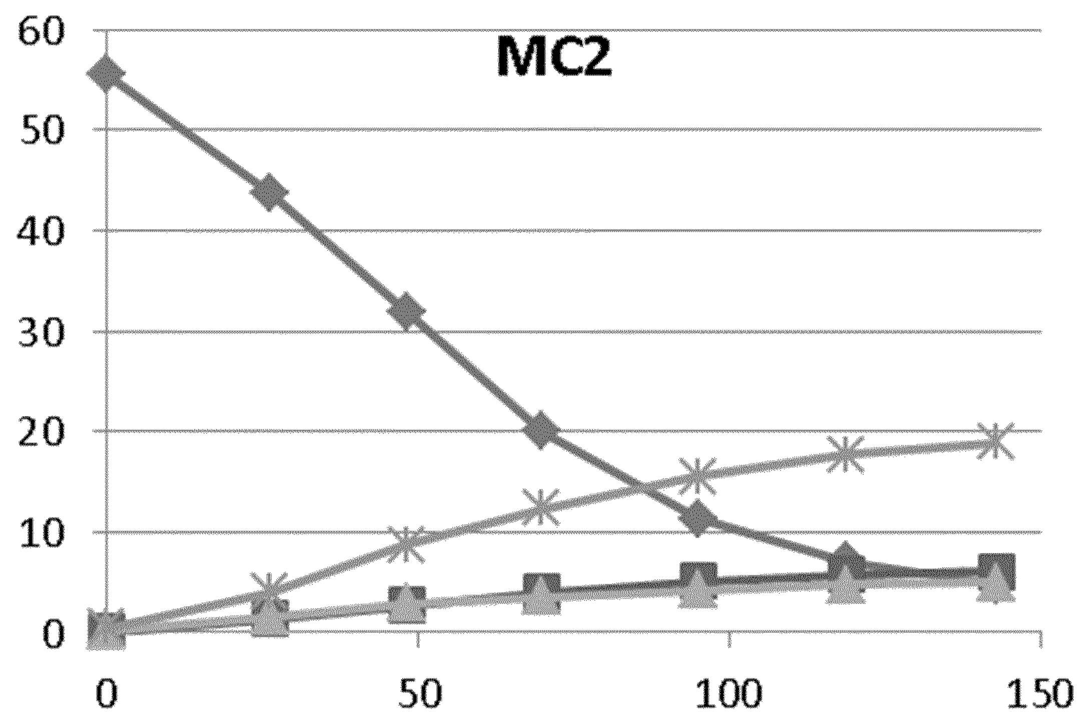
FIG. 23: Fermentation graphs of xylose fermentation by strains MC2 (A), MC3 (B), MC4 (C), MC11 (D), MC14 (E) and MC22 (F) compared with control strain (G). Symbols: diamond—xylose, square—xylitol, triangle—glycerol, star—ethanol.
Figure 23B:
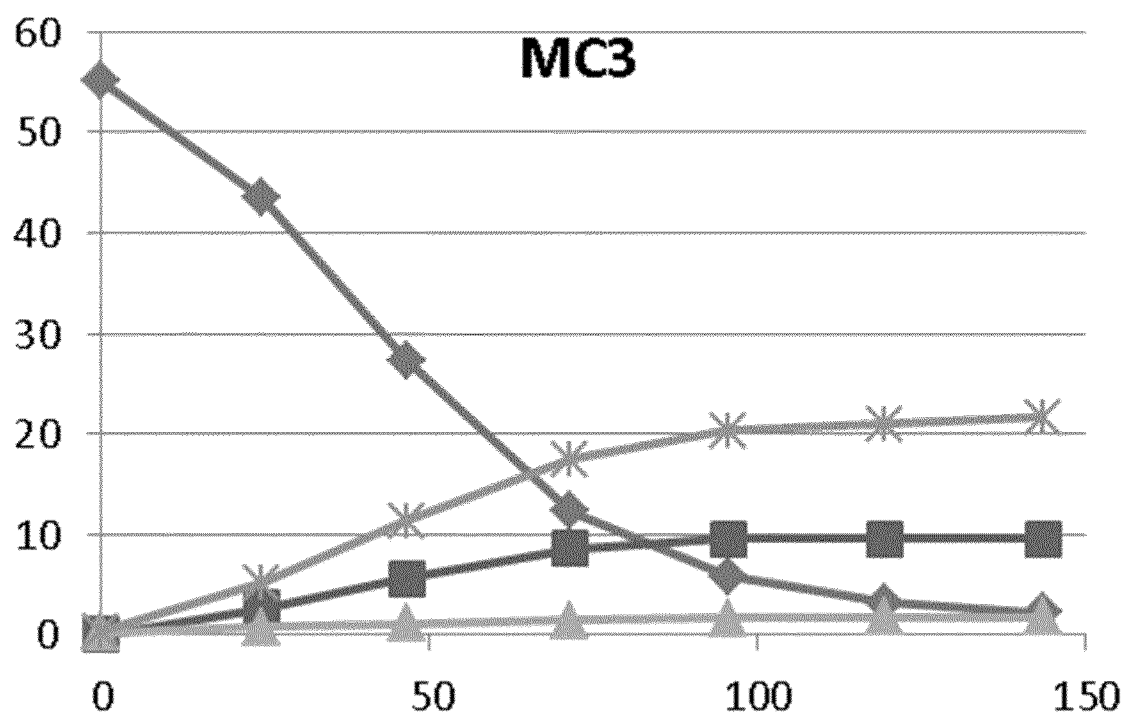
Figure 23C:
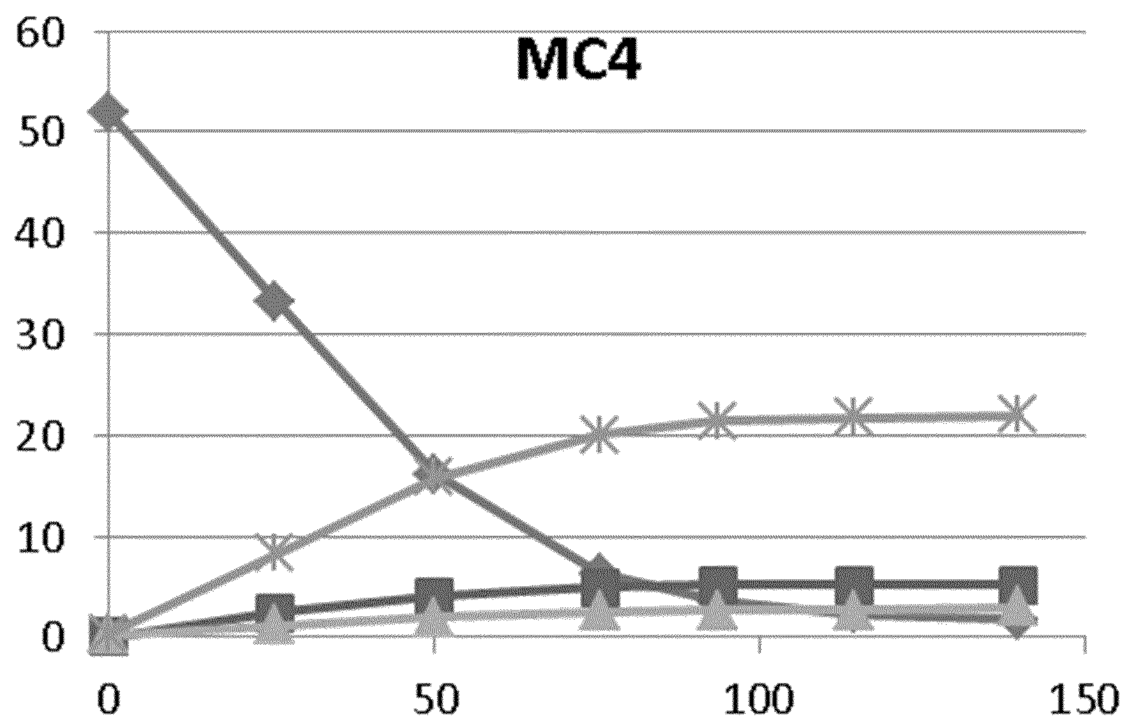
Figure 23D:
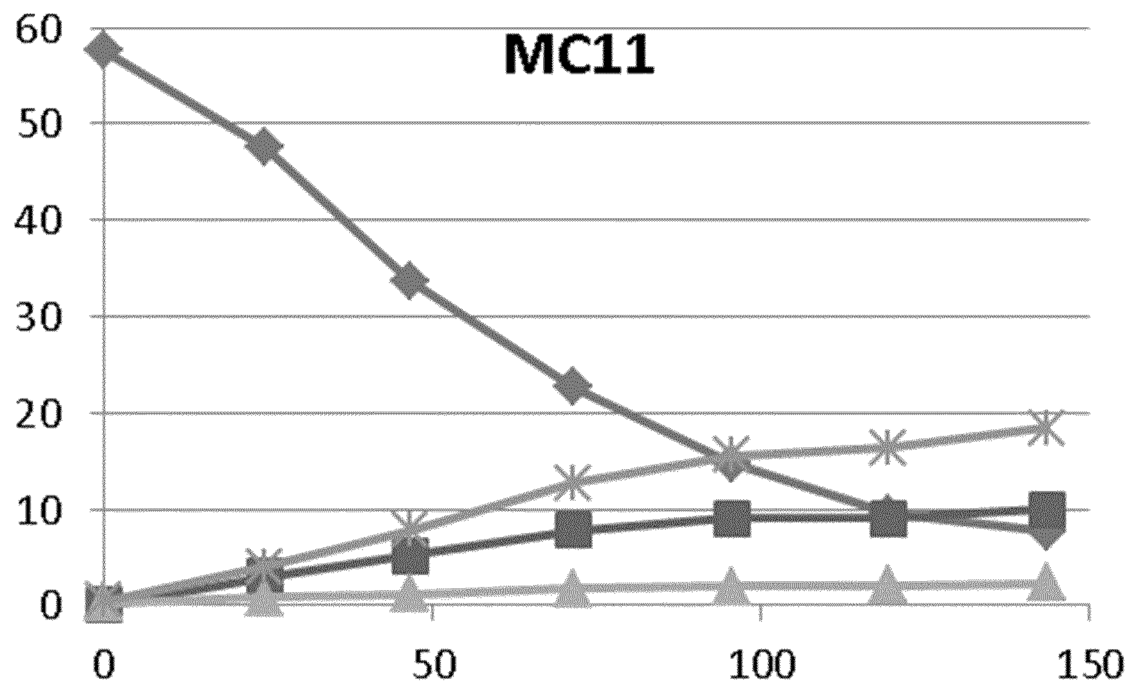
Figure 23E:
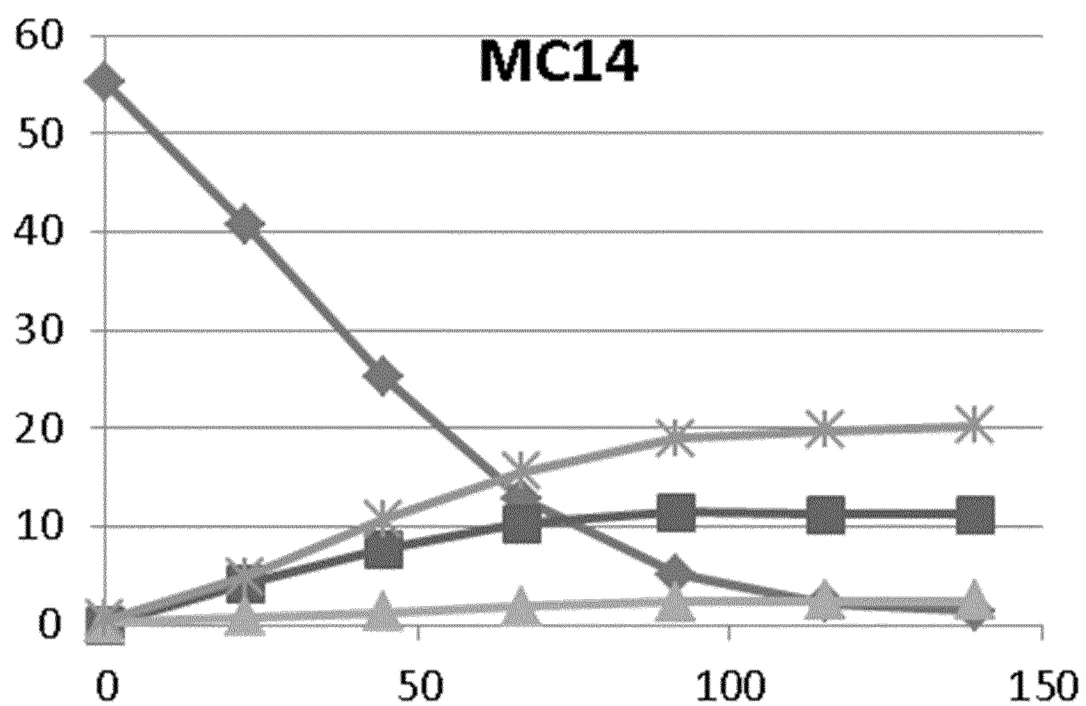
Figure 23F:
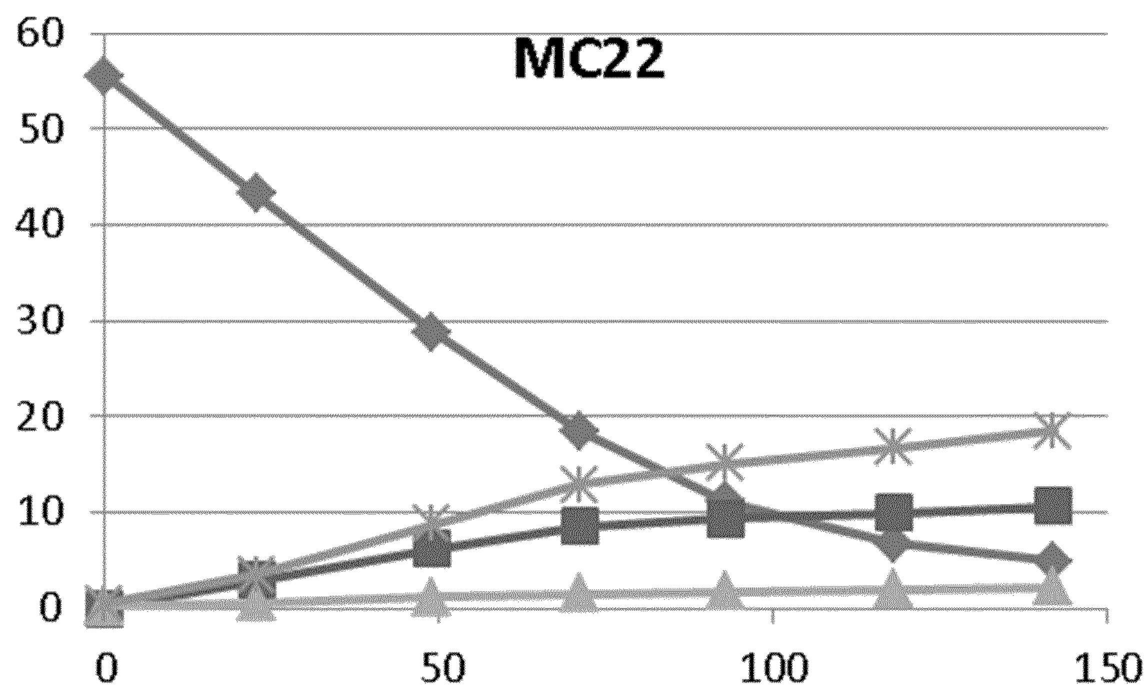
Figure 23G:
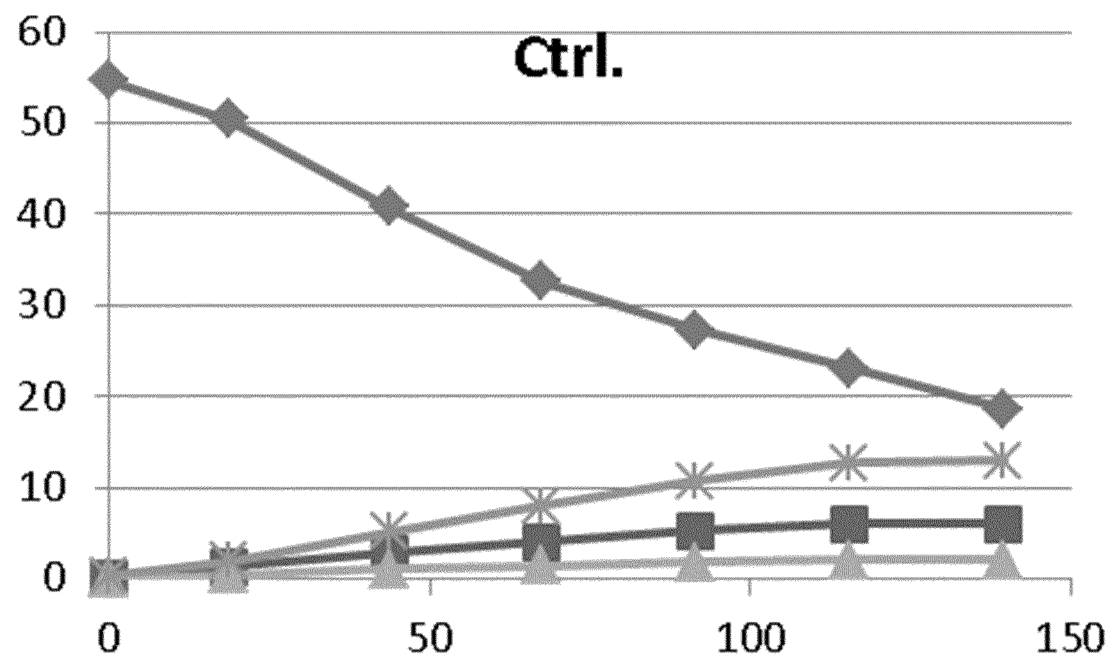

Yeast strains were analysed for anaerobic growth on xylose in 96-well microplate yeast cultures. Prior to experiments, yeast was grown in semi-aerobic precultures in YNB medium with 50 g/l xylose, in microplates, overnight. For measurement of anaerobic growth, cells were inoculated in 200 μl of the same medium where solution of ergosterol and Tween80 had been added at final concentration of 0.03 and 1.2 g/l, respectively. 50 µl mineral oil was added on top of each well to keep culture anaerobic. 20 µl of precultured cells were added. The growth was followed in Multiskan FC (Thermo Scientific) at 30° C. and growth was measured as increase of OD (620 nm). See FIG. 18: For clarity result is presented as normalized OD, against average of all results, for OD at time point of 80 h. Values exceeding 1 indicate that the strain is better than the average of the strains in the experiment.

Example 19: Construction of an *S. cerevisiae* Strain Overexpressing an Enolase, Three of the Genes in the Pentose Phosphate Pathway and a Xylulose Kinase (XK) Gene and Expressing a *Scheffersomyces stipitis* Xylitol Dehydrogenase (XDH) Gene and a Mutated *Scheffersomyces stipitis* Xylose Reductase (XR(N272D)) Gene In this example, the strains, media and genetic techniques described in above were used, except that yeast strains were transformed with the lithium acetate method (Gietz and Schiestl, 2007) and transformed yeast strains were selected on YPD plates containing 500 µg mL-1 geneticin (Gibco Invitrogen, Paisley, UK).

Construction of pC5e0057 Containing a *S. cerevisiae* Enolase (ENO1) Gene

Plasmid pUG6 HXT-PGM2 (WO2010 059095 (A1)) contains the truncated HXT7' promoter and the PGK1terminator from *S. cerevisiae* in pUG6. The DNA cassette HXT7' p-pUG6-PGK1t was PCR amplified having as template pUG6 HXT-PGM2 and using the following primers

```
2_fwd:
                                    (SEQ ID NO: 93)
5'-TGCAGCCCGGGGATCCTTTTT-3'

2_rev:
                                    (SEQ ID NO: 94)
5'-AGGAATTCTAGATCTCCCATGTCTCT-3'.
```

The entire *S. cerevisiae* enolase (ENO1) gene was PCR amplified having as template genomic DNA from CEN.PK and using the following primers.

EN1_fwd
(SEQ ID NO: 95)
5'-GATCCCCGGGCTGCAATGGCTGTCTCTAAAGTTTACGC-3'

EN1_rev
(SEQ ID NO: 96)
5'-AGATCTAGAATTCCTTTATAATTTGTCACCGTGGTGG-3'

The two DNA fragments were fused together by In-Fusion cloning (Clontech, California, Calif., USA). The resulting plasmid was named pC5e0057. Correct orientations and sequences of the inserts were verified by restriction analysis and sequencing.

Construction of C5LTe1051 Overexpressing the Gene Coding for ENO1 and Capable of Growing on Solely Xylose Plasmid pC5e0057 was digested with restriction enzyme Kpnl within the ENO1 gene and it was thereafter transformed into strain C5LTe1035. This resulted in strain C5LTe1051.

Example 20: Construction of an *S. cerevisiae* Strain Overexpressing a 6-Phosphofructokinase, Three of the Genes in the Pentose Phosphate Pathway and a Xylulose Kinase (XK) Gene and Expressing a *Scheffersomyces stipitis* Xylitol Dehydrogenase (XDH) Gene and a Mutated *Scheffersomyces stipitis* Xylose Reductase (XR(N272D)) Gene In this example, the strains, media and genetic techniques described above were used, except that yeast strains were transformed with the lithium acetate method (Gietz and Schiestl, 2007) and transformed yeast strains were selected on YPD plates containing 500 µg mL-1 geneticin (Gibco Invitrogen, Paisley, UK).

Construction of pC5e0058 Containing a *S. cerevisiae* 6-Phosphofructokinase Subunit Beta (PFK2) Gene Plasmid pUG6 HXT-PGM2 (WO 2010/059095 (A1)) contains the truncated HXT7' promoter and the PGK1terminator from *S. cerevisiae* in pUG6. The DNA cassette HXT7'p-pUG6-PGK1t was PCR amplified having as template pUG6 HXT-PGM2 and using the following primers.

```
2_fwd:
                                    (SEQ ID NO: 97)
5'-TGCAGCCCGGGGATCCTTTTT-3'

2_rev:
                                    (SEQ ID NO: 98)
5'-AGGAATTCTAGATCTCCCATGTCTCT-3'
```

The entire *S. cerevisiae* 6-phosphofructokinase subunit beta (PFK2) gene was PCR amplified having as template genomic DNA from CEN.PK and using the following primers.

PF2_fwd
(SEQ ID NO: 99)
5'-GATCCCCGGGCTGCAATGACTGTTACTACTCCTTTTGTGAATG-3'

PF2_rev:
(SEQ ID NO: 100)
5'-AGATCTAGAATTCCTTTAATCAACTCTCTTTCTTCCAACC-3'

The two DNA fragments were fused together by In-Fusion cloning (Clontech, California, Calif., USA). The resulting plasmid was named pC5e0058. Correct orientations and sequences of the inserts were verified by restriction analysis and sequencing.

Construction of C5LTe1052 Overexpressing the Gene Coding for PFK2 and Capable of Growing on Solely Xylose Plasmid pC5e0058 was digested with restriction enzyme Kpnl within the PFK2 gene and it was thereafter transformed into strain C5LTe1035, resulting in strain C5LTe1052.

Example 21: Construction of an *S. cerevisiae* Strain Overexpressing a Glucose-6-Phosphate Isomerase, Three of the Genes in the Pentose Phosphate Pathway and a Xylulose Kinase (XK) Gene and Expressing a *Scheffersomyces stipitis* Xylitol Dehydrogenase (XDH) Gene and a Mutated *Scheffersomyces stipitis* Xylose Reductase (XR(N272D)) Gene In this example, the strains, media and genetic techniques described above were used, except that yeast strains were transformed with the lithium acetate method (Gietz and Schiestl, 2007) and transformed yeast strains were selected on YPD plates containing 500 µg mL-1 geneticin (Gibco Invitrogen, Paisley, UK).

Construction of pC5e0060 Containing a *S. cerevisiae* Glucose-6-Phosphate Isomerase (PGI1) Gene Plasmid pUG6 HXT-PGM2 (WO2010/059095 (A1)) contains the truncated HXT7' promoter and the PGK1terminator from *S. cerevisiae* in pUG6. The DNA cassette HXT7'p-pUG6-PGK1t was PCR amplified having as template pUG6 HXT-PGM2 and using the following primers.

```
2_fwd:
                                        (SEQ ID NO: 101)
5'-TGCAGCCCGGGGATCCTTTTT-3'

2_rev:
                                        (SEQ ID NO: 102)
5'-AGGAATTCTAGATCTCCCATGTCTCT-3'
```

The entire *S. cerevisiae* glucose-6-phosphate isomerase (PGI1) gene was PCR amplified having as template genomic DNA from CEN PK and using the following primers.

PG1_fwd:
(SEQ ID NO: 103)
5'-GATCCCCGGGCTGCAATGTCCAATAACTCATTCACTAACTTCA-3'

PG1_rev:
(SEQ ID NO: 104)
5'-AGATCTAGAATTCCTTCACATCCATTCCTTGAATTG-3'

The two DNA fragments were fused together by In-Fusion cloning (Clontech, California, Calif., USA). The resulting plasmid was named pC5e0060. Correct orientations and sequences of the inserts were verified by restriction analysis and sequencing.

Construction of C5LTe1054 Overexpressing the Gene Coding for PGI1 and Capable of Growing on Solely Xylose Plasmid pC5e0060 was digested with restriction enzyme Kpnl within the PGI1 gene and it was thereafter transformed into strain C5LTe1035. This resulted in strain C5LTe1054.

Example 22: Construction of an *S. cerevisiae* Strain Overexpressing a 6-Phosphofructo-2-Kinase Three of the Genes in the Pentose Phosphate Pathway and a Xylulose Kinase (XK) Gene and Expressing a *Scheffersomyces stipitis* Xylitol Dehydrogenase (XDH) Gene and a Mutated *Scheffersomyces stipitis* Xylose Reductase (XR(N272D)) Gene In this example, the strains, media and genetic techniques described above were used, except that yeast strains were transformed with the lithium acetate method (Gietz and Schiestl, 2007) and transformed yeast strains were selected on YPD plates containing 500 μg mL-1 geneticin (Gibco Invitrogen, Paisley, UK).

Construction of pC5e0060 Containing a *S. cerevisiae* 6-Phosphofructo-2-Kinase (PFK26) Gene Plasmid pUG6 HXT-PGM2 (WO2010/059095 A1) contains the truncated HXT7' promoter and the PGK1terminator from *S. cerevisiae* in pUG6. The DNA cassette HXT7'p-pUG6-PGK1t was PCR amplified having as template pUG6 HXT-PGM2 and using the following primers.

```
2_fwd:
                                        (SEQ ID NO: 105)
5'-TGCAGCCCGGGGATCCTTTTT-3'

2_rev:
                                        (SEQ ID NO: 106)
5'-AGGAATTCTAGATCTCCCATGTCTCT-3'
```

The entire *S. cerevisiae* 6-phosphofructo-2-kinase (PFK26) gene was PCR amplified having as template genomic DNA from CEN PK and using the following primers.

PF26_fwd:
(SEQ ID NO: 107)
5'-GATCCCCGGGCTGCAATGTTCAAACCAGTAGACTTCTCTGA-3'

PF26_rev:
(SEQ ID NO: 108)
5'-AGATCTAGAATTCCTTTAAACGTGACTTTGGCTGC-3'

The two DNA fragments were fused together by In-Fusion cloning (Clontech, California, Calif., USA). The resulting plasmid was named pC5e0061. Correct orientations and sequences of the inserts were verified by restriction analysis and sequencing.

Construction of C5LTe1055 Overexpressing the Gene Coding for PFK26 and Capable of Growing on Solely Xylose Plasmid pC5e0061 was digested with restriction enzyme Kpnl within the PFK26 gene and it was thereafter transformed into strain C5LTe1035. This resulted in strain C5LTe1055.

Example 23: Anaerobic Growth on Xylose

Yeast strains were analysed for anaerobic growth on xylose in 96-well microplate yeast cultures. Prior to experiments, yeast was grown in semi-aerobic pre-cultures in YNB medium with 50 g/l xylose, in microplates, overnight. For measurement of anaerobic growth, cells were inoculated in 250 μl of the same medium where solution of ergosterol and Tween80® had been added at final concentration of 0.03 and 1.2 g/l, respectively. 50 μl mineral oil was added on top of each well to keep culture anaerobic. 10 μl of pre-cultured cells were added. The growth was followed in Multiskan FC (Thermo Scientific) at 30° C. and growth was measured as increase of OD (620 nm). Data is shown graphically in FIG. 19, FIG. 20, FIG. 21, and FIG. 22.

In conclusion, strains with the gene coding for ENO1 or the gene coding for PFK2 or the gene coding for PGI1 or the gene coding for PFK26 grow faster and more under anaerobic conditions than the control strain without overexpression of any of these four genes.

Example 24: Serum Flask Fermentation

Fermentation Procedure:

Cells aerobically grown overnight on YNB medium supplemented with 20 g/L glucose were used to inoculate a shake flask containing 50 mL of YNB medium supplemented with xylose (70 g/L) as carbon source. When the cells were growing exponentially they were used to inoculate a serum flask containing 30 mL of YNB medium supplemented with xylose (55 g/L) and a solution of ergosterol and Tween80 with final concentration of 0.03 and 1.2 g/l, respectively. 7 ml mineral oil was added on top of each serum flask to keep culture anaerobic. Concentrations of xylose, ethanol, glycerol, and xylitol were determined by high performance liquid chromatography (Waters, Milford, Mass., USA).

The results are shown in Table 8 and FIG. 23. Notably, all chosen strains carrying overexpressed genes consumed more xylose and produced more ethanol than the control strain without overexpressed genes.

TABLE 8

| Strain | Xylose consumed in 140 h (g/L) | Ethanol produced in 140 h (g/L) | Ethanol yield (g EtOH/g consumed xylose) |
|---|---|---|---|
| MC4 | 50 | 22 | 0.43 |
| MC22 | 51 | 18 | 0.35 |
| MC2 | 51 | 18 | 0.36 |
| MC14 | 54 | 20 | 0.37 |
| MC3 | 53 | 21 | 0.40 |
| MC11 | 50 | 18 | 0.36 |
| Control | 36 | 13 | 0.35 |

Example 25: Preparation of Strains Carrying PGM1 and PGM3

Yeast strain C5LTe1101 was constructed by transforming yeast strain TMB 3043 (Karhumaa et al. 2005) in its ura3 locus with a DNA fragment containing URA3 gene, TDH3p-XYL1(N272D)-ADH1t, and PGK1p-XYL2-PGK1t. Selection was made on YNB (Yeast nitrogen base 6,7 g/l and 20 g/l glucose, 20 g/l agar) plates supplemented with 200 mg/L leucine.

C5LTe1101 was transformed with DNA fragments obtained with the following PGM1-specific PCR primers

```
                                   (SEQ ID NO: 143)
5'-CTAGAACTAGTGGATCCCCCATGAACGATAGCCAAAACTGC-3'

                                   (SEQ ID NO: 144)
5'-ATATCGAATTCCTGCAGCCCTTATTGGGGGGAAGTGTATTG-3'
```

and with DNA fragments obtained with the following PGM3-specific PCR primers

```
                                   (SEQ ID NO: 145)
5'-CTAGAACTAGTGGATCCCCCATGTTGCAAGGAATTTTAGAAACC

G-3'

                                   (SEQ ID NO: 146)
5'-ATATCGAATTCCTGCAGCCCTCAAAATTTTGTAACTATATTCATTT

CATCTG-3'
```

together with the plasmid p245GPD (Mumberg et al) linearized with SmaI. Selection was made on YNB agar plates 5 with 20 g/l glucose as a carbon source. Selected colonies were tested by colony PCR and clones with PCR-products indicating right size of plasmid insert were chosen.

The nucleic acid and amino acid sequences of PGM1 are shown as SEQ ID NOs: 147 and 148, respectively. The nucleic acid and amino acid sequences of PGM3 are shown as SEQ ID NOs: 149 and 150, respectively.

Example 26: Anaerobic Growth of Strains Carrying PGM1 and PGM3

Figure 24:
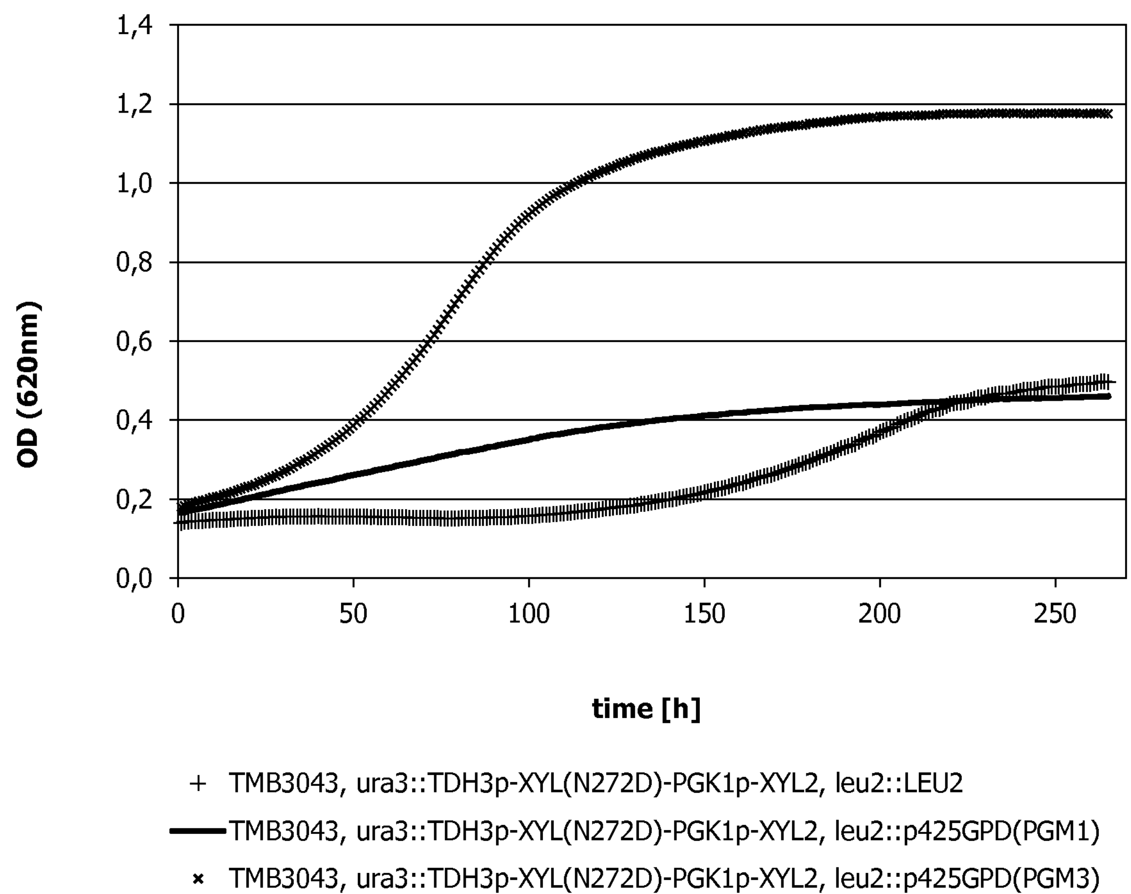
FIG. 24: Graphic representation of anaerobic growth on xylose of control strain and strains carrying PGM1 and PGM3.

Yeast strains obtained in Example 25 were analysed for anaerobic growth on xylose in 96-well microplate yeast cultures. Prior to experiments, yeast was grown in semi-aerobic pre-cultures in YNB medium with 50 g/l xylose, in microplates, overnight. For measurement of anaerobic growth, cells were inoculated in 250 μl of the same medium where a solution of ergosterol and Tween80 had been added at final concentration of 0.03 and 1.2 g/l, respectively. 50 μl mineral oil was added on top of each well to keep the cultures anaerobic. 10 μl of pre-cultured cells were added. The growth was followed in Multiskan FC (Thermo Scientific) at 30° C. and growth was measured as increase of OD (620 nm). The growth curves are presented in FIG. 24.

Example 27: Small Scale Fermentation of Strains Carrying PGM1 and PGM3

Cells aerobically grown overnight on YNB medium supplemented with 20 g/L glucose were used to inoculate a serum flask containing 30 mL of YNB medium supplemented with glucose (20 g/L) and xylose (50 g/L) as carbon source and formic acid (4.5 g/L) at initial concentration of 1 g CDW/L.

Figure 25:
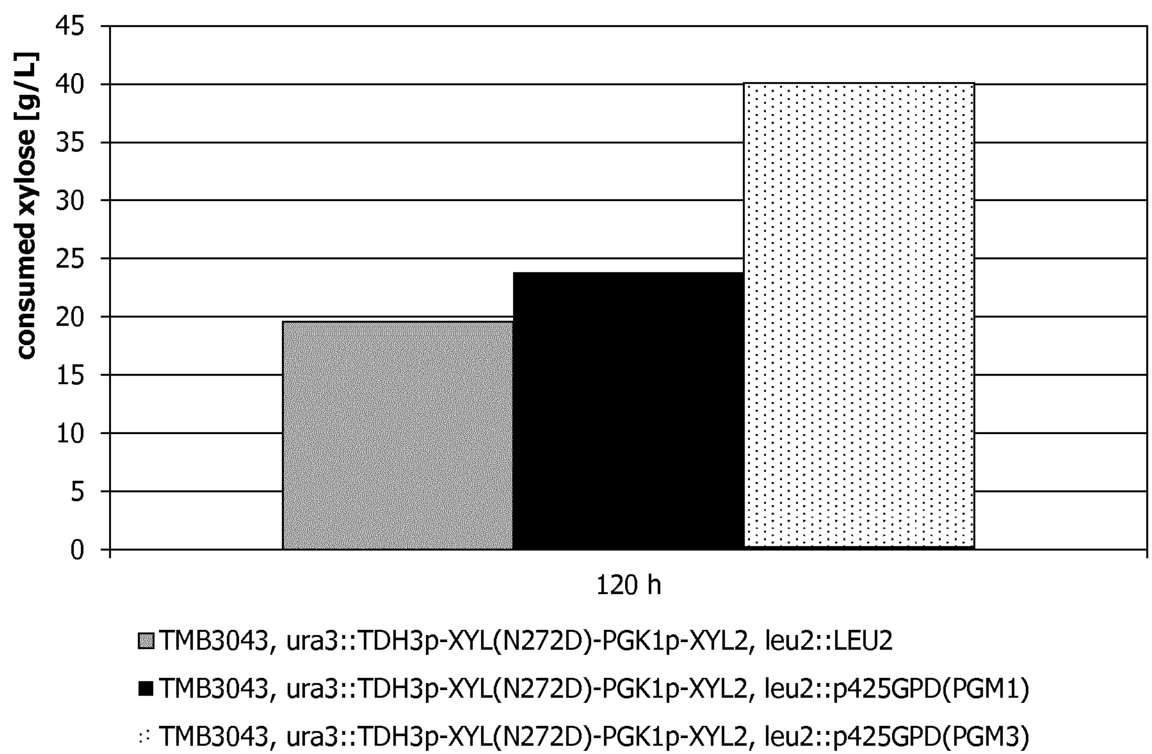
FIG. 25: Graphic representation of consumed xylose after fermentation in mineral medium for 120 h with control strain and strains carrying PGM1 and PGM3.
Figure 26:
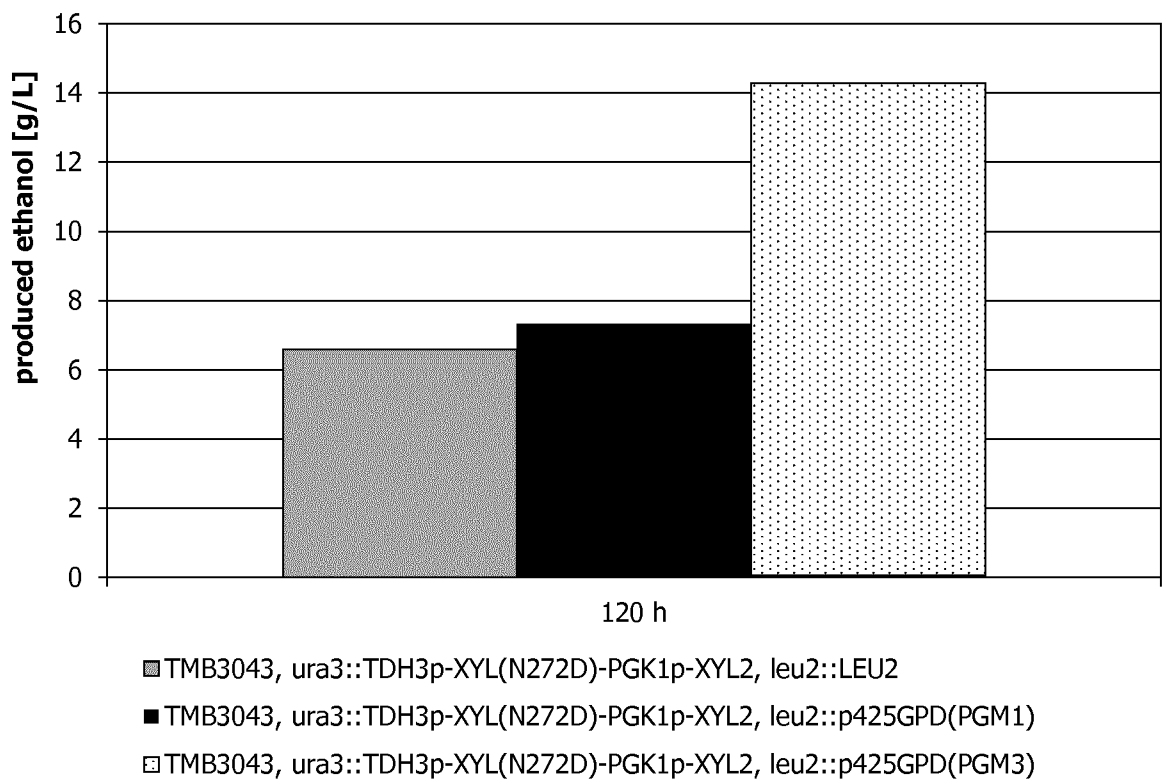
FIG. 26: Graphic representation of produced ethanol after fermentation in mineral medium for 120 h with control strain and strains carrying PGM1 and PGM3.

Concentrations of glucose, xylose, ethanol, glycerol, and xylitol were determined by high performance liquid chromatography (Waters, Milford, Mass., USA). The compounds were separated with a Shodex SUGAR SP0810 Pb2+ copolymer-based column (Showa Denko America, NY, USA) preceded by a Micro-Guard Carbo-C guard column (Bio-Rad, Hercules, Calif., USA). Separation was performed at 80° C., with H2O at a flow rate of 0.6 ml min-1 as mobile phase. Compounds were quantified by refractive index detection (Waters). A seven-point calibration curve was made for each compound to calculate concentrations. Results are presented graphically in FIG. 25 (xylose consumption) and FIG. 26 (ethanol production) as well as in Table 4.

In conclusion, these data show that strains carrying PGM1 or PGM3 consumed more xylose and produced more ethanol than the control strain.

REFERENCES

All references cited herein are incorporated by reference in their entirety. To the extent publications and patents or patent applications incorporated by reference contradict the invention contained in the description, the latter supersedes any contradictory material.

Ausubel et al., Short Protocols in Molecular Biology, 3rd ed., Wiley & Sons, 1995.

Chang and Ho, Appl Biochem Biotechnol. 1988, 17, 313-318.

Eliasson et al., Enzyme and Microbial Technology (2001) 29:288-297.

Gietz and Schiestl, Nature protocols (2) (2007) 31-34.

Hou, Appl Microbiol Biotechnol (2012) 94:205-214.

Inoue et al., Gene 96 (1) (1990) 23-28.

Jin et al., App Environmental Microbiol (2003) 69(1):495-503.

Johansson and Hahn-Hagerdal, Yeast 19 (3) (2002) 225-231.

Johansson et al., Appl Environmental Microbiol (2001) 67(9):4249-4255.

Karhumaa et al., Microb Cell Fact. (2007) 5; 6:5.

Karhumaa et al., Yeast (2005) 22(5):359-68.

Karhumaa et al., Yeast 2009; 26(7):371-82.

Kim et al., Biotechnol Adv. (2013) 31(6):851-61.

Kuyper et al. FEMS Yeast Res. (2005) 5(4-5):399-409.

Linden T, Peetre J, Hahn-Hägerdal B. (1992) Appl Environ Microbiol. 58(5):1661-9.

Lönn et al., Enzyme Microb. Technol. 32 (5) (2003) 567-573.

Madhavan et al., Appl Microbiol Biotechnol. 2009, 82(6), 1067-1078.

Matsushika et al, Enzyme and Microbial Technology (2011) 48:466-471.

Mollapour M, Piper P W. Mol Microbiol. (2001) 42(4):919-30.

Mumberg D, Müller R, Funk M. Gene. 1995 Apr. 14; 156(1):119-22.
Needleman and Wunsch, J. Mol. Biol. (1970), 48:443-453.
Nguyen et al., Mycological Res (2006) 110:1232-1241.
Parachin et al., Metabolic Engineering (2011) 13:508-517.
Rice et al., *Trends Genet* 2000, 16:276-277.
Runquist et al., Appl. Environ. Microbiol. 76 (23) (2010) 7796-7802.
Shamanna and Sanderson, J. Bacteriol. 139 (1979) 64-70.
Tiwari et al., Biochemical and Biophysical Research Communications 366 (2008) 340-345.
Walther et al. FEBS Lett. 2012 Nov. 30; 586(23):4114-8.
Wohlbach et al., Proc Natl Acad Sci USA (2011) 108(32): 13212-7).
Xu et al., Mol Syst Biol 9 (2013) 665.
US 2009/0246857
US 2012/270289 A1
WO 2009/017441
WO 2010/059095
WO 2012/135110
WO 95/13362

SEQUENCES

SEQ ID NO: 5—Artificial *Spathaspora passalidarum* XK Gene

Artificial *Spathaspora passalidarum* XK gene with TPI1 promoter before the ATG-start codon and PGK1terminator after the stop-codon, and coding region based on the amino acid sequence from NCBI Accession Code XP_007373112:

```
TATATCTAGGAACCCATCAGGTTGGTGGAAGATTACCCGTTCTAAGACTT
TTCAGCTTCCTCTATTGATGTTACACCTGGACACCCCTTTTCTGGCATCC
AGTTTTTAATCTTCAGTGGCATGTGAGATTCTCCGAAATTAATTAAAGCA
ATCACACAATTCTCTCGGATACCACCTCGGTTGAAACTGACAGGTGGTTT
GTTACGCATGCTAATGCAAAGGAGCCTATATACCTTTGGCTCGGCTGCTG
TAACAGGGAATATAAAGGGCAGCATAATTTAGGAGTTTAGTGAACTTGCA
ACATTTACTATTTTCCCTTCTTACGTAAATATTTTTCTTTTTAATTCTAA
ATCAATCTTTTTCAATTTTTTGTTTGTATTCTTTTCTTGCTTAAATCTAT
AACTACAAAAAACACATACATAAACTAAAAATGACAGTAGAACTACCCGC
TTCAGAACCTTTGTTTCTTGGGTTTGATCTTAGCACTCAACAGTTGAAAA
TCATAGTGACAAACCAGAAATTAGCTGCACTAAAATCTTACAACGTTGAA
TTCGATGTGGCATTTAAGGAGAAATATGGGATAACCAAGGGAGTCCTAAC
GAACAAAGAGGACGGAGAAGTGGTTTCTCCAGTTGGTATGTGGTTAGATT
CCATAAACCATGTATTCGACCAAATGAAACAAGATGACTTTCCGTTCAAT
CAAGTTGCAGGCATTTCAGGCTCTTGTCAACAACATGGTTCTGTGTTTTG
GTCACATGAAGCTGAGAAGCTTTTATCAGGTTTACAGAAGGATCAAGATC
TGTCGACTCAACTAAAGGACGCTTTATCTTGGGACAAAAGTCCCAATTGG
CAAGATCATTCGACTTTAGAGGAAAGTAAGGCTTTCGTAGATGCTGTAGG
GAGGGAAGAGTTAGCCGATATTACTGGTAGTAGAGATCACTTAAGATTCA
CTGGATTGCAAATTAGGAAGTTTGCCACTAGATCACATCCCGATAAGTAT
GCGAATACTAGTAGAATCTCACTGGTTAGCTCCTTCATAACAAGTGTTCT
```

-continued

```
TCTGGGTGAGATTACCGAATTGGAAGAATCTGATGCTTGTGGCATGAACT
TGTATGACATCAAAGCCGGTGATTTCAATGAAGAATTGTTGGCTCTAGCA
GCCGGTGTTCATCCTAAAGTTGACAACATAACGAAAGATGATCCGAAATA
TAAAGCCGGAATTGAGGACATCAAAGCGAAACTTGGGAAGATCTCCCCAA
TTACATATAAAAGCTCCGGATCCATTGCTTCATATTACGTTGAAAAGTAC
GGTTTGAATCCTAAGTGCCAGATTTACAGCTTTACCGGTGACAATTTGGC
TACAATCTTGAGTTTGCCATTACAGCCTAACGATTGCTTGATTTCGTTAG
GTACTTCGACTACGGTCTTGCTAATCACTAAGAATTACCAACCTTCTTCT
CAATATCACTTGTTTAAGCATCCAACCATACCAGATGGATATATGGGCAT
GATCTGCTATTGCAATGGCTCTTTGGCCAGAGAGAAGATAAGAGATGAAG
TTAATGAATACTATAAGGTGGAAGATAAGAAGAGTTGGGATAAATTTAGT
GAAATTCTGGATAAGTCGACCAAATTCGATAATAAGCTGGGTATTTTCTT
TCCGTTAGGTGAAATCGTTCCACAGGCAAAGGCACAAACTGTCAGAGCAG
TATTGGAGAATGACAAAGTCATAGAAGTAGGTTTGGATACACACGGATTT
GATATTGATCACGACGCAAGAGCTATTGTCGAAAGCCAAGCCTTATCTTG
TAGACTTAGAGCTGGCCCTATGTTATCCAAATCATCACGTGCTTCCGTCA
CATCACCAACGGAGTTAAAAGGCGTATACCATGACATAGTGGCCAAATAT
GGTGACCTGTACACAGATGGTAAACAACAAACCTATGAGTCACTTACATC
TAGGCCAAATCGTTGTTTCTATGTTGGCGGCGGGAGCAATAACATTTCCA
TCATTAGTAAAATGGGTTCTATTCTAGGTCCTGTTCACGGTAACTTTAAA
GTCGATATTCCAAACGCGTGTTCTCTAGGTGGAGCATACAAAGCATCCTG
GTCTTATGAATGTGAACAGAAAGGTGAATGGATTAATTATGACCAATACA
TAAATCAGTTATTGAAAGAATTGAAGTCATTTAACGTGGAGGACAAATGG
TTAGAATACTTTGATGGAGTTGCGCTTTTGGCTAAGATGGAAGAAACCCT
GTTGAAATAAAGATCTCCCATGTCTCTACTGGTGGTGGTGCTTCTTTGGA
ATTATTGGAAGGTAAGGAATTGCCAGGTGTTGCTTTCTTATCCGAAAAGA
AATAAATTGAATTGAATTGAAATCGATAGATCAATTTTTTTCTTTTCTCT
TTCCCCATCCTTTACGCTAAAATAATAGTTTATTTTATTTTTTGAATATT
TTTTATTTATATACGTATATATAGACTATTATTTATCTTTTAATGATTAT
TAAGATTTTTATTAAAAAAAAATTCGCTCCTCTTTTAATGCCTTTATGCA
GTTTTTTTTTCCCATTCGATATTTCTATGTTC
```

SEQ ID NO: 6—*Spathaspora passalidarum* XK

```
MTVELPASEPLFLGFDLSTQQLKIIVTNQKLAALKSYNVEFDVAFKEKYG
ITKGVLTNKEDGEVVSPVGMWLDSINHVFDQMKQDDFPFNQVAGISGSCQ
QHGSVFWSHEAEKLLSGLQKDQDLSTQLKDALSWDKSPNWQDHSTLEESK
AFVDAVGREELADITGSRDHLRFTGLQIRKFATRSHPDKYANTSRISLVS
SFITSVLLGEITELEESDACGMNLYDIKAGDFNEELLALAAGVHPKVDNI
TKDDPKYKAGIEDIKAKLGKISPITYKSSGSIASYYVEKYGLNPKCQIYS
FTGDNLATILSLPLQPNDCLISLGTSTTVLLITKNYQPSSQYHLFKHPTI
PDGYMGMICYCNGSLAREKIRDEVNEYYKVEDKKSWDKFSEILDKSTKFD
```

-continued

```
NKLGIFFPLGEIVPQAKAQTVRAVLENDKVIEVGLDTHGFDIDHDARAIV
ESQALSCRLRAGPMLSKSSRASVTSPTELKGVYHDIVAKYGDLYTDGKQQ
TYESLTSRPNRCFYVGGGSNNISIISKMGSILGPVHGNFKVDIPNACSLG
GAYKASWSYECEQKGEWINYDQYINQLLKELKSFNVEDKWLEYFDGVALL
AKMEETLLK
```

SEQ ID NO: 17—Artificial *Escherichia coli* Xylulose Kinase Gene

Artificial *Escherichia coli* xylulose kinase gene with TPI1 promoter before the ATG-start codon and the PGK1terminator after the stop-codon, and coding region based on the amino acid sequence from NCBI Accession Code YP_001460359:

```
TATATCTAGGAACCCATCAGGTTGGTGGAAGATTACCCGTTCTAAGACTT
TTCAGCTTCCTCTATTGATGTTACACCTGGACACCCCTTTTCTGGCATCC
AGTTTTTAATCTTCAGTGGCATGTGAGATTCTCCGAAATTAATTAAAGCA
ATCACACAATTCTCTCGGATACCACCTCGGTTGAAACTGACAGGTGGTTT
GTTACGCATGCTAATGCAAAGGAGCCTATATACCTTTGGCTCGGCTGCTG
TAACAGGGAATATAAAGGGCAGCATAATTTAGGAGTTTAGTGAACTTGCA
ACATTTACTATTTTCCCTTCTTACGTAAATATTTTTCTTTTTAATTCTAA
ATCAATCTTTTTCAATTTTTTGTTTGTATTCTTTTCTTGCTTAAATCTAT
AACTACAAAAAACACATACATAAACTAAAAATGTATATCGGCATTGATTT
GGGTACTTCTGGCGTAAAGGTTATCCTGCTGAATGAACAGGGTGAAGTGG
TTGCCTCACAAACGGAAAAGTTGACTGTATCTAGGCCACATCCTTTGTGG
AGCGAACAAGATCCAGAACAGTGGTGGCAAGCTACAGATAGAGCAATGAA
AGCGTTAGGTGACCAGCATTCCTTACAGGACGTTAAAGCCTTGGGGATTG
CTGGCCAAATGCATGGTGCGACACTGCTTGATGCCCAACAAAGGGTCTTA
AGGCCTGCAATACTGTGGAATGATGGACGTTGTGCTCAGGAGTGTACCTT
ATTGGAAGCAAGAGTGCCTCAATCCAGGGTGATAACCGGTAACTTGATGA
TGCCTGGATTTACAGCCCCAAAATTGTTATGGGTTCAAAGACACGAACCA
GAGATCTTCCGTCAAATCGACAAGGTCTTATTACCGAAGGACTACTTGAG
ACTACGTATGACTGGTGAATTCGCTTCAGACATGAGTGACGCAGCAGGAA
CCATGTGGTTGGATGTCGCGAAAAGAGATTGGAGTGACGTTATGTTACAA
GCTTGCGATCTATCTAGAGATCAAATGCCAGCTCTGTATGAGGGCTCAGA
AATTACCGGTGCATTATTACCTGAAGTCGCTAAAGCATGGGGTATGGCTA
CTGTCCCAGTTGTTGCCGGTGGTGGTGACAATGCCGCAGGAGCTGTTGGA
GTTGGTATGGTGGATGCAAATCAAGCGATGTTGTCTCTTGGCACATCAGG
CGTCTATTTTGCCGTATCGGAAGGGTTTCTGTCGAAACCAGAATCAGCCG
TACATTCCTTTTGTCACGCTCTTCCACAAAGATGGCATCTAATGAGCGTG
ATGCTTTCTGCAGCATCATGCTTGGATTGGGCCGCTAAATTGACGGGTTT
GAGTAATGTTCCGGCACTTATAGCAGCTGCACAACAAGCAGATGAAAGTG
CTGAACCCGTTTGGTTCTTGCCCTATCTTTCCGGAGAGAGAACACCACAC
AACAATCCTCAAGCCAAAGGTGTGTTCTTTGGGTTAACTCACCAACATGG
TCCAAACGAATTGGCGAGAGCAGTATTGGAAGGAGTAGGGTATGCTCTTG
CTGATGGTATGGATGTTGTCCATGCATGTGGCATAAAGCCGCAATCTGTT
ACGCTTATTGGAGGTGGTGCCAGAAGCGAATACTGGAGACAAATGTTAGC
CGATATTTCCGGTCAACAACTAGACTACAGAACAGGAGGCGATGTAGGGC
CAGCTTTGGGTGCTGCTAGATTGGCTCAGATTGCTGCTAACCCTGAGAAG
TCGTTGATTGAGCTACTACCTCAGTTACCCTTAGAACAGTCTCATCTACC
AGATGCCCAGAGATATGCTGCGTACCAACCTAGAAGAGAGACTTTTCGTA
GGTTATACCAGCAATTACTACCCTTGATGGCGTAAAGATCTCCCATGTCT
CTACTGGTGGTGGTGCTTCTTTGGAATTATTGGAAGGTAAGGAATTGCCA
GGTGTTGCTTTCTTATCCGAAAAGAAATAAATTGAATTGAATTGAAATCG
ATAGATCAATTTTTTTCTTTTCTCTTTCCCCATCCTTTACGCTAAAATAA
TAGTTTATTTTATTTTTTGAATATTTTTTATTTATATACGTATATATAGA
CTATTATTTATCTTTTAATGATTATTAAGATTTTTATTAAAAAAAAATTC
GCTCCTCTTTTAATGCCTTTATGCAGTTTTTTTTTCCCATTCGATATTTC
TATGTTC
```

SEQ ID NO: 18—*Escherichia coli* Xylulose Kinase

```
MYIGIDLGTSGVKVILLNEQGEVVASQTEKLTVSRPHPLWSEQDPEQWWQ
ATDRAMKALGDQHSLQDVKALGIAGQMHGATLLDAQQRVLRPAILWNDGR
CAQECTLLEARVPQSRVITGNLMMPGFTAPKLLWVQRHEPEIFRQIDKVL
LPKDYLRLRMTGEFASDMSDAAGTMWLDVAKRDWSDVMLQACDLSRDQMP
ALYEGSEITGALLPEVAKAWGMATVPVVAGGGDNAAGAVGVGMVDANQAM
LSLGTSGVYFAVSEGFLSKPESAVHSFCHALPQRWHLMSVMLSAASCLDW
AAKLTGLSNVPALIAAAQQADESAEPVWFLPYLSGERTPHNNPQAKGVFF
GLTHQHGPNELARAVLEGVGYALADGMDVVHACGIKPQSVTLIGGGARSE
YWRQMLADISGQQLDYRTGGDVGPALGAARLAQIAANPEKSLIELLPQLP
LEQSHLPDAQRYAAYQPRRETFRRLYQQLLPLMA
```

SEQ ID NO: 21—*Kluyveromyces marxianus* Xylulose Kinase Gene

Artificial *Kluyveromyces marxianus* xylulose kinase gene, with coding region based on the amino acid sequence from NCBI Accession Code ADW23548:

```
ATGTCGACTCCATATTACTTAGGCTTTGATTTGTCAACTCAGCAGTTGAA
ATGTCTAGCAATAGATGATCAGTTAAACATCGTGACTTCAGTTAGCATTG
AATTTGACCGTAATTTCCCAGCTTACAACACAAAGAAAGGGGTATACATC
AAGAATGGTGGTGTGATAGACGCACCAGTTGCTATGTGGTTAGAAGCTGT
TGATTTATGCTTTAGTCAGCTTGCTGAAAGAATCGACTTGAAGAGAGTTC
AATCAATGTCAGGTTCTTGCCAACAACATGGCACCGTCTACTGGAACTGT
GAGCATCTACCAAGTAACCTTGATCCTGCTTCAACCTTGAGAGAGCAACT
TCAAGGCAGTTTATCAAGACCAGTTGCACCCAATTGGCAAGATCATTCCA
CCAAGAAACAATGTGATGAATTGGCAGAATCGGTAGGAGGACCTGAAGAA
CTAGCAAGGATTACAGGTTCTGGAGCACACTATAGATTTTCCGGTTCCCA
```

-continued

AATTGCCAAAATCCATGAAACTGAACCTGAAGTCTATGAGGCTACTAAAC
GTATTTCGTTGGTAAGTAGCTTTCTAGCGTCTGTTTTAGTAGGTGACATT
GTGCCCTTGGAAGAAGCGGATGCTTGTGGCATGAACTTATACGATCTATC
CAAACACGACTTTGACGAAACATTACTGGCTGTCGTTGACCATGATACAG
CGAGATTGAGAAGGAAACTATCAGATCCACCCGTTGGAGCTCCTACCAGA
GAAAGTCCTCTGACCTCCTTGGGTAAAGTCTCTAAGTACTTTCAGGACAA
ATATGGGGTTAACTGTGAATGTGAGATCTTCCCGTTTACTGGCGATAACC
TGGCAACGATTTGTTCCCTACCTTTGCAAAAGAATGATGTCTTGATTAGT
CTAGGTACTTCGACCACGATTTTGTTGGTAACTGACCAATATCACTCTTC
TCCCAATTATCACTTGTTTATACATCCGACAGTGCCAGGTTATTACATGG
GTATGATTTGCTATTGCAATGGGTCTTTGGCTCGTGAGAGAGTAAGAGAT
GATCTGGCTGGACCACAAGCCTCTCAAGCTCCTGGGGAGCAAGTTCCATG
GACTCAATTCAATGACGCATTACTGGATGACTCATTGAGCAATGACAATG
AGATAGGCCTTTACTTCCCTCTTGGTGAGATTGTCCCAAATGTTGATGCC
GTCACCAAAAGATGGACATTCGAAAGAAAAGAGAACCATTCGAACAAAAG
TATCGTTCTTCACGAGTTGGATCAATTCACGCCAAAGAGGAAAGATGCAA
AGAACATAGTGGAAAGTCAGGCCTTAAGCTGTAGAGTGCGTATCTCTCCA
TTGCTGTCTGATGAAACAGATGCCTTAAGCGAAACTCAAGTGTTGTCAAA
GAAGGAGAATACCCAAGTTACGTTTGACTACGATGCATTTCCGTTGTGGA
CGTATGCCAAAAGACCGAATAGAGCGTTCTTTGTTGGTGGTGCCTCCAAG
AATGATGCCATAGTCAGGACAATGGCAAATGTAATAGGTGCTAGGAATGG
AAATTATAGACTTGAAACTCCCAATTCCTGTGCTTTAGGAGGCTGTTATA
AAGCGATGTGGTCATGGTTAAAGGTACATGAACCTACAACTACACCATCT
TTCGATGTTTGGTTAAACGCAAGCTTTAACTGGCAGAGAGATTGCGAATT
CGTGTGCCAGTCTGACGCCGCTAAGTGGGAACAATCTAATGGTAAAATTC
AAGCTTTATCAGAAGCTGAAGCCTATGTTAAAGCTTTAGCACAATCTCAG
GGTCAA

SEQ ID NO: 22—*Kluyveromyces marxianus* Xylulose Kinase

MSTPYYLGFDLSTQQLKCLAIDDQLNIVTSVSIEFDRNFPAYNTKKGVYI
KNGGVIDAPVAMWLEAVDLCFSQLAERIDLKRVQSMSGSCQQHGTVYWNC
EHLPSNLDPASTLREQLQGSLSRPVAPNWQDHSTKKQCDELAESVGGPEE
LARITGSGAHYRFSGSQIAKIHETEPEVYEATKRISLVSSFLASVLVGDI
VPLEEADACGMNLYDLSKHDFDETLLAVVDHDTARLRRKLSDPPVGAPTR
ESPLTSLGKVSKYFQDKYGVNCECEIFPFTGDNLATICSLPLQKNDVLIS
LGTSTTILLVTDQYHSSPNYHLFIHPTVPGYYMGMICYCNGSLARERVRD
DLAGPQASQAPGEQVPWTQFNDALLDDSLSNDNEIGLYFPLGEIVPNVDA
VTKRWTFERKENHSNKSIVLHELDQFTPKRKDAKNIVESQALSCRVRISP
LLSDETDALSETQVLSKKENTQVTFDYDAFPLWTYAKRPNRAFFVGGASK
NDAIVRTMANVIGARNGNYRLETPNSCALGGCYKAMWSWLKVHEPTTTPS

-continued

FDVWLNASFNWQRDCEFVCQSDAAKWEQSNGKIQALSEAEAYVKALAQSQ
GQ

SEQ ID NO: 31—*Saccharomyces cerevisiae* Xylulokinase Gene (XKS1)

ATGTTGTGTTCAGTAATTCAGAGACAGACAAGAGAGGTTTCCAACACAAT
GTCTTTAGACTCATACTATCTTGGGTTTGATCTTTCGACCCAACAACTGA
AATGTCTCGCCATTAACCAGGACCTAAAAATTGTCCATTCAGAAACAGTG
GAATTTGAAAAGGATCTTCCGCATTATCACACAAAGAAGGGTGTCTATAT
ACACGGCGACACTATCGAATGTCCCGTAGCCATGTGGTTAGAGGCTCTAG
ATCTGGTTCTCTCGAAATATCGCGAGGCTAAATTTCCATTGAACAAAGTT
ATGGCCGTCTCAGGGTCCTGCCAGCAGCACGGGTCTGTCTACTGGTCCTC
CCAAGCCGAATCTCTGTTAGAGCAATTGAATAAGAAACCGGAAAAAGATT
TATTGCACTACGTGAGCTCTGTAGCATTTGCAAGGCAAACCGCCCCCAAT
TGGCAAGACCACAGTACTGCAAAGCAATGTCAAGAGTTTGAAGAGTGCAT
AGGTGGGCCTGAAAAAATGGCTCAATTAACAGGGTCCAGAGCCCATTTTA
GATTTACTGGTCCTCAAATTCTGAAAATTGCACAATTAGAACCAGAAGCT
TACGAAAAAACAAAGACCATTTCTTTAGTGTCTAATTTTTTGACTTCTAT
CTTAGTGGGCCATCTTGTTGAATTAGAGGAGGCAGATGCCTGTGGTATGA
ACCTTTATGATATACGTGAAAGAAAATTCAGTGATGAGCTACTACATCTA
ATTGATAGTTCTTCTAAGGATAAAACTATCAGACAAAAATTAATGAGAGC
ACCCATGAAAAATTTGATAGCGGGTACCATCTGTAAATATTTTATTGAGA
AGTACGGTTTCAATACAAACTGCAAGGTCTCTCCCATGACTGGGGATAAT
TTAGCCACTATATGTTCTTTACCCCTGCGGAAGAATGACGTTCTCGTTTC
CCTAGGAACAAGTACTACAGTTCTTCTGGTCACCGATAAGTATCACCCCT
CTCCGAACTATCATCTTTTCATTCATCCAACTCTGCCAAACCATTATATG
GGTATGATTTGTTATTGTAATGGTTCTTTGGCAAGGGAGAGGATAAGAGA
CGAGTTAAACAAAGAACGGGAAAATAATTATGAGAAGACTAACGATTGGA
CTCTTTTTAATCAAGCTGTGCTAGATGACTCAGAAAGTAGTGAAAATGAA
TTAGGTGTATATTTTCCTCTGGGGGAGATCGTTCCTAGCGTAAAAGCCAT
AAACAAAAGGGTTATCTTCAATCCAAAAACGGGTATGATTGAAAGAGAGG
TGGCCAAGTTCAAAGACAAGAGGCACGATGCCAAAAATATTGTAGAATCA
CAGGCTTTAAGTTGCAGGGTAAGAATATCTCCCCTGCTTTCGGATTCAAA
CGCAAGCTCACAACAGAGACTGAACGAAGATACAATCGTGAAGTTTGATT
ACGATGAATCTCCGCTGCGGGACTACCTAAATAAAAGGCCAGAAAGGACT
TTTTTTGTAGGTGGGGCTTCTAAAAACGATGCTATTGTGAAGAAGTTTGC
TCAAGTCATTGGTGCTACAAAGGGTAATTTTAGGCTAGAAACACCAAACT
CATGTGCCCTTGGTGGTTGTTATAAGGCCATGTGGTCATTGTTATATGAC
TCTAATAAAATTGCAGTTCCTTTTGATAAATTTCTGAATGACAATTTTCC
ATGGCATGTAATGGAAAGCATATCCGATGTGGATAATGAAAATTGGGATC

-continued

GCTATAATTCCAAGATTGTCCCCTTAAGCGAACTGGAAAAGACTCTCATC

TAA

SEQ ID NO: 32—*Saccharomyces cerevisiae* Xylulokinase

MLCSVIQRQTREVSNTMSLDSYYLGFDLSTQQLKCLAINQDLKIVHSETV

EFEKDLPHYHTKKGVYIHGDTIECPVAMWLEALDLVLSKYREAKFPLNKV

MAVSGSCQQHGSVYWSSQAESLLEQLNKKPEKDLLHYVSSVAFARQTAPN

WQDHSTAKQCQEFEECIGGPEKMAQLTGSRAHFRFTGPQILKIAQLEPEA

YEKTKTISLVSNFLTSILVGHLVELEEADACGMNLYDIRERKFSDELLHL

IDSSSKDKTIRQKLMRAPMKNLIAGTICKYFIEKYGFNTNCKVSPMTGDN

LATICSLPLRKNDVLVSLGTSTTVLLVTDKYHPSPNYHLFIHPTLPNHYM

GMICYCNGSLARERIRDELNKERENNYEKTNDWTLFNQAVLDDSESSENE

LGVYFPLGEIVPSVKAINKRVIFNPKTGMIEREVAKFKDKRHDAKNIVES

QALSCRVRISPLLSDSNASSQQRLNEDTIVKFDYDESPLRDYLNKRPERT

FFVGGASKNDAIVKKFAQVIGATKGNFRLETPNSCALGGCYKAMWSLLYD

SNKIAVPFDKFLNDNFPWHVMESISDVDNENWDRYNSKIVPLSELEKTLI

*

SEQ ID NO: 49—Codon Optimized *Zygosaccharomyces bailii* YME2 Gene

ATGTTGCCCATTTCTGGACCTTCCAACATGCTGCATGGCCTCGTTTCAGC

CCGTTGTGCAGGGGGTTGGAGGCCACTTATCTCGCATTTGCGTAGGGGAG

TTTTTCCTAAGATGCTTACCATGACAGGTATTGGGGCCAAGAGATTTGTC

TCCAGCGAAATACAGGAGAAAGACGAACAAGCTGGTGAGTCTACTACTGC

TACAGATACTGGTATCATTCATAAAACGGAGCAGGAGACCCTAGTATATT

TCGACAACGTCTATCCACGGACCGCATCTCTATGGAGCCCTGCGCAATGG

TACAATCTACTTCTAACTAATCAATCGAGGGAGGCTGTTAGGCAAAAGAT

CAGCGGTTCGATCCCGCTAGAGACCATTTTTTGGCTTCATTGA

SEQ ID NO: 50-*Zygosaccharomyces bailii* YME2

MLPISGPSNMLHGLVSARCAGGWRPLISHLRRGVFPKMLTMTGIGAKRFV

SSEIQEKDEQAGESTTATDTGIIHKTEQETLVYFDNVYPRTASLWSPAQW

YNLLLTNQSREAVRQKISGSIPLETIFWLH

SEQ ID NO: 131—*Saccharomyces cerevisiae* ENO1 DNA

ATGGCTGTCTCTAAAGTTTACGCTAGATCCGTCTACGACTCCCGTGGTAA

CCCAACCGTCGAAGTCGAATTAACCACCGAAAAGGGTGTTTTCAGATCCA

TTGTCCCATCTGGTGCTTCTACCGGTGTCCACGAAGCTTTGGAAATGAGA

GATGGTGACAAATCCAAGTGGATGGGTAAGGGTGTTTTGCACGCTGTTAA

GAACGTCAACGATGTCATTGCTCCAGCTTTCGTTAAGGCTAACATTGATG

TTAAGGACCAAAAGGCCGTCGATGACTTCTTGATTTCTTTGGACGGTACT

GCCAACAAATCCAAGTTGGGTGCTAACGCTATCTTGGGTGTTTCTTTGGC

-continued

TGCTTCCAGAGCTGCCGCTGCTGAAAAGAATGTCCCATTATACAAGCACT

TGGCTGACTTGTCTAAGTCCAAGACCTCTCCATACGTTTTGCCAGTTCCA

TTCTTGAACGTTTTGAACGGTGGTTCCCACGCTGGTGGTGCTTTGGCTTT

GCAAGAATTTATGATTGCTCCAACTGGTGCTAAGACCTTCGCTGAAGCTT

TGAGAATTGGTTCCGAAGTTTACCACAACTTGAAGTCTTTGACCAAGAAG

AGATACGGTGCTTCTGCCGGTAACGTCGGTGACGAAGGTGGTGTTGCTCC

AAACATTCAAACTGCTGAAGAAGCTTTGGACTTGATTGTTGACGCTATCA

AGGCTGCTGGTCACGACGGTAAGATCAAGATCGGTTTGGACTGTGCTTCC

TCTGAATTCTTCAAGGACGGTAAGTACGACTTGGACTTCAAGAATCCAAA

CTCTGACAAATCCAAGTGGTTGACTGGTCCTCAATTGGCTGACTTGTACC

ACTCCTTGATGAAGAGATACCCAATTGTCTCCATCGAAGATCCATTTGCT

GAAGATGACTGGGAAGCTTGGTCTCACTTCTTCAAGACCGCTGGTATTCA

AATTGTTGCTGATGACTTGACTGTCACCAACCCAAAGAGAATTGCTACCG

CTATCGAAAAGAAGGCTGCCGACGCTTTGTTGTTGAAGGTCAACCAAATC

GGTACCTTGTCTGAATCCATCAAGGCTGCTCAAGACTCTTTCGCTGCCGG

TTGGGGTGTTATGGTTTCCCACAGATCTGGTGAAACTGAAGACACTTTCA

TTGCTGACTTGGTCGTCGGTTTGAGAACTGGTCAAATCAAGACTGGTGCT

CCAGCTAGATCCGAAAGATTGGCTAAATTGAACCAATTGTTGAGAATCGA

AGAAGAATTAGGTGACAACGCTGTTTTCGCTGGTGAAAACTTCCACCACG

GTGACAAATTATAA

SEQ ID NO: 132—*Saccharomyces cerevisiae* ENO1

MAVSKVYARSVYDSRGNPTVEVELTTEKGVFRSIVPSGASTGVHEALEMR

DGDKSKWMGKGVLHAVKNVNDVIAPAFVKANIDVKDQKAVDDFLISLDGT

ANKSKLGANAILGVSLAASRAAAAEKNVPLYKHLADLSKSKTSPYVLPVP

FLNVLNGGSHAGGALALQEFMIAPTGAKTFAEALRIGSEVYHNLKSLTKK

RYGASAGNVGDEGGVAPNIQTAEEALDLIVDAIKAAGHDGKIKIGLDCAS

SEFFKDGKYDLDFKNPNSDKSKWLTGPQLADLYHSLMKRYPIVSIEDPFA

EDDWEAWSHFFKTAGIQIVADDLTVTNPKRIATAIEKKAADALLLKVNQI

GTLSESIKAAQDSFAAGWGVMVSHRSGETEDTFIADLVVGLRTGQIKTGA

PARSERLAKLNQLLRIEEELGDNAVFAGENFHHGDKL*

SEQ ID NO: 133—*Saccharomyces cerevisiae* PFK2 DNA

ATGACTGTTACTACTCCTTTTGTGAATGGTACTTCTTATTGTACCGTCAC

TGCATATTCCGTTCAATCTTATAAAGCTGCCATAGATTTTTACACCAAGT

TTTTGTCATTAGAAAACCGCTCTTCTCCAGATGAAAACTCCACTTTATTG

TCTAACGATTCCATCTCTTTGAAGATCCTTCTACGTCCTGATGAAAAAAT

CAATAAAAATGTTGAGGCTCATTTGAAGGAATTGAACAGTATTACCAAGA

CTCAAGACTGGAGATCACATGCCACCCAATCCTTGGTATTTAACACTTCC

GACATCTTGGCAGTCAAGGACACTCTAAATGCTATGAACGCTCCTCTTCA

AGGCTACCCAACAGAACTATTTCCAATGCAGTTGTACACTTTGGACCCAT

-continued

```
TAGGTAACGTTGTTGGTGTTACTTCTACTAAGAACGCAGTTTCAACCAAG
CCAACTCCACCACCAGCACCAGAAGCTTCTGCTGAGTCTGGTCTTTCCTC
TAAAGTTCACTCTTACACTGATTTGGCTTACCGTATGAAAACCACCGACA
CCTATCCATCTCTGCCAAAGCCATTGAACAGGCCTCAAAAGGCAATTGCC
GTCATGACTTCCGGTGGTGATGCTCCAGGTATGAACTCTAACGTTAGAGC
CATCGTGCGTTCCGCTATCTTCAAAGGTTGTCGTGCCTTTGTTGTCATGG
AAGGTTATGAAGGTTTGGTTCGTGGTGGTCCAGAATACATCAAGGAATTC
CACTGGGAAGACGTCCGTGGTTGGTCTGCTGAAGGTGGTACCAACATTGG
TACTGCCCGTTGTATGGAATTCAAGAAGCGCGAAGGTAGATTATTGGGTG
CCCAACATTTGATTGAGGCCGGTGTCGATGCTTTGATCGTTTGTGGTGGT
GACGGTTCTTTGACTGGTGCTGATCTGTTTAGATCAGAATGGCCTTCTTT
GATCGAGGAATTGTTGAAAACAAACAGAATTTCCAACGAACAATACGAAA
GAATGAAGCATTTGAATATTTGCGGTACTGTCGGTTCTATTGATAACGAT
ATGTCCACCACGGATGCTACTATTGGTGCTTACTCTGCCTTGGACAGAAT
CTGTAAGGCCATCGATTACGTTGAAGCCACTGCCAACTCTCACTCAAGAG
CTTTCGTTGTTGAAGTTATGGGTAGAAACTGTGGTTGGTTAGCTTTATTA
GCTGGTATCGCCACTTCCGCTGACTATATCTTTATTCCAGAGAAGCCAGC
CACTTCCAGCGAATGGCAAGATCAAATGTGTGACATTGTCTCCAAGCACA
GATCAAGGGGTAAGAGAACCACCATTGTTGTTGTTGCAGAAGGTGCTATC
GCTGCTGACTTGACCCCAATTTCTCCAAGCGACGTCCACAAAGTTCTAGT
TGACAGATTAGGTTTGGATACAAGAATTACTACCTTAGGTCACGTTCAAA
GAGGTGGTACTGCTGTTGCTTACGACCGTATCTTGGCTACTTTACAAGGT
CTTGAGGCCGTTAATGCCGTTTTGGAATCCACTCCAGACACCCCATCACC
ATTGATTGCTGTTAACGAAAACAAAATTGTTCGTAAACCATTAATGGAAT
CCGTCAAGTTGACCAAAGCAGTTGCAGAAGCCATTCAAGCTAAGGATTTC
AAGAGAGCTATGTCTTTAAGAGACACTGAGTTCATTGAACATTTAAACAA
TTTCATGGCTATCAACTCTGCTGACCACAACGAACCAAAGCTACCAAAGG
ACAAGAGACTGAAGATTGCCATTGTTAATGTCGGTGCTCCAGCTGGTGGT
ATCAACTCTGCCGTCTACTCGATGGCTACTTACTGTATGTCCCAAGGTCA
CAGACCATACGCTATCTACAATGGTTGGTCTGGTTTGGCAAGACATGAAA
GTGTTCGTTCTTTGAACTGGAAGGATATGTTGGGTTGGCAATCCCGTGGT
GGTTCTGAAATCGGTACTAACAGAGTCACTCCAGAAGAAGCAGATCTAGG
TATGATTGCTTACTATTTCCAAAAGTACGAATTTGATGGTTTGATCATCG
TTGGTGGTTTCGAAGCTTTTGAATCTTTACATCAATTAGAGAGAGCAAGA
GAAAGTTATCCAGCTTTCAGAATCCCAATGGTCTTGATACCAGCTACTTT
GTCTAACAATGTTCCAGGTACTGAATACTCTTTGGGTTCTGATACCGCTT
TGAATGCTCTAATGGAATACTGTGATGTTGTTAAACAATCCGCTTCTTCA
ACCAGAGGTAGAGCCTTCGTTGTCGATTGTCAAGGTGGTAACTCAGGCTA
TTTGGCCACTTACGCTTCTTTGGCTGTTGGTGCTCAAGTCTCTTATGTCC
CAGAAGAAGGTATTTCTTTGGAGCAATTGTCCGAGGATATTGAATACTTA
GCTCAATCTTTTGAAAAGGCAGAAGGTAGAGGTAGATTTGGTAAATTGAT
TTTGAAGAGTACAAACGCTTCTAAGGCTTTATCAGCCACTAAATTGGCTG
AAGTTATTACTGCTGAAGCCGATGGCAGATTTGACGCTAAGCCAGCTTAT
CCAGGTCATGTACAACAAGGTGGTTTGCCATCTCCAATTGATAGAACAAG
AGCCACTAGAATGGCCATTAAAGCTGTCGGCTTCATCAAAGACAACCAAG
CTGCCATTGCTGAAGCTCGTGCTGCCGAAGAAAACTTCAACGCTGATGAC
AAGACCATTTCTGACACTGCTGCTGTCGTTGGTGTTAAGGGTTCACATGT
CGTTTACAACTCCATTAGACAATTGTATGACTATGAAACTGAAGTTTCCA
TGAGAATGCCAAAGGTCATTCACTGGCAAGCTACCAGACTCATTGCTGAC
CATTTGGTTGGAAGAAAGAGAGTTGATTAA
```

SEQ ID NO: 134—*Saccharomyces cerevisiae* PFK2

```
MTVTTPFVNGTSYCTVTAYSVQSYKAAIDFYTKFLSLENRSSPDENSTLL
SNDSISLKILLRPDEKINKNVEAHLKELNSITKTQDWRSHATQSLVFNTS
DILAVKDTLNAMNAPLQGYPTELFPMQLYTLDPLGNVVGVTSTKNAVSTK
PTPPPAPEASAESGLSSKVHSYTDLAYRMKTTDTYPSLPKPLNRPQKAIA
VMTSGGDAPGMNSNVRAIVRSAIFKGCRAFVVMEGYEGLVRGGPEYIKEF
HWEDVRGWSAEGGTNIGTARCMEFKKREGRLLGAQHLIEAGVDALIVCGG
DGSLTGADLFRSEWPSLIEELLKTNRISNEQYERMKHLNICGTVGSIDND
MSTTDATIGAYSALDRICKAIDYVEATANSHSRAFVVEVMGRNCGWLALL
AGIATSADYIFIPEKPATSSEWQDQMCDIVSKHRSRGKRTTIVVVAEGAI
AADLTPISPSDVHKVLVDRLGLDTRITTLGHVQRGGTAVAYDRILATLQG
LEAVNAVLESTPDTPSPLIAVNENKIVRKPLMESVKLTKAVAEAIQAKDF
KRAMSLRDTEFIEHLNNFMAINSADHNEPKLPKDKRLKIAIVNVGAPAGG
INSAVYSMATYCMSQGHRPYAIYNGWSGLARHESVRSLNWKDMLGWQSRG
GSEIGTNRVTPEEADLGMIAYYFQKYEFDGLIIVGGFEAFESLHQLERAR
ESYPAFRIPMVLIPATLSNNVPGTEYSLGSDTALNALMEYCDVVKQSASS
TRGRAFVVDCQGGNSGYLATYASLAVGAQVSYVPEEGISLEQLSEDIEYL
AQSFEKAEGRGRFGKLILKSTNASKALSATKLAEVITAEADGRFDAKPAY
PGHVQQGGLPSPIDRTRATRMAIKAVGFIKDNQAAIAEARAAEENFNADD
KTISDTAAVVGVKGSHVVYNSIRQLYDYETEVSMRMPKVIHWQATRLIAD
HLVGRKRVD*
```

SEQ ID NO: 135—*Saccharomyces cerevisiae* PFK26 DNA

```
ATGTTCAAACCAGTAGACTTCTCTGAAACATCTCCTGTGCCGCCTGATAT
TGATCTTGCTCCTACACAATCTCCACACCATGTGGCACCTAGTCAAGACT
CCAGTTATGATCTTTTATCCCGGAGTTCCGATGATAAAATTGATGCTGAA
AAGGGTCCGCATGATGAATTATCTAAGCACTTACCACTTTTTCAGAAAAG
ACCTTTGAGCGATACTCCTATATCGAGCAATTGGAACTCTCCTGGAATCA
CTGAAGAAAATACACCTTCTGACTCTCCTGAAAATAGCGCTACTAATTTG
AAATCGCTACATCGATTGCATATTAACGACGAAACGCAACTAAAAAATGC
TAAAATTCCCACAAACGATACTACTGACTACATGCCTCCTTCAGATGGAG
```

-continued

CAAATGAGGTAACTCGGATTGATTTGAAAGACATTAAATCACCTACGAGA
CACCATAAAAGAAGACCTACCACCATCGATGTTCCTGGTTTAACAAAGTC
TAAAACATCTCCAGATGGTCTCATATCAAAGGAAGATAGTGGATCAAAGT
TAGTGATTGTCATGGTCGGACTGCCAGCTACGGGAAAGTCATTTATTACA
AATAAATTATCCAGATTTTTAAATTATTCTTTATACTATTGTAAAGTGTT
TAATGTCGGTAACACTAGAAGGAAGTTTGCTAAGGAGCATGGCCTAAAGG
ACCAGGATTCAAAGTTTTTCGAGCCGAAAAACGCCGACTCTACTAGGTTG
AGAGACAAATGGGCCATGGATACTCTGGATGAATTGCTAGATTATTTATT
AGAAGGTTCAGGATCTGTGGGAATTTTTGATGCTACAAATACCTCTCGTG
AAAGAAGAAAAAACGTTCTGGCTAGAATCAGAAAGAGAAGTCCTCATTTG
AAGGTTTTATTTTTAGAATCTGTTTGTTCGGATCATGCACTGGTACAGAA
AAATATTAGACTCAAATTATTTGGTCCAGATTACAAAGGTAAAGATCCTG
AAAGCTCTTTAAAAGATTTTAAAAGTCGCCTGGCAAACTACTTGAAAGCC
TATGAACCAATTGAGGATGACGAAAATTTGCAGTACATCAAAATGATAGA
TGTGGGAAAGAAAGTCATCGCATACAATATTCAAGGGTTTTTAGCTTCGC
AGACGGTATATTATTTGTTAAATTTCAATTTGGCTGACAGACAAATTTGG
ATAACGAGAAGTGGCGAGAGCGAAGATAATGTTAGTGGCCGTATAGGCGG
AAATTCCCATTTGACTCCTCGTGGTCTAAGATTTGCTAAAAGTCTACCAA
AATTCATTGCCAGACAGAGAGAAATATTTTATCAAAATCTCATGCAACAA
AAAAAGAATAATGAAAATACAGATGGGAACATTTATAATGACTTTTTCGT
TTGGACCAGCATGCGTGCTAGGACTATAGGGACTGCTCAATATTTCAACG
AAGATGATTATCCTATCAAACAAATGAAAATGTTAGATGAGTTAAGTGCA
GGTGATTATGATGGTATGACATATCCAGAAATTAAAAACAACTTTCCTGA
AGAATTCGAAAAAAGACAGAAAGATAAGTTGAGATACAGATACCCTGGTA
TTGGCGGTGAATCGTATATGGACGTTATTAATAGACTCAGACCTGTTATC
ACAGAACTAGAAAGAATCGAGGATAACGTTCTTATTATTACACACCGGGT
GGTGGCAAGAGCCTTATTGGGTTATTTTATGAACTTGAGTATGGGTATTA
TTGCCAATTTGGATGTCCCATTACATTGTGTATATTGCCTAGAACCAAAA
CCATATGGAATCACTTGGTCATTATGGGAGTATGATGAAGCATCGGATTC
ATTTTCTAAGGTCCCACAAACGGACTTGAATACCACCAGAGTAAAGGAGG
TTGGCCTTGTTTATAATGAAAGAAGATATTCTGTTATACCAACAGCTCCG
CCAAGTGCAAGAAGCAGCTTTGCAAGTGACTTTTTGTCAAGAAAAAGATC
TAATCCTACTTCTGCATCTTCATCCCAGAGTGAATTATCAGAACAACCCA
AGAATAGCGTTAGTGCTCAAACTGGCAGCAATAATACCACTCTCATTGGG
AGCAACTTTAACATCAAGAATGAAAATGGTGATTCGAGAATACCATTATC
TGCACCACTTATGGCCACTAATACTTCTAATAACATCTTAGATGGTGGAG
GTACCTCAATTTCGATACATCGTCCCAGGGTTGTTCCAAATCAAAACAAC
GTGAATCCTCTTTTGGCTAACAACAATAAAGCGGCTTCTAATGTACCTAA
TGTAAAGAAGTCAGCGGCTACACCAAGGCAAATTTTTGAAATAGATAAAG
TGGACGAAAAGTTATCCATGTTGAAAAATAAAAGTTTTCTATTACATGGA

-continued

AAGGATTATCCTAATAATGCTGATAATAATGACAACGAAGATATAAGGGC
AAAAACCATGAATCGCAGCCAAAGTCACGTTTAA

SEQ ID NO: 136—*Saccharomyces cerevisiae* PFK26

MFKPVDFSETSPVPPDIDLAPTQSPHHVAPSQDSSYDLLSRSSDDKIDAE
KGPHDELSKHLPLFQKRPLSDTPISSNWNSPGITEENTPSDSPENSATNL
KSLHRLHINDETQLKNAKIPTNDTTDYMPPSDGANEVTRIDLKDIKSPTR
HHKRRPTTIDVPGLTKSKTSPDGLISKEDSGSKLVIVMVGLPATGKSFIT
NKLSRFLNYSLYYCKVFNVGNTRRKFAKEHGLKDQDSKFFEPKNADSTRL
RDKWAMDTLDELLDYLLEGSGSVGIFDATNTSRERRKNVLARIRKRSPHL
KVLFLESVCSDHALVQKNIRLKLFGPDYKGKDPESSLKDFKSRLANYLKA
YEPIEDDENLQYIKMIDVGKKVIAYNIQGFLASQTVYYLLNFNLADRQIW
ITRSGESEDNVSGRIGGNSHLTPRGLRFAKSLPKFIARQREIFYQNLMQQ
KKNNENTDGNIYNDFFVWTSMRARTIGTAQYFNEDDYPIKQMKMLDELSA
GDYDGMTYPEIKNNFPEEFEKRQKDKLRYRYPGIGGESYMDVINRLRPVI
TELERIEDNVLIITHRVVARALLGYFMNLSMGIIANLDVPLHCVYCLEPK
PYGITWSLWEYDEASDSFSKVPQTDLNTTRVKEVGLVYNERRYSVIPTAP
PSARSSFASDFLSRKRSNPTSASSSQSELSEQPKNSVSAQTGSNNTTLIG
SNFNIKNENGDSRIPLSAPLMATNTSNNILDGGGTSISIHRPRVVPNQNN
VNPLLANNNKAASNVPNVKKSAATPRQIFEIDKVDEKLSMLKNKSFLLHG
KDYPNNADNNDNEDIRAKTMNRSQSHV*

SEQ ID NO: 137—*Saccharomyces cerevisiae* PGI1 DNA

ATGTCCAATAACTCATTCACTAACTTCAAACTGGCCACTGAATTGCCAGC
CTGGTCTAAGTTGCAAAAAATTTATGAATCTCAAGGTAAGACTTTGTCTG
TCAAGCAAGAATTCCAAAAAGATGCCAAGCGTTTTGAAAAATTGAACAAG
ACTTTCACCAACTATGATGGTTCCAAAATCTTGTTCGACTACTCAAAGAA
CTTGGTCAACGATGAAATCATTGCTGCATTGATTGAACTGGCCAAGGAGG
CTAACGTCACCGGTTTGAGAGATGCTATGTTCAAAGGTGAACACATCAAC
TCCACTGAAGATCGTGCTGTCTACCACGTCGCATTGAGAAACAGAGCTAA
CAAGCCAATGTACGTTGATGGTGTCAACGTTGCTCCAGAAGTCGACTCTG
TCTTGAAGCACATGAAGGAGTTCTCTGAACAAGTTCGTTCTGGTGAATGG
AAGGGTTATACCGGTAAGAAGATCACCGATGTTGTTAACATCGGTATTGG
TGGTTCCGATTTGGGTCCAGTCATGGTCACTGAGGCTTTGAAGCACTACG
CTGGTGTCTTGGATGTCCACTTCGTTTCCAACATTGACGGTACTCACATT
GCTGAAACCTTGAAGGTTGTTGACCCAGAAACTACTTTGTTTTTGATTGC
TTCCAAGACTTTCACTACCGCTGAAACTATCACTAACGCTAACACTGCCA
AGAACTGGTTCTTGTCGAAGACAGGTAATGATCCATCTCACATTGCTAAG
CATTTCGCTGCTTTGTCCACTAACGAAACCGAAGTTGCCAAGTTCGGTAT
TGACACCAAAAACATGTTTGGTTTCGAAAGTTGGGTCGGTGGTCGTTACT
CTGTCTGGTCGGCTATTGGTTTGTCTGTTGCCTTGTACATTGGCTATGAC

-continued

AACTTTGAGGCTTTCTTGAAGGGTGCTGAAGCCGTCGACAACCACTTCAC
CCAAACCCCATTGGAAGACAACATTCCATTGTTGGGTGGTTTGTTGTCTG
TCTGGTACAACAACTTCTTTGGTGCTCAAACCCATTTGGTTGCTCCATTC
GACCAATACTTGCACAGATTCCCAGCCTACTTGCAACAATTGTCAATGGA
ATCTAACGGTAAGTCTGTTACCAGAGGTAACGTGTTTACTGACTACTCTA
CTGGTTCTATCTTGTTTGGTGAACCAGCTACCAACGCTCAACACTCTTTC
TTCCAATTGGTTCACCAAGGTACCAAGTTGATTCCATCTGATTTCATCTT
AGCTGCTCAATCTCATAACCCAATTGAGAACAAATTACATCAAAAGATGT
TGGCTTCAAACTTCTTTGCTCAAGCTGAAGCTTTAATGGTTGGTAAGGAT
GAAGAACAAGTTAAGGCTGAAGGTGCCACTGGTGGTTTGGTCCCACACAA
GGTCTTCTCAGGTAACAGACCAACTACCTCTATCTTGGCTCAAAAGATTA
CTCCAGCTACTTTGGGTGCTTTGATTGCCTACTACGAACATGTTACTTTC
ACTGAAGGTGCCATTTGGAATATCAACTCTTTCGACCAATGGGGTGTTGA
ATTGGGTAAAGTCTTGGCTAAAGTCATCGGCAAGGAATTGGACAACTCCT
CCACCATTTCTACCCACGATGCTTCTACCAACGGTTTAATCAATCAATTC
AAGGAATGGATGTGA

SEQ ID NO: 138—*Saccharomyces cerevisiae* PGI1

MSNNSFTNFKLATELPAWSKLQKIYESQGKTLSVKQEFQKDAKRFEKLNK
TFTNYDGSKILFDYSKNLVNDEIIAALIELAKEANVTGLRDAMFKGEHIN
STEDRAVYHVALRNRANKPMYVDGVNVAPEVDSVLKHMKEFSEQVRSGEW
KGYTGKKITDVVNIGIGGSDLGPVMVTEALKHYAGVLDVHFVSNIDGTHI
AETLKVVDPETTLFLIASKTFTTAETITNANTAKNWFLSKTGNDPSHIAK
HFAALSTNETEVAKFGIDTKNMFGFESWVGGRYSVWSAIGLSVALYIGYD
NFEAFLKGAEAVDNHFTQTPLEDNIPLLGGLLSVWYNNFFGAQTHLVAPF
DQYLHRFPAYLQQLSMESNGKSVTRGNVFTDYSTGSILFGEPATNAQHSF
FQLVHQGTKLIPSDFILAAQSHNPIENKLHQKMLASNFFAQAEALMVGKD
EEQVKAEGATGGLVPHKVFSGNRPTTSILAQKITPATLGALIAYYEHVTF
TEGAIWNINSFDQWGVELGKVLAKVIGKELDNSSTISTHDASTNGLINQF
KEWM*

SEQ ID NO: 139—*Saccharomyces cerevisiae* GPM1 DNA

ATGCCAAAGTTAGTTTTAGTTAGACACGGTCAATCCGAATGGAACGAAAA
GAACTTATTCACCGGTTGGGTTGATGTTAAATTGTCTGCCAAGGGTCAAC
AAGAAGCCGCTAGAGCCGGTGAATTGTTGAAGGAAAAGAAGGTCTACCCA
GACGTCTTGTACACTTCCAAGTTGTCCAGAGCTATCCAAACTGCTAACAT
TGCTTTGGAAAAGGCTGACAGATTATGGATTCCAGTCAACAGATCCTGGA
GATTGAACGAAAGACATTACGGTGACTTACAAGGTAAGGACAAGGCTGAA
ACTTTGAAGAAGTTCGGTGAAGAAAAATTCAACACCTACAGAAGATCCTT
CGATGTTCCACCTCCCCCAATCGACGCTTCTTCTCCATTCTCTCAAAAGG
GTGATGAAAGATACAAGTACGTTGACCCAAATGTCTTGCCAGAAACTGAA
TCTTTGGCTTTGGTCATTGACAGATTGTTGCCATACTGGCAAGATGTCAT
TGCCAAGGACTTGTTGAGTGGTAAGACCGTCATGATCGCCGCTCACGGTA
ACTCCTTGAGAGGTTTGGTTAAGCACTTGGAAGGTATCTCTGATGCTGAC
ATTGCTAAGTTGAACATCCCAACTGGTATTCCATTGGTCTTCGAATTGGA
CGAAAACTTGAAGCCATCTAAGCCATCTTACTACTTGGACCCAGAAGCTG
CCGCTGCTGGTGCCGCTGCTGTTGCCAACCAAGGTAAGAAATAA

SEQ ID NO: 140—*Saccharomyces cerevisiae* GPM1

MPKLVLVRHGQSEWNEKNLFTGWVDVKLSAKGQQEAARAGELLKEKKVYP
DVLYTSKLSRAIQTANIALEKADRLWIPVNRSWRLNERHYGDLQGKDKAE
TLKKFGEEKFNTYRRSFDVPPPPIDASSPFSQKGDERYKYVDPNVLPETE
SLALVIDRLLPYWQDVIAKDLLSGKTVMIAAHGNSLRGLVKHLEGISDAD
IAKLNIPTGIPLVFELDENLKPSKPSYYLDPEAAAAGAAAVANQGKK

SEQ ID NO: 141—*Saccharomyces cerevisiae* TPI1 DNA

ATGGCTAGAACTTTCTTTGTCGGTGGTAACTTTAAATTAAACGGTTCCAA
ACAATCCATTAAGGAAATTGTTGAAAGATTGAACACTGCTTCTATCCCAG
AAAATGTCGAAGTTGTTATCTGTCCTCCAGCTACCTACTTAGACTACTCT
GTCTCTTTGGTTAAGAAGCCACAAGTCACTGTCGGTGCTCAAAACGCCTA
CTTGAAGGCTTCTGGTGCTTTCACCGGTGAAAACTCCGTTGACCAAATCA
AGGATGTTGGTGCTAAGTGGGTTATTTTGGGTCACTCCGAAAGAAGATCT
TACTTCCACGAAGATGACAAGTTCATTGCTGACAAGACCAAGTTCGCTTT
AGGTCAAGGTGTCGGTGTCATCTTGTGTATCGGTGAAACTTTGGAAGAAA
AGAAGGCCGGTAAGACTTTGGATGTTGTTGAAAGACAATTGAACGCTGTC
TTGGAAGAAGTTAAGGACTGGACTAACGTCGTTGTCGCTTACGAACCAGT
CTGGGCCATTGGTACCGGTTTGGCTGCTACTCCAGAAGATGCTCAAGATA
TTCACGCTTCCATCAGAAAGTTCTTGGCTTCCAAGTTGGGTGACAAGGCT
GCCAGCGAATTGAGAATCTTATACGGTGGTTCCGCTAACGGTAGCAACGC
CGTTACCTTCAAGGACAAGGCTGATGTCGATGGTTTCTTGGTCGGTGGTG
CTTCTTTGAAGCCAGAATTTGTTGATATCATCAACTCTAGAAACTAA

SEQ ID NO:142—*Saccharomyces cerevisiae* TPI1

MARTFFVGGNFKLNGSKQSIKEIVERLNTASIPENVEVVICPPATYLDYS
VSLVKKPQVTVGAQNAYLKASGAFTGENSVDQIKDVGAKWVILGHSERRS
YFHEDDKFIADKTKFALGQGVGVILCIGETLEEKKAGKTLDVVERQLNAV
LEEVKDWTNVVVAYEPVWAIGTGLAATPEDAQDIHASIRKFLASKLGDKA
ASELRILYGGSANGSNAVTFKDKADVDGFLVGGASLKPEFVDIINSRN

SEQ ID NO: 147—*Saccharomyces cerevisiae* PGM1 DNA

ATGTCACTTCTAATAGATTCTGTACCAACAGTTGCTTATAAGGACCAAAA
ACCGGGTACTTCAGGTTTACGTAAGAAGACCAAGGTTTTCATGGATGAGC
CTCATTATACTGAGAACTTCATTCAAGCAACAATGCAATCTATCCCTAAT

-continued

GGCTCAGAGGGAACCACTTTAGTTGTTGGAGGAGATGGTCGTTTCTACAA
CGATGTTATCATGAACAAGATTGCCGCAGTAGGTGCTGCAAACGGTGTCA
GAAAGTTAGTCATTGGTCAAGGCGGTTTACTTTCAACACCAGCTGCTTCT
CATATAATTAGAACATACGAGGAAAAGTGTACCGGTGGTGGTATCATATT
AACTGCCTCACACAACCCAGGCGGTCCAGAGAATGATTTAGGTATCAAGT
ATAATTTACCTAATGGTGGGCCAGCTCCAGAGAGTGTCACTAACGCTATC
TGGGAAGCGTCTAAAAAATTAACTCACTATAAAATTATAAAGAACTTCCC
CAAGTTGAATTTGAACAAGCTTGGTAAAAACCAAAAATATGGCCCATTGT
TAGTGGACATAATTGATCCTGCCAAAGCATACGTTCAATTTCTGAAGGAA
ATTTTTGATTTTGACTTAATTAAAAGCTTCTTAGCGAAACAGCGCAAAGA
CAAAGGGTGGAAGTTGTTGTTTGACTCCTTAAATGGTATTACAGGACCAT
ATGGTAAGGCTATATTTGTTGATGAATTTGGTTTACCGGCAGAGGAAGTT
CTTCAAAATTGGCACCCTTTACCTGATTTCGGCGGTTTACATCCCGATCC
GAATCTAACCTATGCACGAACTCTTGTTGACAGGGTTGACCGCGAAAAAA
TTGCCTTTGGAGCAGCCTCCGATGGTGATGGTGATAGGAATATGATTTAC
GGTTATGGCCCTGCTTTCGTTTCGCCAGGTGATTCTGTTGCCATTATTGC
CGAATATGCACCCGAAATTCCATACTTCGCCAAACAAGGTATTTATGGCT
TGGCACGTTCATTTCCTACATCCTCAGCCATTGATCGTGTTGCAGCAAAA
AAGGGATTAAGATGTTACGAAGTTCCAACCGGCTGGAAATTCTTCTGTGC
CTTATTTGATGCTAAAAAGCTATCAATCTGTGGTGAAGAATCCTTCGGTA
CAGGTTCCAATCATATCAGAGAAAAGGACGGTCTATGGGCCATTATTGCT
TGGTTAAATATCTTGGCTATCTACCATAGGCGTAACCCTGAAAAGGAAGC
TTCGATCAAAACTATTCAGGACGAATTTTGGAACGAGTATGGCCGTACTT
TCTTCACAAGATACGATTACGAACATATCGAATGCGAGCAGGCCGAAAAA
GTTGTAGCTCTTTTGAGTGAATTTGTATCAAGGCCAAACGTTTGTGGCTC
CCACTTCCCAGCTGATGAGTCTTTAACCGTTATCGATTGTGGTGATTTTT
CGTATAGAGATCTAGATGGCTCCATCTCTGAAAATCAAGGCCTTTTCGTA
AAGTTTTCGAATGGGACTAAATTTGTTTTGAGGTTATCCGGCACAGGCAG
TTCTGGTGCAACAATAAGATTATACGTAGAAAAGTATACTGATAAAAAGG
AGAACTATGGCCAAACAGCTGACGTCTTCTTGAAACCCGTCATCAACTCC
ATTGTAAAATTCTTAAGATTTAAAGAAATTTTAGGAACAGACGAACCAAC
AGTCCGCACATAG

SEQ ID NO: 148—*Saccharomyces cerevisiae* PGM1

MSLLIDSVPTVAYKDQKPGTSGLRKKTKVFMDEPHYTENFIQATMQSIPN
GSEGTTLVVGGDGRFYNDVIMNKIAAVGAANGVRKLVIGQGGLLSTPAAS
HIIRTYEEKCTGGGIILTASHNPGGPENDLGIKYNLPNGGPAPESVTNAI
WEASKKLTHYKIIKNFPKLNLNKLGKNQKYGPLLVDIIDPAKAYVQFLKE
IFDFDLIKSFLAKQRKDKGWKLLFDSLNGITGPYGKAIFVDEFGLPAEEV
LQNWHPLPDFGGLHPDPNLTYARTLVDRVDREKIAFGAASDGDGDRNMIY
GYGPAFVSPGDSVAIIAEYAPEIPYFAKQGIYGLARSFPTSSAIDRVAAK

-continued

KGLRCYEVPTGWKFFCALFDAKKLSICGEESFGTGSNHIREKDGLWAIIA
WLNILAIYHRRNPEKEASIKTIQDEFWNEYGRTFFTRYDYEHIECEQAEK
VVALLSEFVSRPNVCGSHFPADESLTVIDCGDFSYRDLDGSISENQGLFV
KFSNGTKFVLRLSGTGSSGATIRLYVEKYTDKKENYGQTADVFLKPVINS
IVKFLRFKEILGTDEPTVRT

SEQ ID NO: 149—*Saccharomyces cerevisiae* PGM3 DNA

ATGTTGCAAGGAATTTTAGAAACCGTACCATCTGACTTGAAAGATCCGAT
ATCATTATGGTTTAAGCAAGACCGCAACCCAAAAACTATAGAAGAGGTCA
CCGCTCTCTGCAAAAAATCCGACTGGAATGAGTTACACAAAAGATTTGAT
TCTAGAATTCAGTTTGGCACTGCTGGTTTAAGATCGCAAATGCAAGCTGG
CTTTAGCAGGATGAATACTTTAGTAGTCATACAAGCGTCTCAGGGATTGG
CAACTTATGTAAGACAACAGTTTCCAGACAATTTGGTAGCTGTTGTGGGA
CACGATCATAGATTCCATTCTAAGGAGTTCGCTAGAGCTACTGCTGCTGC
ATTTCTTTTAAAAGGATTTAAGGTACATTATTTGAATCCTGACCACGAAT
TTGTTCATACCCCTTTAGTTCCCTTTGCAGTGGATAAGCTAAAGGCCTCC
GTTGGCGTAATGATAACAGCAAGTCACAACCCAAAAATGGATAATGGATA
TAAAGTATACTATTCCAATGGATGCCAAATCATTCCACCTCACGATCATG
CCATCTCTGATTCCATTGACGCAAATTTAGAACCATGGGCCAATGTGTGG
GATTTCGACGATGTTCTAAATAAGGCTCTCAAACAAGGGAAATTGATGTA
TTCCAGAGAAGAAATGCTGAAGTTATATTTAGAGGAGGTTTCTAAAAATC
TGGTAGAAATCAACCCATTAAAGCTTGAAGTAAAAGCCAAACCTTGGTTC
GTTTACACTCCAATGCATGGGGTTGGATTTGACATTTTCAGCACCATCGT
AAAAAAAACACTGTGCCTGGTAGAAGGTAAGGATTACCTATGTGTTCCTG
AACAACAAAATCCAGATCCTTCTTTCCCAACTGTTGGATTTCCTAACCCT
GAAGAAAAAGGTGCTTTAGACATTGGTATAAACTTGGCTGAAAAACATGA
CATTGACTTACTTGTTGCCAACGACCCTGACGCTGATAGATTCTCTGTTG
CTGTTAAAGATATGCAGTCAGGCGAATGGCGACAACTAACAGGTAACGAA
ATCGGTTTTCTTTTTGCATTTTATGAATATCAGAAATATAAAAGTATGGA
CAAAGAATTTCAGCACGTTCATCCGTTGGCTATGTTAAATTCAACAGTGT
CTTCACAAATGATAAAAAAAAATGGCAGAAATAGAAGGGTTCCATTATGAG
GATACATTAACAGGATTTAAGTGGATCGGAAATCGTGCCATACTCTTGGA
AAAGAAAGGCTATTACGTTCCTTTTGGATTCGAGGAAGCAATAGGCTACA
TGTTTCCAGCAATGGAGCATGATAAGGATGGTATCAGTGCATCCATTGTC
TTCTTGCAAGCCTACTGTAAGTGGAAAATAGACCACAATTTGGACCCGCT
AAATGTCTTAGAAAATGGCTTCAAAAAATATGGCGTGTTCAAAGAGTACA
ATGGCTATTATGTCGTTCCAAATCCAACTGTTACAAAAGATATATTTGAC
TACATCAGGAATGTCTACACTCCTGAGGGCGCGTCATATCCTTCATCTAT
TGGTGAAGAAATCGAAGTACTTTACTATCGAGATTTAACCACTGGTTACC
AATCGGATACCATAAATCATAAACCTACTCTACCCGTCGATCCTACATCA
CAAATGATAACAGTATCTGCTAGACCAAGTAACGGTAGTGAGAATGAGCA

-continued

TATCCGCTTCACTATTCGCGGGTCCGGAACAGAACCAAAACTTAAAGTAT

ATATTGAAGCTTGCGCAAATGAAGAACAAAGAGCCTCTTTCTTGGCGAAA

TTGACTTGGAATGTGCTGAGACGTGAATGGTTTAGACCAGATGAAATGAA

TATAGTTACAAAATTTTGA

SEQ ID NO: 150—*Saccharomyces cerevisiae* PGM3

MLQGILETVPSDLKDPISLWFKQDRNPKTIEEVTALCKKSDWNELHKRFD

SRIQFGTAGLRSQMQAGFSRMNTLVVIQASQGLATYVRQQFPDNLVAVVG

HDHRFHSKEFARATAAAFLLKGFKVHYLNPDHEFVHTPLVPFAVDKLKAS

VGVMITASHNPKMDNGYKVYYSNGCQIIPPHDHAISDSIDANLEPWANVW

-continued

DFDDVLNKALKQGKLMYSREEMLKLYLEEVSKNLVEINPLKLEVKAKPWF

VYTPMHGVGFDIFSTIVKKTLCLVEGKDYLCVPEQQNPDPSFPTVGFPNP

EEKGALDIGINLAEKHDIDLLVANDPDADRFSVAVKDMQSGEWRQLTGNE

IGFLFAFYEYQKYKSMDKEFQHVHPLAMLNSTVSSQMIKKMAEIEGFHYE

DTLTGFKWIGNRAILLEKKGYYVPFGFEEAIGYMFPAMEHDKDGISASIV

FLQAYCKWKIDHNLDPLNVLENGFKKYGVFKEYNGYYVVPNPTVTKDIFD

YIRNVYTPEGASYPSSIGEEIEVLYYRDLTTGYQSDTINHKPTLPVDPTS

QMITVSARPSNGSENEHIRFTIRGSGTEPKLKVYIEACANEEQRASFLAK

LTWNVLRREWFRPDEMNIVTKF

What is claimed is:

1. A recombinant *Saccharomyces* cell which is capable of fermenting xylose and which comprises a heterologous gene encoding a xylulokinase (XK) having xylulokinase activity, wherein the XK:

has an amino acid sequence at least 95% sequence identical to the amino acid sequence of SEQ ID NO: 6 or at least 95% sequence identical to the amino acid sequence of SEQ ID NO: 22;

provides an enzymatic activity for converting D-xylulose to xylulose 5-phosphate at least twice that provided by the *S. cerevisiae* XK of SEQ ID NO: 32 under the same conditions, and provides for an anaerobic growth rate of the recombinant cell on xylose which is higher than that provided by the *S. cerevisiae* XK of SEQ ID NO: 32 under the same conditions.

2. The recombinant cell of claim 1, wherein the XK further provides for an aerobic growth rate of the cell on xylose which is higher than that provided by the *S. cerevisiae* XK of SEQ ID NO: 32 under the same conditions.

3. The recombinant cell of claim 1, wherein the XK comprises the amino acid sequence of SEQ ID NO: 6, or the amino acid sequence of SEQ ID NO: 22.

4. The recombinant cell of claim 1, wherein the amino acid sequence of the XK has at least 97% sequence identity with the amino acid sequence of SEQ ID NO: 6.

5. The recombinant cell of claim 1, wherein the amino acid sequence of the XK has at least 99% sequence identity with the amino acid sequence of SEQ ID NO: 6.

6. The recombinant cell of claim 1, wherein the XK is a fragment of the polypeptide of SEQ ID NO: 6 or the polypeptide of SEQ ID NO: 22, wherein the fragment has xylulokinase activity.

7. The recombinant cell of claim 1, wherein the amino acid sequence of the XK has at least 97% sequence identity with the amino acid sequence of SEQ ID NO: 22.

8. The recombinant cell of claim 1, wherein the amino acid sequence of the XK has at least 99% sequence identity with the amino acid sequence of SEQ ID NO: 22.

9. A recombinant *Saccharomyces* cell which is capable of fermenting xylose and which comprises a heterologous gene encoding a xylulokinase (XK) having xylulokinase activity, wherein the amino acid sequence of the XK has at least 95% sequence identity with the amino acid sequence of SEQ ID NO: 6 or at least 95% sequence identity with the amino acid sequence of SEQ ID NO: 22.

10. The recombinant cell of claim 9, wherein the amino acid sequence of the XK has at least 97% sequence identity with the amino acid sequence of SEQ ID NO: 6.

11. The recombinant cell of claim 9, wherein the amino acid sequence of the XK has at least 97% sequence identity with the amino acid sequence of SEQ ID NO: 22.

12. The recombinant cell of claim 9, wherein the XK is a fragment of the polypeptide of SEQ ID NO: 6 or the polypeptide of SEQ ID NO: 22, wherein the fragment has xylulokinase activity.

13. The recombinant cell of claim 9, wherein the XK comprises the amino acid sequence of SEQ ID NO: 6 or the amino acid sequence of SEQ ID NO: 22.

14. A method for producing a fermentation product, comprising (a) contacting the recombinant cell of claim 1 with a medium comprising a carbon source comprising xylose or arabinose under anaerobic conditions, and (b) isolating the fermentation product from the medium.

15. The method of claim 14, wherein the amino acid sequence of the XK has at least 97% sequence identity with the amino acid sequence of SEQ ID NO: 6.

16. The method of claim 14, wherein the amino acid sequence of the XK has at least 99% sequence identity with the amino acid sequence of SEQ ID NO: 6.

17. The method of claim 14, wherein the amino acid sequence of the XK has at least 97% sequence identity with the amino acid sequence of SEQ ID NO: 22.

18. The method of claim 14, wherein the amino acid sequence of the XK has at least 99% sequence identity with the amino acid sequence of SEQ ID NO: 22.

19. The method of claim 14, wherein the XK comprises the amino acid sequence of SEQ ID NO: 6 or the amino acid sequence of SEQ ID NO: 22.

20. The method of claim 14, wherein the XK is a fragment of the polypeptide of SEQ ID NO: 6 or the polypeptide of SEQ ID NO: 22, wherein the fragment has xylulokinase activity.

* * * * *

SEQUENCE LISTING

```
<160> NUMBER OF SEQ ID NOS: 150

<210> SEQ ID NO 1
<211> LENGTH: 33
<212> TYPE: DNA
<213> ORGANISM: Artificial Sequence
<220> FEATURE:
<223> OTHER INFORMATION: Artificial DNA Primer

<400> SEQUENCE: 1

ggtaccgagc tctaactgat ctatccaaaa ctg                                  33


<210> SEQ ID NO 2
<211> LENGTH: 39
<212> TYPE: DNA
<213> ORGANISM: Artificial Sequence
<220> FEATURE:
<223> OTHER INFORMATION: Artificial DNA Primer

<400> SEQUENCE: 2

ggtaccgatc agcatgcgat cgctcgacat ttgatatac                            39


<210> SEQ ID NO 3
<211> LENGTH: 33
<212> TYPE: DNA
<213> ORGANISM: Artificial Sequence
<220> FEATURE:
<223> OTHER INFORMATION: Artificial DNA Primer

<400> SEQUENCE: 3

ccgcgggagc tctaactgat ctatccaaaa ctg                                  33


<210> SEQ ID NO 4
<211> LENGTH: 39
<212> TYPE: DNA
<213> ORGANISM: Artificial Sequence
<220> FEATURE:
<223> OTHER INFORMATION: Artificial DNA Primer

<400> SEQUENCE: 4

ccgcgggatc agcatgcgat cgctcgacat ttgatatac                            39


<210> SEQ ID NO 5
<211> LENGTH: 2582
<212> TYPE: DNA
<213> ORGANISM: Spathaspora passalidarum
```

<400> SEQUENCE: 5

```
tatatctagg aacccatcag gttggtggaa gattacccgt tctaagactt ttcagcttcc     60
tctattgatg ttacacctgg acaccccttt tctggcatcc agtttttaat cttcagtggc    120
atgtgagatt ctccgaaatt aattaaagca atcacacaat tctctcggat accacctcgg    180
ttgaaactga caggtggttt gttacgcatg ctaatgcaaa ggagcctata tacctttggc    240
tcggctgctg taacagggaa tataaagggc agcataattt aggagtttag tgaacttgca    300
acatttacta ttttcccttc ttacgtaaat atttttcttt ttaattctaa atcaatcttt    360
ttcaattttt tgtttgtatt cttttcttgc ttaaatctat aactacaaaa aacacataca    420
taaactaaaa atgacagtag aactacccgc ttcagaacct ttgtttcttg ggtttgatct    480
tagcactcaa cagttgaaaa tcatagtgac aaaccagaaa ttagctgcac taaaatctta    540
caacgttgaa ttcgatgtgg catttaagga gaaatatggg ataaccaagg gagtcctaac    600
gaacaaagag gacggagaag tggtttctcc agttggtatg tggttagatt ccataaacca    660
tgtattcgac caaatgaaac aagatgactt tccgttcaat caagttgcag gcatttcagg    720
ctcttgtcaa caacatggtt ctgtgttttg gtcacatgaa gctgagaagc ttttatcagg    780
tttacagaag gatcaagatc tgtcgactca actaaaggac gctttatctt gggacaaaag    840
tcccaattgg caagatcatt cgactttaga ggaaagtaag gctttcgtag atgctgtagg    900
gagggaagag ttagccgata ttactggtag tagagatcac ttaagattca ctggattgca    960
aattaggaag tttgccacta gatcacatcc cgataagtat gcgaatacta gtagaatctc   1020
actggttagc tccttcataa caagtgttct tctgggtgag attaccgaat tggaagaatc   1080
tgatgcttgt ggcatgaact tgtatgacat caaagccggt gatttcaatg aagaattgtt   1140
ggctctagca gccggtgttc atcctaaagt tgacaacata acgaaagatg atccgaaata   1200
taaagccgga attgaggaca tcaaagcgaa acttgggaag atctccccaa ttacatataa   1260
aagctccgga tccattgctt catattacgt tgaaaagtac ggtttgaatc ctaagtgcca   1320
gatttacagc tttaccggtg acaatttggc tacaatcttg agtttgccat tacagcctaa   1380
cgattgcttg atttcgttag gtacttcgac tacggtcttg ctaatcacta agaattacca   1440
accttcttct caatatcact tgtttaagca tccaaccata ccagatggat atatgggcat   1500
gatctgctat tgcaatggct ctttggccag agagaagata agagatgaag ttaatgaata   1560
ctataaggtg gaagataaga agagttggga taaatttagt gaaattctgg ataagtcgac   1620
caaattcgat aataagctgg gtattttctt tccgttaggt gaaatcgttc cacaggcaaa   1680
ggcacaaact gtcagagcag tattggagaa tgacaaagtc atagaagtag gtttggatac   1740
acacggattt gatattgatc acgacgcaag agctattgtc gaaagccaag ccttatcttg   1800
tagacttaga gctggcccta tgttatccaa atcatcacgt gcttccgtca catcaccaac   1860
ggagttaaaa ggcgtatacc atgacatagt ggccaaatat ggtgacctgt acacagatgg   1920
taaacaacaa acctatgagt cacttacatc taggccaaat cgttgtttct atgttggcgg   1980
cgggagcaat aacatttcca tcattagtaa aatgggttct attctaggtc ctgttcacgg   2040
taactttaaa gtcgatattc caaacgcgtg ttctctaggt ggagcataca aagcatcctg   2100
gtcttatgaa tgtgaacaga aaggtgaatg gattaattat gaccaataca taaatcagtt   2160
attgaaagaa ttgaagtcat ttaacgtgga ggacaaatgg ttagaatact ttgatggagt   2220
tgcgcttttg gctaagatgg aagaaaccct gttgaaataa agatctccca tgtctctact   2280
ggtggtggtg cttctttgga attattggaa ggtaaggaat tgccaggtgt tgctttctta   2340
```

```
tccgaaaaga aataaattga attgaattga aatcgataga tcaatttttt tcttttctct   2400

ttccccatcc tttacgctaa aataatagtt tattttattt tttgaatatt ttttatttat   2460

atacgtatat atagactatt atttatcttt taatgattat taagattttt attaaaaaaa   2520

aattcgctcc tcttttaatg cctttatgca gttttttttt cccattcgat atttctatgt   2580

tc                                                                 2582


<210> SEQ ID NO 6
<211> LENGTH: 609
<212> TYPE: PRT
<213> ORGANISM: Spathaspora passalidarum

<400> SEQUENCE: 6

Met Thr Val Glu Leu Pro Ala Ser Glu Pro Leu Phe Leu Gly Phe Asp
1               5                   10                  15

Leu Ser Thr Gln Gln Leu Lys Ile Ile Val Thr Asn Gln Lys Leu Ala
            20                  25                  30

Ala Leu Lys Ser Tyr Asn Val Glu Phe Asp Val Ala Phe Lys Glu Lys
        35                  40                  45

Tyr Gly Ile Thr Lys Gly Val Leu Thr Asn Lys Glu Asp Gly Glu Val
    50                  55                  60

Val Ser Pro Val Gly Met Trp Leu Asp Ser Ile Asn His Val Phe Asp
65                  70                  75                  80

Gln Met Lys Gln Asp Asp Phe Pro Phe Asn Gln Val Ala Gly Ile Ser
                85                  90                  95

Gly Ser Cys Gln Gln His Gly Ser Val Phe Trp Ser His Glu Ala Glu
            100                 105                 110

Lys Leu Leu Ser Gly Leu Gln Lys Asp Gln Asp Leu Ser Thr Gln Leu
        115                 120                 125

Lys Asp Ala Leu Ser Trp Asp Lys Ser Pro Asn Trp Gln Asp His Ser
    130                 135                 140

Thr Leu Glu Glu Ser Lys Ala Phe Val Asp Ala Val Gly Arg Glu Glu
145                 150                 155                 160

Leu Ala Asp Ile Thr Gly Ser Arg Asp His Leu Arg Phe Thr Gly Leu
                165                 170                 175

Gln Ile Arg Lys Phe Ala Thr Arg Ser His Pro Asp Lys Tyr Ala Asn
            180                 185                 190

Thr Ser Arg Ile Ser Leu Val Ser Ser Phe Ile Thr Ser Val Leu Leu
        195                 200                 205

Gly Glu Ile Thr Glu Leu Glu Glu Ser Asp Ala Cys Gly Met Asn Leu
    210                 215                 220

Tyr Asp Ile Lys Ala Gly Asp Phe Asn Glu Glu Leu Leu Ala Leu Ala
225                 230                 235                 240

Ala Gly Val His Pro Lys Val Asp Asn Ile Thr Lys Asp Asp Pro Lys
                245                 250                 255

Tyr Lys Ala Gly Ile Glu Asp Ile Lys Ala Lys Leu Gly Lys Ile Ser
            260                 265                 270

Pro Ile Thr Tyr Lys Ser Ser Gly Ser Ile Ala Ser Tyr Tyr Val Glu
        275                 280                 285

Lys Tyr Gly Leu Asn Pro Lys Cys Gln Ile Tyr Ser Phe Thr Gly Asp
    290                 295                 300

Asn Leu Ala Thr Ile Leu Ser Leu Pro Leu Gln Pro Asn Asp Cys Leu
305                 310                 315                 320
```

```
Ile Ser Leu Gly Thr Ser Thr Thr Val Leu Leu Ile Thr Lys Asn Tyr
                325                 330                 335

Gln Pro Ser Ser Gln Tyr His Leu Phe Lys His Pro Thr Ile Pro Asp
            340                 345                 350

Gly Tyr Met Gly Met Ile Cys Tyr Cys Asn Gly Ser Leu Ala Arg Glu
        355                 360                 365

Lys Ile Arg Asp Glu Val Asn Glu Tyr Tyr Lys Val Glu Asp Lys Lys
    370                 375                 380

Ser Trp Asp Lys Phe Ser Glu Ile Leu Asp Lys Ser Thr Lys Phe Asp
385                 390                 395                 400

Asn Lys Leu Gly Ile Phe Phe Pro Leu Gly Glu Ile Val Pro Gln Ala
                405                 410                 415

Lys Ala Gln Thr Val Arg Ala Val Leu Glu Asn Asp Lys Val Ile Glu
            420                 425                 430

Val Gly Leu Asp Thr His Gly Phe Asp Ile Asp His Asp Ala Arg Ala
        435                 440                 445

Ile Val Glu Ser Gln Ala Leu Ser Cys Arg Leu Arg Ala Gly Pro Met
    450                 455                 460

Leu Ser Lys Ser Ser Arg Ala Ser Val Thr Ser Pro Thr Glu Leu Lys
465                 470                 475                 480

Gly Val Tyr His Asp Ile Val Ala Lys Tyr Gly Asp Leu Tyr Thr Asp
                485                 490                 495

Gly Lys Gln Gln Thr Tyr Glu Ser Leu Thr Ser Arg Pro Asn Arg Cys
            500                 505                 510

Phe Tyr Val Gly Gly Gly Ser Asn Asn Ile Ser Ile Ile Ser Lys Met
        515                 520                 525

Gly Ser Ile Leu Gly Pro Val His Gly Asn Phe Lys Val Asp Ile Pro
    530                 535                 540

Asn Ala Cys Ser Leu Gly Gly Ala Tyr Lys Ala Ser Trp Ser Tyr Glu
545                 550                 555                 560

Cys Glu Gln Lys Gly Glu Trp Ile Asn Tyr Asp Gln Tyr Ile Asn Gln
                565                 570                 575

Leu Leu Lys Glu Leu Lys Ser Phe Asn Val Glu Asp Lys Trp Leu Glu
            580                 585                 590

Tyr Phe Asp Gly Val Ala Leu Leu Ala Lys Met Glu Glu Thr Leu Leu
        595                 600                 605

Lys
```

<210> SEQ ID NO 7
<211> LENGTH: 36
<212> TYPE: DNA
<213> ORGANISM: Artificial Sequence
<220> FEATURE:
<223> OTHER INFORMATION: Artificial DNA Primer

<400> SEQUENCE: 7

```
tcttccacac ctgcagtata tctaggaacc catcag                           36
```

<210> SEQ ID NO 8
<211> LENGTH: 40
<212> TYPE: DNA
<213> ORGANISM: Artificial Sequence
<220> FEATURE:
<223> OTHER INFORMATION: Artificial DNA Primer

<400> SEQUENCE: 8

```
atcagttaga ctgcaggaac atagaaatat cgaatgggaa                       40
```

<210> SEQ ID NO 9
<211> LENGTH: 36
<212> TYPE: DNA
<213> ORGANISM: Artificial Sequence
<220> FEATURE:
<223> OTHER INFORMATION: Artificial DNA Primer

<400> SEQUENCE: 9
tcttccacac ctgcagtata tctaggaacc catcag 36

<210> SEQ ID NO 10
<211> LENGTH: 48
<212> TYPE: DNA
<213> ORGANISM: Artificial Sequence
<220> FEATURE:
<223> OTHER INFORMATION: Artificial DNA Primer

<400> SEQUENCE: 10
ctgtctctga attactgaac acaacatttt tagtttatgt atgtgttt 48

<210> SEQ ID NO 11
<211> LENGTH: 48
<212> TYPE: DNA
<213> ORGANISM: Artificial Sequence
<220> FEATURE:
<223> OTHER INFORMATION: Artificial DNA Primer

<400> SEQUENCE: 11
gcgaactgga aaagactctc atctaaagat ctcccatgtc tctactgg 48

<210> SEQ ID NO 12
<211> LENGTH: 40
<212> TYPE: DNA
<213> ORGANISM: Artificial Sequence
<220> FEATURE:
<223> OTHER INFORMATION: Artificial DNA Primer

<400> SEQUENCE: 12
atcagttaga ctgcaggaac atagaaatat cgaatgggaa 40

<210> SEQ ID NO 13
<211> LENGTH: 48
<212> TYPE: DNA
<213> ORGANISM: Artificial Sequence
<220> FEATURE:
<223> OTHER INFORMATION: Artificial DNA Primer

<400> SEQUENCE: 13
aaacacatac ataaactaaa aatgttgtgt tcagtaattc agagacag 48

<210> SEQ ID NO 14
<211> LENGTH: 48
<212> TYPE: DNA
<213> ORGANISM: Artificial Sequence
<220> FEATURE:
<223> OTHER INFORMATION: Artificial DNA Primer

<400> SEQUENCE: 14
ccagtagaga catgggagat ctttagatga gagtcttttc cagttcgc 48

<210> SEQ ID NO 15
<211> LENGTH: 36
<212> TYPE: DNA
<213> ORGANISM: Artificial Sequence
<220> FEATURE:
<223> OTHER INFORMATION: Artificial DNA Primer

<400> SEQUENCE: 15
tcttccacac ctgcagtata tctaggaacc catcag 36

<210> SEQ ID NO 16
<211> LENGTH: 40
<212> TYPE: DNA
<213> ORGANISM: Artificial Sequence
<220> FEATURE:
<223> OTHER INFORMATION: Artificial DNA Primer

<400> SEQUENCE: 16
atcagttaga ctgcaggaac atagaaatat cgaatgggaa 40

<210> SEQ ID NO 17
<211> LENGTH: 2207
<212> TYPE: DNA
<213> ORGANISM: Escherichia coli

<400> SEQUENCE: 17
tatatctagg aacccatcag gttggtggaa gattacccgt tctaagactt ttcagcttcc 60
tctattgatg ttacacctgg acaccccttt tctggcatcc agtttttaat cttcagtggc 120
atgtgagatt ctccgaaatt aattaaagca atcacacaat tctctcggat accacctcgg 180
ttgaaactga caggtggttt gttacgcatg ctaatgcaaa ggagcctata tacctttggc 240
tcggctgctg taacagggaa tataaagggc agcataattt aggagtttag tgaacttgca 300
acatttacta ttttcccttc ttacgtaaat atttttcttt ttaattctaa atcaatcttt 360
ttcaattttt tgtttgtatt cttttcttgc ttaaatctat aactacaaaa aacacataca 420
taaactaaaa atgtatatcg gcattgattt gggtacttct ggcgtaaagg ttatcctgct 480
gaatgaacag ggtgaagtgg ttgcctcaca aacggaaaag ttgactgtat ctaggccaca 540
tcctttgtgg agcgaacaag atccagaaca gtggtggcaa gctacagata gagcaatgaa 600
agcgttaggt gaccagcatt ccttacagga cgttaaagcc ttggggattg ctggccaaat 660
gcatggtgcg acactgcttg atgcccaaca aagggtctta aggcctgcaa tactgtggaa 720
tgatggacgt tgtgctcagg agtgtacctt attggaagca agagtgcctc aatccagggt 780
gataaccggt aacttgatga tgcctggatt tacagcccca aaattgttat gggttcaaag 840
acacgaacca gagatcttcc gtcaaatcga caaggtctta ttaccgaagg actacttgag 900
actacgtatg actggtgaat tcgcttcaga catgagtgac gcagcaggaa ccatgtggtt 960
ggatgtcgcg aaaagagatt ggagtgacgt tatgttacaa gcttgcgatc tatctagaga 1020
tcaaatgcca gctctgtatg agggctcaga aattaccggt gcattattac ctgaagtcgc 1080
taaagcatgg ggtatggcta ctgtcccagt tgttgccggt ggtggtgaca atgccgcagg 1140
agctgttgga gttggtatgg tggatgcaaa tcaagcgatg ttgtctcttg gcacatcagg 1200
cgtctatttt gccgtatcgg aagggtttct gtcgaaacca gaatcagccg tacattcctt 1260
ttgtcacgct cttccacaaa gatggcatct aatgagcgtg atgctttctg cagcatcatg 1320
cttggattgg gccgctaaat tgacgggttt gagtaatgtt ccggcactta tagcagctgc 1380
acaacaagca gatgaaagtg ctgaacccgt ttggttcttg ccctatcttt ccggagagag 1440
aacaccacac aacaatcctc aagccaaagg tgtgttcttt gggttaactc accaacatgg 1500
tccaaacgaa ttggcgagag cagtattgga aggagtaggg tatgctcttg ctgatggtat 1560
ggatgttgtc catgcatgtg gcataaagcc gcaatctgtt acgcttattg gaggtggtgc 1620
cagaagcgaa tactggagac aaatgttagc cgatatttcc ggtcaacaac tagactacag 1680

```
aacaggaggc gatgtagggc cagctttggg tgctgctaga ttggctcaga ttgctgctaa   1740

ccctgagaag tcgttgattg agctactacc tcagttaccc ttagaacagt ctcatctacc   1800

agatgcccag agatatgctg cgtaccaacc tagaagagag acttttcgta ggttatacca   1860

gcaattacta cccttgatgg cgtaaagatc tcccatgtct ctactggtgg tggtgcttct   1920

ttggaattat tggaaggtaa ggaattgcca ggtgttgctt tcttatccga aaagaaataa   1980

attgaattga attgaaatcg atagatcaat ttttttcttt tctctttccc catcctttac   2040

gctaaaataa tagtttattt tattttttga atattttta tttatatacg tatatataga   2100

ctattattta tcttttaatg attattaaga tttttattaa aaaaaaattc gctcctcttt   2160

taatgccttt atgcagtttt tttttcccat tcgatatttc tatgttc                 2207
```

<210> SEQ ID NO 18
<211> LENGTH: 484
<212> TYPE: PRT
<213> ORGANISM: Escherichia coli

<400> SEQUENCE: 18

```
Met Tyr Ile Gly Ile Asp Leu Gly Thr Ser Gly Val Lys Val Ile Leu
1               5                   10                  15

Leu Asn Glu Gln Gly Glu Val Val Ala Ser Gln Thr Glu Lys Leu Thr
            20                  25                  30

Val Ser Arg Pro His Pro Leu Trp Ser Glu Gln Asp Pro Glu Gln Trp
        35                  40                  45

Trp Gln Ala Thr Asp Arg Ala Met Lys Ala Leu Gly Asp Gln His Ser
    50                  55                  60

Leu Gln Asp Val Lys Ala Leu Gly Ile Ala Gly Gln Met His Gly Ala
65                  70                  75                  80

Thr Leu Leu Asp Ala Gln Gln Arg Val Leu Arg Pro Ala Ile Leu Trp
                85                  90                  95

Asn Asp Gly Arg Cys Ala Gln Glu Cys Thr Leu Leu Glu Ala Arg Val
            100                 105                 110

Pro Gln Ser Arg Val Ile Thr Gly Asn Leu Met Met Pro Gly Phe Thr
        115                 120                 125

Ala Pro Lys Leu Leu Trp Val Gln Arg His Glu Pro Glu Ile Phe Arg
    130                 135                 140

Gln Ile Asp Lys Val Leu Leu Pro Lys Asp Tyr Leu Arg Leu Arg Met
145                 150                 155                 160

Thr Gly Glu Phe Ala Ser Asp Met Ser Asp Ala Ala Gly Thr Met Trp
                165                 170                 175

Leu Asp Val Ala Lys Arg Asp Trp Ser Asp Val Met Leu Gln Ala Cys
            180                 185                 190

Asp Leu Ser Arg Asp Gln Met Pro Ala Leu Tyr Glu Gly Ser Glu Ile
        195                 200                 205

Thr Gly Ala Leu Leu Pro Glu Val Ala Lys Ala Trp Gly Met Ala Thr
    210                 215                 220

Val Pro Val Val Ala Gly Gly Gly Asp Asn Ala Ala Gly Ala Val Gly
225                 230                 235                 240

Val Gly Met Val Asp Ala Asn Gln Ala Met Leu Ser Leu Gly Thr Ser
                245                 250                 255

Gly Val Tyr Phe Ala Val Ser Glu Gly Phe Leu Ser Lys Pro Glu Ser
            260                 265                 270

Ala Val His Ser Phe Cys His Ala Leu Pro Gln Arg Trp His Leu Met
        275                 280                 285
```

```
Ser Val Met Leu Ser Ala Ala Ser Cys Leu Asp Trp Ala Ala Lys Leu
    290                 295                 300

Thr Gly Leu Ser Asn Val Pro Ala Leu Ile Ala Ala Ala Gln Gln Ala
305                 310                 315                 320

Asp Glu Ser Ala Glu Pro Val Trp Phe Leu Pro Tyr Leu Ser Gly Glu
                325                 330                 335

Arg Thr Pro His Asn Asn Pro Gln Ala Lys Gly Val Phe Phe Gly Leu
            340                 345                 350

Thr His Gln His Gly Pro Asn Glu Leu Ala Arg Ala Val Leu Glu Gly
        355                 360                 365

Val Gly Tyr Ala Leu Ala Asp Gly Met Asp Val Val His Ala Cys Gly
    370                 375                 380

Ile Lys Pro Gln Ser Val Thr Leu Ile Gly Gly Gly Ala Arg Ser Glu
385                 390                 395                 400

Tyr Trp Arg Gln Met Leu Ala Asp Ile Ser Gly Gln Gln Leu Asp Tyr
                405                 410                 415

Arg Thr Gly Gly Asp Val Gly Pro Ala Leu Gly Ala Ala Arg Leu Ala
            420                 425                 430

Gln Ile Ala Ala Asn Pro Glu Lys Ser Leu Ile Glu Leu Leu Pro Gln
        435                 440                 445

Leu Pro Leu Glu Gln Ser His Leu Pro Asp Ala Gln Arg Tyr Ala Ala
    450                 455                 460

Tyr Gln Pro Arg Arg Glu Thr Phe Arg Arg Leu Tyr Gln Gln Leu Leu
465                 470                 475                 480

Pro Leu Met Ala


<210> SEQ ID NO 19
<211> LENGTH: 36
<212> TYPE: DNA
<213> ORGANISM: Artificial Sequence
<220> FEATURE:
<223> OTHER INFORMATION: Artificial DNA Primer

<400> SEQUENCE: 19

tcttccacac ctgcagtata tctaggaacc catcag                               36


<210> SEQ ID NO 20
<211> LENGTH: 40
<212> TYPE: DNA
<213> ORGANISM: Artificial Sequence
<220> FEATURE:
<223> OTHER INFORMATION: Artificial DNA Primer

<400> SEQUENCE: 20

atcagttaga ctgcaggaac atagaaatat cgaatgggaa                           40


<210> SEQ ID NO 21
<211> LENGTH: 1806
<212> TYPE: DNA
<213> ORGANISM: Kluyveromyces marxianus

<400> SEQUENCE: 21

atgtcgactc catattactt aggctttgat ttgtcaactc agcagttgaa atgtctagca     60

atagatgatc agttaaacat cgtgacttca gttagcattg aatttgaccg taatttccca    120

gcttacaaca caaagaaagg ggtatacatc aagaatggtg gtgtgataga cgcaccagtt    180

gctatgtggt tagaagctgt tgatttatgc tttagtcagc ttgctgaaag aatcgacttg    240

aagagagttc aatcaatgtc aggttcttgc caacaacatg gcaccgtcta ctggaactgt    300
```

```
gagcatctac caagtaacct tgatcctgct tcaaccttga gagagcaact tcaaggcagt    360

ttatcaagac cagttgcacc caattggcaa gatcattcca ccaagaaaca atgtgatgaa    420

ttggcagaat cggtaggagg acctgaagaa ctagcaagga ttacaggttc tggagcacac    480

tatagatttt ccggttccca aattgccaaa atccatgaaa ctgaacctga agtctatgag    540

gctactaaac gtatttcgtt ggtaagtagc tttctagcgt ctgttttagt aggtgacatt    600

gtgcccttgg aagaagcgga tgcttgtggc atgaacttat acgatctatc caaacacgac    660

tttgacgaaa cattactggc tgtcgttgac catgatacag cgagattgag aaggaaacta    720

tcagatccac ccgttggagc tcctaccaga gaaagtcctc tgacctcctt gggtaaagtc    780

tctaagtact ttcaggacaa atatggggtt aactgtgaat gtgagatctt cccgtttact    840

ggcgataacc tggcaacgat ttgttcccta cctttgcaaa agaatgatgt cttgattagt    900

ctaggtactt cgaccacgat tttgttggta actgaccaat atcactcttc tcccaattat    960

cacttgttta tacatccgac agtgccaggt tattacatgg gtatgatttg ctattgcaat   1020

gggtctttgg ctcgtgagag agtaagagat gatctggctg gaccacaagc ctctcaagct   1080

cctggggagc aagttccatg gactcaattc aatgacgcat tactggatga ctcattgagc   1140

aatgacaatg agataggcct ttacttccct cttggtgaga ttgtcccaaa tgttgatgcc   1200

gtcaccaaaa gatggacatt cgaaagaaaa gagaaccatt cgaacaaaag tatcgttctt   1260

cacgagttgg atcaattcac gccaaagagg aaagatgcaa agaacatagt ggaaagtcag   1320

gccttaagct gtagagtgcg tatctctcca ttgctgtctg atgaaacaga tgccttaagc   1380

gaaactcaag tgttgtcaaa gaaggagaat acccaagtta cgtttgacta cgatgcattt   1440

ccgttgtgga cgtatgccaa aagaccgaat agagcgttct ttgttggtgg tgcctccaag   1500

aatgatgcca tagtcaggac aatggcaaat gtaataggtg ctaggaatgg aaattataga   1560

cttgaaactc ccaattcctg tgctttagga ggctgttata aagcgatgtg gtcatggtta   1620

aaggtacatg aacctacaac tacaccatct ttcgatgttt ggttaaacgc aagctttaac   1680

tggcagagag attgcgaatt cgtgtgccag tctgacgccg ctaagtggga acaatctaat   1740

ggtaaaattc aagctttatc agaagctgaa gcctatgtta aagctttagc acaatctcag   1800

ggtcaa                                                              1806
```

```
<210> SEQ ID NO 22
<211> LENGTH: 602
<212> TYPE: PRT
<213> ORGANISM: Kluyveromyces marxianus

<400> SEQUENCE: 22

Met Ser Thr Pro Tyr Tyr Leu Gly Phe Asp Leu Ser Thr Gln Gln Leu
1               5                   10                  15

Lys Cys Leu Ala Ile Asp Asp Gln Leu Asn Ile Val Thr Ser Val Ser
            20                  25                  30

Ile Glu Phe Asp Arg Asn Phe Pro Ala Tyr Asn Thr Lys Lys Gly Val
        35                  40                  45

Tyr Ile Lys Asn Gly Gly Val Ile Asp Ala Pro Val Ala Met Trp Leu
    50                  55                  60

Glu Ala Val Asp Leu Cys Phe Ser Gln Leu Ala Glu Arg Ile Asp Leu
65                  70                  75                  80

Lys Arg Val Gln Ser Met Ser Gly Ser Cys Gln Gln His Gly Thr Val
                85                  90                  95
```

```
Tyr Trp Asn Cys Glu His Leu Pro Ser Asn Leu Asp Pro Ala Ser Thr
            100                 105                 110

Leu Arg Glu Gln Leu Gln Gly Ser Leu Ser Arg Pro Val Ala Pro Asn
        115                 120                 125

Trp Gln Asp His Ser Thr Lys Lys Gln Cys Asp Glu Leu Ala Glu Ser
    130                 135                 140

Val Gly Gly Pro Glu Glu Leu Ala Arg Ile Thr Gly Ser Gly Ala His
145                 150                 155                 160

Tyr Arg Phe Ser Gly Ser Gln Ile Ala Lys Ile His Glu Thr Glu Pro
                165                 170                 175

Glu Val Tyr Glu Ala Thr Lys Arg Ile Ser Leu Val Ser Ser Phe Leu
            180                 185                 190

Ala Ser Val Leu Val Gly Asp Ile Val Pro Leu Glu Glu Ala Asp Ala
        195                 200                 205

Cys Gly Met Asn Leu Tyr Asp Leu Ser Lys His Asp Phe Asp Glu Thr
    210                 215                 220

Leu Leu Ala Val Val Asp His Asp Thr Ala Arg Leu Arg Arg Lys Leu
225                 230                 235                 240

Ser Asp Pro Pro Val Gly Ala Pro Thr Arg Glu Ser Pro Leu Thr Ser
                245                 250                 255

Leu Gly Lys Val Ser Lys Tyr Phe Gln Asp Lys Tyr Gly Val Asn Cys
            260                 265                 270

Glu Cys Glu Ile Phe Pro Phe Thr Gly Asp Asn Leu Ala Thr Ile Cys
        275                 280                 285

Ser Leu Pro Leu Gln Lys Asn Asp Val Leu Ile Ser Leu Gly Thr Ser
    290                 295                 300

Thr Thr Ile Leu Leu Val Thr Asp Gln Tyr His Ser Ser Pro Asn Tyr
305                 310                 315                 320

His Leu Phe Ile His Pro Thr Val Pro Gly Tyr Tyr Met Gly Met Ile
                325                 330                 335

Cys Tyr Cys Asn Gly Ser Leu Ala Arg Glu Arg Val Arg Asp Asp Leu
            340                 345                 350

Ala Gly Pro Gln Ala Ser Gln Ala Pro Gly Glu Gln Val Pro Trp Thr
        355                 360                 365

Gln Phe Asn Asp Ala Leu Leu Asp Asp Ser Leu Ser Asn Asp Asn Glu
    370                 375                 380

Ile Gly Leu Tyr Phe Pro Leu Gly Glu Ile Val Pro Asn Val Asp Ala
385                 390                 395                 400

Val Thr Lys Arg Trp Thr Phe Glu Arg Lys Glu Asn His Ser Asn Lys
                405                 410                 415

Ser Ile Val Leu His Glu Leu Asp Gln Phe Thr Pro Lys Arg Lys Asp
            420                 425                 430

Ala Lys Asn Ile Val Glu Ser Gln Ala Leu Ser Cys Arg Val Arg Ile
        435                 440                 445

Ser Pro Leu Leu Ser Asp Glu Thr Asp Ala Leu Ser Glu Thr Gln Val
    450                 455                 460

Leu Ser Lys Lys Glu Asn Thr Gln Val Thr Phe Asp Tyr Asp Ala Phe
465                 470                 475                 480

Pro Leu Trp Thr Tyr Ala Lys Arg Pro Asn Arg Ala Phe Phe Val Gly
                485                 490                 495

Gly Ala Ser Lys Asn Asp Ala Ile Val Arg Thr Met Ala Asn Val Ile
            500                 505                 510
```

```
Gly Ala Arg Asn Gly Asn Tyr Arg Leu Glu Thr Pro Asn Ser Cys Ala
        515                 520                 525

Leu Gly Gly Cys Tyr Lys Ala Met Trp Ser Trp Leu Lys Val His Glu
    530                 535                 540

Pro Thr Thr Thr Pro Ser Phe Asp Val Trp Leu Asn Ala Ser Phe Asn
545                 550                 555                 560

Trp Gln Arg Asp Cys Glu Phe Val Cys Gln Ser Asp Ala Ala Lys Trp
                565                 570                 575

Glu Gln Ser Asn Gly Lys Ile Gln Ala Leu Ser Glu Ala Glu Ala Tyr
            580                 585                 590

Val Lys Ala Leu Ala Gln Ser Gln Gly Gln
        595                 600
```

<210> SEQ ID NO 23
<211> LENGTH: 36
<212> TYPE: DNA
<213> ORGANISM: Artificial Sequence
<220> FEATURE:
<223> OTHER INFORMATION: Artificial DNA Primer

<400> SEQUENCE: 23
tcttccacac ctgcagtata tctaggaacc catcag 36

<210> SEQ ID NO 24
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 24
gcctaagtaa tatggagtcg acatttttag tttatgtatg tgttt 45

<210> SEQ ID NO 25
<211> LENGTH: 48
<212> TYPE: DNA
<213> ORGANISM: Artificial Sequence
<220> FEATURE:
<223> OTHER INFORMATION: Artificial DNA Primer

<400> SEQUENCE: 25
ctttagcaca atctcagggt caataaagat ctcccatgtc tctactgg 48

<210> SEQ ID NO 26
<211> LENGTH: 40
<212> TYPE: DNA
<213> ORGANISM: Artificial Sequence
<220> FEATURE:
<223> OTHER INFORMATION: Artificial DNA Primer

<400> SEQUENCE: 26
atcagttaga ctgcaggaac atagaaatat cgaatgggaa 40

<210> SEQ ID NO 27
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 27
aaacacatac ataaactaaa aatgtcgact ccatattact taggc 45

<210> SEQ ID NO 28
<211> LENGTH: 48
<212> TYPE: DNA
<213> ORGANISM: Artificial Sequence
<220> FEATURE:
<223> OTHER INFORMATION: Artificial DNA Primer

<400> SEQUENCE: 28
ccagtagaga catgggagat ctttattgac cctgagattg tgctaaag 48

<210> SEQ ID NO 29
<211> LENGTH: 36
<212> TYPE: DNA
<213> ORGANISM: Artificial Sequence
<220> FEATURE:
<223> OTHER INFORMATION: Artificial DNA Primer

<400> SEQUENCE: 29
tcttccacac ctgcagtata tctaggaacc catcag 36

<210> SEQ ID NO 30
<211> LENGTH: 40
<212> TYPE: DNA
<213> ORGANISM: Artificial Sequence
<220> FEATURE:
<223> OTHER INFORMATION: Artificial DNA Primer

<400> SEQUENCE: 30
atcagttaga ctgcaggaac atagaaatat cgaatgggaa 40

<210> SEQ ID NO 31
<211> LENGTH: 1803
<212> TYPE: DNA
<213> ORGANISM: Saccharomyces cerevisiae

<400> SEQUENCE: 31
atgttgtgtt cagtaattca gagacagaca agagaggttt ccaacacaat gtctttagac 60
tcatactatc ttgggtttga tctttcgacc caacaactga aatgtctcgc cattaaccag 120
gacctaaaaa ttgtccattc agaaacagtg gaatttgaaa aggatcttcc gcattatcac 180
acaaagaagg gtgtctatat acacggcgac actatcgaat gtcccgtagc catgtggtta 240
gaggctctag atctggttct ctcgaaatat cgcgaggcta aatttccatt gaacaaagtt 300
atggccgtct cagggtcctg ccagcagcac gggtctgtct actggtcctc ccaagccgaa 360
tctctgttag agcaattgaa taagaaaccg gaaaaagatt tattgcacta cgtgagctct 420
gtagcatttg caaggcaaac cgcccccaat tggcaagacc acagtactgc aaagcaatgt 480
caagagtttg aagagtgcat aggtgggcct gaaaaaatgg ctcaattaac agggtccaga 540
gcccatttta gatttactgg tcctcaaatt ctgaaaattg cacaattaga accagaagct 600
tacgaaaaaa caaagaccat ttctttagtg tctaattttt tgacttctat cttagtgggc 660
catcttgttg aattagagga ggcagatgcc tgtggtatga acctttatga tatacgtgaa 720
agaaaattca gtgatgagct actacatcta attgatagtt cttctaagga taaaactatc 780
agacaaaaat taatgagagc acccatgaaa aatttgatag cgggtaccat ctgtaaatat 840
tttattgaga agtacggttt caatacaaac tgcaaggtct ctcccatgac tggggataat 900
ttagccacta tatgttcttt acccctgcgg aagaatgacg ttctcgtttc cctaggaaca 960
agtactacag ttcttctggt caccgataag tatcacccct ctccgaacta tcatcttttc 1020
attcatccaa ctctgccaaa ccattatatg ggtatgattt gttattgtaa tggttctttg 1080

```
gcaagggaga ggataagaga cgagttaaac aaagaacggg aaaataatta tgagaagact   1140

aacgattgga ctctttttaa tcaagctgtg ctagatgact cagaaagtag tgaaaatgaa   1200

ttaggtgtat attttcctct gggggagatc gttcctagcg taaaagccat aaacaaaagg   1260

gttatcttca atccaaaaac gggtatgatt gaaagagagg tggccaagtt caaagacaag   1320

aggcacgatg ccaaaaatat tgtagaatca caggctttaa gttgcagggt aagaatatct   1380

cccctgcttt cggattcaaa cgcaagctca caacagagac tgaacgaaga tacaatcgtg   1440

aagtttgatt acgatgaatc tccgctgcgg gactacctaa ataaaaggcc agaaaggact   1500

tttttgtag gtggggcttc taaaaacgat gctattgtga agaagtttgc tcaagtcatt   1560

ggtgctacaa agggtaattt taggctagaa acaccaaact catgtgccct tggtggttgt   1620

tataaggcca tgtggtcatt gttatatgac tctaataaaa ttgcagttcc ttttgataaa   1680

tttctgaatg acaattttcc atggcatgta atggaaagca tatccgatgt ggataatgaa   1740

aattgggatc gctataattc caagattgtc cccttaagcg aactggaaaa gactctcatc   1800

taa                                                                 1803
```

<210> SEQ ID NO 32
<211> LENGTH: 600
<212> TYPE: PRT
<213> ORGANISM: Saccharomyces cerevisiae

<400> SEQUENCE: 32

```
Met Leu Cys Ser Val Ile Gln Arg Gln Thr Arg Glu Val Ser Asn Thr
1               5                   10                  15

Met Ser Leu Asp Ser Tyr Tyr Leu Gly Phe Asp Leu Ser Thr Gln Gln
            20                  25                  30

Leu Lys Cys Leu Ala Ile Asn Gln Asp Leu Lys Ile Val His Ser Glu
        35                  40                  45

Thr Val Glu Phe Glu Lys Asp Leu Pro His Tyr His Thr Lys Lys Gly
    50                  55                  60

Val Tyr Ile His Gly Asp Thr Ile Glu Cys Pro Val Ala Met Trp Leu
65                  70                  75                  80

Glu Ala Leu Asp Leu Val Leu Ser Lys Tyr Arg Glu Ala Lys Phe Pro
                85                  90                  95

Leu Asn Lys Val Met Ala Val Ser Gly Ser Cys Gln Gln His Gly Ser
            100                 105                 110

Val Tyr Trp Ser Ser Gln Ala Glu Ser Leu Leu Glu Gln Leu Asn Lys
        115                 120                 125

Lys Pro Glu Lys Asp Leu Leu His Tyr Val Ser Ser Val Ala Phe Ala
    130                 135                 140

Arg Gln Thr Ala Pro Asn Trp Gln Asp His Ser Thr Ala Lys Gln Cys
145                 150                 155                 160

Gln Glu Phe Glu Glu Cys Ile Gly Gly Pro Glu Lys Met Ala Gln Leu
                165                 170                 175

Thr Gly Ser Arg Ala His Phe Arg Phe Thr Gly Pro Gln Ile Leu Lys
            180                 185                 190

Ile Ala Gln Leu Glu Pro Glu Ala Tyr Glu Lys Thr Lys Thr Ile Ser
        195                 200                 205

Leu Val Ser Asn Phe Leu Thr Ser Ile Leu Val Gly His Leu Val Glu
    210                 215                 220
```

```
Leu Glu Glu Ala Asp Ala Cys Gly Met Asn Leu Tyr Asp Ile Arg Glu
225                 230                 235                 240

Arg Lys Phe Ser Asp Glu Leu Leu His Leu Ile Asp Ser Ser Ser Lys
                245                 250                 255

Asp Lys Thr Ile Arg Gln Lys Leu Met Arg Ala Pro Met Lys Asn Leu
            260                 265                 270

Ile Ala Gly Thr Ile Cys Lys Tyr Phe Ile Glu Lys Tyr Gly Phe Asn
        275                 280                 285

Thr Asn Cys Lys Val Ser Pro Met Thr Gly Asp Asn Leu Ala Thr Ile
    290                 295                 300

Cys Ser Leu Pro Leu Arg Lys Asn Asp Val Leu Val Ser Leu Gly Thr
305                 310                 315                 320

Ser Thr Thr Val Leu Leu Val Thr Asp Lys Tyr His Pro Ser Pro Asn
                325                 330                 335

Tyr His Leu Phe Ile His Pro Thr Leu Pro Asn His Tyr Met Gly Met
            340                 345                 350

Ile Cys Tyr Cys Asn Gly Ser Leu Ala Arg Glu Arg Ile Arg Asp Glu
        355                 360                 365

Leu Asn Lys Glu Arg Glu Asn Asn Tyr Glu Lys Thr Asn Asp Trp Thr
    370                 375                 380

Leu Phe Asn Gln Ala Val Leu Asp Asp Ser Glu Ser Ser Glu Asn Glu
385                 390                 395                 400

Leu Gly Val Tyr Phe Pro Leu Gly Glu Ile Val Pro Ser Val Lys Ala
                405                 410                 415

Ile Asn Lys Arg Val Ile Phe Asn Pro Lys Thr Gly Met Ile Glu Arg
            420                 425                 430

Glu Val Ala Lys Phe Lys Asp Lys Arg His Asp Ala Lys Asn Ile Val
        435                 440                 445

Glu Ser Gln Ala Leu Ser Cys Arg Val Arg Ile Ser Pro Leu Leu Ser
    450                 455                 460

Asp Ser Asn Ala Ser Ser Gln Gln Arg Leu Asn Glu Asp Thr Ile Val
465                 470                 475                 480

Lys Phe Asp Tyr Asp Glu Ser Pro Leu Arg Asp Tyr Leu Asn Lys Arg
                485                 490                 495

Pro Glu Arg Thr Phe Phe Val Gly Gly Ala Ser Lys Asn Asp Ala Ile
            500                 505                 510

Val Lys Lys Phe Ala Gln Val Ile Gly Ala Thr Lys Gly Asn Phe Arg
        515                 520                 525

Leu Glu Thr Pro Asn Ser Cys Ala Leu Gly Gly Cys Tyr Lys Ala Met
    530                 535                 540

Trp Ser Leu Leu Tyr Asp Ser Asn Lys Ile Ala Val Pro Phe Asp Lys
545                 550                 555                 560

Phe Leu Asn Asp Asn Phe Pro Trp His Val Met Glu Ser Ile Ser Asp
                565                 570                 575

Val Asp Asn Glu Asn Trp Asp Arg Tyr Asn Ser Lys Ile Val Pro Leu
            580                 585                 590

Ser Glu Leu Glu Lys Thr Leu Ile
        595                 600
```

<210> SEQ ID NO 33
<211> LENGTH: 33
<212> TYPE: DNA
<213> ORGANISM: Artificial Sequence
<220> FEATURE:
<223> OTHER INFORMATION: Artificial DNA Primer

<400> SEQUENCE: 33
ggtaccgagc tctaactgat ctatccaaaa ctg 33

<210> SEQ ID NO 34
<211> LENGTH: 39
<212> TYPE: DNA
<213> ORGANISM: Artificial Sequence
<220> FEATURE:
<223> OTHER INFORMATION: Artificial DNA Primer

<400> SEQUENCE: 34
ggtaccgatc agcatgcgat cgctcgacat ttgatatac 39

<210> SEQ ID NO 35
<211> LENGTH: 33
<212> TYPE: DNA
<213> ORGANISM: Artificial Sequence
<220> FEATURE:
<223> OTHER INFORMATION: Artificial DNA Primer

<400> SEQUENCE: 35
ccgcgggagc tctaactgat ctatccaaaa ctg 33

<210> SEQ ID NO 36
<211> LENGTH: 39
<212> TYPE: DNA
<213> ORGANISM: Artificial Sequence
<220> FEATURE:
<223> OTHER INFORMATION: Artificial DNA Primer

<400> SEQUENCE: 36
ccgcgggatc agcatgcgat cgctcgacat ttgatatac 39

<210> SEQ ID NO 37
<211> LENGTH: 36
<212> TYPE: DNA
<213> ORGANISM: Artificial Sequence
<220> FEATURE:
<223> OTHER INFORMATION: Artificial DNA Primer

<400> SEQUENCE: 37
tcttccacac ctgcagtata tctaggaacc catcag 36

<210> SEQ ID NO 38
<211> LENGTH: 48
<212> TYPE: DNA
<213> ORGANISM: Artificial Sequence
<220> FEATURE:
<223> OTHER INFORMATION: Artificial DNA Primer

<400> SEQUENCE: 38
ctgtctctga attactgaac acaacatttt tagtttatgt atgtgttt 48

<210> SEQ ID NO 39
<211> LENGTH: 48
<212> TYPE: DNA
<213> ORGANISM: Artificial Sequence
<220> FEATURE:
<223> OTHER INFORMATION: Artificial DNA Primer

<400> SEQUENCE: 39
gcgaactgga aaagactctc atctaaagat ctcccatgtc tctactgg 48

<210> SEQ ID NO 40
<211> LENGTH: 40
<212> TYPE: DNA
<213> ORGANISM: Artificial Sequence
<220> FEATURE:
<223> OTHER INFORMATION: Artificial DNA Primer

<400> SEQUENCE: 40
atcagttaga ctgcaggaac atagaaatat cgaatgggaa 40

<210> SEQ ID NO 41
<211> LENGTH: 48
<212> TYPE: DNA
<213> ORGANISM: Artificial Sequence
<220> FEATURE:
<223> OTHER INFORMATION: Artificial DNA Primer

<400> SEQUENCE: 41
aaacacatac ataaactaaa aatgttgtgt tcagtaattc agagacag 48

<210> SEQ ID NO 42
<211> LENGTH: 48
<212> TYPE: DNA
<213> ORGANISM: Artificial Sequence
<220> FEATURE:
<223> OTHER INFORMATION: Artificial DNA Primer

<400> SEQUENCE: 42
ccagtagaga catgggagat ctttagatga gagtcttttc cagttcgc 48

<210> SEQ ID NO 43
<211> LENGTH: 36
<212> TYPE: DNA
<213> ORGANISM: Artificial Sequence
<220> FEATURE:
<223> OTHER INFORMATION: Artificial DNA Primer

<400> SEQUENCE: 43
tcttccacac ctgcagtata tctaggaacc catcag 36

<210> SEQ ID NO 44
<211> LENGTH: 40
<212> TYPE: DNA
<213> ORGANISM: Artificial Sequence
<220> FEATURE:
<223> OTHER INFORMATION: Artificial DNA Primer

<400> SEQUENCE: 44
atcagttaga ctgcaggaac atagaaatat cgaatgggaa 40

<210> SEQ ID NO 45
<211> LENGTH: 37
<212> TYPE: DNA
<213> ORGANISM: Artificial Sequence
<220> FEATURE:
<223> OTHER INFORMATION: Artificial DNA Primer

<400> SEQUENCE: 45
gatccccggg ctgcaatgtt gcccatttct ggacctt 37

<210> SEQ ID NO 46
<211> LENGTH: 37
<212> TYPE: DNA
<213> ORGANISM: Artificial Sequence
<220> FEATURE:
<223> OTHER INFORMATION: Artificial DNA Primer

<400> SEQUENCE: 46

```
cgctgcaggt cgacgtgtta catgcgtaca cgcgtct                              37
```

<210> SEQ ID NO 47
<211> LENGTH: 18
<212> TYPE: DNA
<213> ORGANISM: Artificial Sequence
<220> FEATURE:
<223> OTHER INFORMATION: Artificial DNA Primer

<400> SEQUENCE: 47

```
cgtcgacctg cagcgtac                                                   18
```

<210> SEQ ID NO 48
<211> LENGTH: 21
<212> TYPE: DNA
<213> ORGANISM: Artificial Sequence
<220> FEATURE:
<223> OTHER INFORMATION: Artificial DNA Primer

<400> SEQUENCE: 48

```
tgcagcccgg ggatcctttt t                                               21
```

<210> SEQ ID NO 49
<211> LENGTH: 393
<212> TYPE: DNA
<213> ORGANISM: Zygosaccharomyces bailii

<400> SEQUENCE: 49

```
atgttgccca tttctggacc ttccaacatg ctgcatggcc tcgtttcagc ccgttgtgca     60

gggggttgga ggccacttat ctcgcatttg cgtaggggag tttttcctaa gatgcttacc    120

atgacaggta ttggggccaa gagatttgtc tccagcgaaa tacaggagaa agacgaacaa    180

gctggtgagt ctactactgc tacagatact ggtatcattc ataaaacgga gcaggagacc    240

ctagtatatt tcgacaacgt ctatccacgg accgcatctc tatggagccc tgcgcaatgg    300

tacaatctac ttctaactaa tcaatcgagg gaggctgtta ggcaaaagat cagcggttcg    360

atcccgctag agaccatttt ttggcttcat tga                                 393
```

<210> SEQ ID NO 50
<211> LENGTH: 130
<212> TYPE: PRT
<213> ORGANISM: Zygosaccharomyces bailii

<400> SEQUENCE: 50

```
Met Leu Pro Ile Ser Gly Pro Ser Asn Met Leu His Gly Leu Val Ser
1               5                   10                  15

Ala Arg Cys Ala Gly Gly Trp Arg Pro Leu Ile Ser His Leu Arg Arg
            20                  25                  30

Gly Val Phe Pro Lys Met Leu Thr Met Thr Gly Ile Gly Ala Lys Arg
        35                  40                  45

Phe Val Ser Ser Glu Ile Gln Glu Lys Asp Glu Gln Ala Gly Glu Ser
    50                  55                  60

Thr Thr Ala Thr Asp Thr Gly Ile Ile His Lys Thr Glu Gln Glu Thr
65                  70                  75                  80

Leu Val Tyr Phe Asp Asn Val Tyr Pro Arg Thr Ala Ser Leu Trp Ser
                85                  90                  95

Pro Ala Gln Trp Tyr Asn Leu Leu Leu Thr Asn Gln Ser Arg Glu Ala
            100                 105                 110
```

```
Val Arg Gln Lys Ile Ser Gly Ser Ile Pro Leu Glu Thr Ile Phe Trp
        115                 120                 125

Leu His
    130


<210> SEQ ID NO 51
<211> LENGTH: 33
<212> TYPE: DNA
<213> ORGANISM: Artificial Sequence
<220> FEATURE:
<223> OTHER INFORMATION: Artificial DNA Primer

<400> SEQUENCE: 51

ggtaccgagc tctaactgat ctatccaaaa ctg                                    33


<210> SEQ ID NO 52
<211> LENGTH: 39
<212> TYPE: DNA
<213> ORGANISM: Artificial Sequence
<220> FEATURE:
<223> OTHER INFORMATION: Artificial DNA Primer

<400> SEQUENCE: 52

ggtaccgatc agcatgcgat cgctcgacat ttgatatac                              39


<210> SEQ ID NO 53
<211> LENGTH: 33
<212> TYPE: DNA
<213> ORGANISM: Artificial Sequence
<220> FEATURE:
<223> OTHER INFORMATION: Artificial DNA Primer

<400> SEQUENCE: 53

ccgcgggagc tctaactgat ctatccaaaa ctg                                    33


<210> SEQ ID NO 54
<211> LENGTH: 39
<212> TYPE: DNA
<213> ORGANISM: Artificial Sequence
<220> FEATURE:
<223> OTHER INFORMATION: Artificial DNA Primer

<400> SEQUENCE: 54

ccgcgggatc agcatgcgat cgctcgacat ttgatatac                              39


<210> SEQ ID NO 55
<211> LENGTH: 36
<212> TYPE: DNA
<213> ORGANISM: Artificial Sequence
<220> FEATURE:
<223> OTHER INFORMATION: Artificial DNA Primer

<400> SEQUENCE: 55

tcttccacac ctgcagtata tctaggaacc catcag                                 36


<210> SEQ ID NO 56
<211> LENGTH: 48
<212> TYPE: DNA
<213> ORGANISM: Artificial Sequence
<220> FEATURE:
<223> OTHER INFORMATION: Artificial DNA Primer

<400> SEQUENCE: 56

ctgtctctga attactgaac acaacatttt tagtttatgt atgtgttt                    48
```

<210> SEQ ID NO 57
<211> LENGTH: 48
<212> TYPE: DNA
<213> ORGANISM: Artificial Sequence
<220> FEATURE:
<223> OTHER INFORMATION: Artificial DNA Primer

<400> SEQUENCE: 57
gcgaactgga aaagactctc atctaaagat ctcccatgtc tctactgg 48

<210> SEQ ID NO 58
<211> LENGTH: 40
<212> TYPE: DNA
<213> ORGANISM: Artificial Sequence
<220> FEATURE:
<223> OTHER INFORMATION: Artificial DNA Primer

<400> SEQUENCE: 58
atcagttaga ctgcaggaac atagaaatat cgaatgggaa 40

<210> SEQ ID NO 59
<211> LENGTH: 48
<212> TYPE: DNA
<213> ORGANISM: Artificial Sequence
<220> FEATURE:
<223> OTHER INFORMATION: Artificial DNA Primer

<400> SEQUENCE: 59
aaacacatac ataaactaaa aatgttgtgt tcagtaattc agagacag 48

<210> SEQ ID NO 60
<211> LENGTH: 48
<212> TYPE: DNA
<213> ORGANISM: Artificial Sequence
<220> FEATURE:
<223> OTHER INFORMATION: Artificial DNA Primer

<400> SEQUENCE: 60
ccagtagaga catgggagat ctttagatga gagtcttttc cagttcgc 48

<210> SEQ ID NO 61
<211> LENGTH: 36
<212> TYPE: DNA
<213> ORGANISM: Artificial Sequence
<220> FEATURE:
<223> OTHER INFORMATION: Artificial DNA Primer

<400> SEQUENCE: 61
tcttccacac ctgcagtata tctaggaacc catcag 36

<210> SEQ ID NO 62
<211> LENGTH: 40
<212> TYPE: DNA
<213> ORGANISM: Artificial Sequence
<220> FEATURE:
<223> OTHER INFORMATION: Artificial DNA Primer

<400> SEQUENCE: 62
atcagttaga ctgcaggaac atagaaatat cgaatgggaa 40

<210> SEQ ID NO 63
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 63
ctagaactag tggatccccc atgtcattcg acgacttaca caaag 45

<210> SEQ ID NO 64
<211> LENGTH: 41
<212> TYPE: DNA
<213> ORGANISM: Artificial Sequence
<220> FEATURE:
<223> OTHER INFORMATION: Artificial DNA Primer

<400> SEQUENCE: 64
atatcgaatt cctgcagccc tcatgctaca agcgcacaca a 41

<210> SEQ ID NO 65
<211> LENGTH: 48
<212> TYPE: DNA
<213> ORGANISM: Artificial Sequence
<220> FEATURE:
<223> OTHER INFORMATION: Artificial DNA Primer

<400> SEQUENCE: 65
ctagaactag tggatccccc atgtccaata actcattcac taacttca 48

<210> SEQ ID NO 66
<211> LENGTH: 41
<212> TYPE: DNA
<213> ORGANISM: Artificial Sequence
<220> FEATURE:
<223> OTHER INFORMATION: Artificial DNA Primer

<400> SEQUENCE: 66
atatcgaatt cctgcagccc tcacatccat tccttgaatt g 41

<210> SEQ ID NO 67
<211> LENGTH: 46
<212> TYPE: DNA
<213> ORGANISM: Artificial Sequence
<220> FEATURE:
<223> OTHER INFORMATION: Artificial DNA Primer

<400> SEQUENCE: 67
ctagaactag tggatccccc atgttcaaac cagtagactt ctctga 46

<210> SEQ ID NO 68
<211> LENGTH: 40
<212> TYPE: DNA
<213> ORGANISM: Artificial Sequence
<220> FEATURE:
<223> OTHER INFORMATION: Artificial DNA Primer

<400> SEQUENCE: 68
atatcgaatt cctgcagccc ttaaacgtga ctttggctgc 40

<210> SEQ ID NO 69
<211> LENGTH: 48
<212> TYPE: DNA
<213> ORGANISM: Artificial Sequence
<220> FEATURE:
<223> OTHER INFORMATION: Artificial DNA Primer

<400> SEQUENCE: 69
ctagaactag tggatccccc atgactgtta ctactccttt tgtgaatg 48

<210> SEQ ID NO 70
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 70
atatcgaatt cctgcagccc ttaatcaact ctctttcttc caacc 45

<210> SEQ ID NO 71
<211> LENGTH: 41
<212> TYPE: DNA
<213> ORGANISM: Artificial Sequence
<220> FEATURE:
<223> OTHER INFORMATION: Artificial DNA Primer

<400> SEQUENCE: 71
ctagaactag tggatccccc atgggtggtt cttccgattc a 41

<210> SEQ ID NO 72
<211> LENGTH: 41
<212> TYPE: DNA
<213> ORGANISM: Artificial Sequence
<220> FEATURE:
<223> OTHER INFORMATION: Artificial DNA Primer

<400> SEQUENCE: 72
atatcgaatt cctgcagccc tcaagcaaat ccgttgcttt c 41

<210> SEQ ID NO 73
<211> LENGTH: 46
<212> TYPE: DNA
<213> ORGANISM: Artificial Sequence
<220> FEATURE:
<223> OTHER INFORMATION: Artificial DNA Primer

<400> SEQUENCE: 73
ctagaactag tggatccccc atgggtgttg aacaaatctt aaagag 46

<210> SEQ ID NO 74
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 74
atatcgaatt cctgcagccc ttaatcaact ctctttcttc caacc 45

<210> SEQ ID NO 75
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 75
ctagaactag tggatccccc atgatcagaa ttgctattaa cggtttc 47

<210> SEQ ID NO 76
<211> LENGTH: 42
<212> TYPE: DNA
<213> ORGANISM: Artificial Sequence
<220> FEATURE:
<223> OTHER INFORMATION: Artificial DNA Primer

<400> SEQUENCE: 76
atatcgaatt cctgcagccc ttaagccttg gcaacatatt cg 42

<210> SEQ ID NO 77
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 77
ctagaactag tggatccccc atggttagag ttgctattaa cggtttc 47

<210> SEQ ID NO 78
<211> LENGTH: 40
<212> TYPE: DNA
<213> ORGANISM: Artificial Sequence
<220> FEATURE:
<223> OTHER INFORMATION: Artificial DNA Primer

<400> SEQUENCE: 78
atatcgaatt cctgcagccc ttaagccttg gcaacgtgtt 40

<210> SEQ ID NO 79
<211> LENGTH: 48
<212> TYPE: DNA
<213> ORGANISM: Artificial Sequence
<220> FEATURE:
<223> OTHER INFORMATION: Artificial DNA Primer

<400> SEQUENCE: 79
ctagaactag tggatccccc atgccaaagt tagttttagt tagacacg 48

<210> SEQ ID NO 80
<211> LENGTH: 44
<212> TYPE: DNA
<213> ORGANISM: Artificial Sequence
<220> FEATURE:
<223> OTHER INFORMATION: Artificial DNA Primer

<400> SEQUENCE: 80
atatcgaatt cctgcagccc ttatttctta ccttggttgg caac 44

<210> SEQ ID NO 81
<211> LENGTH: 44
<212> TYPE: DNA
<213> ORGANISM: Artificial Sequence
<220> FEATURE:
<223> OTHER INFORMATION: Artificial DNA Primer

<400> SEQUENCE: 81
ctagaactag tggatccccc atgactgcaa gcacaccatc caat 44

<210> SEQ ID NO 82
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 82
atatcgaatt cctgcagccc ttaaggattt tttatgaaac cctca 45

<210> SEQ ID NO 83
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 83
ctagaactag tggatccccc atgactgtta ctgacacttt taaactg 47

<210> SEQ ID NO 84
<211> LENGTH: 42
<212> TYPE: DNA
<213> ORGANISM: Artificial Sequence
<220> FEATURE:
<223> OTHER INFORMATION: Artificial DNA Primer

<400> SEQUENCE: 84
atatcgaatt cctgcagccc tcatggattc ttttcgaaac cc 42

<210> SEQ ID NO 85
<211> LENGTH: 43
<212> TYPE: DNA
<213> ORGANISM: Artificial Sequence
<220> FEATURE:
<223> OTHER INFORMATION: Artificial DNA Primer

<400> SEQUENCE: 85
ctagaactag tggatccccc atggctgtct ctaaagttta cgc 43

<210> SEQ ID NO 86
<211> LENGTH: 42
<212> TYPE: DNA
<213> ORGANISM: Artificial Sequence
<220> FEATURE:
<223> OTHER INFORMATION: Artificial DNA Primer

<400> SEQUENCE: 86
atatcgaatt cctgcagccc ttataatttg tcaccgtggt gg 42

<210> SEQ ID NO 87
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 87
ctagaactag tggatccccc atgtctagat tagaaagatt gacctca 47

<210> SEQ ID NO 88
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 88
atatcgaatt cctgcagccc ttaaacggta gagacttgca aagtg 45

<210> SEQ ID NO 89
<211> LENGTH: 40
<212> TYPE: DNA
<213> ORGANISM: Artificial Sequence
<220> FEATURE:
<223> OTHER INFORMATION: Artificial DNA Primer

<400> SEQUENCE: 89
ctagaactag tggatccccc atgccagagt ccagattgca 40

<210> SEQ ID NO 90
<211> LENGTH: 48
<212> TYPE: DNA
<213> ORGANISM: Artificial Sequence
<220> FEATURE:
<223> OTHER INFORMATION: Artificial DNA Primer

<400> SEQUENCE: 90
atatcgaatt cctgcagccc ctagaattct tgaccaacag tagaaatg 48

<210> SEQ ID NO 91
<211> LENGTH: 44
<212> TYPE: DNA
<213> ORGANISM: Artificial Sequence
<220> FEATURE:
<223> OTHER INFORMATION: Artificial DNA Primer

<400> SEQUENCE: 91
ctagaactag tggatccccc atgtctgaaa ttactttggg taaa 44

<210> SEQ ID NO 92
<211> LENGTH: 43
<212> TYPE: DNA
<213> ORGANISM: Artificial Sequence
<220> FEATURE:
<223> OTHER INFORMATION: Artificial DNA Primer

<400> SEQUENCE: 92
atatcgaatt cctgcagccc ttattgctta gcgttggtag cag 43

<210> SEQ ID NO 93
<211> LENGTH: 48
<212> TYPE: DNA
<213> ORGANISM: Artificial Sequence
<220> FEATURE:
<223> OTHER INFORMATION: Artificial DNA Primer

<400> SEQUENCE: 93
ctagaactag tggatccccc atgtctgaaa ttactcttgg aaaatact 48

<210> SEQ ID NO 94
<211> LENGTH: 43
<212> TYPE: DNA
<213> ORGANISM: Artificial Sequence
<220> FEATURE:
<223> OTHER INFORMATION: Artificial DNA Primer

<400> SEQUENCE: 94
atatcgaatt cctgcagccc ttattgtttg gcatttgtag cgg 43

<210> SEQ ID NO 95
<211> LENGTH: 46
<212> TYPE: DNA
<213> ORGANISM: Artificial Sequence
<220> FEATURE:
<223> OTHER INFORMATION: Artificial DNA Primer

<400> SEQUENCE: 95
ctagaactag tggatccccc atgactaagc tacactttga cactgc 46

<210> SEQ ID NO 96
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 96
atatcgaatt cctgcagccc ttacaactta attctgacag cttttac 47

<210> SEQ ID NO 97
<211> LENGTH: 41
<212> TYPE: DNA
<213> ORGANISM: Artificial Sequence
<220> FEATURE:
<223> OTHER INFORMATION: Artificial DNA Primer

<400> SEQUENCE: 97
ctagaactag tggatccccc atgccttcgc aagtcattcc t 41

<210> SEQ ID NO 98
<211> LENGTH: 46
<212> TYPE: DNA
<213> ORGANISM: Artificial Sequence
<220> FEATURE:
<223> OTHER INFORMATION: Artificial DNA Primer

<400> SEQUENCE: 98
atatcgaatt cctgcagccc tcatttagaa gtctcaacaa catatc 46

<210> SEQ ID NO 99
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 99
ctagaactag tggatccccc atgtcttatc ctgagaaatt tgaaggt 47

<210> SEQ ID NO 100
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 100
atatcgaatt cctgcagccc ctagtctgaa aattctttgt cgtagcc 47

<210> SEQ ID NO 101
<211> LENGTH: 43
<212> TYPE: DNA
<213> ORGANISM: Artificial Sequence
<220> FEATURE:
<223> OTHER INFORMATION: Artificial DNA Primer

<400> SEQUENCE: 101
ctagaactag tggatccccc atggctagaa ctttctttgt cgg 43

<210> SEQ ID NO 102
<211> LENGTH: 48
<212> TYPE: DNA
<213> ORGANISM: Artificial Sequence
<220> FEATURE:
<223> OTHER INFORMATION: Artificial DNA Primer

<400> SEQUENCE: 102
atatcgaatt cctgcagccc ttagtttcta gagttgatga tatcaaca 48

<210> SEQ ID NO 103
<211> LENGTH: 43
<212> TYPE: DNA
<213> ORGANISM: Artificial Sequence
<220> FEATURE:
<223> OTHER INFORMATION: Artificial DNA Primer

<400> SEQUENCE: 103
ctagaactag tggatccccc atgtctgctg ctgctgatag att 43

<210> SEQ ID NO 104
<211> LENGTH: 48
<212> TYPE: DNA
<213> ORGANISM: Artificial Sequence
<220> FEATURE:
<223> OTHER INFORMATION: Artificial DNA Primer

<400> SEQUENCE: 104
atatcgaatt cctgcagccc ctaatcttca tgtagatcta attcttca 48

<210> SEQ ID NO 105
<211> LENGTH: 44
<212> TYPE: DNA
<213> ORGANISM: Artificial Sequence
<220> FEATURE:
<223> OTHER INFORMATION: Artificial DNA Primer

<400> SEQUENCE: 105
ctagaactag tggatccccc atgcttgctg tcagaagatt aaca 44

<210> SEQ ID NO 106
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 106
atatcgaatt cctgcagccc ctattcgtca tcgatgtcta gctct 45

<210> SEQ ID NO 107
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 107
ctagaactag tggatccccc atgggattga ctactaaacc tctatct 47

<210> SEQ ID NO 108
<211> LENGTH: 42
<212> TYPE: DNA
<213> ORGANISM: Artificial Sequence
<220> FEATURE:
<223> OTHER INFORMATION: Artificial DNA Primer

<400> SEQUENCE: 108
atatcgaatt cctgcagccc ttaccatttc aacagatcgt cc 42

<210> SEQ ID NO 109
<211> LENGTH: 48
<212> TYPE: DNA
<213> ORGANISM: Artificial Sequence
<220> FEATURE:
<223> OTHER INFORMATION: Artificial DNA Primer

<400> SEQUENCE: 109
ctagaactag tggatccccc atggatccta atagtaacag ttctagcg 48

<210> SEQ ID NO 110
<211> LENGTH: 53
<212> TYPE: DNA
<213> ORGANISM: Artificial Sequence
<220> FEATURE:
<223> OTHER INFORMATION: Artificial DNA Primer

<400> SEQUENCE: 110
atatcgaatt cctgcagccc ttatttcaaa tcattatttt catttacagg ttg 53

<210> SEQ ID NO 111
<211> LENGTH: 41
<212> TYPE: DNA
<213> ORGANISM: Artificial Sequence
<220> FEATURE:
<223> OTHER INFORMATION: Artificial DNA Primer

<400> SEQUENCE: 111
ctagaactag tggatccccc atgaacgata gccaaaactg c 41

<210> SEQ ID NO 112
<211> LENGTH: 41
<212> TYPE: DNA
<213> ORGANISM: Artificial Sequence
<220> FEATURE:
<223> OTHER INFORMATION: Artificial DNA Primer

<400> SEQUENCE: 112
atatcgaatt cctgcagccc ttattggggg gaagtgtatt g 41

<210> SEQ ID NO 113
<211> LENGTH: 41
<212> TYPE: DNA
<213> ORGANISM: Artificial Sequence
<220> FEATURE:
<223> OTHER INFORMATION: Artificial DNA Primer

<400> SEQUENCE: 113
ctagaactag tggatccccc atgcaaagcc catatccaat g 41

<210> SEQ ID NO 114
<211> LENGTH: 40
<212> TYPE: DNA
<213> ORGANISM: Artificial Sequence
<220> FEATURE:
<223> OTHER INFORMATION: Artificial DNA Primer

<400> SEQUENCE: 114
atatcgaatt cctgcagccc tcagtccatg tgtgggaagg 40

<210> SEQ ID NO 115
<211> LENGTH: 41
<212> TYPE: DNA
<213> ORGANISM: Artificial Sequence
<220> FEATURE:
<223> OTHER INFORMATION: Artificial DNA Primer

<400> SEQUENCE: 115
ctagaactag tggatccccc atgtttgttt caccacctcc a 41

<210> SEQ ID NO 116
<211> LENGTH: 41
<212> TYPE: DNA
<213> ORGANISM: Artificial Sequence
<220> FEATURE:
<223> OTHER INFORMATION: Artificial DNA Primer

<400> SEQUENCE: 116
atatcgaatt cctgcagccc ctaggacatt ccatcaggct t 41

<210> SEQ ID NO 117
<211> LENGTH: 46
<212> TYPE: DNA
<213> ORGANISM: Artificial Sequence
<220> FEATURE:
<223> OTHER INFORMATION: Artificial DNA Primer

<400> SEQUENCE: 117
ctagaactag tggatccccc atgtctatcc cagaaactca aaaagg 46

<210> SEQ ID NO 118
<211> LENGTH: 49
<212> TYPE: DNA
<213> ORGANISM: Artificial Sequence
<220> FEATURE:
<223> OTHER INFORMATION: Artificial DNA Primer

<400> SEQUENCE: 118
atatcgaatt cctgcagccc ttatttagaa gtgtcacaac gtatctacc 49

<210> SEQ ID NO 119
<211> LENGTH: 41
<212> TYPE: DNA
<213> ORGANISM: Artificial Sequence
<220> FEATURE:
<223> OTHER INFORMATION: Artificial DNA Primer

<400> SEQUENCE: 119
ctagaactag tggatccccc atgaacgata gccaaaactg c 41

<210> SEQ ID NO 120
<211> LENGTH: 41
<212> TYPE: DNA
<213> ORGANISM: Artificial Sequence
<220> FEATURE:
<223> OTHER INFORMATION: Artificial DNA Primer

<400> SEQUENCE: 120
atatcgaatt cctgcagccc ttattggggg gaagtgtatt g 41

<210> SEQ ID NO 121
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 121
ctagaactag tggatccccc atgttgcaag gaattttaga aaccg 45

<210> SEQ ID NO 122
<211> LENGTH: 52
<212> TYPE: DNA
<213> ORGANISM: Artificial Sequence
<220> FEATURE:
<223> OTHER INFORMATION: Artificial DNA Primer

<400> SEQUENCE: 122
atatcgaatt cctgcagccc tcaaaatttt gtaactatat tcatttcatc tg 52

<210> SEQ ID NO 123
<211> LENGTH: 46
<212> TYPE: DNA
<213> ORGANISM: Artificial Sequence
<220> FEATURE:
<223> OTHER INFORMATION: Artificial DNA Primer

<400> SEQUENCE: 123
ctagaactag tggatccccc atgaatacaa acgttccaat attcag 46

<210> SEQ ID NO 124
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 124
atatcgaatt cctgcagccc ttattgttcg tacaaacaag taccc 45

<210> SEQ ID NO 125
<211> LENGTH: 48
<212> TYPE: DNA
<213> ORGANISM: Artificial Sequence
<220> FEATURE:
<223> OTHER INFORMATION: Artificial DNA Primer

<400> SEQUENCE: 125
ctagaactag tggatccccc atgactaaat ctcattcaga agaagtga 48

<210> SEQ ID NO 126
<211> LENGTH: 46
<212> TYPE: DNA
<213> ORGANISM: Artificial Sequence
<220> FEATURE:
<223> OTHER INFORMATION: Artificial DNA Primer

<400> SEQUENCE: 126
atatcgaatt cctgcagccc ttataattca tatagacagc tgccca 46

<210> SEQ ID NO 127
<211> LENGTH: 48
<212> TYPE: DNA
<213> ORGANISM: Artificial Sequence
<220> FEATURE:
<223> OTHER INFORMATION: Artificial DNA Primer

<400> SEQUENCE: 127
ctagaactag tggatccccc atgaagctac tgtcttctat cgaacaag 48

<210> SEQ ID NO 128
<211> LENGTH: 44
<212> TYPE: DNA
<213> ORGANISM: Artificial Sequence
<220> FEATURE:
<223> OTHER INFORMATION: Artificial DNA Primer

<400> SEQUENCE: 128
atatcgaatt cctgcagccc ttactctttt tttgggtttg gtgg 44

<210> SEQ ID NO 129
<211> LENGTH: 46
<212> TYPE: DNA
<213> ORGANISM: Artificial Sequence
<220> FEATURE:
<223> OTHER INFORMATION: Artificial DNA Primer

<400> SEQUENCE: 129
ctagaactag tggatccccc atgactgctg aagaatttga tttttc 46

<210> SEQ ID NO 130
<211> LENGTH: 50
<212> TYPE: DNA
<213> ORGANISM: Artificial Sequence
<220> FEATURE:
<223> OTHER INFORMATION: Artificial DNA Primer

<400> SEQUENCE: 130
atatcgaatt cctgcagccc ttacagtctt tgtagataat gaatctgacc 50

<210> SEQ ID NO 131
<211> LENGTH: 1314
<212> TYPE: DNA
<213> ORGANISM: Saccharomyces cerevisiae

<400> SEQUENCE: 131
atggctgtct ctaaagttta cgctagatcc gtctacgact cccgtggtaa cccaaccgtc 60
gaagtcgaat taaccaccga aaagggtgtt ttcagatcca ttgtcccatc tggtgcttct 120
accggtgtcc acgaagcttt ggaaatgaga gatggtgaca aatccaagtg gatgggtaag 180
ggtgttttgc acgctgttaa gaacgtcaac gatgtcattg ctccagcttt cgttaaggct 240
aacattgatg ttaaggacca aaaggccgtc gatgacttct tgatttcttt ggacggtact 300
gccaacaaat ccaagttggg tgctaacgct atcttgggtg tttctttggc tgcttccaga 360
gctgccgctg ctgaaaagaa tgtcccatta tacaagcact tggctgactt gtctaagtcc 420
aagacctctc catacgtttt gccagttcca ttcttgaacg ttttgaacgg tggttcccac 480
gctggtggtg ctttggcttt gcaagaattt atgattgctc caactggtgc taagaccttc 540
gctgaagctt tgagaattgg ttccgaagtt taccacaact tgaagtcttt gaccaagaag 600
agatacggtg cttctgccgg taacgtcggt gacgaaggtg gtgttgctcc aaacattcaa 660
actgctgaag aagctttgga cttgattgtt gacgctatca aggctgctgg tcacgacggt 720
aagatcaaga tcggtttgga ctgtgcttcc tctgaattct tcaaggacgg taagtacgac 780
ttggacttca agaatccaaa ctctgacaaa tccaagtggt tgactggtcc tcaattggct 840
gacttgtacc actccttgat gaagagatac ccaattgtct ccatcgaaga tccatttgct 900
gaagatgact gggaagcttg gtctcacttc ttcaagaccg ctggtattca aattgttgct 960
gatgacttga ctgtcaccaa cccaaagaga attgctaccg ctatcgaaaa gaaggctgcc 1020
gacgctttgt tgttgaaggt caaccaaatc ggtaccttgt ctgaatccat caaggctgct 1080
caagactctt tcgctgccgg ttggggtgtt atggtttccc acagatctgg tgaaactgaa 1140
gacactttca ttgctgactt ggtcgtcggt ttgagaactg gtcaaatcaa gactggtgct 1200
ccagctagat ccgaaagatt ggctaaattg aaccaattgt tgagaatcga agaagaatta 1260
ggtgacaacg ctgttttcgc tggtgaaaac ttccaccacg gtgacaaatt ataa 1314

<210> SEQ ID NO 132
<211> LENGTH: 437
<212> TYPE: PRT
<213> ORGANISM: Saccharomyces cerevisiae

<400> SEQUENCE: 132

```
Met Ala Val Ser Lys Val Tyr Ala Arg Ser Val Tyr Asp Ser Arg Gly
1               5                   10                  15

Asn Pro Thr Val Glu Val Glu Leu Thr Thr Glu Lys Gly Val Phe Arg
            20                  25                  30

Ser Ile Val Pro Ser Gly Ala Ser Thr Gly Val His Glu Ala Leu Glu
        35                  40                  45

Met Arg Asp Gly Asp Lys Ser Lys Trp Met Gly Lys Gly Val Leu His
    50                  55                  60

Ala Val Lys Asn Val Asn Asp Val Ile Ala Pro Ala Phe Val Lys Ala
65                  70                  75                  80

Asn Ile Asp Val Lys Asp Gln Lys Ala Val Asp Asp Phe Leu Ile Ser
                85                  90                  95

Leu Asp Gly Thr Ala Asn Lys Ser Lys Leu Gly Ala Asn Ala Ile Leu
            100                 105                 110

Gly Val Ser Leu Ala Ala Ser Arg Ala Ala Ala Ala Glu Lys Asn Val
        115                 120                 125

Pro Leu Tyr Lys His Leu Ala Asp Leu Ser Lys Ser Lys Thr Ser Pro
    130                 135                 140

Tyr Val Leu Pro Val Pro Phe Leu Asn Val Leu Asn Gly Gly Ser His
145                 150                 155                 160

Ala Gly Gly Ala Leu Ala Leu Gln Glu Phe Met Ile Ala Pro Thr Gly
                165                 170                 175

Ala Lys Thr Phe Ala Glu Ala Leu Arg Ile Gly Ser Glu Val Tyr His
            180                 185                 190

Asn Leu Lys Ser Leu Thr Lys Lys Arg Tyr Gly Ala Ser Ala Gly Asn
        195                 200                 205

Val Gly Asp Glu Gly Gly Val Ala Pro Asn Ile Gln Thr Ala Glu Glu
    210                 215                 220

Ala Leu Asp Leu Ile Val Asp Ala Ile Lys Ala Ala Gly His Asp Gly
225                 230                 235                 240

Lys Ile Lys Ile Gly Leu Asp Cys Ala Ser Ser Glu Phe Phe Lys Asp
                245                 250                 255

Gly Lys Tyr Asp Leu Asp Phe Lys Asn Pro Asn Ser Asp Lys Ser Lys
            260                 265                 270

Trp Leu Thr Gly Pro Gln Leu Ala Asp Leu Tyr His Ser Leu Met Lys
        275                 280                 285

Arg Tyr Pro Ile Val Ser Ile Glu Asp Pro Phe Ala Glu Asp Asp Trp
    290                 295                 300

Glu Ala Trp Ser His Phe Phe Lys Thr Ala Gly Ile Gln Ile Val Ala
305                 310                 315                 320

Asp Asp Leu Thr Val Thr Asn Pro Lys Arg Ile Ala Thr Ala Ile Glu
                325                 330                 335

Lys Lys Ala Ala Asp Ala Leu Leu Leu Lys Val Asn Gln Ile Gly Thr
            340                 345                 350

Leu Ser Glu Ser Ile Lys Ala Ala Gln Asp Ser Phe Ala Ala Gly Trp
        355                 360                 365

Gly Val Met Val Ser His Arg Ser Gly Glu Thr Glu Asp Thr Phe Ile
    370                 375                 380
```

```
Ala Asp Leu Val Val Gly Leu Arg Thr Gly Gln Ile Lys Thr Gly Ala
385                 390                 395                 400

Pro Ala Arg Ser Glu Arg Leu Ala Lys Leu Asn Gln Leu Leu Arg Ile
                405                 410                 415

Glu Glu Glu Leu Gly Asp Asn Ala Val Phe Ala Gly Glu Asn Phe His
            420                 425                 430

His Gly Asp Lys Leu
        435


<210> SEQ ID NO 133
<211> LENGTH: 2880
<212> TYPE: DNA
<213> ORGANISM: Saccharomyces cerevisiae

<400> SEQUENCE: 133

atgactgtta ctactccttt tgtgaatggt acttcttatt gtaccgtcac tgcatattcc      60

gttcaatctt ataaagctgc catagatttt tacaccaagt tttgtcatt agaaaaccgc     120

tcttctccag atgaaaactc cactttattg tctaacgatt ccatctcttt gaagatcctt     180

ctacgtcctg atgaaaaaat caataaaaat gttgaggctc atttgaagga attgaacagt     240

attaccaaga ctcaagactg gagatcacat gccacccaat ccttggtatt taacacttcc     300

gacatcttgg cagtcaagga cactctaaat gctatgaacg ctcctcttca aggctaccca     360

acagaactat ttccaatgca gttgtacact ttggacccat taggtaacgt tgttggtgtt     420

acttctacta agaacgcagt ttcaaccaag ccaactccac caccagcacc agaagcttct     480

gctgagtctg gtctttcctc taaagttcac tcttacactg atttggctta ccgtatgaaa     540

accaccgaca cctatccatc tctgccaaag ccattgaaca ggcctcaaaa ggcaattgcc     600

gtcatgactt ccggtggtga tgctccaggt atgaactcta acgttagagc catcgtgcgt     660

tccgctatct tcaaaggttg tcgtgccttt gttgtcatgg aaggttatga aggtttggtt     720

cgtggtggtc cagaatacat caaggaattc cactgggaag acgtccgtgg ttggtctgct     780

gaaggtggta ccaacattgg tactgcccgt tgtatggaat tcaagaagcg cgaaggtaga     840

ttattgggtg cccaacattt gattgaggcc ggtgtcgatg ctttgatcgt ttgtggtggt     900

gacggttctt tgactggtgc tgatctgttt agatcagaat ggccttcttt gatcgaggaa     960

ttgttgaaaa caaacagaat ttccaacgaa caatacgaaa gaatgaagca tttgaatatt    1020

tgcggtactg tcggttctat tgataacgat atgtccacca cggatgctac tattggtgct    1080

tactctgcct tggacagaat ctgtaaggcc atcgattacg ttgaagccac tgccaactct    1140

cactcaagag ctttcgttgt tgaagttatg ggtagaaact gtggttggtt agctttatta    1200

gctggtatcg ccacttccgc tgactatatc tttattccag agaagccagc cacttccagc    1260

gaatggcaag atcaaatgtg tgacattgtc tccaagcaca gatcaagggg taagagaacc    1320

accattgttg ttgttgcaga aggtgctatc gctgctgact tgaccccaat ttctccaagc    1380

gacgtccaca aagttctagt tgacagatta ggtttggata caagaattac taccttaggt    1440

cacgttcaaa gaggtggtac tgctgttgct tacgaccgta tcttggctac tttacaaggt    1500

cttgaggccg ttaatgccgt tttggaatcc actccagaca ccccatcacc attgattgct    1560

gttaacgaaa acaaaattgt tcgtaaacca ttaatggaat ccgtcaagtt gaccaaagca    1620

gttgcagaag ccattcaagc taaggatttc aagagagcta tgtctttaag agacactgag    1680

ttcattgaac atttaaacaa tttcatggct atcaactctg ctgaccacaa cgaaccaaag    1740

ctaccaaagg acaagagact gaagattgcc attgttaatg tcggtgctcc agctggtggt    1800
```

```
atcaactctg ccgtctactc gatggctact tactgtatgt cccaaggtca cagaccatac   1860

gctatctaca atggttggtc tggtttggca agacatgaaa gtgttcgttc tttgaactgg   1920

aaggatatgt tgggttggca atcccgtggt ggttctgaaa tcggtactaa cagagtcact   1980

ccagaagaag cagatctagg tatgattgct tactatttcc aaaagtacga atttgatggt   2040

ttgatcatcg ttggtggttt cgaagctttt gaatctttac atcaattaga gagagcaaga   2100

gaaagttatc cagctttcag aatcccaatg gtcttgatac cagctacttt gtctaacaat   2160

gttccaggta ctgaatactc tttgggttct gataccgctt tgaatgctct aatggaatac   2220

tgtgatgttg ttaaacaatc cgcttcttca accagaggta gagccttcgt tgtcgattgt   2280

caaggtggta actcaggcta tttggccact tacgcttctt tggctgttgg tgctcaagtc   2340

tcttatgtcc cagaagaagg tatttctttg gagcaattgt ccgaggatat tgaatactta   2400

gctcaatctt ttgaaaaggc agaaggtaga ggtagatttg gtaaattgat tttgaagagt   2460

acaaacgctt ctaaggcttt atcagccact aaattggctg aagttattac tgctgaagcc   2520

gatggcagat ttgacgctaa gccagcttat ccaggtcatg tacaacaagg tggtttgcca   2580

tctccaattg atagaacaag agccactaga atggccatta aagctgtcgg cttcatcaaa   2640

gacaaccaag ctgccattgc tgaagctcgt gctgccgaag aaaacttcaa cgctgatgac   2700

aagaccattt ctgacactgc tgctgtcgtt ggtgttaagg gttcacatgt cgtttacaac   2760

tccattagac aattgtatga ctatgaaact gaagtttcca tgagaatgcc aaaggtcatt   2820

cactggcaag ctaccagact cattgctgac catttggttg gaagaaagag agttgattaa   2880
```

```
<210> SEQ ID NO 134
<211> LENGTH: 959
<212> TYPE: PRT
<213> ORGANISM: Saccharomyces cerevisiae

<400> SEQUENCE: 134

Met Thr Val Thr Thr Pro Phe Val Asn Gly Thr Ser Tyr Cys Thr Val
1               5                   10                  15

Thr Ala Tyr Ser Val Gln Ser Tyr Lys Ala Ala Ile Asp Phe Tyr Thr
            20                  25                  30

Lys Phe Leu Ser Leu Glu Asn Arg Ser Ser Pro Asp Glu Asn Ser Thr
        35                  40                  45

Leu Leu Ser Asn Asp Ser Ile Ser Leu Lys Ile Leu Leu Arg Pro Asp
    50                  55                  60

Glu Lys Ile Asn Lys Asn Val Glu Ala His Leu Lys Glu Leu Asn Ser
65                  70                  75                  80

Ile Thr Lys Thr Gln Asp Trp Arg Ser His Ala Thr Gln Ser Leu Val
                85                  90                  95

Phe Asn Thr Ser Asp Ile Leu Ala Val Lys Asp Thr Leu Asn Ala Met
            100                 105                 110

Asn Ala Pro Leu Gln Gly Tyr Pro Thr Glu Leu Phe Pro Met Gln Leu
        115                 120                 125

Tyr Thr Leu Asp Pro Leu Gly Asn Val Val Gly Val Thr Ser Thr Lys
    130                 135                 140

Asn Ala Val Ser Thr Lys Pro Thr Pro Pro Pro Ala Pro Glu Ala Ser
145                 150                 155                 160

Ala Glu Ser Gly Leu Ser Ser Lys Val His Ser Tyr Thr Asp Leu Ala
                165                 170                 175

Tyr Arg Met Lys Thr Thr Asp Thr Tyr Pro Ser Leu Pro Lys Pro Leu
            180                 185                 190
```

```
Asn Arg Pro Gln Lys Ala Ile Ala Val Met Thr Ser Gly Gly Asp Ala
        195                 200                 205

Pro Gly Met Asn Ser Asn Val Arg Ala Ile Val Arg Ser Ala Ile Phe
    210                 215                 220

Lys Gly Cys Arg Ala Phe Val Val Met Glu Gly Tyr Glu Gly Leu Val
225                 230                 235                 240

Arg Gly Gly Pro Glu Tyr Ile Lys Glu Phe His Trp Glu Asp Val Arg
                245                 250                 255

Gly Trp Ser Ala Glu Gly Gly Thr Asn Ile Gly Thr Ala Arg Cys Met
            260                 265                 270

Glu Phe Lys Lys Arg Glu Gly Arg Leu Leu Gly Ala Gln His Leu Ile
        275                 280                 285

Glu Ala Gly Val Asp Ala Leu Ile Val Cys Gly Gly Asp Gly Ser Leu
    290                 295                 300

Thr Gly Ala Asp Leu Phe Arg Ser Glu Trp Pro Ser Leu Ile Glu Glu
305                 310                 315                 320

Leu Leu Lys Thr Asn Arg Ile Ser Asn Glu Gln Tyr Glu Arg Met Lys
                325                 330                 335

His Leu Asn Ile Cys Gly Thr Val Gly Ser Ile Asp Asn Asp Met Ser
            340                 345                 350

Thr Thr Asp Ala Thr Ile Gly Ala Tyr Ser Ala Leu Asp Arg Ile Cys
        355                 360                 365

Lys Ala Ile Asp Tyr Val Glu Ala Thr Ala Asn Ser His Ser Arg Ala
    370                 375                 380

Phe Val Val Glu Val Met Gly Arg Asn Cys Gly Trp Leu Ala Leu Leu
385                 390                 395                 400

Ala Gly Ile Ala Thr Ser Ala Asp Tyr Ile Phe Ile Pro Glu Lys Pro
                405                 410                 415

Ala Thr Ser Ser Glu Trp Gln Asp Gln Met Cys Asp Ile Val Ser Lys
            420                 425                 430

His Arg Ser Arg Gly Lys Arg Thr Thr Ile Val Val Val Ala Glu Gly
        435                 440                 445

Ala Ile Ala Ala Asp Leu Thr Pro Ile Ser Pro Ser Asp Val His Lys
    450                 455                 460

Val Leu Val Asp Arg Leu Gly Leu Asp Thr Arg Ile Thr Thr Leu Gly
465                 470                 475                 480

His Val Gln Arg Gly Gly Thr Ala Val Ala Tyr Asp Arg Ile Leu Ala
                485                 490                 495

Thr Leu Gln Gly Leu Glu Ala Val Asn Ala Val Leu Glu Ser Thr Pro
            500                 505                 510

Asp Thr Pro Ser Pro Leu Ile Ala Val Asn Glu Asn Lys Ile Val Arg
        515                 520                 525

Lys Pro Leu Met Glu Ser Val Lys Leu Thr Lys Ala Val Ala Glu Ala
    530                 535                 540

Ile Gln Ala Lys Asp Phe Lys Arg Ala Met Ser Leu Arg Asp Thr Glu
545                 550                 555                 560

Phe Ile Glu His Leu Asn Asn Phe Met Ala Ile Asn Ser Ala Asp His
                565                 570                 575

Asn Glu Pro Lys Leu Pro Lys Asp Lys Arg Leu Lys Ile Ala Ile Val
            580                 585                 590

Asn Val Gly Ala Pro Ala Gly Gly Ile Asn Ser Ala Val Tyr Ser Met
        595                 600                 605
```

```
Ala Thr Tyr Cys Met Ser Gln Gly His Arg Pro Tyr Ala Ile Tyr Asn
    610                 615                 620

Gly Trp Ser Gly Leu Ala Arg His Glu Ser Val Arg Ser Leu Asn Trp
625                 630                 635                 640

Lys Asp Met Leu Gly Trp Gln Ser Arg Gly Gly Ser Glu Ile Gly Thr
                645                 650                 655

Asn Arg Val Thr Pro Glu Glu Ala Asp Leu Gly Met Ile Ala Tyr Tyr
            660                 665                 670

Phe Gln Lys Tyr Glu Phe Asp Gly Leu Ile Ile Val Gly Gly Phe Glu
        675                 680                 685

Ala Phe Glu Ser Leu His Gln Leu Glu Arg Ala Arg Glu Ser Tyr Pro
    690                 695                 700

Ala Phe Arg Ile Pro Met Val Leu Ile Pro Ala Thr Leu Ser Asn Asn
705                 710                 715                 720

Val Pro Gly Thr Glu Tyr Ser Leu Gly Ser Asp Thr Ala Leu Asn Ala
                725                 730                 735

Leu Met Glu Tyr Cys Asp Val Val Lys Gln Ser Ala Ser Ser Thr Arg
            740                 745                 750

Gly Arg Ala Phe Val Val Asp Cys Gln Gly Gly Asn Ser Gly Tyr Leu
        755                 760                 765

Ala Thr Tyr Ala Ser Leu Ala Val Gly Ala Gln Val Ser Tyr Val Pro
    770                 775                 780

Glu Glu Gly Ile Ser Leu Glu Gln Leu Ser Glu Asp Ile Glu Tyr Leu
785                 790                 795                 800

Ala Gln Ser Phe Glu Lys Ala Glu Gly Arg Gly Arg Phe Gly Lys Leu
                805                 810                 815

Ile Leu Lys Ser Thr Asn Ala Ser Lys Ala Leu Ser Ala Thr Lys Leu
            820                 825                 830

Ala Glu Val Ile Thr Ala Glu Ala Asp Gly Arg Phe Asp Ala Lys Pro
        835                 840                 845

Ala Tyr Pro Gly His Val Gln Gln Gly Gly Leu Pro Ser Pro Ile Asp
    850                 855                 860

Arg Thr Arg Ala Thr Arg Met Ala Ile Lys Ala Val Gly Phe Ile Lys
865                 870                 875                 880

Asp Asn Gln Ala Ala Ile Ala Glu Ala Arg Ala Ala Glu Glu Asn Phe
                885                 890                 895

Asn Ala Asp Asp Lys Thr Ile Ser Asp Thr Ala Ala Val Val Gly Val
            900                 905                 910

Lys Gly Ser His Val Val Tyr Asn Ser Ile Arg Gln Leu Tyr Asp Tyr
        915                 920                 925

Glu Thr Glu Val Ser Met Arg Met Pro Lys Val Ile His Trp Gln Ala
    930                 935                 940

Thr Arg Leu Ile Ala Asp His Leu Val Gly Arg Lys Arg Val Asp
945                 950                 955


<210> SEQ ID NO 135
<211> LENGTH: 2484
<212> TYPE: DNA
<213> ORGANISM: Saccharomyces cerevisiae

<400> SEQUENCE: 135

atgttcaaac cagtagactt ctctgaaaca tctcctgtgc cgcctgatat tgatcttgct      60

cctacacaat ctccacacca tgtggcacct agtcaagact ccagttatga tcttttatcc     120

cggagttccg atgataaaat tgatgctgaa aagggtccgc atgatgaatt atctaagcac     180
```

```
ttaccacttt ttcagaaaag acctttgagc gatactccta tatcgagcaa ttggaactct    240
cctggaatca ctgaagaaaa tacaccttct gactctcctg aaaatagcgc tactaatttg    300
aaatcgctac atcgattgca tattaacgac gaaacgcaac taaaaaatgc taaaattccc    360
acaaacgata ctactgacta catgcctcct tcagatggag caaatgaggt aactcggatt    420
gatttgaaag acattaaatc acctacgaga caccataaaa gaagacctac caccatcgat    480
gttcctggtt taacaaagtc taaaacatct ccagatggtc tcatatcaaa ggaagatagt    540
ggatcaaagt tagtgattgt catggtcgga ctgccagcta cgggaaagtc atttattaca    600
aataaattat ccagattttt aaattattct ttatactatt gtaaagtgtt taatgtcggt    660
aacactagaa ggaagtttgc taaggagcat ggcctaaagg accaggattc aaagtttttc    720
gagccgaaaa acgccgactc tactaggttg agagacaaat gggccatgga tactctggat    780
gaattgctag attatttatt agaaggttca ggatctgtgg gaatttttga tgctacaaat    840
acctctcgtg aaagaagaaa aaacgttctg gctagaatca gaaagagaag tcctcatttg    900
aaggttttat ttttagaatc tgtttgttcg gatcatgcac tggtacagaa aaatattaga    960
ctcaaattat ttggtccaga ttacaaaggt aaagatcctg aaagctcttt aaaagatttt   1020
aaaagtcgcc tggcaaacta cttgaaagcc tatgaaccaa ttgaggatga cgaaaatttg   1080
cagtacatca aaatgataga tgtgggaaag aaagtcatcg catacaatat tcaagggttt   1140
ttagcttcgc agacggtata ttatttgtta aatttcaatt tggctgacag acaaatttgg   1200
ataacgagaa gtggcgagag cgaagataat gttagtggcc gtataggcgg aaattcccat   1260
ttgactcctc gtggtctaag atttgctaaa agtctaccaa aattcattgc cagacagaga   1320
gaaatatttt atcaaaatct catgcaacaa aaaaagaata atgaaaatac agatgggaac   1380
atttataatg actttttcgt ttggaccagc atgcgtgcta ggactatagg gactgctcaa   1440
tatttcaacg aagatgatta tcctatcaaa caaatgaaaa tgttagatga gttaagtgca   1500
ggtgattatg atggtatgac atatccagaa attaaaaaca actttcctga agaattcgaa   1560
aaaagacaga aagataagtt gagatacaga taccctggta ttggcggtga atcgtatatg   1620
gacgttatta atagactcag acctgttatc acagaactag aaagaatcga ggataacgtt   1680
cttattatta cacaccgggt ggtggcaaga gccttattgg gttattttat gaacttgagt   1740
atgggtatta ttgccaattt ggatgtccca ttacattgtg tatattgcct agaaccaaaa   1800
ccatatggaa tcacttggtc attatgggag tatgatgaag catcggattc attttctaag   1860
gtcccacaaa cggacttgaa taccaccaga gtaaaggagg ttggccttgt ttataatgaa   1920
agaagatatt ctgttatacc aacagctccg ccaagtgcaa gaagcagctt tgcaagtgac   1980
tttttgtcaa gaaaaagatc taatcctact tctgcatctt catcccagag tgaattatca   2040
gaacaaccca agaatagcgt tagtgctcaa actggcagca ataataccac tctcattggg   2100
agcaacttta acatcaagaa tgaaaatggt gattcgagaa taccattatc tgcaccactt   2160
atggccacta atacttctaa taacatctta gatggtggag gtacctcaat ttcgatacat   2220
cgtcccaggg ttgttccaaa tcaaaacaac gtgaatcctc ttttggctaa caacaataaa   2280
gcggcttcta atgtacctaa tgtaaagaag tcagcggcta caccaaggca aatttttgaa   2340
atagataaag tggacgaaaa gttatccatg ttgaaaaata aaagttttct attacatgga   2400
aaggattatc ctaataatgc tgataataat gacaacgaag atataagggc aaaaaccatg   2460
aatcgcagcc aaagtcacgt ttaa                                          2484
```

```
<210> SEQ ID NO 136
<211> LENGTH: 827
<212> TYPE: PRT
<213> ORGANISM: Saccharomyces cerevisiae

<400> SEQUENCE: 136

Met Phe Lys Pro Val Asp Phe Ser Glu Thr Ser Pro Val Pro Pro Asp
1               5                   10                  15

Ile Asp Leu Ala Pro Thr Gln Ser Pro His His Val Ala Pro Ser Gln
            20                  25                  30

Asp Ser Ser Tyr Asp Leu Leu Ser Arg Ser Ser Asp Asp Lys Ile Asp
        35                  40                  45

Ala Glu Lys Gly Pro His Asp Glu Leu Ser Lys His Leu Pro Leu Phe
    50                  55                  60

Gln Lys Arg Pro Leu Ser Asp Thr Pro Ile Ser Ser Asn Trp Asn Ser
65                  70                  75                  80

Pro Gly Ile Thr Glu Glu Asn Thr Pro Ser Asp Ser Pro Glu Asn Ser
                85                  90                  95

Ala Thr Asn Leu Lys Ser Leu His Arg Leu His Ile Asn Asp Glu Thr
            100                 105                 110

Gln Leu Lys Asn Ala Lys Ile Pro Thr Asn Asp Thr Thr Asp Tyr Met
        115                 120                 125

Pro Pro Ser Asp Gly Ala Asn Glu Val Thr Arg Ile Asp Leu Lys Asp
    130                 135                 140

Ile Lys Ser Pro Thr Arg His His Lys Arg Arg Pro Thr Thr Ile Asp
145                 150                 155                 160

Val Pro Gly Leu Thr Lys Ser Lys Thr Ser Pro Asp Gly Leu Ile Ser
                165                 170                 175

Lys Glu Asp Ser Gly Ser Lys Leu Val Ile Val Met Val Gly Leu Pro
            180                 185                 190

Ala Thr Gly Lys Ser Phe Ile Thr Asn Lys Leu Ser Arg Phe Leu Asn
        195                 200                 205

Tyr Ser Leu Tyr Tyr Cys Lys Val Phe Asn Val Gly Asn Thr Arg Arg
    210                 215                 220

Lys Phe Ala Lys Glu His Gly Leu Lys Asp Gln Asp Ser Lys Phe Phe
225                 230                 235                 240

Glu Pro Lys Asn Ala Asp Ser Thr Arg Leu Arg Asp Lys Trp Ala Met
                245                 250                 255

Asp Thr Leu Asp Glu Leu Leu Asp Tyr Leu Leu Glu Gly Ser Gly Ser
            260                 265                 270

Val Gly Ile Phe Asp Ala Thr Asn Thr Ser Arg Glu Arg Arg Lys Asn
        275                 280                 285

Val Leu Ala Arg Ile Arg Lys Arg Ser Pro His Leu Lys Val Leu Phe
    290                 295                 300

Leu Glu Ser Val Cys Ser Asp His Ala Leu Val Gln Lys Asn Ile Arg
305                 310                 315                 320

Leu Lys Leu Phe Gly Pro Asp Tyr Lys Gly Lys Asp Pro Glu Ser Ser
                325                 330                 335

Leu Lys Asp Phe Lys Ser Arg Leu Ala Asn Tyr Leu Lys Ala Tyr Glu
            340                 345                 350

Pro Ile Glu Asp Asp Glu Asn Leu Gln Tyr Ile Lys Met Ile Asp Val
        355                 360                 365

Gly Lys Lys Val Ile Ala Tyr Asn Ile Gln Gly Phe Leu Ala Ser Gln
    370                 375                 380
```

```
Thr Val Tyr Tyr Leu Leu Asn Phe Asn Leu Ala Asp Arg Gln Ile Trp
385                 390                 395                 400

Ile Thr Arg Ser Gly Glu Ser Glu Asp Asn Val Ser Gly Arg Ile Gly
                405                 410                 415

Gly Asn Ser His Leu Thr Pro Arg Gly Leu Arg Phe Ala Lys Ser Leu
            420                 425                 430

Pro Lys Phe Ile Ala Arg Gln Arg Glu Ile Phe Tyr Gln Asn Leu Met
        435                 440                 445

Gln Gln Lys Lys Asn Asn Glu Asn Thr Asp Gly Asn Ile Tyr Asn Asp
    450                 455                 460

Phe Phe Val Trp Thr Ser Met Arg Ala Arg Thr Ile Gly Thr Ala Gln
465                 470                 475                 480

Tyr Phe Asn Glu Asp Asp Tyr Pro Ile Lys Gln Met Lys Met Leu Asp
                485                 490                 495

Glu Leu Ser Ala Gly Asp Tyr Asp Gly Met Thr Tyr Pro Glu Ile Lys
            500                 505                 510

Asn Asn Phe Pro Glu Glu Phe Glu Lys Arg Gln Lys Asp Lys Leu Arg
        515                 520                 525

Tyr Arg Tyr Pro Gly Ile Gly Gly Glu Ser Tyr Met Asp Val Ile Asn
    530                 535                 540

Arg Leu Arg Pro Val Ile Thr Glu Leu Glu Arg Ile Glu Asp Asn Val
545                 550                 555                 560

Leu Ile Ile Thr His Arg Val Val Ala Arg Ala Leu Leu Gly Tyr Phe
                565                 570                 575

Met Asn Leu Ser Met Gly Ile Ile Ala Asn Leu Asp Val Pro Leu His
            580                 585                 590

Cys Val Tyr Cys Leu Glu Pro Lys Pro Tyr Gly Ile Thr Trp Ser Leu
        595                 600                 605

Trp Glu Tyr Asp Glu Ala Ser Asp Ser Phe Ser Lys Val Pro Gln Thr
    610                 615                 620

Asp Leu Asn Thr Thr Arg Val Lys Glu Val Gly Leu Val Tyr Asn Glu
625                 630                 635                 640

Arg Arg Tyr Ser Val Ile Pro Thr Ala Pro Pro Ser Ala Arg Ser Ser
                645                 650                 655

Phe Ala Ser Asp Phe Leu Ser Arg Lys Arg Ser Asn Pro Thr Ser Ala
            660                 665                 670

Ser Ser Ser Gln Ser Glu Leu Ser Glu Gln Pro Lys Asn Ser Val Ser
        675                 680                 685

Ala Gln Thr Gly Ser Asn Asn Thr Thr Leu Ile Gly Ser Asn Phe Asn
    690                 695                 700

Ile Lys Asn Glu Asn Gly Asp Ser Arg Ile Pro Leu Ser Ala Pro Leu
705                 710                 715                 720

Met Ala Thr Asn Thr Ser Asn Asn Ile Leu Asp Gly Gly Gly Thr Ser
                725                 730                 735

Ile Ser Ile His Arg Pro Arg Val Val Pro Asn Gln Asn Asn Val Asn
            740                 745                 750

Pro Leu Leu Ala Asn Asn Asn Lys Ala Ala Ser Asn Val Pro Asn Val
        755                 760                 765

Lys Lys Ser Ala Ala Thr Pro Arg Gln Ile Phe Glu Ile Asp Lys Val
    770                 775                 780

Asp Glu Lys Leu Ser Met Leu Lys Asn Lys Ser Phe Leu Leu His Gly
785                 790                 795                 800
```

```
Lys Asp Tyr Pro Asn Asn Ala Asp Asn Asn Asp Asn Glu Asp Ile Arg
                805                 810                 815

Ala Lys Thr Met Asn Arg Ser Gln Ser His Val
            820                 825
```

<210> SEQ ID NO 137
<211> LENGTH: 1665
<212> TYPE: DNA
<213> ORGANISM: Saccharomyces cerevisiae

<400> SEQUENCE: 137

```
atgtccaata actcattcac taacttcaaa ctggccactg aattgccagc ctggtctaag      60

ttgcaaaaaa tttatgaatc tcaaggtaag actttgtctg tcaagcaaga attccaaaaa     120

gatgccaagc gttttgaaaa attgaacaag actttcacca actatgatgg ttccaaaatc     180

ttgttcgact actcaaagaa cttggtcaac gatgaaatca ttgctgcatt gattgaactg     240

gccaaggagg ctaacgtcac cggtttgaga gatgctatgt tcaaaggtga acacatcaac     300

tccactgaag atcgtgctgt ctaccacgtc gcattgagaa acagagctaa caagccaatg     360

tacgttgatg gtgtcaacgt tgctccagaa gtcgactctg tcttgaagca catgaaggag     420

ttctctgaac aagttcgttc tggtgaatgg aagggttata ccggtaagaa gatcaccgat     480

gttgttaaca tcggtattgg tggttccgat ttgggtccag tcatggtcac tgaggctttg     540

aagcactacg ctggtgtctt ggatgtccac ttcgtttcca acattgacgg tactcacatt     600

gctgaaacct tgaaggttgt tgacccagaa actactttgt tttgattgc ttccaagact      660

ttcactaccg ctgaaactat cactaacgct aacactgcca agaactggtt cttgtcgaag     720

acaggtaatg atccatctca cattgctaag catttcgctg ctttgtccac taacgaaacc     780

gaagttgcca agttcggtat tgacaccaaa aacatgtttg gtttcgaaag ttgggtcggt     840

ggtcgttact ctgtctggtc ggctattggt ttgtctgttg ccttgtacat tggctatgac     900

aactttgagg ctttcttgaa gggtgctgaa gccgtcgaca accacttcac ccaaacccca     960

ttggaagaca acattccatt gttgggtggt ttgttgtctg tctggtacaa caacttcttt    1020

ggtgctcaaa cccatttggt tgctccattc gaccaatact tgcacagatt cccagcctac    1080

ttgcaacaat tgtcaatgga atctaacggt aagtctgtta ccagaggtaa cgtgtttact    1140

gactactcta ctggttctat cttgtttggt gaaccagcta ccaacgctca acactctttc    1200

ttccaattgg ttcaccaagg taccaagttg attccatctg atttcatctt agctgctcaa    1260

tctcataacc caattgagaa caaattacat caaaagatgt tggcttcaaa cttctttgct    1320

caagctgaag ctttaatggt tggtaaggat gaagaacaag ttaaggctga aggtgccact    1380

ggtggtttgg tcccacacaa ggtcttctca ggtaacagac caactacctc tatcttggct    1440

caaaagatta ctccagctac tttgggtgct ttgattgcct actacgaaca tgttactttc    1500

actgaaggtg ccatttggaa tatcaactct ttcgaccaat ggggtgttga attgggtaaa    1560

gtcttggcta aagtcatcgg caaggaattg gacaactcct ccaccatttc tacccacgat    1620

gcttctacca acggtttaat caatcaattc aaggaatgga tgtga                    1665
```

<210> SEQ ID NO 138
<211> LENGTH: 554
<212> TYPE: PRT
<213> ORGANISM: Saccharomyces cerevisiae

<400> SEQUENCE: 138

```
Met Ser Asn Asn Ser Phe Thr Asn Phe Lys Leu Ala Thr Glu Leu Pro
1               5                   10                  15

Ala Trp Ser Lys Leu Gln Lys Ile Tyr Glu Ser Gln Gly Lys Thr Leu
            20                  25                  30

Ser Val Lys Gln Glu Phe Gln Lys Asp Ala Lys Arg Phe Glu Lys Leu
        35                  40                  45

Asn Lys Thr Phe Thr Asn Tyr Asp Gly Ser Lys Ile Leu Phe Asp Tyr
    50                  55                  60

Ser Lys Asn Leu Val Asn Asp Glu Ile Ile Ala Ala Leu Ile Glu Leu
65                  70                  75                  80

Ala Lys Glu Ala Asn Val Thr Gly Leu Arg Asp Ala Met Phe Lys Gly
                85                  90                  95

Glu His Ile Asn Ser Thr Glu Asp Arg Ala Val Tyr His Val Ala Leu
            100                 105                 110

Arg Asn Arg Ala Asn Lys Pro Met Tyr Val Asp Gly Val Asn Val Ala
        115                 120                 125

Pro Glu Val Asp Ser Val Leu Lys His Met Lys Glu Phe Ser Glu Gln
    130                 135                 140

Val Arg Ser Gly Glu Trp Lys Gly Tyr Thr Gly Lys Lys Ile Thr Asp
145                 150                 155                 160

Val Val Asn Ile Gly Ile Gly Gly Ser Asp Leu Gly Pro Val Met Val
                165                 170                 175

Thr Glu Ala Leu Lys His Tyr Ala Gly Val Leu Asp Val His Phe Val
            180                 185                 190

Ser Asn Ile Asp Gly Thr His Ile Ala Glu Thr Leu Lys Val Val Asp
        195                 200                 205

Pro Glu Thr Thr Leu Phe Leu Ile Ala Ser Lys Thr Phe Thr Thr Ala
    210                 215                 220

Glu Thr Ile Thr Asn Ala Asn Thr Ala Lys Asn Trp Phe Leu Ser Lys
225                 230                 235                 240

Thr Gly Asn Asp Pro Ser His Ile Ala Lys His Phe Ala Ala Leu Ser
                245                 250                 255

Thr Asn Glu Thr Glu Val Ala Lys Phe Gly Ile Asp Thr Lys Asn Met
            260                 265                 270

Phe Gly Phe Glu Ser Trp Val Gly Gly Arg Tyr Ser Val Trp Ser Ala
        275                 280                 285

Ile Gly Leu Ser Val Ala Leu Tyr Ile Gly Tyr Asp Asn Phe Glu Ala
    290                 295                 300

Phe Leu Lys Gly Ala Glu Ala Val Asp Asn His Phe Thr Gln Thr Pro
305                 310                 315                 320

Leu Glu Asp Asn Ile Pro Leu Leu Gly Gly Leu Leu Ser Val Trp Tyr
                325                 330                 335

Asn Asn Phe Phe Gly Ala Gln Thr His Leu Val Ala Pro Phe Asp Gln
            340                 345                 350

Tyr Leu His Arg Phe Pro Ala Tyr Leu Gln Gln Leu Ser Met Glu Ser
        355                 360                 365

Asn Gly Lys Ser Val Thr Arg Gly Asn Val Phe Thr Asp Tyr Ser Thr
    370                 375                 380

Gly Ser Ile Leu Phe Gly Glu Pro Ala Thr Asn Ala Gln His Ser Phe
385                 390                 395                 400

Phe Gln Leu Val His Gln Gly Thr Lys Leu Ile Pro Ser Asp Phe Ile
                405                 410                 415
```

```
Leu Ala Ala Gln Ser His Asn Pro Ile Glu Asn Lys Leu His Gln Lys
            420                 425                 430

Met Leu Ala Ser Asn Phe Phe Ala Gln Ala Glu Ala Leu Met Val Gly
        435                 440                 445

Lys Asp Glu Glu Gln Val Lys Ala Glu Gly Ala Thr Gly Gly Leu Val
    450                 455                 460

Pro His Lys Val Phe Ser Gly Asn Arg Pro Thr Thr Ser Ile Leu Ala
465                 470                 475                 480

Gln Lys Ile Thr Pro Ala Thr Leu Gly Ala Leu Ile Ala Tyr Tyr Glu
                485                 490                 495

His Val Thr Phe Thr Glu Gly Ala Ile Trp Asn Ile Asn Ser Phe Asp
            500                 505                 510

Gln Trp Gly Val Glu Leu Gly Lys Val Leu Ala Lys Val Ile Gly Lys
        515                 520                 525

Glu Leu Asp Asn Ser Ser Thr Ile Ser Thr His Asp Ala Ser Thr Asn
    530                 535                 540

Gly Leu Ile Asn Gln Phe Lys Glu Trp Met
545                 550
```

<210> SEQ ID NO 139
<211> LENGTH: 744
<212> TYPE: DNA
<213> ORGANISM: Saccharomyces cerevisiae

<400> SEQUENCE: 139

```
atgccaaagt tagttttagt tagacacggt caatccgaat ggaacgaaaa gaacttattc     60

accggttggg ttgatgttaa attgtctgcc aagggtcaac aagaagccgc tagagccggt    120

gaattgttga aggaaaagaa ggtctaccca gacgtcttgt acacttccaa gttgtccaga    180

gctatccaaa ctgctaacat tgctttggaa aaggctgaca gattatggat tccagtcaac    240

agatcctgga gattgaacga aagacattac ggtgacttac aaggtaagga caaggctgaa    300

actttgaaga agttcggtga agaaaaattc aacacctaca gaagatcctt cgatgttcca    360

cctcccccaa tcgacgcttc ttctccattc tctcaaaagg gtgatgaaag atacaagtac    420

gttgacccaa atgtcttgcc agaaactgaa tctttggctt tggtcattga cagattgttg    480

ccatactggc aagatgtcat tgccaaggac ttgttgagtg gtaagaccgt catgatcgcc    540

gctcacggta actccttgag aggtttggtt aagcacttgg aaggtatctc tgatgctgac    600

attgctaagt tgaacatccc aactggtatt ccattggtct tcgaattgga cgaaaacttg    660

aagccatcta agccatctta ctacttggac ccagaagctg ccgctgctgg tgccgctgct    720

gttgccaacc aaggtaagaa ataa                                           744
```

<210> SEQ ID NO 140
<211> LENGTH: 247
<212> TYPE: PRT
<213> ORGANISM: Saccharomyces cerevisiae

<400> SEQUENCE: 140

```
Met Pro Lys Leu Val Leu Val Arg His Gly Gln Ser Glu Trp Asn Glu
1               5                   10                  15

Lys Asn Leu Phe Thr Gly Trp Val Asp Val Lys Leu Ser Ala Lys Gly
            20                  25                  30

Gln Gln Glu Ala Ala Arg Ala Gly Glu Leu Leu Lys Glu Lys Lys Val
        35                  40                  45
```

```
Tyr Pro Asp Val Leu Tyr Thr Ser Lys Leu Ser Arg Ala Ile Gln Thr
    50                  55                  60

Ala Asn Ile Ala Leu Glu Lys Ala Asp Arg Leu Trp Ile Pro Val Asn
65                  70                  75                  80

Arg Ser Trp Arg Leu Asn Glu Arg His Tyr Gly Asp Leu Gln Gly Lys
                85                  90                  95

Asp Lys Ala Glu Thr Leu Lys Lys Phe Gly Glu Glu Lys Phe Asn Thr
            100                 105                 110

Tyr Arg Arg Ser Phe Asp Val Pro Pro Pro Pro Ile Asp Ala Ser Ser
        115                 120                 125

Pro Phe Ser Gln Lys Gly Asp Glu Arg Tyr Lys Tyr Val Asp Pro Asn
    130                 135                 140

Val Leu Pro Glu Thr Glu Ser Leu Ala Leu Val Ile Asp Arg Leu Leu
145                 150                 155                 160

Pro Tyr Trp Gln Asp Val Ile Ala Lys Asp Leu Leu Ser Gly Lys Thr
                165                 170                 175

Val Met Ile Ala Ala His Gly Asn Ser Leu Arg Gly Leu Val Lys His
            180                 185                 190

Leu Glu Gly Ile Ser Asp Ala Asp Ile Ala Lys Leu Asn Ile Pro Thr
        195                 200                 205

Gly Ile Pro Leu Val Phe Glu Leu Asp Glu Asn Leu Lys Pro Ser Lys
    210                 215                 220

Pro Ser Tyr Tyr Leu Asp Pro Glu Ala Ala Ala Ala Gly Ala Ala Ala
225                 230                 235                 240

Val Ala Asn Gln Gly Lys Lys
                245
```

<210> SEQ ID NO 141
<211> LENGTH: 747
<212> TYPE: DNA
<213> ORGANISM: Saccharomyces cerevisiae

<400> SEQUENCE: 141

```
atggctagaa ctttctttgt cggtggtaac tttaaattaa acggttccaa acaatccatt      60

aaggaaattg ttgaaagatt gaacactgct tctatcccag aaaatgtcga agttgttatc     120

tgtcctccag ctacctactt agactactct gtctctttgg ttaagaagcc acaagtcact     180

gtcggtgctc aaaacgccta cttgaaggct tctggtgctt tcaccggtga aaactccgtt     240

gaccaaatca aggatgttgg tgctaagtgg gttattttgg gtcactccga aagaagatct     300

tacttccacg aagatgacaa gttcattgct gacaagacca agttcgcttt aggtcaaggt     360

gtcggtgtca tcttgtgtat cggtgaaact ttggaagaaa agaaggccgg taagactttg     420

gatgttgttg aaagacaatt gaacgctgtc ttggaagaag ttaaggactg gactaacgtc     480

gttgtcgctt acgaaccagt ctgggccatt ggtaccggtt tggctgctac tccagaagat     540

gctcaagata ttcacgcttc catcagaaag ttcttggctt ccaagttggg tgacaaggct     600

gccagcgaat tgagaatctt atacggtggt tccgctaacg gtagcaacgc cgttaccttc     660

aaggacaagg ctgatgtcga tggtttcttg gtcggtggtg cttctttgaa gccagaattt     720

gttgatatca tcaactctag aaactaa                                         747
```

<210> SEQ ID NO 142
<211> LENGTH: 248
<212> TYPE: PRT
<213> ORGANISM: Saccharomyces cerevisiae

<400> SEQUENCE: 142

```
Met Ala Arg Thr Phe Phe Val Gly Gly Asn Phe Lys Leu Asn Gly Ser
1               5                   10                  15

Lys Gln Ser Ile Lys Glu Ile Val Glu Arg Leu Asn Thr Ala Ser Ile
            20                  25                  30

Pro Glu Asn Val Glu Val Val Ile Cys Pro Pro Ala Thr Tyr Leu Asp
        35                  40                  45

Tyr Ser Val Ser Leu Val Lys Lys Pro Gln Val Thr Val Gly Ala Gln
    50                  55                  60

Asn Ala Tyr Leu Lys Ala Ser Gly Ala Phe Thr Gly Glu Asn Ser Val
65                  70                  75                  80

Asp Gln Ile Lys Asp Val Gly Ala Lys Trp Val Ile Leu Gly His Ser
                85                  90                  95

Glu Arg Arg Ser Tyr Phe His Glu Asp Asp Lys Phe Ile Ala Asp Lys
            100                 105                 110

Thr Lys Phe Ala Leu Gly Gln Gly Val Gly Val Ile Leu Cys Ile Gly
        115                 120                 125

Glu Thr Leu Glu Glu Lys Lys Ala Gly Lys Thr Leu Asp Val Val Glu
    130                 135                 140

Arg Gln Leu Asn Ala Val Leu Glu Glu Val Lys Asp Trp Thr Asn Val
145                 150                 155                 160

Val Val Ala Tyr Glu Pro Val Trp Ala Ile Gly Thr Gly Leu Ala Ala
                165                 170                 175

Thr Pro Glu Asp Ala Gln Asp Ile His Ala Ser Ile Arg Lys Phe Leu
            180                 185                 190

Ala Ser Lys Leu Gly Asp Lys Ala Ala Ser Glu Leu Arg Ile Leu Tyr
        195                 200                 205

Gly Gly Ser Ala Asn Gly Ser Asn Ala Val Thr Phe Lys Asp Lys Ala
    210                 215                 220

Asp Val Asp Gly Phe Leu Val Gly Gly Ala Ser Leu Lys Pro Glu Phe
225                 230                 235                 240

Val Asp Ile Ile Asn Ser Arg Asn
                245
```

<210> SEQ ID NO 143
<211> LENGTH: 41
<212> TYPE: DNA
<213> ORGANISM: Artificial Sequence
<220> FEATURE:
<223> OTHER INFORMATION: Artificial DNA Primer

<400> SEQUENCE: 143
ctagaactag tggatccccc atgaacgata gccaaaactg c 41

<210> SEQ ID NO 144
<211> LENGTH: 41
<212> TYPE: DNA
<213> ORGANISM: Artificial Sequence
<220> FEATURE:
<223> OTHER INFORMATION: Artificial DNA Primer

<400> SEQUENCE: 144
atatcgaatt cctgcagccc ttattggggg gaagtgtatt g 41

<210> SEQ ID NO 145
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 145
ctagaactag tggatccccc atgttgcaag gaattttaga aaccg 45

<210> SEQ ID NO 146
<211> LENGTH: 52
<212> TYPE: DNA
<213> ORGANISM: Artificial Sequence
<220> FEATURE:
<223> OTHER INFORMATION: Artificial DNA Primer

<400> SEQUENCE: 146
atatcgaatt cctgcagccc tcaaaatttt gtaactatat tcatttcatc tg 52

<210> SEQ ID NO 147
<211> LENGTH: 3426
<212> TYPE: DNA
<213> ORGANISM: Saccharomyces cerevisiae

<400> SEQUENCE: 147
atgtcacttc taatagattc tgtaccaaca gttgcttata aggaccaaaa accgggtact 60
tcaggtttac gtaagaagac caaggttttc atggatgagc ctcattatac tgagaacttc 120
attcaagcaa caatgcaatc tatccctaat ggctcagagg gaaccacttt agttgttgga 180
ggagatggtc gtttctacaa cgatgttatc atgaacaaga ttgccgcagt aggtgctgca 240
aacggtgtca gaaagttagt cattggtcaa ggcggtttac tttcaacacc agctgcttct 300
catataatta gaacatacga ggaaaagtgt accggtggtg gtatcatatt aactgcctca 360
cacaacccag gcggtccaga gaatgattta ggtatcaagt ataatttacc taatggtggg 420
ccagctccag agagtgtcac taacgctatc tgggaagcgt ctaaaaaatt aactcactat 480
aaaattataa agaacttccc caagttgaat ttgaacaagc ttggtaaaaa ccaaaaatat 540
ggcccattgt tagtggacat aattgatcct gccaaagcat acgttcaatt tctgaaggaa 600
atttttgatt ttgacttaat taaaagcttc ttagcgaaac agcgcaaaga caaagggtgg 660
aagttgttgt ttgactcctt aaatggtatt acaggaccat atggtaaggc tatatttgtt 720
gatgaatttg gtttaccggc agaggaagtt cttcaaaatt ggcacccttt acctgatttc 780
ggcggtttac atcccgatcc gaatctaacc tatgcacgaa ctcttgttga cagggttgac 840
cgcgaaaaaa ttgcctttgg agcagcctcc gatggtgatg gtgataggaa tatgatttac 900
ggttatggcc ctgctttcgt ttcgccaggt gattctgttg ccattattgc cgaatatgca 960
cccgaaattc catacttcgc caaacaaggt atttatggct tggcacgttc atttcctaca 1020
tcctcagcca ttgatcgtgt tgcagcaaaa aagggattaa gatgttacga agttccaacc 1080
ggctggaaat tcttctgtgc cttatttgat gctaaaaagc tatcaatctg tggtgaagaa 1140
tccttcggta caggttccaa tcatatcaga gaaaaggacg gtctatgggc cattattgct 1200
tggttaaata tcttggctat ctaccatagg cgtaaccctg aaaaggaagc ttcgatcaaa 1260
actattcagg acgaattttg gaacgagtat ggccgtactt tcttcacaag atacgattac 1320
gaacatatcg aatgcgagca ggccgaaaaa gttgtagctc ttttgagtga atttgtatca 1380
aggccaaacg tttgtggctc ccacttccca gctgatgagt ctttaaccgt tatcgattgt 1440
ggtgattttt cgtatagaga tctagatggc tccatctctg aaaatcaagg ccttttcgta 1500
aagttttcga atgggactaa atttgttttg aggttatccg gcacaggcag ttctggtgca 1560

```
acaataagat tatacgtaga aaagtatact gataaaaagg agaactatgg ccaaacagct   1620

gacgtcttct tgaaacccgt catcaactcc attgtaaaat tcttaagatt taaagaaatt   1680

ttaggaacag acgaaccaac agtccgcaca tagatgtcac ttctaataga ttctgtacca   1740

acagttgctt ataaggacca aaaaccgggt acttcaggtt tacgtaagaa gaccaaggtt   1800

ttcatggatg agcctcatta tactgagaac ttcattcaag caacaatgca atctatccct   1860

aatggctcag agggaaccac tttagttgtt ggaggagatg gtcgtttcta caacgatgtt   1920

atcatgaaca agattgccgc agtaggtgct gcaaacggtg tcagaaagtt agtcattggt   1980

caaggcggtt tactttcaac accagctgct tctcatataa ttagaacata cgaggaaaag   2040

tgtaccggtg gtggtatcat attaactgcc tcacacaacc caggcggtcc agagaatgat   2100

ttaggtatca agtataattt acctaatggt gggccagctc cagagagtgt cactaacgct   2160

atctgggaag cgtctaaaaa attaactcac tataaaatta taaagaactt ccccaagttg   2220

aatttgaaca agcttggtaa aaaccaaaaa tatggcccat tgttagtgga cataattgat   2280

cctgccaaag catacgttca atttctgaag gaaatttttg attttgactt aattaaaagc   2340

ttcttagcga aacagcgcaa agacaaaggg tggaagttgt tgtttgactc cttaaatggt   2400

attacaggac catatggtaa ggctatattt gttgatgaat ttggtttacc ggcagaggaa   2460

gttcttcaaa attggcaccc tttacctgat ttcggcggtt tacatcccga tccgaatcta   2520

acctatgcac gaactcttgt tgacagggtt gaccgcgaaa aaattgcctt tggagcagcc   2580

tccgatggtg atggtgatag gaatatgatt tacggttatg gccctgcttt cgtttcgcca   2640

ggtgattctg ttgccattat tgccgaatat gcacccgaaa ttccatactt cgccaaacaa   2700

ggtatttatg gcttggcacg ttcatttcct acatcctcag ccattgatcg tgttgcagca   2760

aaaaagggat taagatgtta cgaagttcca accggctgga aattcttctg tgccttattt   2820

gatgctaaaa agctatcaat ctgtggtgaa gaatccttcg gtacaggttc caatcatatc   2880

agagaaaagg acggtctatg ggccattatt gcttggttaa atatcttggc tatctaccat   2940

aggcgtaacc ctgaaaagga agcttcgatc aaaactattc aggacgaatt ttggaacgag   3000

tatggccgta ctttcttcac aagatacgat tacgaacata tcgaatgcga gcaggccgaa   3060

aaagttgtag ctcttttgag tgaatttgta tcaaggccaa acgtttgtgg ctcccacttc   3120

ccagctgatg agtctttaac cgttatcgat tgtggtgatt tttcgtatag agatctagat   3180

ggctccatct ctgaaaatca aggccttttc gtaaagtttt cgaatgggac taaatttgtt   3240

ttgaggttat ccggcacagg cagttctggt gcaacaataa gattatacgt agaaaagtat   3300

actgataaaa aggagaacta tggccaaaca gctgacgtct tcttgaaacc cgtcatcaac   3360

tccattgtaa aattcttaag atttaaagaa attttaggaa cagacgaacc aacagtccgc   3420

acatag                                                              3426
```

<210> SEQ ID NO 148
<211> LENGTH: 570
<212> TYPE: PRT
<213> ORGANISM: Saccharomyces cerevisiae

<400> SEQUENCE: 148

```
Met Ser Leu Leu Ile Asp Ser Val Pro Thr Val Ala Tyr Lys Asp Gln
1               5                   10                  15

Lys Pro Gly Thr Ser Gly Leu Arg Lys Lys Thr Lys Val Phe Met Asp
            20                  25                  30
```

```
Glu Pro His Tyr Thr Glu Asn Phe Ile Gln Ala Thr Met Gln Ser Ile
        35                  40                  45

Pro Asn Gly Ser Glu Gly Thr Thr Leu Val Val Gly Gly Asp Gly Arg
    50                  55                  60

Phe Tyr Asn Asp Val Ile Met Asn Lys Ile Ala Ala Val Gly Ala Ala
65                  70                  75                  80

Asn Gly Val Arg Lys Leu Val Ile Gly Gln Gly Gly Leu Leu Ser Thr
                85                  90                  95

Pro Ala Ala Ser His Ile Ile Arg Thr Tyr Glu Glu Lys Cys Thr Gly
            100                 105                 110

Gly Gly Ile Ile Leu Thr Ala Ser His Asn Pro Gly Gly Pro Glu Asn
        115                 120                 125

Asp Leu Gly Ile Lys Tyr Asn Leu Pro Asn Gly Gly Pro Ala Pro Glu
    130                 135                 140

Ser Val Thr Asn Ala Ile Trp Glu Ala Ser Lys Lys Leu Thr His Tyr
145                 150                 155                 160

Lys Ile Ile Lys Asn Phe Pro Lys Leu Asn Leu Asn Lys Leu Gly Lys
                165                 170                 175

Asn Gln Lys Tyr Gly Pro Leu Leu Val Asp Ile Ile Asp Pro Ala Lys
            180                 185                 190

Ala Tyr Val Gln Phe Leu Lys Glu Ile Phe Asp Phe Asp Leu Ile Lys
        195                 200                 205

Ser Phe Leu Ala Lys Gln Arg Lys Asp Lys Gly Trp Lys Leu Leu Phe
    210                 215                 220

Asp Ser Leu Asn Gly Ile Thr Gly Pro Tyr Gly Lys Ala Ile Phe Val
225                 230                 235                 240

Asp Glu Phe Gly Leu Pro Ala Glu Glu Val Leu Gln Asn Trp His Pro
                245                 250                 255

Leu Pro Asp Phe Gly Gly Leu His Pro Asp Pro Asn Leu Thr Tyr Ala
            260                 265                 270

Arg Thr Leu Val Asp Arg Val Asp Arg Glu Lys Ile Ala Phe Gly Ala
        275                 280                 285

Ala Ser Asp Gly Asp Gly Asp Arg Asn Met Ile Tyr Gly Tyr Gly Pro
    290                 295                 300

Ala Phe Val Ser Pro Gly Asp Ser Val Ala Ile Ile Ala Glu Tyr Ala
305                 310                 315                 320

Pro Glu Ile Pro Tyr Phe Ala Lys Gln Gly Ile Tyr Gly Leu Ala Arg
                325                 330                 335

Ser Phe Pro Thr Ser Ser Ala Ile Asp Arg Val Ala Ala Lys Lys Gly
            340                 345                 350

Leu Arg Cys Tyr Glu Val Pro Thr Gly Trp Lys Phe Phe Cys Ala Leu
        355                 360                 365

Phe Asp Ala Lys Lys Leu Ser Ile Cys Gly Glu Glu Ser Phe Gly Thr
    370                 375                 380

Gly Ser Asn His Ile Arg Glu Lys Asp Gly Leu Trp Ala Ile Ile Ala
385                 390                 395                 400

Trp Leu Asn Ile Leu Ala Ile Tyr His Arg Arg Asn Pro Glu Lys Glu
                405                 410                 415

Ala Ser Ile Lys Thr Ile Gln Asp Glu Phe Trp Asn Glu Tyr Gly Arg
            420                 425                 430

Thr Phe Phe Thr Arg Tyr Asp Tyr Glu His Ile Glu Cys Glu Gln Ala
        435                 440                 445
```

```
Glu Lys Val Val Ala Leu Leu Ser Glu Phe Val Ser Arg Pro Asn Val
    450                 455                 460

Cys Gly Ser His Phe Pro Ala Asp Glu Ser Leu Thr Val Ile Asp Cys
465                 470                 475                 480

Gly Asp Phe Ser Tyr Arg Asp Leu Asp Gly Ser Ile Ser Glu Asn Gln
                485                 490                 495

Gly Leu Phe Val Lys Phe Ser Asn Gly Thr Lys Phe Val Leu Arg Leu
            500                 505                 510

Ser Gly Thr Gly Ser Ser Gly Ala Thr Ile Arg Leu Tyr Val Glu Lys
        515                 520                 525

Tyr Thr Asp Lys Lys Glu Asn Tyr Gly Gln Thr Ala Asp Val Phe Leu
    530                 535                 540

Lys Pro Val Ile Asn Ser Ile Val Lys Phe Leu Arg Phe Lys Glu Ile
545                 550                 555                 560

Leu Gly Thr Asp Glu Pro Thr Val Arg Thr
                565                 570


<210> SEQ ID NO 149
<211> LENGTH: 1869
<212> TYPE: DNA
<213> ORGANISM: Saccharomyces cerevisiae

<400> SEQUENCE: 149

atgttgcaag gaattttaga aaccgtacca tctgacttga aagatccgat atcattatgg      60

tttaagcaag accgcaaccc aaaaactata gaagaggtca ccgctctctg caaaaaatcc     120

gactggaatg agttacacaa aagatttgat tctagaattc agtttggcac tgctggttta     180

agatcgcaaa tgcaagctgg ctttagcagg atgaatactt tagtagtcat acaagcgtct     240

cagggattgg caacttatgt aagacaacag tttccagaca atttggtagc tgttgtggga     300

cacgatcata gattccattc taaggagttc gctagagcta ctgctgctgc atttctttta     360

aaaggattta aggtacatta tttgaatcct gaccacgaat ttgttcatac ccctttagtt     420

ccctttgcag tggataagct aaaggcctcc gttggcgtaa tgataacagc aagtcacaac     480

ccaaaaatgg ataatggata taaagtatac tattccaatg gatgccaaat cattccacct     540

cacgatcatg ccatctctga ttccattgac gcaaatttag aaccatgggc caatgtgtgg     600

gatttcgacg atgttctaaa taaggctctc aaacaaggga aattgatgta ttccagagaa     660

gaaatgctga agttatattt agaggaggtt tctaaaaatc tggtagaaat caacccatta     720

aagcttgaag taaaagccaa accttggttc gtttacactc caatgcatgg gggttggatt     780

gacattttca gcaccatcgt aaaaaaaaca ctgtgcctgg tagaaggtaa ggattaccta     840

tgtgttcctg aacaacaaaa tccagatcct tctttcccaa ctgttggatt tcctaaccct     900

gaagaaaaag gtgctttaga cattggtata aacttggctg aaaaacatga cattgactta     960

cttgttgcca acgaccctga cgctgataga ttctctgttg ctgttaaaga tatgcagtca    1020

ggcgaatggc gacaactaac aggtaacgaa atcggttttc tttttgcatt ttatgaatat    1080

cagaaatata aaagtatgga caaagaattt cagcacgttc atccgttggc tatgttaaat    1140

tcaacagtgt cttcacaaat gataaaaaaa atggcagaaa tagaagggtt ccattatgag    1200

gatacattaa caggatttaa gtggatcgga aatcgtgcca tactcttgga aaagaaaggc    1260

tattacgttc cttttggatt cgaggaagca ataggctaca tgtttccagc aatggagcat    1320

gataaggatg gtatcagtgc atccattgtc ttcttgcaag cctactgtaa gtggaaaata    1380

gaccacaatt tggacccgct aaatgtctta gaaaatggct tcaaaaaata tggcgtgttc    1440
```

```
aaagagtaca atggctatta tgtcgttcca aatccaactg ttacaaaaga tatatttgac   1500

tacatcagga atgtctacac tcctgagggc gcgtcatatc cttcatctat tggtgaagaa   1560

atcgaagtac tttactatcg agatttaacc actggttacc aatcggatac cataaatcat   1620

aaacctactc tacccgtcga tcctacatca caaatgataa cagtatctgc tagaccaagt   1680

aacggtagtg agaatgagca tatccgcttc actattcgcg ggtccggaac agaaccaaaa   1740

cttaaagtat atattgaagc ttgcgcaaat gaagaacaaa gagcctcttt cttggcgaaa   1800

ttgacttgga atgtgctgag acgtgaatgg tttagaccag atgaaatgaa tatagttaca   1860

aaattttga                                                           1869
```

<210> SEQ ID NO 150
<211> LENGTH: 622
<212> TYPE: PRT
<213> ORGANISM: Saccharomyces cerevisiae

<400> SEQUENCE: 150

```
Met Leu Gln Gly Ile Leu Glu Thr Val Pro Ser Asp Leu Lys Asp Pro
1               5                   10                  15

Ile Ser Leu Trp Phe Lys Gln Asp Arg Asn Pro Lys Thr Ile Glu Glu
            20                  25                  30

Val Thr Ala Leu Cys Lys Lys Ser Asp Trp Asn Glu Leu His Lys Arg
        35                  40                  45

Phe Asp Ser Arg Ile Gln Phe Gly Thr Ala Gly Leu Arg Ser Gln Met
    50                  55                  60

Gln Ala Gly Phe Ser Arg Met Asn Thr Leu Val Val Ile Gln Ala Ser
65                  70                  75                  80

Gln Gly Leu Ala Thr Tyr Val Arg Gln Gln Phe Pro Asp Asn Leu Val
                85                  90                  95

Ala Val Val Gly His Asp His Arg Phe His Ser Lys Glu Phe Ala Arg
            100                 105                 110

Ala Thr Ala Ala Ala Phe Leu Leu Lys Gly Phe Lys Val His Tyr Leu
        115                 120                 125

Asn Pro Asp His Glu Phe Val His Thr Pro Leu Val Pro Phe Ala Val
    130                 135                 140

Asp Lys Leu Lys Ala Ser Val Gly Val Met Ile Thr Ala Ser His Asn
145                 150                 155                 160

Pro Lys Met Asp Asn Gly Tyr Lys Val Tyr Tyr Ser Asn Gly Cys Gln
                165                 170                 175

Ile Ile Pro Pro His Asp His Ala Ile Ser Asp Ser Ile Asp Ala Asn
            180                 185                 190

Leu Glu Pro Trp Ala Asn Val Trp Asp Phe Asp Asp Val Leu Asn Lys
        195                 200                 205

Ala Leu Lys Gln Gly Lys Leu Met Tyr Ser Arg Glu Glu Met Leu Lys
    210                 215                 220

Leu Tyr Leu Glu Glu Val Ser Lys Asn Leu Val Glu Ile Asn Pro Leu
225                 230                 235                 240

Lys Leu Glu Val Lys Ala Lys Pro Trp Phe Val Tyr Thr Pro Met His
                245                 250                 255

Gly Val Gly Phe Asp Ile Phe Ser Thr Ile Val Lys Lys Thr Leu Cys
            260                 265                 270

Leu Val Glu Gly Lys Asp Tyr Leu Cys Val Pro Glu Gln Gln Asn Pro
        275                 280                 285
```

-continued

```
Asp Pro Ser Phe Pro Thr Val Gly Phe Pro Asn Pro Glu Glu Lys Gly
    290                 295                 300

Ala Leu Asp Ile Gly Ile Asn Leu Ala Glu Lys His Asp Ile Asp Leu
305                 310                 315                 320

Leu Val Ala Asn Asp Pro Asp Ala Asp Arg Phe Ser Val Ala Val Lys
                325                 330                 335

Asp Met Gln Ser Gly Glu Trp Arg Gln Leu Thr Gly Asn Glu Ile Gly
            340                 345                 350

Phe Leu Phe Ala Phe Tyr Glu Tyr Gln Lys Tyr Lys Ser Met Asp Lys
        355                 360                 365

Glu Phe Gln His Val His Pro Leu Ala Met Leu Asn Ser Thr Val Ser
    370                 375                 380

Ser Gln Met Ile Lys Lys Met Ala Glu Ile Glu Gly Phe His Tyr Glu
385                 390                 395                 400

Asp Thr Leu Thr Gly Phe Lys Trp Ile Gly Asn Arg Ala Ile Leu Leu
                405                 410                 415

Glu Lys Lys Gly Tyr Tyr Val Pro Phe Gly Phe Glu Glu Ala Ile Gly
            420                 425                 430

Tyr Met Phe Pro Ala Met Glu His Asp Lys Asp Gly Ile Ser Ala Ser
        435                 440                 445

Ile Val Phe Leu Gln Ala Tyr Cys Lys Trp Lys Ile Asp His Asn Leu
    450                 455                 460

Asp Pro Leu Asn Val Leu Glu Asn Gly Phe Lys Lys Tyr Gly Val Phe
465                 470                 475                 480

Lys Glu Tyr Asn Gly Tyr Tyr Val Val Pro Asn Pro Thr Val Thr Lys
                485                 490                 495

Asp Ile Phe Asp Tyr Ile Arg Asn Val Tyr Thr Pro Glu Gly Ala Ser
            500                 505                 510

Tyr Pro Ser Ser Ile Gly Glu Glu Ile Glu Val Leu Tyr Tyr Arg Asp
        515                 520                 525

Leu Thr Thr Gly Tyr Gln Ser Asp Thr Ile Asn His Lys Pro Thr Leu
    530                 535                 540

Pro Val Asp Pro Thr Ser Gln Met Ile Thr Val Ser Ala Arg Pro Ser
545                 550                 555                 560

Asn Gly Ser Glu Asn Glu His Ile Arg Phe Thr Ile Arg Gly Ser Gly
                565                 570                 575

Thr Glu Pro Lys Leu Lys Val Tyr Ile Glu Ala Cys Ala Asn Glu Glu
            580                 585                 590

Gln Arg Ala Ser Phe Leu Ala Lys Leu Thr Trp Asn Val Leu Arg Arg
        595                 600                 605

Glu Trp Phe Arg Pro Asp Glu Met Asn Ile Val Thr Lys Phe
    610                 615                 620
```